US011801243B2

(12) United States Patent
Guichard et al.

(10) Patent No.: US 11,801,243 B2
(45) Date of Patent: Oct. 31, 2023

(54) BROMODOMAIN INHIBITORS FOR ANDROGEN RECEPTOR-DRIVEN CANCERS

(71) Applicant: FORMA Therapeutics, Inc., Watertown, MA (US)

(72) Inventors: Sylvie Guichard, Watertown, MA (US); Maureen Caligiuri, Watertown, MA (US); Anna Ericsson, Shrewsbury, MA (US); Qunli Xu, Watertown, MA (US); Hesham Mohamed, Watertown, MA (US)

(73) Assignee: Forma Therapeutics, Inc., Watertown, MA (US)

(*) Notice: Subject to any disclaimer, the term of this patent is extended or adjusted under 35 U.S.C. 154(b) by 35 days.

(21) Appl. No.: 17/482,720

(22) Filed: Sep. 23, 2021

(65) Prior Publication Data

US 2022/0088005 A1 Mar. 24, 2022

Related U.S. Application Data

(60) Provisional application No. 63/082,963, filed on Sep. 24, 2020, provisional application No. 63/082,418, filed on Sep. 23, 2020, provisional application No. 63/082,412, filed on Sep. 23, 2020, provisional application No. 63/082,414, filed on Sep. 23, 2020.

(51) Int. Cl.
*A61K 31/4745* (2006.01)
*A61P 35/00* (2006.01)

(52) U.S. Cl.
CPC .......... *A61K 31/4745* (2013.01); *A61P 35/00* (2018.01)

(58) Field of Classification Search
None
See application file for complete search history.

(56) References Cited

U.S. PATENT DOCUMENTS

| | | |
|---|---|---|
| 6,011,029 A | 1/2000 | Ding et al. |
| 7,101,869 B2 | 9/2006 | Blumenkopf et al. |
| 7,709,489 B2 | 5/2010 | Aranyi et al. |
| 9,211,333 B2 | 12/2015 | Zhang et al. |
| 9,763,922 B2 | 9/2017 | Adler et al. |
| 9,975,896 B2 | 5/2018 | Marineau et al. |
| 10,336,722 B2 | 7/2019 | Bair et al. |
| 10,562,916 B2 | 2/2020 | Campbell et al. |
| 10,870,648 B2 | 12/2020 | Schiller et al. |
| 2004/0214825 A1 | 10/2004 | McCall et al. |
| 2006/0106020 A1 | 5/2006 | Rodgers et al. |
| 2006/0167047 A1 | 7/2006 | Timmers et al. |
| 2007/0179165 A1 | 8/2007 | Gyorkos et al. |
| 2007/0203236 A1 | 8/2007 | Smith et al. |
| 2007/0254961 A1 | 11/2007 | Tapas et al. |
| 2009/0326020 A1 | 12/2009 | Yan et al. |
| 2010/0166781 A1 | 7/2010 | Setiadi et al. |
| 2010/0179325 A1 | 7/2010 | Suzuki et al. |
| 2010/0216853 A1 | 8/2010 | Marmorstein et al. |
| 2010/0267672 A1 | 10/2010 | Jung et al. |
| 2011/0257196 A1 | 10/2011 | Yan et al. |
| 2012/0108581 A1 | 5/2012 | Ashikawa et al. |
| 2012/0258953 A1 | 10/2012 | Aay et al. |
| 2013/0158003 A1 | 6/2013 | Campbell et al. |
| 2013/0324580 A1 | 12/2013 | Zhang et al. |
| 2016/0158207 A1 | 9/2016 | Adler et al. |
| 2016/0257692 A1 | 9/2016 | Bair et al. |
| 2020/0216445 A1 | 7/2020 | Schiller et al. |

FOREIGN PATENT DOCUMENTS

| | | |
|---|---|---|
| EP | 2 412 710 A1 | 1/2012 |
| JP | 2013-526615 | 6/2013 |
| JP | 2016-540831 | 12/2016 |
| JP | 2017-537100 | 12/2017 |
| WO | WO 1995/020589 A1 | 8/1995 |
| WO | WO 2002/040614 A1 | 5/2002 |
| WO | WO 2003/033517 A1 | 4/2003 |
| WO | WO 2003/045929 A1 | 6/2003 |
| WO | WO 2004/043392 A2 | 5/2004 |
| WO | WO 2005/066162 A1 | 7/2005 |
| WO | WO 2007/120339 A1 | 10/2007 |
| WO | WO 2007/133653 A2 | 11/2007 |
| WO | WO 2008/009348 A1 | 1/2008 |
| WO | WO 2009/000413 A1 | 12/2008 |
| WO | WO 2009/064251 A1 | 5/2009 |
| WO | WO 2009/152072 A1 | 12/2009 |

(Continued)

OTHER PUBLICATIONS

Scher et al, The New England Journal of Medicine, vol. 367, No. 13, Sep. 27 2012.*
Proverbs-Singh et al, Endocr Relat Cancer, 22(3): R87-R106. doi:10.1530/ERC-14-0543; Jan. 15, 2016.*
European Search Report from corresponding application EP 20 77 3477 (dated Nov. 21, 2022).
Moustakim et al.,, "Discovery of a PCAF Bromodomain Chemical Probe", Angewandte chemie, Dec. 14, 2016 , pp. 845-849, vol. 129.
Extended European Search Report from corresponding application EP 19 18 3741 (dated Aug. 1, 2019).

(Continued)

*Primary Examiner* — Zinna Northington Davis
(74) *Attorney, Agent, or Firm* — Wiggin and Dana LLP

(57) ABSTRACT

Methods for treating certain androgen receptor-positive forms of cancer using inhibitors of the CREB binding protein bromodomain are disclosed. In some methods, the AR-positive forms of cancer may be breast cancer, including triple negative forms, hormone receptor positive forms, and HER2-positive forms. In other methods, the AR-positive forms of cancer may be prostate cancer, including metastatic castration resistant prostate cancer. In some embodiments, methods of treating prostate cancer comprise the step of administering to a patient in need thereof the compound (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid, or a pharmaceutically acceptable salt thereof.

23 Claims, 39 Drawing Sheets

(56) References Cited

FOREIGN PATENT DOCUMENTS

| WO | WO 2010/110380 A1 | 9/2010 |
|---|---|---|
| WO | WO 2010/118208 A1 | 10/2010 |
| WO | WO 2010/138490 A1 | 12/2010 |
| WO | WO 2011/085039 A2 | 7/2011 |
| WO | WO 2011/109059 A1 | 9/2011 |
| WO | WO 2011/150156 A2 | 12/2011 |
| WO | WO 2012/019093 A1 | 2/2012 |
| WO | WO 2012/080729 A2 | 6/2012 |
| WO | WO 2012/082837 A1 | 6/2012 |
| WO | WO 2012/116135 A1 | 8/2012 |
| WO | WO 2013/004995 A1 | 1/2013 |
| WO | WO 2013/006485 A1 | 1/2013 |
| WO | WO 2013/148114 A1 | 10/2013 |
| WO | WO 2014/045305 A1 | 3/2014 |
| WO | WO 2014/133414 A2 | 9/2014 |
| WO | WO 2014/182929 A1 | 11/2014 |
| WO | WO 2015/002754 A2 | 1/2015 |
| WO | WO 2015/004533 A2 | 1/2015 |
| WO | WO 2015/013635 A2 | 1/2015 |
| WO | WO 2015/022322 A1 | 2/2015 |
| WO | WO 2015/073763 A1 | 5/2015 |
| WO | WO 2015/074064 A2 | 5/2015 |
| WO | WO 2015/074081 A1 | 5/2015 |
| WO | WO 2016/044694 A1 | 3/2016 |
| WO | WO 2016/086200 A1 | 6/2016 |
| WO | WO 2016/110821 A1 | 7/2016 |
| WO | WO 2016/128908 A1 | 8/2016 |
| WO | WO 2016/170323 A1 | 10/2016 |
| WO | WO 2016/170324 A1 | 10/2016 |
| WO | WO 2017/197056 A1 | 11/2017 |
| WO | WO 2017/197240 A1 | 11/2017 |
| WO | WO 2017/205536 A2 | 11/2017 |
| WO | WO 2018/073586 A1 | 4/2018 |
| WO | WO 2018/073587 A1 | 4/2018 |
| WO | WO 2019/055869 A1 | 3/2019 |
| WO | WO 2019/055877 A1 | 3/2019 |

OTHER PUBLICATIONS

International Search Report from related application PCT/US2018/051235 (dated Feb. 25, 2019).
International Search Report from related application PCT/US2018/051214 (dated Dec. 4, 2018).
International Search Report from related application PCT/US2017/034320 (dated Nov. 15, 2017).
International Search Report from related application PCT/US2014/066198 (dated May 18, 2015).
International Search Report from related Application No. PCT/US2019/039936 (dated Sep. 23, 2019).
International Search Report from related Application No. PCT/US2020/022783 (dated Jun. 10, 2020).
International Search Report from related Application No. PCT/US2020/022818 (dated Jun. 15, 2020).
International Search Report from related Application No. PCT/US2020/022823 (dated Jun. 15, 2020).
PubChem CID: 138472436, create date, Aug. 20, 2019, p. 2 formula.
PubChem CID 136574372, deposited Jan. 24, 2019, pp. 1-8, p. 2.
"AR: Androgen Receptor", Depmap Portal, https://depmap.org/portal/gene/AR?tab=characterization (release 19Q2), dated May 28, 2020.
"Gene Set: Hallmark_Androgen Response", Gene Set Enrichment Analysis, http://software.broadinstitute.org/gsea/msigdb/cards/HALLMARK_ANDROGEN_RESPONSE.html, (dated May 28, 2020).
Bowers, et al. Virtual Ligand Screening of the p300/CBP Histone Acetyltransferase: Identification of a Selective Small Molecule Inhibitor, Chemistry & Biology 17, pp. 471-482, May 28, 2010.

Chekler, Eugene L. et al. "Transcriptional Profiling of a Selective CREB Binding Protein Bromodomain Inhibitor Highlights Therapeutic Opportunities", Chemistry and Biology, 2015, 22(12), 1588-1596.
Crawford et al. "Discovery of A Potent and Selective Vivo Probe (GNE-272) for the Bromodomains fo CBP/EP300", J. Med. Chem., 2016, 56 pgs.
Duncan, A. Hay et al. "Discovery and Optimization of Small Molecule Ligands for the CBP/p300 Bromodomains", J. Am. Chem. Soc., 2014, 136(26), 9308-9319.
Fan et al. "p300 Modulates the BRCA1 Inhibition of Estrogen Receptor Activity", Cancer Research, 2002, 62, 141-151.
Garcia-Carpizo et al. "CREBBP/EP300 bromodomain inhibition affects the proliferation of AR positive breast cancer cell lines", Molecular Cancer Research, 2019.
Goff, Corinne Le et al. "Synthesis of some novel fused tetracyclic quinolonecarboxylic acids via 7-methyl-6,7,8,9-tetrahydro-3H-imidazo[4,5-f]quinoline and 6-methyl-5,6,7,8-tetrahydro-1H-imidazo[4,5-g]quinoline", Journal of Heterocyclic Chemistry, 1994, 31(1), 153-160.
Hammitzsch, "CBP30, a selective CBP/p300 bromodomain inhibitor, suppresses human Th 17 responses," Proceedings of the National Academy of Sciences 112.34 (2015): 10768-10773.
Jiang et al., "Small molecule Nas-e targeting cAMP response element binding protein (CREB) and CREB-binding protein interaction inhibits breast cancer bone metastasis" Journal of Cellular and Molecular Medicine, Nov. 20, 2018, vol. 23, pp. 1224-1234.
Jin et al. "Therapeutic Targeting of the CBP/p300 Bromodomain Blocks the Growth of Castration-Resistant Prostate Cancer", Cancer Research, 2017, 77(20), 5564-5575.
Kumar et al. "Androgen Receptor Immunohistochemistry as a Companion Diagnostic Approach to Predict Clinical Response to Enzalutamide in Triple-Negative Breast Cancer", JCO Precision Oncology, 2017, DOI: 10.1200/PO.17.00075.
Lasko et al. "Discovery of a selective catalytic p300/CBP inhibitor that targets lineage-specific tumours", Nature, 2017, vol. 000, 17 pgs.
Robinson et al., "Androgen receptor driven transcription in molecular apocrine breast cancer is mediated by FoxA1", The EMBO Journal, 2011, 30, 3019-3027
Safarpour, Damoun et al. "Androgen receptor (AR) expression in 400 breast carcinomas: is routine AR assessment justified?", Am J Cancer Res, 2014, 4(4), 353-368.
Scher, Howard et al. "Association of AR-V7 on Circulating Tumor Cells as a Treatment-Specific Biomarker With Outcomes and Survival in Castration-Resistant Prostate Cancer", JAMA Oncology, 2016, 2(11), 1441-1449.
Scher et al. "Assessment of the Validity of Nuclear-Localized Androgen Receptor Splice Variant 7 in Circulating Tumor Cells as a Predictive Biomarker for Castration-Resistant Prostate Cancer" JAMA Oncology, 2018, 4(9), 1179-1186.
Snow et al., "Discovery of 2-Phenylamino-imidazo[4,5-h]isoquinolin-9-ones: a New Class of Inhibitors of Lck Kinase", Journal of Medicinal Chemistry, vol. 45, pp. 3394-3405, (2002).
Solankee et al. "Synthesis and evaluation of some novel S-triazine based chalcones and their derivatives",Der Pharma Chemica, 2011, 3(6), 317-324.
Traina et al. "Enzalutamide for the Treatment of Androgen Receptor-Expressing Triple-Negative Breast Cancer" Journal of Clinical Oncology, 2018, 36(9), 884-890.
Tucci, Marcello et al. "Enzalutamide-resistant castration-resistant prostate cancer: challenges and solutions", OncoTargets and Therapy, 2018, 11, 7353-7368.
Wong et al. "Anti-tumor activity of targeted and cytotoxic agents in murine subcutaneous tumor models correlates with clinical response", Clinical Cancer Research, 2012.

* cited by examiner

FIGURE 2

| Cmpd. No. | Structure and Compound Name | LCMS (m/z) [M+H]+ | 1H NMR | CBP IC50 (µM) (mean) | BRD4 IC50 (µM) (mean) |
|---|---|---|---|---|---|
| 1 | 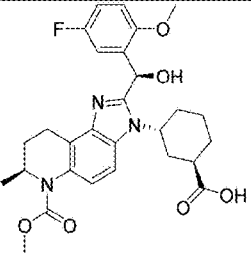 (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 526 | 1H-NMR (CD3OD, 400 MHz) δ (ppm): 7.56-7.47 (m, 1H), 7.47-7.31 (m, 1H), 7.21-7.09 (m, 1H), 7.09-6.89 (m, 2H), 6.53(s, 1H), 4.81-4.61(m, 2H), 3.85(s, 3H), 3.78(s, 3H), 3.31-3.18(m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.15 (d, J = 6.8 Hz, 3H) | ++++ | ++ |
| 2 | 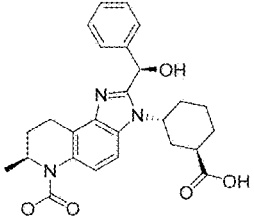 3-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 478 | 1H-NMR (CD3OD, 400 MHz) δ (ppm): 7.51-7.25 (m, 7H), 6.20 (s, 1H), 4.98-4.72 (m, 2H), 3.79(s, 3H), 3.33-3.25(m, 1H), 3.06-2.81 (m, 2H), 2.41-2.20 (m, 2H), 2.18-2.05 (m, 3H), 1.81-1.72 (m, 1H), 1.70-1.53 (m, 2H), 1.48-1.25 (m, 2H), 1.16 (d, J = 6.4 Hz, 3H) | ++++ | + |
| 3 | 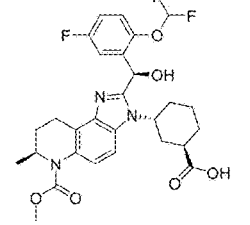 3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 562 | 1H-NMR (CD3OD, 400 MHz) δ (ppm): 7.62 (d, J = 9.2 Hz, 1H), 7.53 (d, J = 8.8 Hz, 1H), 7.41(d, J = 9.2Hz, 1H) 7.20-7.13 (m, 2H), 6.67-6.30 (m, 2H), 4.98-4.95 (m, 1H), 4.76-4.71 (m, 1H), 3.78 (s, 3H), 3.15-2.86 (m, 3H), 2.46-2.20 (m, 5H), 1.81-1.53 (m, 5H), 1.13 (d, J = 6.8 Hz, 3H) | ++++ | ++ |

FIGURE 2 (continued)

| Cmpd. No. | Structure and Compound Name | LCMS (m/z) [M+H]+ | ¹H NMR | CBP IC$_{50}$ (µM) (mean) | BRD4 IC$_{50}$ (µM) (mean) |
|---|---|---|---|---|---|
| 4 | 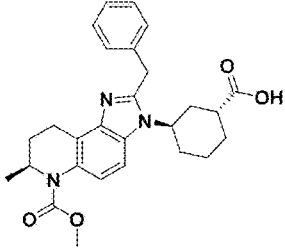 (1R,3R)-3-[(7S)-2-benzyl-6-(methoxycarbonyl)-7-methyl-3H,6H,7H,8H,9H-imidazo[4,5-f]quinolin-3-yl]cyclohexane-1-carboxylic acid | 462 | ¹H NMR (CD$_3$OD, 400 MHz) δ (ppm): 7.47 (d, J = 9.0 Hz, 1H), 7.39 (d, J = 8.9 Hz, 1H), 7.35–7.19 (m, 5H), 4.84–4.68 (m, 2H), 4.45-4.25 (m, 2H), 3.79 (s, 3H), 3.22-3.14 (m, 1H), 2.98-2.85 (m, 2H), 2.40–2.02 (m, 5H), 1.83–1.70 (m, 1H), 1.64-1.54 (m, 2H), 1.33–1.13 (m, 5H) | ++++ | + |
| 17 | 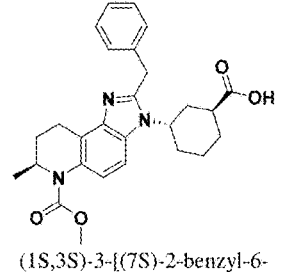 (1S,3S)-3-[(7S)-2-benzyl-6-(methoxycarbonyl)-7-methyl-3H,6H,7H,8H,9H-imidazo[4,5-f]quinolin-3-yl]cyclohexane-1-carboxylic acid | 462 | ¹H NMR (CD$_3$OD, 400 MHz) δ (ppm): 7.47 (d, J = 9.0 Hz, 1H), 7.39 (d, J = 8.9 Hz, 1H), 7.35–7.19 (m, 5H), 4.84–4.68 (m, 2H), 4.45-4.25 (m, 2H), 3.79 (s, 3H), 3.22-3.14 (m, 1H), 2.98-2.85 (m, 2H), 2.40–2.02 (m, 5H), 1.83–1.70 (m, 1H), 1.64-1.54 (m, 2H), 1.33–1.13 (m, 5H) | +++ | + |
| 18 | 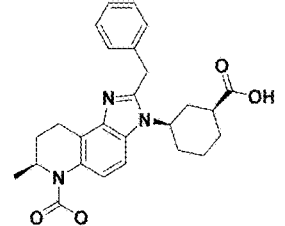 (1S,3R)-3-[(7S)-2-benzyl-6-(methoxycarbonyl)-7-methyl-3H,6H,7H,8H,9H-imidazo[4,5-f]quinolin-3-yl]cyclohexane-1-carboxylic acid | 462 | ¹H NMR (CD$_3$OD, 400 MHz) δ (ppm): 7.51-7.20 (m, 7H), 4.82-4.74 (m, 1H), 4.43 (s, 2H), 4.38-4.24 (m, 1H), 3.79 (s, 3H) 3.28-3.20 (m, 1H), 3.02-2.94 (m, 1H) 2.37-1.95 (m, 5H), 1.94-1.67 (m, 3H), 1.50-1.28 (m, 3H), 1.17 (d, J=6.7 Hz, 3H) | ++ | + |

FIGURE 2 (continued)

| Cmpd. No. | Structure and Compound Name | LCMS (m/z) [M+H]⁺ | ¹H NMR | CBP IC₅₀ (μM) (mean) | BRD4 IC₅₀ (μM) (mean) |
|---|---|---|---|---|---|
| 19 | 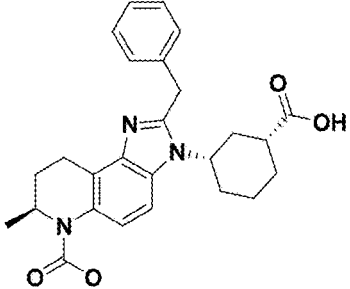<br>(1R,3S)-3-[(7S)-2-benzyl-6-(methoxycarbonyl)-7-methyl-3H,6H,7H,8H,9H-imidazo[4,5-f]quinolin-3-yl]cyclohexane-1-carboxylic acid | 462 | ¹H NMR (CD₃OD, 400 MHz) δ (ppm): 7.51-7.20 (m, 7H), 4.82-4.74 (m, 1H), 4.43 (s, 2H), 4.38-4.25 (m, 1H), 3.79 (s, 3H) 3.28-3.18 (m, 1H), 3.02-2.92 (m, 1H) 2.38-1.95 (m, 5H), 1.93-1.70 (m, 3H), 1.50-1.28 (m, 3H), 1.17 (d, J=6.6 Hz, 3H) | +++ | + |
| 413 | 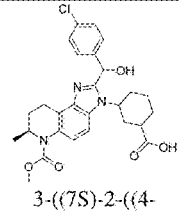<br>3-((7S)-2-((4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1ˢᵗ eluting isomer | 512 | ¹H NMR (CD₃OD, 400 MHz) δ (ppm): 7.49 (d, J = 9.0 Hz, 1H), 7.42-7.33 (m, 5H), 6.19 (s, 1H), 4.92-4.90 (m, 1H), 4.82-4.72 (m, 1H), 3.79 (s, 3H), 3.34-3.20 (m, 1H), 3.02-2.94 (m, 1H), 2.90-2.87 (m, 1H), 2.36-2.09 (m, 4H), 1.99-1.96 (m, 1H), 1.80-1.42 (m, 5H), 1.16 (d, J = 6.6 Hz, 3H). | ++++ | ++ |
| 414 | 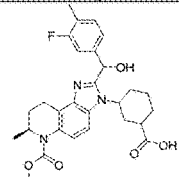<br>3-((7S)-2-((3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1ˢᵗ eluting isomer | 510 | ¹H NMR (CD₃OD, 400 MHz) δ (ppm): 7.53-7.38 (m, 2H), 7.22-7.19 (m, 1H), 7.09-7.04 (m, 2H), 6.16 (s, 1H), 4.86-4.70 (m, 2H), 3.79 (s, 3H), 3.30-3.21 (m, 1H), 3.01-2.92 (m, 1H), 2.88-2.84 (m, 1H), 2.43-2.23 (m, 5H), 2.15-2.04 (m, 2H), 2.01-1.97 (m, 1H), 1.81-1.60 (m, 3H), 1.56-1.38 (m, 2H), 1.16 (d, J = 6.8 Hz, 3H) | ++++ | ++ |

FIGURE 2 (continued)

| Cmpd. No. | Structure and Compound Name | LCMS (m/z) [M+H]+ | 1H NMR | CBP IC50 (μM) (mean) | BRD4 IC50 (μM) (mean) |
|---|---|---|---|---|---|
| 415 | 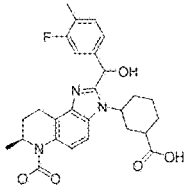 3-((7S)-2-((3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 510 | 1H NMR (CD3OD, 400 MHz) δ (ppm): 7.61-7.52 (m, 2H), 7.33-7.18 (m, 2H), 7.11-7.09 (m, 1H), 6.26 (s, 1H), 5.02-4.99 (m, 1H), 4.80-4.79 (m, 1H), 3.80 (s, 3H), 3.21-3.16 (m, 1H), 3.08-2.90 (m, 2H), 2.49-2.41 (m, 1H), 2.35-2.22 (m, 5H), 2.14-2.03 (m, 2H), 1.81-1.79 (m, 1H), 1.63-1.58 (m, 2H), 1.45-1.30 (m, 1H), 1.21-1.18 (m, 1H), 1.16 (d, $J$ = 6.8 Hz, 3H) | ++++ | ++ |
| 416 | 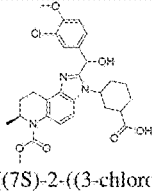 3-((7S)-2-((3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 542 | 1H-NMR (CD3OD, 400 MHz) δ (ppm): 7.71-7.54 (m, 2H), 7.54-7.42 (m, 1H), 7.42-7.29 (m, 1H), 7.19-6.97 (m, 1H), 6.20(s, 1H), 4.99-4.89(m, 1H), 4.82-4.74(m, 1H), 3.98(s, 3H), 3.89(s, 3H), 3.29-3.19(m, 1H), 3.11-2.93 (m, 2H), 2.48-2.22 (m, 2H), 2.22-2.08 (m, 3H), 1.91-1.69 (m, 3H), 1.38-1.24 (m, 2H), 1.18 (d, $J$ = 6.8 Hz, 3H) | ++++ | ++ |
| 417 | 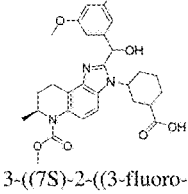 3-((7S)-2-((3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 526 | 1H-NMR (CD3OD, 400 MHz) δ (ppm): 7.51-7.42 (m, 2H), 6.94 (s, 1H), 6.79-6.72 (m, 1H), 6.55-6.62 (m, 1H), 6.19 (s, 1H), 5.03-4.90 (m, 1H), 4.84-4.70 (m, 1H), 3.82 (s, 3H), 3.81 (s, 3H), 3.28-3.10 (m, 1H), 3.05-2.95 (m, 2H), 2.52-2.43 (m, 2H), 2.38-2.27 (m, 1H), 2.17-1.96 (m, 2H), 1.81-1.66 (m, 1H), 1.64-1.58 (m, 2H), 1.43-1.30 (m, 1H), 1.15 (d, $J$ = 6.8 Hz, 3H), 1.02-0.98 (m, 1H) | ++++ | ++ |

FIGURE 2 (continued)

| Cmpd. No. | Structure and Compound Name | LCMS (m/z) [M+H]⁺ | ¹H NMR | CBP IC₅₀ (μM) (mean) | BRD4 IC₅₀ (μM) (mean) |
|---|---|---|---|---|---|
| 418 | 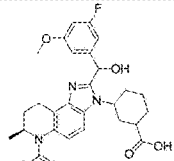 3-((7S)-2-((3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 526 | ¹H-NMR (CD₃OD, 400 MHz) δ (ppm): 7.55-7.37 (m, 2H), 6.80 (s, 1H), 6.77-6.72 (m, 1H), 6.66-6.59 (m, 1H), 6.15 (s, 1H), 4.85-4.70 (m, 2H), 3.80 (s, 6H), 3.28-3.19 (m, 1H), 3.05-2.95 (m, 1H), 2.91-2.87 (m, 1H), 2.42-2.03 (m, 5H), 1.81-1.60 (m, 3H), 1.56-1.38 (m, 2H), 1.16 (d, J = 6.8 Hz, 3H) | ++++ | ++ |
| 420 | 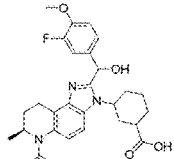 3-((7S)-2-((3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 526 | ¹H-NMR (CD₃OD, 400 MHz) δ (ppm): 7.53-7.39 (m, 2H), 7.17-7.05 (m, 3H), 6.14 (s, 1H), 4.89-4.67 (m, 2H), 3.86 (s, 3H), 3.79 (s, 3H), 3.32-3.21 (m, 1H), 3.04-2.93 (m, 1H), 2.91-2.89 (s, 1H), 2.40-2.22 (m, 2H), 2.22-2.10 (m, 2H), 2.10-2.05 (m, 1H), 1.81-1.60 (m, 3H), 1.52-1.40 (m, 2H), 1.16 (d, J = 6.8 Hz, 3H) | ++++ | ++ |
| 421 | 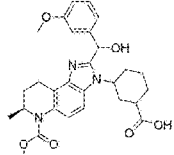 3-((7S)-2-((3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 542 | ¹H-NMR (CD₃OD, 400 MHz) δ (ppm): 7.52-7.42 (m, 2H), 7.00-6.89 (m, 3H), 6.13 (s, 1H), 4.85-4.73 (m, 2H), 3.81 (s, 3H), 3.79 (s, 3H), 3.33-3.22 (m, 1H), 3.04-2.90 (m, 2H), 2.42-2.22 (m, 2H), 2.16-2.07 (m, 3H), 1.78-1.54 (m, 3H), 1.48-1.32 (m, 2H), 1.17 (d, J = 6.8 Hz, 3H) | ++++ | ++ |
| 423 | 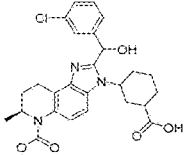 3-((7S)-2-((3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 512 | ¹H-NMR (CD₃OD, 400 MHz) δ (ppm): 7.47-7.30 (m, 6H), 6.22 (s, 1H), 4.92-4.90 (m, 1H), 4.78-4.74 (m, 1H), 3.78 (m, 3H), 3.33-3.24 (m, 1H), 3.01-2.82 (m, 2H), 2.34-2.14 (m, 5H), 1.76-1.38 (m, 5H), 1.16 (d, J = 6.4 Hz, 3H) | ++++ | ++ |

FIGURE 2 (continued)

| Cmpd. No. | Structure and Compound Name | LCMS (m/z) [M+H]+ | 1H NMR | CBP IC50 (μM) (mean) | BRD4 IC50 (μM) (mean) |
|---|---|---|---|---|---|
| 428 | 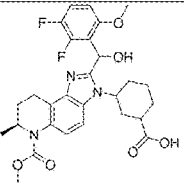 3-((7S)-2-((2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 544 | 1H-NMR (CD3OD, 400 MHz) δ (ppm): 7.58-7.44 (m, 1H), 7.44-7.34 (m, 1H), 7.31-7.19 (m, 1H), 6.96-6.78 (m, 1H), 6.57(s, 1H), 4.81-4.66(m, 1H), 4.52-4.29(m, 1H), 3.87(s, 3H), 3.79(s, 3H), 3.33-3.21(m, 1H), 3.08-2.84 (m, 2H), 2.59-2.41 (m, 1H), 2.39-2.22 (m, 2H), 2.22-2.12 (m, 1H), 2.12-1.96 (m, 1H), 1.82-1.68 (m, 1H), 1.69-1.52 (m, 2H),1.24-1.07 (m, 4H), 1.24-0.99 (m, 1H) | ++++ | ++ |
| 430 | 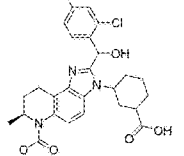 3-((7S)-2-((2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | | 1H-NMR (CD3OD, 400 MHz) δ (ppm): 7.74 (d, J = 9.2 Hz, 1H), 7.52 (d, J = 8.8 Hz, 1H), 7.41 (d, J = 8.8 Hz, 1H), 6.99-6.97 (m, 2H), 6.40 (s, 1H), 4.85-4.81 (m, 1H), 4.74-4.71 (m, 1H), 3.82 (s, 3H), 3.78 (s, 3H), 3.20-3.13(m, 1H), 2.95-2.90 (m, 1H), 2.89-2.85 (m, 1H), 2.47-2.45 (m, 1H), 2.30-2.17 (m, 4H), 1.75-1.64 (m, 4H), 1.54-1.45 (m, 1H), 1.14 (d, J = 6.8 Hz, 3H). LCMS (ES, m/z): 542 [M+H]+. | ++++ | ++ |
| 431 | 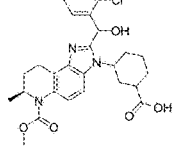 3-((7S)-2-((2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 542 | 1H-NMR (CD3OD, 400 MHz) δ (ppm): 7.59 (d, J = 9.2 Hz, 1H), 7.41 (d, J = 9.2 Hz, 1H), 7.24 (d, J = 8.8 Hz, 1H), 7.02 (s, 1H), 6.84 (d, J = 8.8 Hz, 1H), 6.50 (s, 1H), 4.77-4.72 (m, 1H), 4.54-4.53 (m, 1H), 3.80 (s, 3H), 3.79 (s, 3H), 3.29-3.23(m, 1H), 2.98-2.91 (m, 2H), 2.47-2.45 (m, 1H), 2.36-2.33 (m, 1H), 2.28-2.17 (m, 2H), 2.08-2.03 (m, 1H), 1.72-1.65 (m, 3H), 1.37-1.21 (m, 1H), 1.21-1.18 (m, 1H), 1.15 (d, J = 6.8 Hz, 3H) | ++++ | ++ |

FIGURE 2 (continued)

| Cmpd. No. | Structure and Compound Name | LCMS (m/z) [M+H]+ | ¹H NMR | CBP IC$_{50}$ (μM) (mean) | BRD4 IC$_{50}$ (μM) (mean) |
|---|---|---|---|---|---|
| 432 | 3-((7S)-2-((3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | 514 | ¹H NMR (CD$_3$OD, 400 MHz) δ (ppm): 7.51 (d, J = 9.0 Hz, 1H), 7.44 (d, J = 9.0 Hz, 1H), 7.40-7.31 (m, 1H), 7.23-7.18 (m, 1H), 7.15-7.11 (m, 1H), 6.18 (s, 1H), 4.93-4.91 (m, 1H), 4.80-4.76 (m, 1H), 3.79 (s, 3H), 3.26-3.21 (m, 1H), 3.01-2.94 (m, 1H), 2.86-2.84 (m, 1H), 2.41-2.09 (m, 4H), 1.92-1.89 (m, 1H), 1.78-1.48 (m, 5H), 1.16 (d, J = 6.4 Hz, 3H) | ++++ | + |
| 433 | 3-((7S)-2-((3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | 542 | ¹H-NMR (CD$_3$OD, 400 MHz) δ (ppm): 7.62-7.51 (m, 2H), 7.12-7.07 (m, 1H), 7.03-6.97 (m, 1H), 6.86-6.80 (m, 1H), 6.20 (s, 1H), 5.03-4.92 (m, 1H), 4.78 (m, 1H), 3.81 (s, 3H), 3.79 (s, 3H), 3.24-3.22 (m, 1H), 3.06-2.96 (m, 2H), 2.53-2.36 (m, 2H), 2.32-2.28 (m, 1H), 2.14-2.12 (m, 1H), 2.04-2.00 (m, 1H), 1.83-1.71 (m, 1H), 1.61-1.52 (m, 2H), 1.40-1.31 (m, 1H), 1.16 (d, J = 6.8 Hz, 3H), 1.05-0.97 (m, 1H) | ++++ | ++ |
| 437 | 3-((7S)-2-((3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | 542 | ¹H-NMR (CD$_3$OD, 400 MHz) δ (ppm): 7.64-7.39 (m, 3H), 7.39-7.21 (m, 1H), 7.16-6.89 (m, 1H), 6.17 (s, 1H), 5.03-4.91 (m, 1H), 4.82-4.68 (m, 1H), 3.87 (s, 3H), 3.78 (s, 3H), 3.29-3.12 (m, 1H), 3.02-2.89 (m, 2H), 2.51-2.21 (m, 3H), 2.19-1.93 (m, 2H), 1.84-1.71 (m, 1H), 1.69-1.54 (m, 2H), 1.51-1.36 (m, 1H), 1.16 (d, J = 6.4 Hz, 3H), 1.10-0.97 (m, 1H) | ++++ | ++ |
| 438 | 3-((7S)-2-((3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | 526 | ¹H-NMR (CD$_3$OD, 400 MHz) δ (ppm): 7.52-7.40 (m, 2H), 7.32-7.24 (m, 1H), 7.16-7.10 (m, 1H), 7.08-7.00 (m, 1H), 6.17 (s, 1H), 4.98-4.90 (m, 1H), 4.82-4.71 (m, 1H), 3.86 (s, 3H), 3.79 (s, 3H), 3.30-3.17 (m, 1H), 3.04-2.94 (m, 2H), 2.50-2.29 (m, 2H), 2.27-2.18 (m, 1H), 2.13-1.95 (m, 2H), 1.80-1.68 (m, 1H), 1.61-1.54 (m, 2H), 1.44-1.27 (m, 1H), 1.15 (d, J = 6.8 Hz, 3H), 1.09-1.06 (m, 1H) | ++++ | ++ |

FIGURE 2 (continued)

| Cmpd. No. | Structure and Compound Name | LCMS (m/z) [M+H]+ | 1H NMR | CBP IC50 (μM) (mean) | BRD4 IC50 (μM) (mean) |
|---|---|---|---|---|---|
| 442 | 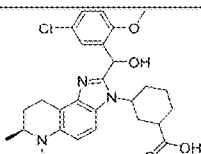<br>3-((7S)-2-((5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 542 | 1H-NMR (CD3OD, 400 MHz) δ (ppm): 7.59-7.47 (m, 1H), 7.47-7.32 (m, 2H), 7.12-6.99 (m, 1H), 7.09-6.93 (m, 1H), 6.51(s, 1H), 4.82-4.57(m, 2H), 3.87(s, 3H), 3.78(s, 3H), 3.32-3.18(m, 1H), 3.05-2.79 (m, 2H), 2.57-2.41 (m, 1H), 2.41-2.31 (m, 1H), 2.31-2.05 (m, 3H), 1.82-1.67 (m, 3H), 1.52-1.22 (m, 2H), 1.16 (d, J = 6.8 Hz, 3H) | ++++ | ++ |
| 444 | 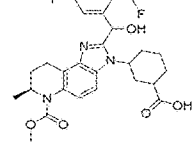<br>3-((7S)-2-((2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 546 | 1H-NMR (CD3OD, 400 MHz) δ (ppm): 7.86-7.83 (m, 3H), 7.51-7.34 (m, 2H), 7.29-7.23 (m, 1H), 6.64-6.62 (m, 1H), 4.89-4.76 (m, 3H), 3.83(s, 3H), 3.27-3.02(m, 3H), 2.48-2.14(m, 5H), 1.90-1.85 (m, 1H), 1.76-1.69 (m, 2H), 1.27-1.15 (m, 5H) | ++++ | ++ |
| 445 | 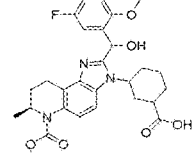<br>3-((7S)-2-((5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 554 | 1H-NMR (CD3OD, 400 MHz) δ (ppm): 7.58-7.52 (m, 1H), 7.45-7.40 (m, 1H), 7.31-7.29 (m, 1H), 7.08-6.90 (m, 2H), 6.38 (s, 1H), 4.86-4.75 (m, 2H), 4.62-4.50 (m, 1H), 3.79 (s, 3H), 3.30 – 3.17 (m, 1H), 2.95 – 2.86 (m, 2H), 2.48- 2.44 (m, 1H), 2.32-2.24 (m, 4H), 1.80 – 1.50 (m, 5H), 1.18 (d, J = 6.0 Hz, 3H), 1.13 (d, J = 6.4 Hz, 3H), 1.03 (d, J = 6.0 Hz, 3H) | ++++ | ++ |
| 449 | 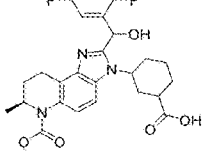<br>3-((7S)-2-((2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 514 | 1H-NMR (CD3OD, 400 MHz) δ (ppm): 7.55-7.50 (m, 1H), 7.43-7.41 (m, 1H), 7.36-7.32 (m, 1H), 7.14-7.08 (m, 2H), 6.42 (s, 1H), 4.87-4.72(m, 2H), 3.78 (s, 3H),3..33-3.20 (m, 1H), 2.96-2.88 (m, 2H), 2.47-2.2.42 (m, 1H), 2.32-2.12 (m, 4H), 1.80-1.67 (m, 3H), 1.59-1.48 (m, 2H), 1.15 (d, J = 6.4 Hz, 3H) | ++++ | + |

FIGURE 2 (continued)

| Cmpd. No. | Structure and Compound Name | LCMS (m/z) [M+H]+ | ¹H NMR | CBP IC$_{50}$ (µM) (mean) | BRD4 IC$_{50}$ (µM) (mean) |
|---|---|---|---|---|---|
| 452 | 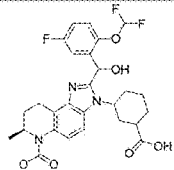<br>3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | 562 | ¹H-NMR (CD$_3$OD, 400 MHz) δ (ppm): 7.54 (d, J = 8.8 Hz, 1H), 7.47-7.42 (m, 2H), 7.40-7.12 (m, 2H), 6.85-6.45 (m, 1H), 6.44 (s, 1H), 4.94-4.91 (m, 1H), 4.76-4.71 (m, 1H), 3.78 (s, 3H), 3.22-2.84 (m, 3H), 2.46-2.23 (m, 5H), 1.84-1.61 (m, 5H), 1.14 (d, J = 6.4 Hz, 3H) | ++++ | ++ |
| 463 | 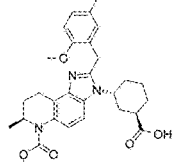<br>(1R,3R)-3-((S)-2-(5-fluoro-2-methoxybenzyl)-6-(methoxycarbonyl)-7-methyl-6,7,8,9-tetrahydro-3H-imidazo[4,5-f]quinolin-3-yl)cyclohexane-1-carboxylic acid | 510 | ¹H-NMR (CD$_3$OD, 400 MHz) δ (ppm): 7.68-7.66 (m, 2H), 7.10-6.96 (m, 3H), 4.85-4.75 (m, 2H), 4.54-4.38 (m, 2H), 3.82 (s, 3H), 3.80 (s, 3H), 3.16-3.12 (m, 1H), 3.06-2.94 (m, 2H), 2.44-2.39 (m, 1H), 2.34-2.11 (m, 4H), 1.84-1.65 (m, 3H), 1.33-1.25 (m, 2H), 1.17 (d, J = 6.8 Hz, 3H) | ++++ | + |
| 464 | 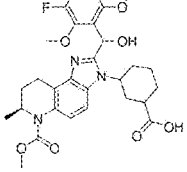<br>3-((7S)-2-((3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | 556 | ¹H-NMR (CD$_3$OD, 400 MHz) δ (ppm): 7.49-7.41 (m, 2H), 7.17-7.12 (m, 1H), 6.77-6.74 (m, 1H), 6.55(s, 1H), 4.86-4.76(m, 1H), 4.38-4.34(m, 1H), 3.84(s, 3H), 3.79(s, 3H), 3.53(s, 3H), 3.33-3.25(m, 1H), 3.05-2.98(m, 1H), 2.94-2.92 (m, 1H), 2.50-2.48 (m, 1H), 2.31-2.18(m, 3H), 2.02-1.93(m, 1H), 1.79-1.75 (m, 1H), 1.61-1.58 (m, 2H), 1.18-1.16 (m, 4H), 0.99-0.96 (m, 1H) | ++++ | ++ |
| 470 | 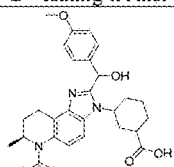<br>3-((7S)-2-(hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | 508 | ¹H-NMR (DMSO, 400 MHz) δ (ppm): 7.49-7.45 (m, 1H), 7.32-7.27 (m, 3H), 6.89-6.86 (m, 2H), 6.50-6.20 (m, 1H), 6.03 (s, 1H), 4.86-4.79 (m, 1H), 4.67-4.62 (m, 1H), 3.72 (s, 3H), 3.67 (s, 3H), 3.08-3.01 (m, 1H), 2.88-2.82 (m, 2H), 2.34-2.29 (m, 1H), 2.18-2.10 (m, 2H), 1.95-1.88 (m, 2H), 1.66-1.61 (m, 1H), 1.58-1.48 (m, 2H), 1.26-1.22 (m, 1H), 1.06 (d, J = 6.8 Hz, 3H), 1.94-0.90 (m, 1H) | ++++ | ++ |

FIGURE 2 (continued)

| Cmpd. No. | Structure and Compound Name | LCMS (m/z) [M+H]+ | ¹H NMR | CBP IC$_{50}$ (μM) (mean) | BRD4 IC$_{50}$ (μM) (mean) |
|---|---|---|---|---|---|
| 471 | 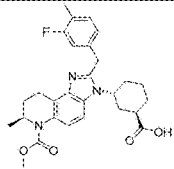 (1R,3R)-3-((S)-2-(3-fluoro-4-methylbenzyl)-6-(methoxycarbonyl)-7-methyl-6,7,8,9-tetrahydro-3H-imidazo[4,5-f]quinolin-3-yl)cyclohexane-1-carboxylic acid | 494 | ¹H-NMR (CD₃OD, 400 MHz) δ (ppm): 7.46 (d, J = 8.8 Hz, 1H), 7.39 (d, J = 8.8 Hz, 1H), 7.19-7.10 (m, 1H), 6.97-6.87 (m, 2H), 4.81-4.62 (m, 2H), 4.42-4.23 (m, 2H), 3.76 (s, 3H), 3.25-3.10 (m, 1H), 3.02-2.88 (m, 2H), 2.37-2.06 (m, 8H), 1.81-1.59 (m, 3H), 1.34-1.20 (m, 2H), 1.13 (d, J = 6.4 Hz, 3H) | ++++ | + |
| 472 | 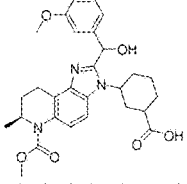 3-((7S)-2-(hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 508 | ¹H-NMR (CD₃OD, 400 MHz) δ (ppm): 7.50-7.40(m, 2H), 7.27-7.08 (m, 2H), 6.94-6.84(m, 2H), 6.23(s, 1H), 4.91-4.88(m, 1H), 3.79 (s, 6H), 3.34-2.96 (m, 2H), 2.78-2.68 (m, 1H), 2.36-2.05 (m, 5H), 1.78-1.55 (m, 3H), 1.31-1.15 (m, 6H) | ++++ | ++ |
| 479 | 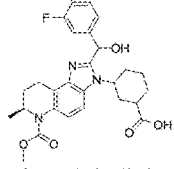 3-((7S)-2-((3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1ˢᵗ eluting isomer | 514 | ¹H NMR (CD₃OD, 400 MHz) δ (ppm): 7.54-7.38 (m, 3H), 7.22-7.14 (m, 2H), 6.20 (s, 1H), 4.96-4.93 (m, 1H), 4.79-4.74 (m, 1H), 3.78 (s, 3H), 3.24-3.18 (m, 1H), 3.01-2.94 (m, 2H), 2.50-2.21 (m, 3H), 2.17-1.97 (m, 2H), 1.78-1.72 (m, 1H), 1.63-1.55 (m, 2H), 1.49-1.31 (m, 1H), 1.14 (d, J = 6.8 Hz, 3H), 1.09-1.04 (m, 1H) | ++++ | + |
| 481 | 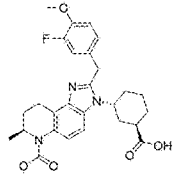 (1R,3R)-3-((S)-2-(3-fluoro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | 510 | ¹H-NMR (CD₃OD, 400 MHz) δ (ppm): 7.48-7.38(m, 2H), 7.04-7.01(m, 3H), 4.86-4.67(m, 2H), 4.40-4.15(m, 2H), 3.85(s, 3H), 3.76(s, 3H), 3.30-3.10(m, 1H), 2.99-2.89(m, 2H), 2.48-2.05(m, 5H),1.85-1.65(m, 3H), 1.40-1.20(m, 2H), 1.13(d, J=6.4 Hz, 3H) | ++++ | + |

FIGURE 2 (continued)

| Cmpd. No. | Structure and Compound Name | LCMS (m/z) [M+H]+ | ¹H NMR | CBP IC$_{50}$ (μM) (mean) | BRD4 IC$_{50}$ (μM) (mean) |
|---|---|---|---|---|---|
| 488 | 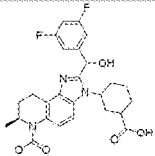 3-((7S)-2-((3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 514 | ¹H-NMR (CD$_3$OD, 400 MHz) δ (ppm): 7.63–7.47 (m, 2H), 7.12 (d, J = 6.8 Hz, 3H), 6.90-6.87 (m, 1H), 6.26 (s, 1H), 5.04 – 4.93 (m, 1H), 4.81-4.78 (m, 1H), 3.79 (s, 3H), 3.24-3.15 (m, 1H), 3.02-2.98 (m, 2H), 2.52-2.06 (m, 5H), 1.81-1.59 (m, 3H), 1.52-1.42 (m, 1H), 1.22-1.17 (m, 1H), 1.15 (d, J = 6.4 Hz, 3H) | ++++ | ++ |
| 489 | 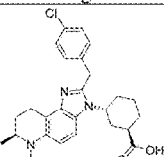 (1R,3R)-3-((S)-2-(4-chlorobenzyl)-6-(methoxycarbonyl)-7-methyl-6,7,8,9-tetrahydro-3H-imidazo[4,5-f]quinolin-3-yl)cyclohexane-1-carboxylic acid | 496 | ¹H-NMR (CD$_3$OD, 400 MHz) δ (ppm): 7.46 (d, J = 8.8 Hz, 1H), 7.38 (d, J = 9.2 Hz, 1H), 7.30 (d, J = 8.4 Hz, 2H), 7.23 (d, J = 8.4 Hz, 2H), 4.81-4.62(m, 2H), 4.45-4.22(m, 2H), 3.79(s, 3H), 3.28-3.12(m, 1H), 3.00-2.86 (m, 2H), 2.35-2.10 (m, 5H), 1.81-1.61 (m, 3H), 1.33-1.20 (m, 2H), 1.16 (d, J = 6.8 Hz, 3H) | ++++ | + |
| 493 | 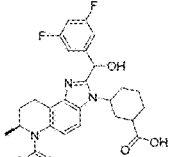 3-((7S)-2-((3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 514 | ¹H-NMR (CD$_3$OD, 400 MHz) δ (ppm): 7.67–7.45 (m, 2H), 7.02 (d, J = 6.4 Hz, 3H), 6.94-6.91 (m, 1H), 6.23 (s, 1H), 4.93-4.92 (m, 1H), 4.81-4.79 (m, 1H), 3.80 (s, 3H), 3.28–3.18 (m, 1H), 3.01-2.88 (m, 2H), 2.42-2.12 (m, 4H), 2.03-1.99 (m, 1H), 1.83-1.63 (m, 4H), 1.52-1.42 (m, 1H), 1.17 (d, J = 6.8 Hz, 3H) | ++++ | ++ |
| 501 | 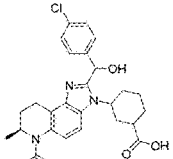 3-((7S)-2-((4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 512 | ¹H-NMR (CD$_3$OD, 400 MHz) δ (ppm): 7.52-7.33 (m, 6H), 6.22 (s, 1H), 4.84-4.73 (m, 2H), 3.78 (s, 3H), 3.27-3.16 (m, 1H), 3.04-2.92 (m, 1H), 2.90-2.88 (m, 1H), 2.46-2.35 (m, 2H), 2.30-2.22 (m, 1H), 2.15-2.02 (m, 2H), 1.82-1.71 (m, 1H), 1.63-1.55 (m, 2H), 1.40-1.28 (m, 1H), 1.15 (d, J = 6.8 Hz, 3H), 1.14-1.01(m, 1H) | ++++ | ++ |

FIGURE 2 (continued)

| Cmpd. No. | Structure and Compound Name | LCMS (m/z) [M+H]+ | ¹H NMR | CBP IC$_{50}$ (μM) (mean) | BRD4 IC$_{50}$ (μM) (mean) |
|---|---|---|---|---|---|
| 502 | 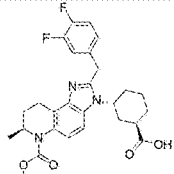<br>(1R,3R)-3-((S)-2-(3,4-difluorobenzyl)-6-(methoxycarbonyl)-7-methyl-6,7,8,9-tetrahydro-3H-imidazo[4,5-f]quinolin-3-yl)cyclohexane-1-carboxylic acid | 498 | ¹H-NMR (CD$_3$OD, 400 MHz) δ (ppm): 7.48 (d, J = 8.8 Hz, 1H), 7.40 (d, J = 9.2 Hz, 1H), 7.23-7.18 (m, 2H), 7.05-7.02 (m, 1H), 4.78-4.65(m, 2H), 4.40-4.22(m, 2H), 3.79(s, 3H), 3.26-3.15(m, 1H), 3.03-2.96 (m, 2H), 2.38-2.12 (m, 5H), 1.79-1.62 (m, 3H), 1.41-1.23 (m, 2H), 1.16 (d, J = 6.4 Hz, 3H) | ++++ | + |
| 512 | 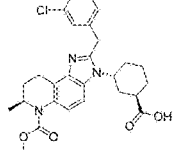<br>(1R,3R)-3-((S)-2-(3-chloro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | 526 | ¹H-NMR (d6-DMSO, 400 MHz) δ (ppm): 7.90–7.84 (m, 1H), 7.69–7.62 (m, 1H), 7.00 (s, 2H), 6.93 (s, 1H), 4.91-4.81 (m, 1H), 4.78–4.68 (m, 1H), 4.68–4.60 (m, 1H), 4.39-4.31 (m, 1H), 3.77 (s, 3H), 3.71 (s, 3H), 3.05-2.93 (m, 3H), 2.36-2.24 (m, 1H), 2.24-2.05 (m, 3H), 2.04-1.96 (m, 1H), 1.86-1.65 (m, 3H), 1.40-1.33 (m, 1H), 1.27-1.13 (m, 1H), 1.09 (d, J=6.4 Hz, 3H) | ++++ | + |
| 523 | 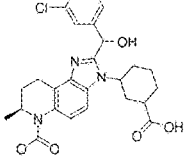<br>3-((7S)-2-((3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 512 | ¹H-NMR (CD$_3$OD, 400 MHz) δ (ppm): 7.51-7.30 (m, 6H), 6.24 (s, 1H), 4.93-4.74 (m, 2H), 3.78 (s, 3H), 3.33-3.17 (m, 1H), 3.01-2.94 (m, 1H), 2.82 (m, 1H), 2.37-2.35 (m, 2H), 2.29-2.24 (m, 2H), 2.08-2.05 (m, 1H), 1.77-1.72 (m, 1H), 1.60-1.54 (m, 2H), 1.34-1.30 (m, 1H), 1.15 (d, J = 6.8 Hz, 3H), 1.14-1.05 (m, 1H) | ++++ | ++ |
| 528 | 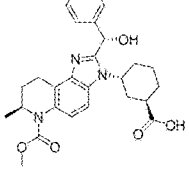<br>(1R,3R)-3-((S)-2-((S)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | 478 | ¹H-NMR (CD$_3$OD, 400 MHz) δ (ppm): 7.57-7.40 (m, 4H), 7.30-7.28 (m, 3H), 6.12(s, 1H), 4.95-4.90 (m, 1H), 4.84-4.79(m, 1H), 3.79(s, 3H), 3.33-3.25(m, 1H), 3.03-2.82 (m, 2H), 2.49-2.30 (m, 2H), 2.29-2.21 (m, 1H), 2.12-2.07 (m, 1H), 1.99-1.90 (m, 1H), 1.85-1.79 (m, 1H), 1.64-1.49 (m, 2H), 1.40-1.29 (m, 1H), 1.16 (d, J = 6.4 Hz, 3H), 0.95-0.89 (m, 1H) | ++++ | ++ |

FIGURE 2 (continued)

| Cmpd. No. | Structure and Compound Name | LCMS (m/z) [M+H]+ | ¹H NMR | CBP IC$_{50}$ (µM) (mean) | BRD4 IC$_{50}$ (µM) (mean) |
|---|---|---|---|---|---|
| 533 | 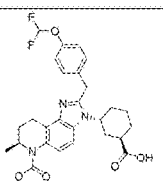<br>(1R,3R)-3-((S)-2-(4-(difluoromethoxy)benzyl)-6-(methoxycarbonyl)-7-methyl-6,7,8,9-tetrahydro-3H-imidazo[4,5-f]quinolin-3-yl)cyclohexane-1-carboxylic acid | 528 | ¹H-NMR (d6-DMSO, 400 MHz) δ (ppm): 12.60 (br, 1H), 7.91–7.84 (m, 1H), 7.69–7.62 (m, 1H), 7.43–7.38 (m, 2H), 7.32–7.05 (m, 3H), 4.85–4.65 (m, 3H), 4.43–4.36 (m, 1H), 3.71 (s, 3H), 3.07–2.91 (m, 3H), 2.35–2.25 (m, 1H), 2.22–2.08 (m, 3H), 2.04–1.96 (m, 1H), 1.82–1.66 (m, 3H), 1.49–1.41 (m, 1H), 1.29–1.21 (m, 1H), 1.09 (d, J = 6.4 Hz, 3H) | ++++ | + |
| 537 | 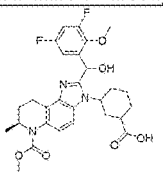<br>3-((7S)-2-((3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | 544 | ¹H NMR (CD$_3$OD, 400 MHz) δ (ppm): 7.63 (d, J = 8.8 Hz, 1H), 7.55 (d, J = 9.2 Hz, 1H), 7.21-7.19 (m, 1H), 7.08-7.04 (m, 1H), 6.46 (s, 1H), 4.94-4.92 (m, 1H), 4.80-4.78 (m, 1H), 3.79 (s, 3H), 3.78 (s, 3H), 3.27-3.21 (m, 1H), 3.05 – 2.89 (m, 2H), 2.51-2.41 (m, 1H), 2.38 – 2.15 (m, 4H), 1.80-1.69 (m, 3H), 1.52-1.43 (m, 2H), 1.15 (d, J = 6.4 Hz, 3H) | ++++ | ++ |
| 538 | 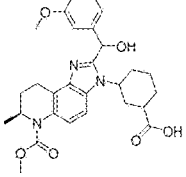<br>3-((7S)-2-(hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | 508 | ¹H-NMR (CD$_3$OD, 400 MHz) δ (ppm): 7.47-7.24(m, 3H), 7.04-6.86 (m, 3H), 6.21(s, 1H), 4.87-4.73(m, 1H), 3.77 (s, 6H), 3.33-3.32 (m, 1H), 3.00-2.77 (m, 2H), 2.29-2.05 (m, 5H), 1.75-1.31 (m, 5H), 1.79-1.45 (m, 4H) | ++++ | + |
| 541 | 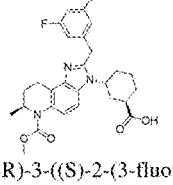<br>(1R,3R)-3-((S)-2-(3-fluoro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | 510 | ¹H-NMR (CD$_3$OD, 400 MHz) δ (ppm): 7.49 (d, J = 8.8 Hz, 1H), 7.40 (d, J = 8.8 Hz, 1H), 6.70-6.68 (m, 1H), 6.67-6.51 (m, 2H), 4.82-4.72 (m, 1H), 4.50-4.31 (m, 2H), 3.76 (s, 3H), 3.74 (s, 3H), 3.28-3.12 (m, 1H), 3.04-2.92 (m, 1H), 2.78-2.76 (m, 1H), 2.40-2.21 (m, 4H), 2.21-2.02 (m, 1H), 1.83-1.69 (m, 1H), 1.69-1.50 (m, 2H), 1.48-1.20 (m, 3H), 1.15 (d, J = 6.4 Hz, 3H) | ++++ | + |

FIGURE 2 (continued)

| Cmpd. No. | Structure and Compound Name | LCMS (m/z) [M+H]+ | 1H NMR | CBP IC50 (μM) (mean) | BRD4 IC50 (μM) (mean) |
|---|---|---|---|---|---|
| 549 | 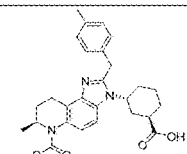<br>(1R,3R)-3-((S)-6-(methoxycarbonyl)-7-methyl-2-(4-methylbenzyl)-6,7,8,9-tetrahydro-3H-imidazo[4,5-f]quinolin-3-yl)cyclohexane-1-carboxylic acid | 476 | 1H-NMR (CD3OD, 300 MHz) δ (ppm): 7.45-7.35(m, 2H), 7.12-7.08(m, 4H), 4.86-4.60(m, 2H), 4.39-4.23(m, 2H), 3.76(s, 3H), 3.30-3.10(m, 1H), 2.99-2.86(m, 2H), 2.40-2.00(m, 8H),1.80-1.52(m, 3H) , 1.35-1.12(m, 5H) | ++++ | + |
| 564 | 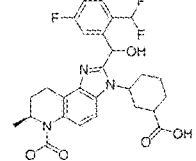<br>3-((7S)-2-((2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 546 | 1H-NMR (CD3OD, 400 MHz) δ (ppm): 7.89-7.83 (m, 2H), 7.77-7.72 (m, 1H), 7.53-7.50 (m, 1H), 7.34-7.31 (m, 1H), 7.21-6.93 (m, 1H), 6.74-6.72 (m, 1H), 4.95-4.93 (m, 1H), 4.85-4.81 (m, 2H), 3.83 (s, 3H), 3.19-3.12(m, 1H), 3.02-2.95 (m, 2H), 2.50-2.48 (m, 1H), 2.30-2.16(m, 4H), 1.89-1.73 (m, 4H), 1.50-1.42 (m, 1H), 1.16 (d, J = 6.4 Hz, 3H) | ++++ | + |
| 568 | 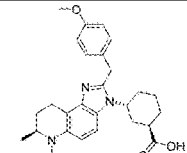<br>(1R,3R)-3-((S)-2-(4-methoxybenzyl)-6-(methoxycarbonyl)-7-methyl-6,7,8,9-tetrahydro-3H-imidazo[4,5-f]quinolin-3-yl)cyclohexane-1-carboxylic acid | 492 | 1H-NMR (CD3OD, 400 MHz) δ (ppm): 7.43 (d, J = 9.2 Hz, 1H), 7.36 (d, J = 8.8 Hz, 1H), 7.16 (d, J = 8.8 Hz, 2H), 6.84 (d, J = 9.2 Hz, 2H), 4.81-4.63 (m, 2H), 4.40-4.19 (m, 2H), 3.82-3.70 (m, 6H), 3.26-3.12 (m, 1H), 3.02-2.85 (m, 2H), 2.37-1.98 (m, 5H), 1.80-1.69 (m, 1H), 1.68-1.55 (m, 2H), 1.37-1.09 (m, 5H) | ++++ | + |
| 572 | 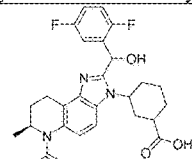<br>3-((7S)-2-((2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 514 | 1H-NMR (CD3OD, 400 MHz) δ (ppm): 7.68-7.64 (m, 1H), 7.53-7.50 (m, 1H), 7.43-7.40 (m, 1H), 7.08-7.05 (m, 2H), 6.39 (s, 1H), 5.01-4.95 (m, 1H), 4.87-4.72 (m, 1H), 3.81 (s, 3H), 3.31-3.13(m, 1H), 2.97-2.96 (m, 1H), 2.94-2.86 (m, 1H), 2.50-2.46 (m, 1H), 2.44-2.32 (m, 1H), 2.28-2.17 (m, 3H), 1.74-1.60 (m, 3H), 1.53-1.15 (m, 2H), 1.14 (d, J = 6.4 Hz, 3H) | ++++ | + |

FIGURE 2 (continued)

| Cmpd. No. | Structure and Compound Name | LCMS (m/z) [M+H]⁺ | ¹H NMR | CBP IC₅₀ (μM) (mean) | BRD4 IC₅₀ (μM) (mean) |
|---|---|---|---|---|---|
| 601 | 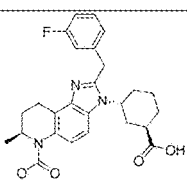<br>(1R,3R)-3-((S)-2-(3-fluorobenzyl)-6-(methoxycarbonyl)-7-methyl-6,7,8,9-tetrahydro-3H-imidazo[4,5-f]quinolin-3-yl)cyclohexane-1-carboxylic acid | 480 | ¹H-NMR (CD₃OD, 300 MHz) δ (ppm): 7.55-7.26 (m, 3H), 7.09-6.96 (m, 3H), 4.81-4.65(m, 2H), 4.49-4.32(m, 2H), 3.79(s, 3H), 3.28-3.17(m, 1H), 3.03-2.96 (m, 2H), 2.45-2.10 (m, 5H), 1.81-1.68 (m, 3H), 1.33-1.20 (m, 2H), 1.16 (d, J = 6.6 Hz, 3H) | +++ | + |
| 616 | 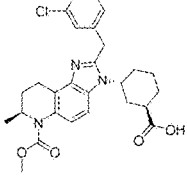<br>(1R,3R)-3-((S)-2-(3-chlorobenzyl)-6-(methoxycarbonyl)-7-methyl-6,7,8,9-tetrahydro-3H-imidazo[4,5-f]quinolin-3-yl)cyclohexane-1-carboxylic acid | 496 | ¹H-NMR (CD₃OD, 400 MHz) δ (ppm): 7.48-7.45(m, 1H), 7.40-7.38(m, 1H), 7.30-7.23(m, 3H), 7.18-7.17(m, 1H), 4.77-4.68(m, 2H), 4.44-4.40(m, 1H), 4.33-4.29(m, 1H), 3.76(s, 3H), 3.19-3.15(m, 1H), 2.98-2.94(m, 2H), 2.33-2.13(m, 5H), 1.76-1.64(m, 3H), 1.24-1.23(m, 2H), 1.13(d, J= 6.8 Hz, 3H) | +++ | + |
| 621 | 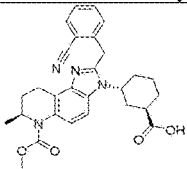<br>(1R,3R)-3-((S)-2-(2-cyanobenzyl)-6-(methoxycarbonyl)-7-methyl-6,7,8,9-tetrahydro-3H-imidazo[4,5-f]quinolin-3-yl)cyclohexane-1-carboxylic acid | 487 | ¹H-NMR (CD₃OD, 400 MHz) δ (ppm): 7.79 (d, J = 7.6 Hz, 1H), 7.64-7.43 (m, 4H), 7.15-7.13 (m, 1H), 4.83-4.61 (m, 4H), 3.79 (s, 3H), 3.28-2.92 (m, 3H), 2.41-2.17 (m, 5H), 1.79-1.66 (m, 4H), 1.47-1.37 (m, 1H), 1.16(d, J = 6.0 Hz, 3H) | +++ | + |
| 630 | 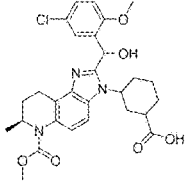<br>3-((7S)-2-((5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 542 | ¹H-NMR (CD₃OD, 400 MHz) δ (ppm): 7.86-7.73(m, 1H), 7.58-7.48 (m, 1H), 7.48-7.34 (m, 1H), 7.34-7.23 (m, 1H), 6.99-6.84 (m, 1H), 6.37(s, 1H), 5.08-4.92(m, 1H), 4.81-4.61(m, 1H), 3.78(s, 3H), 3.64(s, 3H), 3.27-3.04 (m, 1H), 3.01-2.93 (m, 1H), 2.93-2.82 (m, 1H), 2.59-2.39 (m, 1H), 2.39-2.28(m, 1H), 2.28-2.07(m, 3H), 1.85-1.60 (m, 3H), 1.59-1.38 (m, 2H), 1.14 (d, J = 6.8 Hz, 3H) | +++ | ++ |

FIGURE 2 (continued)

| Cmpd. No. | Structure and Compound Name | LCMS (m/z) [M+H]⁺ | ¹H NMR | CBP IC₅₀ (μM) (mean) | BRD4 IC₅₀ (μM) (mean) |
|---|---|---|---|---|---|
| 638 | 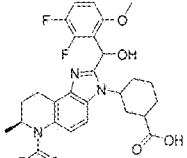 3-((7S)-2-((2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 544 | ¹H-NMR (CD₃OD, 400 MHz) δ (ppm): 7.62-7.51 (m, 1H), 7.49-7.34 (m, 1H), 7.31-7.11 (m, 1H), 6.91-6.78 (m, 1H), 6.58(s, 1H), 4.89-4.81(m, 1H), 4.78-4.66(m, 1H), 3.83(s, 3H), 3.78(s, 3H), 3.27-3.12(m, 1H), 3.01-2.89 (m, 1H), 2.89-2.76 (m, 1H), 2.54-2.41 (m, 1H), 2.41-2.27 (m, 1H), 2.27-2.12 (m, 3H), 2.12-2.02 (m, 1H),1.95-1.83 (m, 1H), 1.78-1.61 (m, 3H),1.14 (d, J = 6.4 Hz, 3H) | +++ | + |
| 641 | 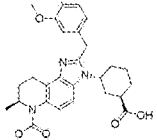 (1R,3R)-3-((S)-2-(3,4-dimethoxybenzyl)-6-(methoxycarbonyl)-7-methyl-6,7,8,9-tetrahydro-3H-imidazo[4,5-f]quinolin-3-yl)cyclohexane-1-carboxylic acid | 522 | ¹H-NMR (CD₃OD, 400 MHz) δ (ppm): 7.43 (d, J = 9.2 Hz, 1H), 7.33 (d, J = 8.8 Hz, 1H), 6.96 (s, 1H), 6.94-6.76 (m, 2H), 4.97-4.88 (m, 1H), 4.80-4.68 (m, 1H), 4.37-4.25 (m, 2H), 3.83-3.71 (m, 9H), 3.26-3.14 (m, 1H), 3.00-2.88 (m, 1H), 2.76-2.74 (m, 1H), 2.34-2.13 (m, 4H), 2.10-1.93 (m, 1H), 1.78-1.67 (m, 1H), 1.61-1.45 (m, 2H), 1.42-1.25 (m, 1H), 1.18-1.03 (m, 4H) | +++ | + |
| 649 | 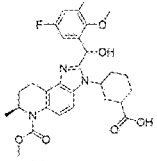 3-((7S)-2-((3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1ˢᵗ eluting isomer | 544 | ¹H NMR (CD₃OD, 400 MHz) δ (ppm): 7.90 (s, 2H), 7.42-7.38 (m, 1H), 7.15-7.10 (m, 1H), 6.51 (s, 1H), 5.09-5.02 (m, 1H), 4.88-4.86 (m, 1H), 3.83 (s, 3H), 3.72 (s, 3H), 3.24-2.94 (m, 3H), 2.53-2.49 (m, 1H), 2.31-2.12 (m, 4H), 1.92-1.89 (m, 1H), 1.81-1.71 (m, 2H), 1.56-1.37 (m, 2H), 1.19 (d, J = 6.8 Hz, 3H) | +++ | + |
| 1· | 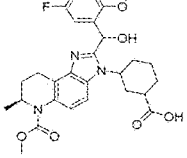 3-((7S)-2-((5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2ⁿᵈ eluting isomer | 526 | ¹H-NMR (CD₃OD, 400 MHz) δ (ppm): 7.69-7.44 (m, 2H), 7.44-7.29 (m, 1H), 7.12-6.99 (m, 1H), 6.98-6.82 (m, 1H), 6.37(s, 1H), 5.03-4.91(m, 1H), 4.81-4.69(m, 1H), 3.78(s, 3H), 3.61(s, 3H), 3.22-3.04(m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J = 6.4 Hz, 3H) | +++ | + |

FIGURE 2 (continued)

| Cmpd. No. | Structure and Compound Name | LCMS (m/z) [M+H]+ | ¹H NMR | CBP IC$_{50}$ (μM) (mean) | BRD4 IC$_{50}$ (μM) (mean) |
|---|---|---|---|---|---|
| 662 | 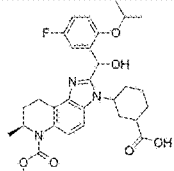 3-((7S)-2-((5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 554 | ¹H NMR (CD$_3$OD, 400 MHz) δ (ppm): δ 7.61 (m, 1H), 7.52-7.42 (m, 2H), 7.05-6.98 (m, 1H), 6.90-6.85 (m, 1H), 6.32 (s, 1H), 4.96-4.85 (m, 1H), 4.81-4.76 (m, 1H), 4.49-4.43 (m, 1H), 3.79 (s, 3H), 3.20-3.16 (m, 1H), 2.98 – 2.85 (m, 2H), 2.51 – 2.35 (m, 2H), 2.29 – 2.07 (m, 3H), 1.78 – 1.60 (m, 3H), 1.50-1.39 (m, 2H), 1.18 (d, J = 6.8 Hz, 3H), 1.12 (d, J = 6.0 Hz, 3H), 0.65 (d, J = 6.0 Hz, 3H) | +++ | ++ |
| 675 | 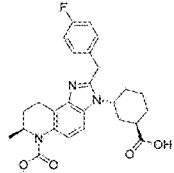 (1R,3R)-3-((S)-2-(4-fluorobenzyl)-6-(methoxycarbonyl)-7-methyl-6,7,8,9-tetrahydro-3H-imidazo[4,5-f]quinolin-3-yl)cyclohexane-1-carboxylic acid | 480 | ¹H-NMR (CD$_3$OD, 300 MHz) δ (ppm): 7.50 – 7.30 (m, 2H), 7.27 – 7.17 (m, 2H), 7.07 – 6.92 (m, 2H), 4.77 – 4.54 (m, 2H), 4.41 – 4.15 (m, 2H), 3.74 (s, 3H), 3.23 – 3.07 (m, 1H), 2.98 – 2.84 (m, 2H), 2.37 – 2.04 (m, 5H), 1.79 – 1.55 (m, 3H), 1.30 – 1.16 (m, 2H), 1.11 (d, J = 6.9 Hz, 3H) | +++ | + |
| 682 | 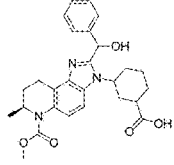 3-((7S)-2-(hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | 508 | ¹H-NMR (DMSO, 400 MHz) δ (ppm): 7.48-7.45 (m, 1H), 7.31-7.24 (m, 3H), 6.89-6.86 (m, 2H), 6.21-6.16 (m, 1H), 5.97-5.96 (m, 1H), 4.83-4.75 (m, 1H), 4.68-4.63 (m, 1H), 3.72 (s, 3H), 3.67 (s, 3H), 3.13-3.06 (m, 1H), 2.89-2.81 (m, 2H), 2.27-2.11 (m, 2H), 2.07-1.87 (m, 3H), 1.68-1.57 (m, 3H), 1.36-1.24 (m, 2H), 1.07 (d, J = 6.4 Hz, 3H) | +++ | + |
| 718 | 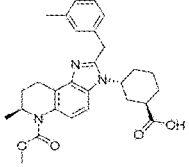 (1R,3R)-3-((S)-6-(methoxycarbonyl)-7-methyl-2-(3-methylbenzyl)-6,7,8,9-tetrahydro-3H-imidazo[4,5-f]quinolin-3-yl)cyclohexane-1-carboxylic acid | 476 | ¹H-NMR (CD$_3$OD, 300 MHz) δ (ppm): 7.51-7.41(m, 2H), 7.17-7.03(m, 4H), 4.77-4.69(m, 2H), 4.43-4.29(m, 2H), 3.76(s, 3H), 3.21-3.14(m, 1H), 2.99-2.92(m, 2H), 2.43-2.03(m, 8H), 1.77-1.57(m, 3H), 1.28-1.12(m, 5H) | +++ | + |

| Cmpd. No. | Structure and Compound Name | LCMS (m/z) [M+H]⁺ | ¹H NMR | CBP IC₅₀ (μM) (mean) | BRD4 IC₅₀ (μM) (mean) |
|---|---|---|---|---|---|
| 770 | <br>3-((7S)-2-((3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>1ˢᵗ eluting isomer | 556 | ¹H-NMR (CD₃OD, 400 MHz) δ (ppm): 7.55-7.50 (m, 1H), 7.43-7.41 (m, 1H), 7.17-7.12 (m, 1H), 6.79-6.77(m, 1H), 6.54 (s, 1H), 4.87-4.70 (m, 2H), 3.83-3.50 (m, 9H), 3.33-3.16 (m, 1H), 2.93-2.82 (m, 2H), 2.51-2.46 (m, 1H), 2.35-2.32 (m, 1H), 2.22-2.20 (m, 3H), 2.05-2.02 (m, 1H), 1.92-1.88 (m, 1H), 1.70-1.68 (m, 3H) 1.44 (d, $J$ = 4.0 Hz, 3H) | +++ | + |

FIGURE 3A

*Parameters for XRPD Analysis*

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV, 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

FIGURE 3B

*Parameters for TGA and DSC Analysis*

| Parameters | TGA | DSC |
|---|---|---|
| Method | Ramp | Ramp |
| Sample pan | Platinum, open | Aluminum, crimped |
| Temperature | RT - desired temperature | 25 °C - desired temperature |
| Heating rate | 10 °C/min | 10 °C/min |
| Purge gas | $N_2$ | $N_2$ |

FIGURE 3C

*Parameters for DVS Analysis*

| Parameters | Values |
|---|---|
| Temperature | 25 °C |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0%RH-95%RH-0%RH |
| RH step size | 10% |

FIGURE 3D

*Parameters for HPLC Analysis*

| Parameters | Values |
|---|---|
| Mobile Phase A | 10 mM Ammonium Acetate |
| Mobile Phase B | Acetonitrile |
| Column | Waters XSelect Phenyl-Hexyl, 3.5 μm, 4.6x150 mm |
| Column Temperature | 35 °C |
| LC Gradient | 0 min   10% B<br>5 min   30% B<br>15 min   45% B<br>21 min   80% B<br>22 min   80% B<br>22.1 min   10% B |
| Runtime | 25 min |
| LC Flow Rate | 1 mL/min |
| UV Wavelength | 238 nm |
| Ionization Mode | Electrospray Ionization- Positive Mode |
| Injection Volume | 8 μL |

FIGURE 4

| XRPD Peaks for the Hydrochloric Acid Addition Salts ||||||
| | TYPE A || TYPE B || TYPE C ||
| Peak No. | Position [°2Θ] | Relative Intensity [%] | Position [°2Θ] | Relative Intensity [%] | Position [°2Θ] | Relative Intensity [%] |
| --- | --- | --- | --- | --- | --- | --- |
| 1 | 7.27 | 11 | 8.00 | 100 | 7.05 | 7 |
| 2 | 8.98 | 100 | 11.68 | 8 | 8.09 | 100 |
| 3 | 10.60 | 85 | 12.36 | 46 | 9.90 | 7 |
| 4 | 11.44 | 29 | 13.59 | 18 | 11.47 | 9 |
| 5 | 12.05 | 30 | 14.68 | 13 | 11.77 | 6 |
| 6 | 14.54 | 20 | 15.23 | 5 | 12.16 | 16 |
| 7 | 14.93 | 29 | 16.02 | 31 | 12.42 | 17 |
| 8 | 15.60 | 7 | 16.29 | 37 | 13.69 | 5 |
| 9 | 17.51 | 53 | 16.45 | 21 | 14.85 | 15 |
| 10 | 17.69 | 79 | 16.74 | 9 | 16.15 | 7 |
| 11 | 18.01 | 11 | 17.35 | 7 | 16.40 | 20 |
| 12 | 20.17 | 8 | 18.72 | 7 | 16.69 | 9 |
| 13 | 20.44 | 10 | 18.98 | 5 | 16.90 | 8 |
| 14 | 20.59 | 11 | 19.59 | 58 | 17.70 | 14 |
| 15 | 21.35 | 80 | 20.12 | 9 | 19.05 | 17 |
| 16 | 21.67 | 11 | 20.56 | 12 | 19.58 | 7 |
| 17 | 21.88 | 24 | 21.33 | 10 | 19.84 | 47 |
| 18 | 23.24 | 25 | 21.80 | 24 | 20.16 | 5 |
| 19 | 23.46 | 11 | 22.41 | 6 | 21.99 | 21 |
| 20 | 23.93 | 20 | 23.03 | 36 | 23.28 | 27 |
| 21 | 24.26 | 8 | 24.77 | 19 | 24.98 | 22 |
| 22 | 25.33 | 21 | 25.23 | 8 | 25.51 | 9 |
| 23 | 26.79 | 11 | 28.03 | 6 | 28.39 | 6 |
| 24 | 27.12 | 13 | 28.31 | 6 | 31.44 | 8 |
| 25 | 27.46 | 6 | 31.10 | 8 | | |
| 26 | 28.45 | 12 | 32.68 | 6 | | |
| 27 | 29.38 | 6 | | | | |
| 28 | 30.08 | 22 | | | | |
| 29 | 31.97 | 9 | | | | |
| 30 | 32.67 | 12 | | | | |

FIGURE 5

| XRPD Peaks for the Freeform Type A Crystalline Solid |||
|---|---|---|
| Peak No. | Position [°2Θ] | Relative intensity [%] |
| 1 | 11.11 | 26 |
| 2 | 11.40 | 11 |
| 3 | 14.11 | 100 |
| 4 | 14.41 | 24 |
| 5 | 14.91 | 44 |
| 6 | 15.23 | 59 |
| 7 | 18.21 | 6 |
| 8 | 19.00 | 5 |
| 9 | 19.70 | 8 |
| 10 | 19.87 | 16 |
| 11 | 20.48 | 37 |
| 12 | 22.41 | 7 |
| 13 | 23.14 | 34 |
| 14 | 23.20 | 23 |
| 15 | 24.22 | 13 |
| 16 | 25.08 | 14 |
| 17 | 26.24 | 10 |
| 18 | 28.37 | 6 |
| 19 | 28.95 | 7 |

FIGURE 6A
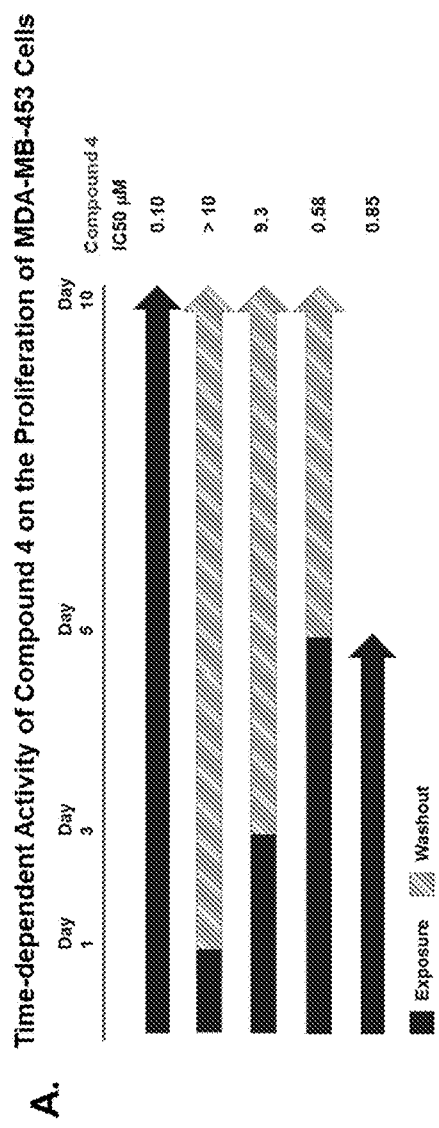
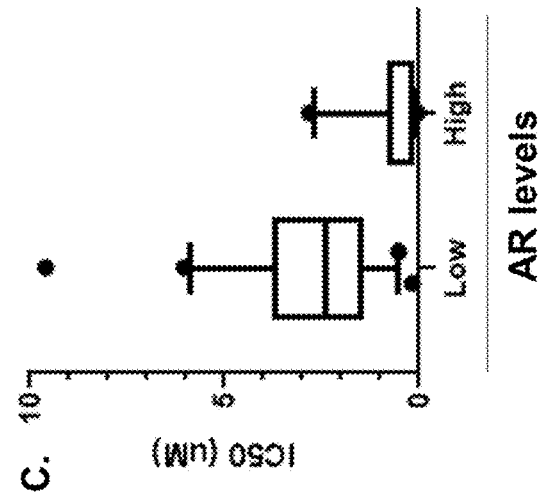
FIGURE 6B
FIGURE 6C

FIGURE 12A
| Gene set Enrichment 24 hr | Rank |
|---|---|
| HALLMARK_MYC_TARGETS_V1 | 1 |
| HALLMARK_E2F_TARGETS | 2 |
| HALLMARK_MYC_TARGETS_V2 | 3 |
| HALLMARK_ESTROGEN_RESPONSE_LATE | 4 |
| HALLMARK_ESTROGEN_RESPONSE_EARLY | 5 |
| HALLMARK_ANDROGEN_RESPONSE | 14 |
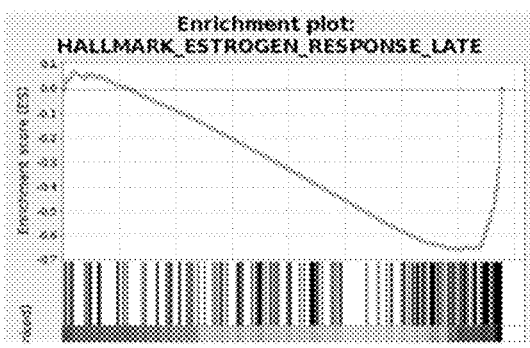 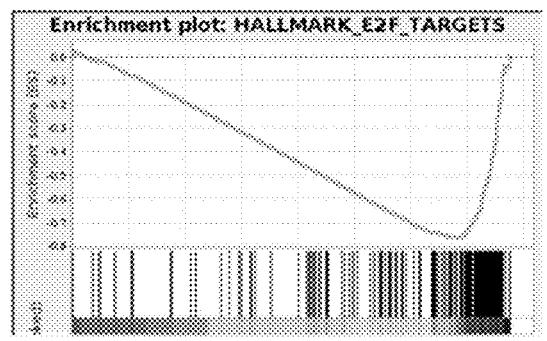
NES=-1.84; FDR<0.001        NES=-2.1; FDR<0.001
FIGURE 12B
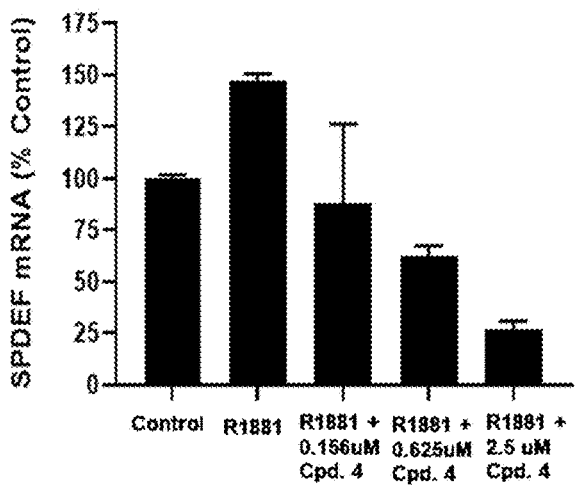 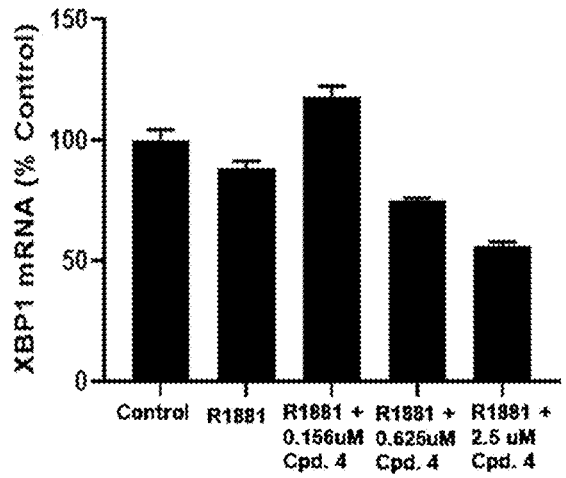

FIGURE 16
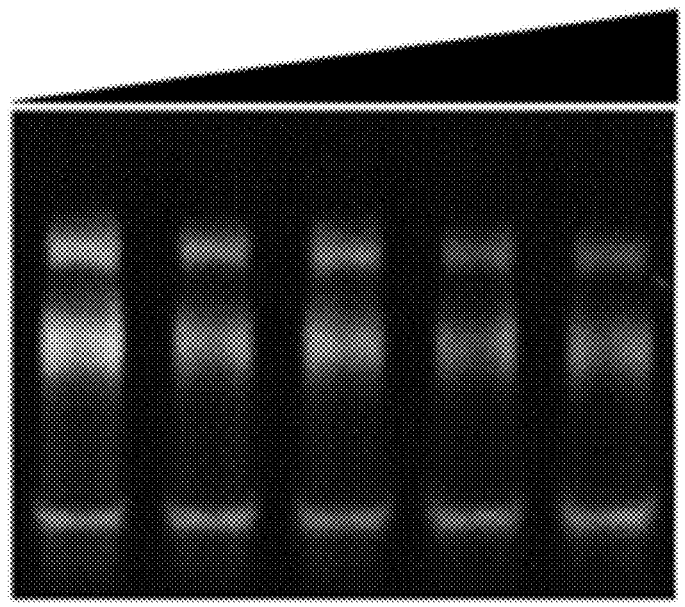
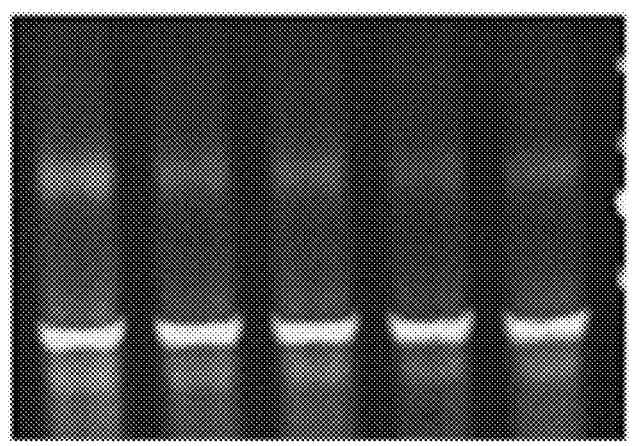

BROMODOMAIN INHIBITORS FOR ANDROGEN RECEPTOR-DRIVEN CANCERS

CROSS-REFERENCE TO RELATED APPLICATIONS

This application claims the benefit of U.S. Provisional Application No. 63/082,412, filed Sep. 23, 2020, U.S. Provisional Application No. 63/082,414, filed Sep. 23, 2020, U.S. Provisional Application No. 63/082,418, filed Sep. 23, 2020, and U.S. Provisional Application No. 63/082,963, filed Sep. 24, 2020, each of which is incorporated herein by reference in their entirety.

TECHNICAL FIELD

This disclosure relates to methods of treating certain androgen receptor positive forms of cancer using inhibitors of the CREB binding protein (CBP) bromodomain.

BACKGROUND

Growth and proliferation of hormone sensitive tumors are dependent on oncogenic signaling programs driven by corresponding nuclear receptors. The androgen receptor (AR), a key driver in prostate cancer and subsets of breast cancers, controls the expression of about 100 androgen-responsive target genes. Expression of these AR target genes is important for normal tissue development and cellular activities but can have pathological effects that underlie tumor initiation and progression. While the direct targeting of androgen biosynthesis and androgen interaction with AR has demonstrated clinical utility, acquired resistance to these therapies can circumvent ligand-driven AR function while retaining continued dependence on AR-driven transcriptional programs. In particular, AR regulates expression of genes essential for the growth and survival of prostate cancers and AR-positive breast cancers.

CREB binding protein (CBP) and E1A binding protein (p300) are closely related multi-domain proteins that contain acetyltransferase activity and acetyl-lysine binding bromodomains. These proteins function as coactivators of numerous oncogenic transcription factors including the androgen receptor. CBP and p300 increase H3K27 acetylation, thereby relaxing chromatin and increasing transcriptional activity. CBP and p300 have also been shown to acetylate AR, thereby stabilizing the receptor. CBP and p300 also interact directly with AR at both the N- and C-terminus of AR, including with truncated forms of AR lacking the ligand-binding domain.

Nuclear hormone receptors, including AR, are part of multi-protein complexes involving co-activators and co-repressors which control the impact of the nuclear receptor on its downstream target genes. Within the AR-associated multi-protein complex, CBP/p300 are critical co-activators of AR, modifying the chromatin environment surrounding the nuclear receptor to increase its intrinsic transcriptional activity and recruiting additional co-factors. More specifically, CREB binding protein (CBP) and EP300 (p300) are closely related multi-domain proteins that function broadly as transcriptional co-activators. They carry acetyl-lysine binding bromodomains which impart a scaffolding or positioning function on these proteins and have proven to be suitable for the design of small molecule inhibitors of their biological function. These paralogs are highly homologous at the amino acid level and share many overlapping functions. They are histone acetyl transferases (HATs), catalyzing the post-translational modification of histone and non-histone proteins. As bromodomain carrying HATs, these proteins function as both epigenetic readers and writers. The non-histone protein substrates of CBP/p300 consist of numerous transcription factors, including nuclear receptors such as AR. CBP/p300 function as co-activators of AR-signaling in part by acetylating AR, which activates its transcriptional activity and promotes enhanced protein stability. In addition, they acetylate histone H3 at lysine 27 (Ac-H3K27) to provide a docking site for the bromodomain, thus providing a scaffold to bridge the nuclear receptor to the basal transcriptional machinery. Acetylation of histone leads to the generation of a transcriptionally permissive environment on chromatin. The localization of CBP/p300 to AR dependent super-enhancers thus leads to increased localized Ac-H3K27 which further increases transcription at these loci.

Prostate and breast cancers are frequently dependent upon gene expression programs respectively driven by the AR, or by the estrogen and progesterone receptors (ER and PR). Consequently, direct and indirect antagonists of steroid hormone biosynthesis and receptor interaction are central to the treatment of these diseases. Nuclear hormone receptors, including AR, participate in multiprotein complexes of co-activators and co-repressors to modulate the activity of their target genes. Within these complexes, CBP/p300 are critical and essential co-activators, modifying the chromatin environment surrounding the nuclear receptor to increase its transcriptional activity and recruit additional co-factors. Prostate cancer resistance to anti-androgen therapies is multi-factorial (including autocrine ligand production, intra-tumoral androgen biosynthesis, AR gene amplification, somatic mutation in the ligand binding domain (LBD) of AR and altered splicing of AR messenger ribonucleic acid (mRNA) resulting in loss of the LBD, the so-called AR variant 7 (AR-v7) form). These mechanisms of resistance remain dependent upon AR-mediated transcriptional programs and therefore CBP/p300. In fact, CBP and p300 were shown to be upregulated and associated with castration resistance. The persistent dependence on AR function within these resistant populations warrants novel therapeutic approaches targeting AR functions distinct from ligand binding.

A subset of triple-negative breast cancers express the AR, which can substitute for the estrogen receptor (ER) to drive its oncogenic transcriptional signature. AR-positive breast cancer have lower Ki67 expression and are less sensitive to chemotherapy than other types of TNBC, due to a lower proliferative index. AR antagonists have been tested clinically and have shown some early activity in AR-positive breast cancers. AR dependency of a model of AR-positive breast cancer has been demonstrated both in vitro and in vivo.

Prostate cancer is the second and third leading cause of cancer death for men in the United States, or U.S., and in Europe, respectively, and metastatic castrate-resistant prostate cancer (mCRPC) is the most advanced form of the disease. Prostate cancer cell growth is driven by activity of the androgen receptor, or AR, and primary treatments of mCRPC include therapies, such as Zytiga (abiraterone acetate) and Xtandi (enzalutamide), that reduce androgen synthesis or inhibit androgen binding and activation of the AR. Specifically, for men with metastatic castration resistant prostate cancer, there are currently three broad therapeutic approaches: taxanes, anti-androgens, and immunotherapy. The standard treatment of metastatic disease is surgical or chemical castration in the form of androgen-deprivation therapy (ADT). Despite initial success and disease regression, resistance to therapy ultimately develops and the disease transitions to castration-resistant prostate cancer (CRPC). Androgen receptor (AR) activation and autocrine and/or paracrine androgen synthesis are potential mechanisms of recurrence of prostate cancer during ADT. Chemotherapy and AR signaling inhibitors are the mainstay of treatment in a CRPC setting. At time of failure of these approaches the development of AR inhibitor resistance and subsequent disease progression is common. Studies have shown that approximately 20% to 40% of mCRPC patients demonstrate primary resistance to these therapies, and virtually all patients who demonstrate initial clinical responses eventually acquire resistance.

Prostate cancers are frequently dependent upon gene expression programs driven by the Androgen Receptor (AR). Consequently, direct and indirect antagonists of steroid hormone biosynthesis and androgen receptor interaction are central to the treatment of these diseases. Nuclear hormone receptors, including AR, participate in multiprotein complexes of co-activators and co-repressors to modulate the activity of their target genes. Within these complexes, CBP/p300 are critical and essential co-activators, modifying the chromatin environment surrounding the nuclear hormone receptor to increase its transcriptional activity and recruit additional co-factors. Prostate cancer resistance to anti-androgen therapies is multi-factorial (including autocrine ligand production, intra-tumoral androgen biosynthesis, AR gene amplification, somatic mutation in the ligand binding domain (LBD) of AR and altered splicing of AR messenger ribonucleic acid (mRNA) resulting in loss of the LBD, as in the so-called AR variant 7 (AR-v7) form. These mechanisms of resistance remain dependent upon AR-mediated transcriptional programs and therefore CBP/p300. The persistent dependence on AR function within these resistant populations warrants novel therapeutic approaches targeting AR functions distinct from ligand binding. The dependence of prostate cancer on AR signaling is well-established and is the basis for the development of androgen deprivation therapy (ADT), including with agents such as luteinizing hormone releasing hormone (LHRH) receptor agonists and antagonists, and/or cytochrome P450 (CYP) 17 inhibitors capable of antagonizing androgen biosynthesis. These therapies are the mainstay of prostate cancer treatment.

Prostate cancer can become castration-resistant. AR antagonists such as enzalutamide, apalutamide or darolutamide are effective therapies in CRPC. However, the 5-year survival rate for subjects with metastatic castration-resistant prostate cancer (mCRPC) progressing on or after first line chemotherapy is estimated as being less than 2%. This is due to resistance to anti-androgen therapies arising from autocrine ligand production and/or intra-tumoral androgen biosynthesis, as well as aberrations in AR including AR gene amplification, somatic mutation in the ligand binding domain (LBD) of AR, and/or altered splicing of AR messenger ribonucleic acid (mRNA) resulting in loss of the LBD, as in the so-called AR variant 7 (AR-v7) form. Tumors at this stage can remain dependent upon AR-mediated transcriptional programs. This persistent dependence on AR function within these resistant populations recommends novel therapeutic approaches targeting AR functions distinct from ligand binding.

There are no approved therapeutics specifically aimed at mCRPC patients for whom androgen antagonists and taxane therapies have proven ineffective. These include patients with tumors harboring structurally altered androgen receptors, including the AR-v7 splice form, that continue to promote the AR transcriptional program in a ligand-independent manner, unaffected by androgen antagonists. Multiple third-party studies have demonstrated that the CBP/p300 protein complex is an upstream co-activator of the AR and upregulation of this AR co-activator is one of the mechanisms that can lead to mCRPC. This population, therefore, represents a long-felt, unmet clinical need. Stated another way, there remains an unmet medical need for novel and potent compounds for treating prostate cancer by inhibiting CBP/p300.

SUMMARY

Methods for the treatment of patients with AR-positive tumors, including prostate cancer, can comprise the administration of a compound disclosed herein to a patient in need thereof. For example, compounds and methods are provided herein for inhibiting cyclic adenosine monophosphate (cAMP)-response element binding protein (CREB) binding protein (CBP)/E1A binding protein p300 (p300) bromodomain (BRD) interactions with acetylated lysines on histones (e.g. H3K27Ac), including methods to disrupt androgen receptor (AR)-related transcriptional programming and induce antiproliferative, and apoptotic effects in AR-dependent tumors. Given the co-regulatory relationship between AR and CBP/P300, inhibition of CBP/P300 activity offers a rational approach to suppress AR-dependent oncogenic programs in AR-dependent tumors, such as those found in some forms of AR-positive breast and prostate cancers. Accordingly, methods for the treatment of certain AR-positive cancers using compositions comprising CBP inhibitor compounds are disclosed herein (FIG. 1).

Disclosed herein are methods for treating a patient diagnosed with an AR-positive cancer including the step of administering to the patient in need thereof a therapeutically effective amount of a pharmaceutical composition comprising a CBP inhibitor compound of formula (I):

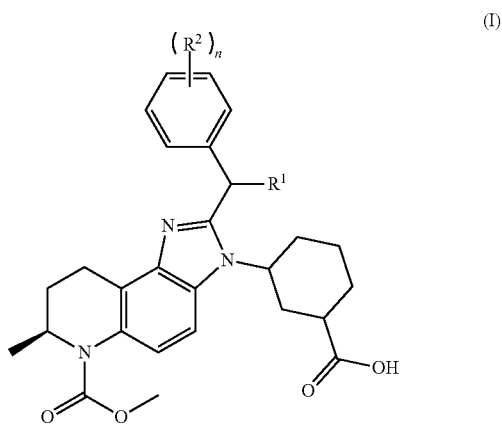

and pharmaceutically acceptable salts thereof, wherein:
$R^1$ is H or —OH;
each $R^2$ is independently selected from $C_1$-$C_6$ alkyl (e.g., methyl), halogen, —CN, and —OR$^3$, (e.g., methoxy) wherein the alkyl is optionally substituted with one or more halogen;
each $R^3$ is independently H or $C_1$-$C_6$ alkyl (e.g., methyl), wherein the alkyl is optionally substituted with one or more halogen; and n is an integer selected from 0, 1, 2, 3, 4 or 5, wherein n is preferably 0, 1, 2, or 3.

In some embodiments, the pharmaceutical composition includes compound 1:

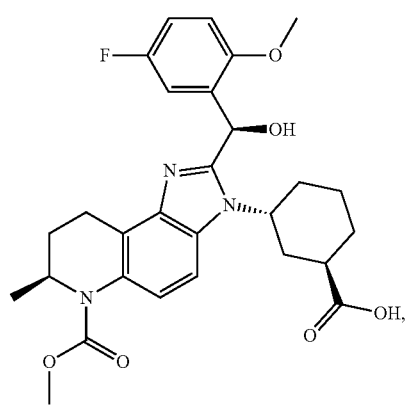

(1)

or a pharmaceutically acceptable salt thereof.

The applicants discovered certain methods of treatment comprising the administration of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid ("Compound 1"), or a pharmaceutically acceptable salt thereof, to a patient in need thereof to disrupt androgen receptor-related transcriptional programming and induce antiproliferative, and potentially apoptotic effects in AR-dependent tumors, such as prostate cancer tumors.

Compound 1 is a potent and selective oral inhibitor of cyclic adenosine monophosphate (cAMP)-response element binding protein (CREB) binding protein (CBP)/E1A binding protein p300 (p300) bromodomain (BRD) interactions with acetylated lysines on histones that can disrupt androgen receptor (AR)-related transcriptional programming and induce antiproliferative, and potentially apoptotic effects in AR-dependent tumors. Compound 1 is a potent and selective oral inhibitor of CBP/p300 bromodomain (BRD) interactions with acetylated lysines on histones that antagonizes AR-driven transcriptional activity in preclinical models of prostate cancer, both in vitro and in vivo, and demonstrates preclinical antitumor activity.

Accordingly, methods of treatment include the administration of a therapeutically effective amount of Compound 1 to a patient diagnosed with metastatic castration resistant prostate cancer (mCRPC). In some embodiments, methods of treating patients diagnosed with AR-positive tumors, including prostate cancer, comprise the step of administering Compound 1 or a pharmaceutically acceptable salt thereof to the patient in need thereof. In some embodiments, Compound 1 (or a pharmaceutically acceptable salt thereof) can be administered in an oral unit dosage form, to the patient in need thereof, as a single agent for the treatment of men with mCRPC.

In one aspect, methods of treatment provide the oral administration to a patient in need thereof of a pharmaceutical composition comprising a non-amorphous, solid form of a pharmaceutically acceptable salt of Compound 1, such as a hydrochloride salt of Compound 1:

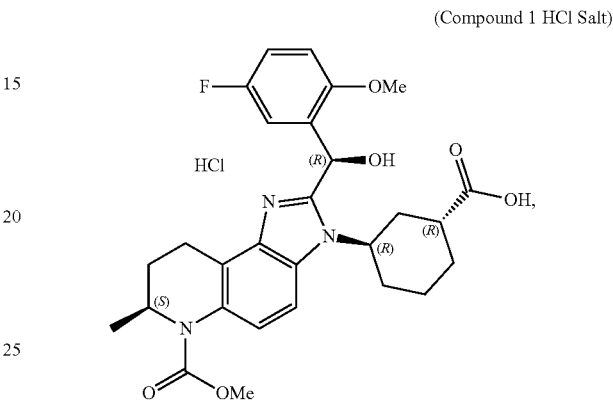

(Compound 1 HCl Salt)

or as another pharmaceutically acceptable salt thereof. For example, in some methods, Compound 1, or the pharmaceutically acceptable salt thereof, is administered to a patient in need thereof in an oral unit dosage form containing a crystalline solid form (as provided herein) of the free base or the hydrochloric acid addition salt (also known as a hydrochloride addition salt) of Compound 1, such as (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid hydrochloride.

In some embodiments, the pharmaceutical composition includes compound 2:

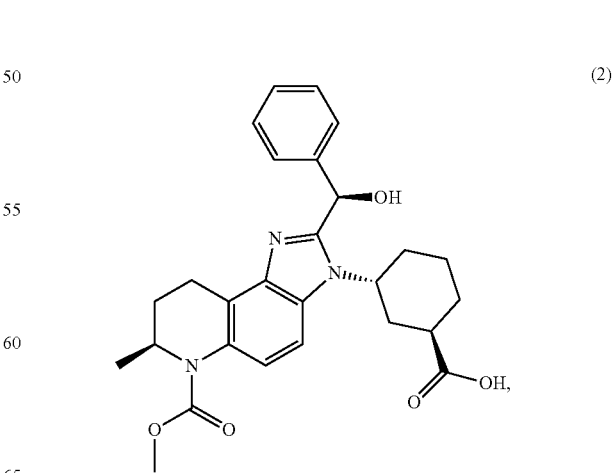

(2)

or a pharmaceutically acceptable salt thereof.

In some embodiments, the pharmaceutical composition includes compound 3:

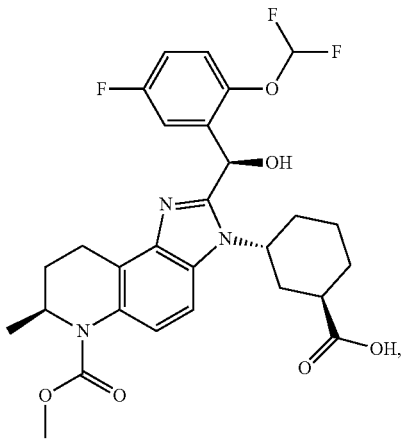

(3)

or a pharmaceutically acceptable salt thereof.

In some embodiments, the pharmaceutical composition includes compound 4:

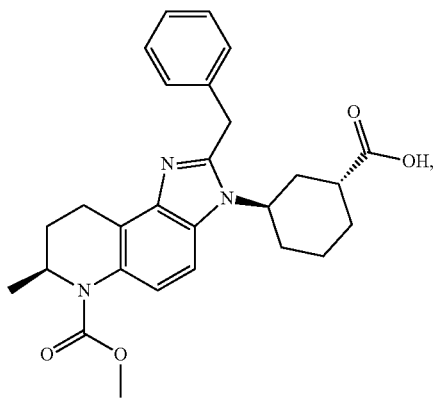

(4)

or a pharmaceutically acceptable salt thereof.

Compound 4 has a single-digit nanomolar potency against CBP and p300, and is highly selective over BRD4 and other bromodomain proteins representative of the branches of the bromodomain tree, as shown in the examples disclosed herein. Compound 4 induces the rapid reduction of H3K27 acetylation in an AR-positive triple-negative breast cancer model. High-content analysis reveals that this reduction of H3K27 acetylation occurs throughout the entire population of cells. Additionally, the reduction of H3K27 acetylation is reversible, returning to baseline within 24 to 48 hours after removal of the compound.

Gene set enrichment analysis of RNAseq data revealed enrichment of ER- and AR-target genes in AR-positive triple-negative breast cancer cells treated with compound 4. SPDEF and XBP1, representative of AR- and ER-target genes, respectively, were validated by qPCR after cells were exposed to the AR agonist R1881 with and without simultaneous exposure to compound 4. ChIP-seq analysis revealed reduced CBP and p300 binding upstream of the ER-regulated gene, AQP3. This is concurrent with reduction in H3K27 acetylation at this location. These changes were also associated with the reduction of AQP3 mRNA levels.

Compound 4 is a potent inhibitor of the proliferation of an AR-positive triple negative breast cancer cell model. This AR-modulator also potently inhibits the proliferation of AR-positive prostate cancer models, including an AR-v7 expressing cell model. Compound 4 induces time-dependent inhibition of proliferation, with maximum inhibition observed after ten days of continuous exposure. Five days of exposure defines the minimal period to achieve sustained growth inhibition. Compound 4 is forty-times as potent as the AR-antagonist enzalutamide in this model, and is preferentially active against cells expressing high levels of AR.

A dose- and time-dependent pharmacokinetic (PK) and pharmacodynamic (PD) relationship was observed from an oral administration of compound 4 to mice harboring an AR-positive triple negative breast cancer xenograft. The level of unbound compound 4 in plasma correlated with modulation of H3K27 acetylation and ER- and AR-target genes. This was associated with a reduced proliferative index, as measured by Ki67 immunohistochemical (IHC) staining. Additionally, compound 4 induced tumor stasis in the AR-positive triple negative breast cancer xenografts.

In some embodiments, the AR-positive cancer is a form of AR-positive breast cancer, including, but not limited to, triple-negative, hormone receptor positive, and HER2-positive forms of breast cancer.

A method of treating triple-negative breast cancer comprising administering to the patient in need thereof a therapeutically effective amount of compound 4, or a therapeutically effective amount thereof, is disclosed herein.

In some embodiments, the AR-positive cancer is a form of AR-positive prostate cancer, including, but not limited to, metastatic castration-resistant prostate cancer (mCRPC). In some embodiments, the metastatic castration resistant prostate cancer may harbor the AR-v7 splice form of the protein.

In some embodiments, the pharmaceutical composition is administered to patients at a therapeutically effective dose. The CBP Inhibitor of Formula (I) can be used in a therapeutically effective amount to inhibit CBP and antagonize androgen receptor signaling. In some embodiments, a therapeutically effective amount can be administered to a patient diagnosed with prostate cancer, including patients diagnosed with mCRPC (e.g., mCRPC expressing the AR-v7 splice form). AR is an oncogenic driver in prostate cancer and progression of the disease towards castration- and drug-resistance is associated with aberrations of AR such as amplification of AR, mutations in the LBD and increase in a splice variant of AR lacking the LBD (AR-v7).

BRIEF DESCRIPTION OF THE DRAWINGS

The present application contains drawings for a better understanding of the principles of the disclosure:

FIG. 3(A) is a table of the parameters used for X-ray powder diffraction analysis of the solid forms disclosed herein.

FIG. 3(B) is a table of the parameters used for thermogravimetric and differential scanning calorimetry analysis of the solid forms disclosed herein.

FIG. 3(C) is a table of the parameters used for dynamic vapor sorption analysis of the solid forms disclosed herein.

FIG. 3(D) is a table of the parameters used for the HPLC analysis of the amorphous free base compound disclosed herein.

FIG. 4 is a table of the X-ray powder diffraction peaks with a greater than 5% relative intensity of the type A, B, and C hydrochloric acid addition salt forms disclosed herein.

FIG. 5 is a table of the X-ray powder diffraction peaks with a greater than 5% relative intensity of the crystalline freeform type A solid form disclosed herein.

FIG. 6(A) shows the time-dependent inhibition of AR+ triple-negative breast cancer cell proliferation in cells treated with compound 4.

FIG. 6(B) shows a comparison of the anti-proliferative effects of compound 4 compared to enzalutamide in AR+ triple-negative breast cancer cells.

FIG. 6(C) shows the activity of compound 4 in cells with high-levels of AR compared to cells with low-levels of AR.

FIG. 12(A) shows gene set enrichment analysis of RNAseq data from cells treated with compound 4.

FIG. 12(B) shows qPCR analysis of SPDEF and XBP1 mRNA levels in cells exposed to R1881 in the presence and absence of compound 4.

FIG. 16 is an immunoblot showing AR and AR-v7 expression levels in an AR-v7+ prostate cancer cell line after 24 h exposure to increasing concentrations of Compound 3.

DETAILED DESCRIPTION

Figure 1:
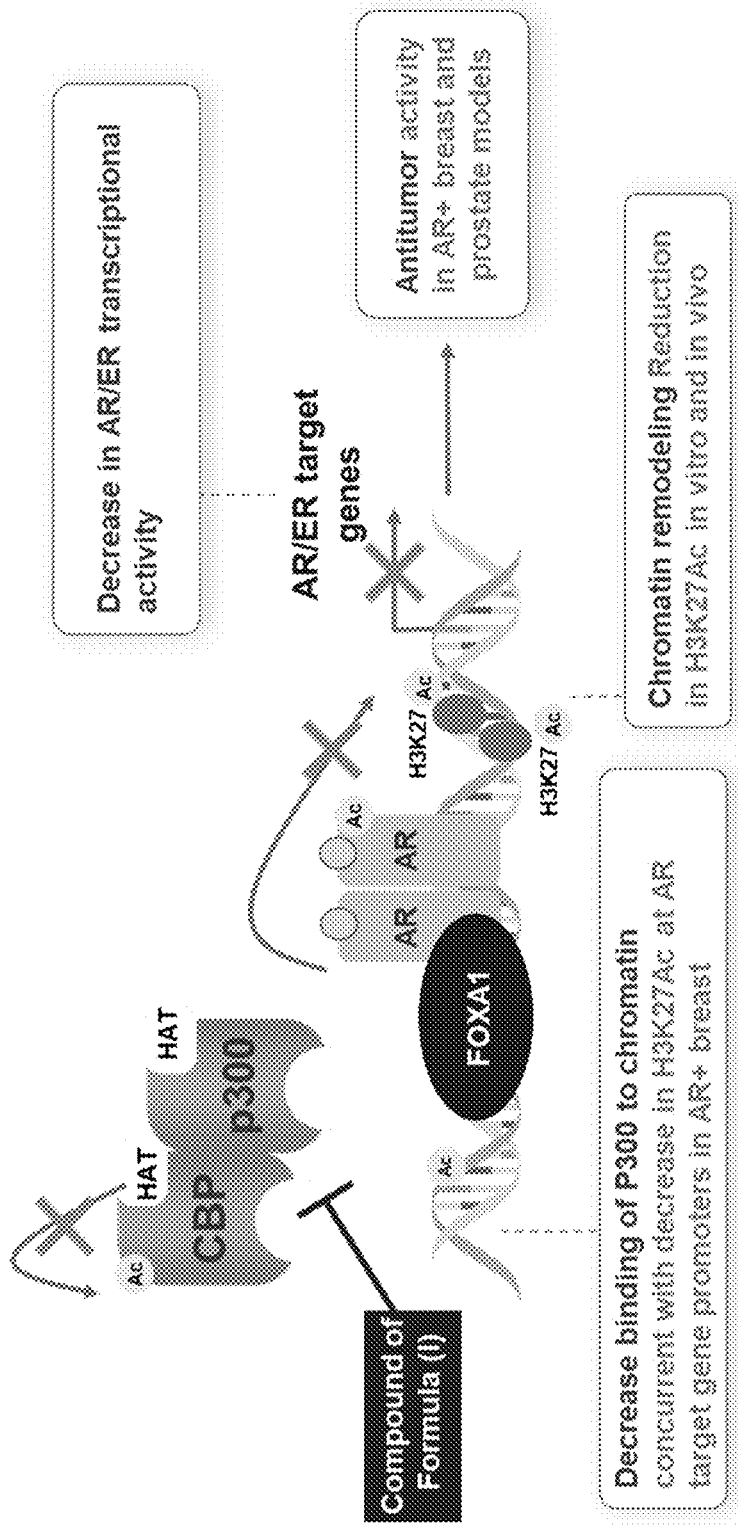
FIG. 1 shows a schematic representation that summarizes the effects of treatment with a compound of formula (I).

The present disclosure relates to salts and solid forms of compounds and compositions that are capable of modulating the activity of the CBP/p300 family bromodomains. The present disclosure also relates to the ability of CBP inhibitor compounds to inhibit proliferation of androgen receptor (AR) overexpressing models of breast and prostate cancers. Methods for the treatment of certain AR-positive cancers using compositions comprising CBP inhibitor compounds are disclosed.

The methods of the present disclosure can be used in the treatment of a variety of CBP/p300 bromodomain dependent diseases and disorders by inhibiting the activity of a CBP/p300 bromodomains. Inhibition of CBP/p300 bromodomains provides a novel approach to the treatment of diseases including, but not limited to, cancer. Cyclic adenosine monophosphate (cAMP)-response element binding protein (CREB) binding protein (CBP) and E1A binding protein p300 (p300) are essential co-activators of AR-mediated transcription. The catalytic core of these proteins contains a bromodomain (BRD) and a histone acetyltransferase (HAT) domain. The BRD of CBP/p300 binds acetylated lysines on histones, positioning CBP/p300 on the chromatin so the HAT can acetylate proximal substrates, including histone H3 at lysine 27 (H3K27Ac). This results in a more accessible, transcriptionally permissive chromatin environment. CBP/p300 also binds AR at both the N-terminus and the ligand-binding domain of the receptor, including truncated forms of AR like the AR-v7 variant. CBP/p300 also acetylates and stabilizes AR. Overall, CBP/p300 promotes AR transcriptional activity and increases AR target gene expression driving proliferation in AR-driven tumors.

In one aspect, a method for treating a patient diagnosed with an AR-positive cancer is disclosed and includes the step of administering to the patient in need thereof a therapeutically effective amount of a pharmaceutical composition comprising a CBP inhibitor compound of formula (I), as described above.

A CBP inhibitor compound is defined herein as a compound having one or more of the following characteristics when tested according to the HTRF biochemical assay protocol of Example 3 below: (1) a CBP $IC_{50}$ value less than 1 μM; and (2) a CBP $IC_{50}$ value between 0.001 and 1 μM. In some embodiments, CBP inhibitor compounds of the present disclosure may have $IC_{50}$ values less than 0.01 μM against the CBP bromodomain when tested in the HTRF biochemical assay of Example 3 below. In some embodiments, the CBP inhibitor compound is a selective CBP inhibitor compound, defined as a CBP inhibitor compound with an $IC_{50}$ value against the BRD4 bromodomain that is greater than the $IC_{50}$ value of the compound against the CBP bromodomain, preferably wherein the BRD4 $IC_{50}$ value is greater than 1 μM (e.g., 1 micromolar to 10 micromolar, or greater) when tested via the HTRF biochemical assay of Example 3 below. In some embodiments, compounds of formula (I) can be Selective CBP Inhibitor Compounds, wherein the BRD4 $IC_{50}$ value is greater than 500 nM (e.g., 500 nanomolar to 10 micromolar, or greater), wherein the $IC_{50}$ values are determined as in the procedures set forth in the assay described in Example 3.

Unless otherwise indicated herein, all isomeric forms of specified chemical compounds are provided by the present disclosure, including mixtures thereof (e.g., S, R and racemic orientations at each chiral center). If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of formula (I) and Group A, unless otherwise indicated, may exist in their tautomeric form. All such tautomeric forms are contemplated herein as part of the present disclosure.

The compounds of formula (I), unless otherwise indicated, may contain one or more stereocenters, and, therefore, exist in different stereoisomeric forms. It is intended that unless otherwise indicated all stereoisomeric forms of the compounds of formula (I) and Group A, as well as mixtures thereof, including racemic mixtures, form part of the present disclosure. In addition, the present disclosure embraces all geometric and positional isomers. For example, if a compound of formula (I) or Group A incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers based on their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula (I) or Group A may be atropisomers (e.g., substituted biaryls) and are considered as part of this disclosure. Enantiomers can also be separated by use of a chiral HPLC column.

The compounds of formula (I) or Group A may form acid addition salts, which may be pharmaceutically acceptable salts. The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of formula (I) or Group A can be a capsule. In some embodiments, an oral dosage form of a compound of formula (I) or Group A is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

A CBP Inhibitor compound of the present disclosure can be dosed at a therapeutically effective level. A Selective CBP Inhibitor compound of the present disclosure can be dosed at a therapeutically effective level.

A therapeutically effective amount may vary from patient to patient, and is defined as an amount sufficient to elicit a desired effect within the patient. Non-limiting examples of such desired effects within a patient include a reduction in tumor volume, the inhibition of AR-dependent and/or ER-dependent gene expression, a reduction in histone acetylation, a reduction in the intracellular protein level of AR or aberrant forms of AR, such as the AR-v7 splice form protein, and/or an increase in the degradation of AR or aberrant forms of AR, such as the AR-v7 splice form protein.

In some embodiments, the disclosure features methods of treating, preventing or ameliorating a disease or disorder in which CBP/p300 bromodomains play a role by administering to a patient in need thereof a therapeutically effective amount of Compound 1 or a pharmaceutically acceptable salt thereof.

In some embodiments, methods of treating a patient diagnosed with prostate cancer can include administering a therapeutically effective amount of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid ("Compound 1") or a pharmaceutically acceptable salt thereof.

In some embodiments, methods of treating a patient diagnosed with metastatic castration-resistant prostate cancer (mCRPC) include administering a therapeutically effective amount of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl] cyclohexane-1-carboxylic acid hydrochloride. For example, some methods of treatment include the oral administration to a patient diagnosed with mCRPC of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid hydrochloride as an active pharmaceutical ingredient (API) in an oral unit dosage form, such as a capsule or tablet, in combination with one or more pharmaceutically acceptable excipients.

Compounds of the Disclosure

In one aspect, the disclosure relates to compounds of formula (I):

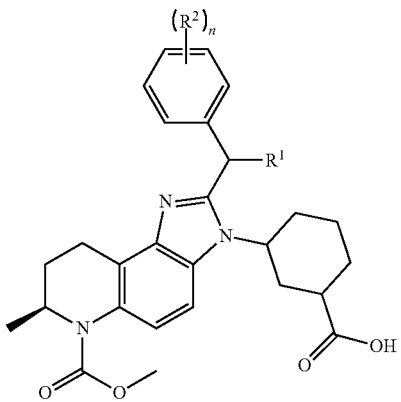

(I)

or a pharmaceutically acceptable salt thereof, wherein:
R$^1$ is H or —OH;
each R$^2$ is independently selected from C$_1$-C$_6$ alkyl, halogen, —CN, and —OR$^3$, wherein the alkyl is optionally substituted with one or more halogen;
each R$^3$ is independently H or C$_1$-C$_6$ alkyl, wherein the alkyl is optionally substituted with one or more halogen; and
n is an integer selected from 0-5, wherein n is preferably 0, 1, 2, or, 3.

In some embodiments, R$^1$ is H or —OH; each R$^2$ is independently selected from —F, —Cl, —CH$_3$, —CHF$_2$, —CN, and —OR$^3$; each R$^3$ is independently selected from —CH$_3$, —CHF$_2$, and —CH(CH$_3$)$_2$, and n is selected from 0, 1, 2, and 3.

In some embodiments, compounds of Formula (I) are provided wherein R$^2$ is —Cl, —CH$_3$, —CHF$_2$, —CN, —OCH$_3$, —OCHF$_2$, —OCH(CH$_3$)$_2$. In some embodiments, R$^2$ is —F, —CH$_3$, —CHF$_2$, —CN, or —OR$^3$. In some embodiments, R$^2$ is —F, —Cl, —CHF$_2$, —CN, or —OR$^3$. In some embodiments, R$^2$ is —F, —Cl, —CH$_3$, —CN, or —OR$^3$. In some embodiments, R$^2$ is —F, —Cl, —CH$_3$, —CHF$_2$, or —OR$^3$. In some embodiments, R$^2$ is —F, —Cl, —CH$_3$, —CHF$_2$, or —CN.

In one embodiment, the disclosure provides compounds of formula (Ib):

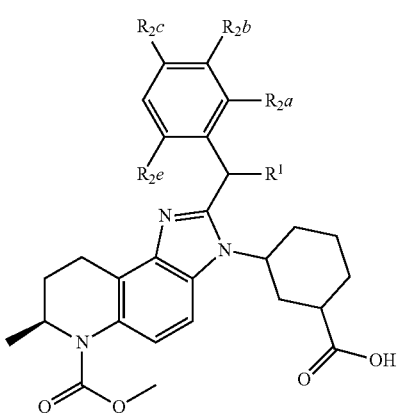

(Ib)

or a pharmaceutically acceptable salt thereof, wherein:
R$^1$ is H or —OH;
R$^{2a}$ is selected from H, C$_1$-C$_6$ alkyl (e.g., methyl), halogen (e.g., F or Cl), and —OR$^3$, wherein the alkyl is optionally substituted with one or more halogen (e.g., CHF$_2$);
R$^{2b}$ is selected from H, C$_1$-C$_6$ alkyl (e.g., methyl), halogen (e.g., F or Cl), and —OR$^3$, wherein the alkyl is optionally substituted with one or more halogen (e.g., CHF$_2$);
R$^{2c}$ is selected from H, C$_1$-C$_6$ alkyl (e.g., methyl), halogen (e.g., F or Cl), and —OR$^3$, wherein the alkyl is optionally substituted with one or more halogen;
R$^{2d}$ is selected from H or halogen (e.g., F or Cl);
R$^{2e}$ is selected from H, C$_1$-C$_6$ alkyl (e.g., methyl), halogen (e.g., F or Cl), —CN, and —OR$^3$, wherein the alkyl is optionally substituted with one or more halogen (e.g., methyl); and
R$^3$ is H or C$_1$-C$_6$ alkyl (e.g., methyl), wherein the alkyl is optionally substituted with one or more halogen (e.g., CHF$_2$).

In one embodiment, the disclosure provides compounds of formula (Ib):

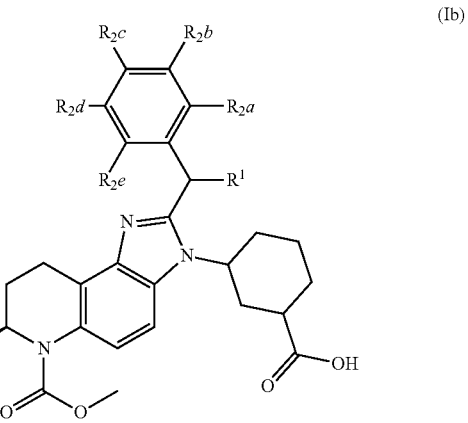

(Ib)

or a pharmaceutically acceptable salt thereof, wherein:
R$^1$ is —OH;
R$^{2a}$ is selected from H, C$_1$-C$_6$ alkyl (e.g., methyl), halogen (e.g., F or Cl), and —OR$^3$, wherein the alkyl is optionally substituted with one or more halogen (e.g., CHF$_2$);
R$^{2b}$ is selected from H, C$_1$-C$_6$ alkyl (e.g., methyl), halogen (e.g., F or Cl), and —OR$^3$, wherein the alkyl is optionally substituted with one or more halogen (e.g., CHF$_2$);
R$^{2c}$ is selected from H, C$_1$-C$_6$ alkyl (e.g., methyl), halogen (e.g., F or Cl), and —OR$^3$, wherein the alkyl is optionally substituted with one or more halogen;
R$^{2d}$ is selected from H or halogen (e.g., F or Cl);
R$^{2e}$ is selected from H, C$_1$-C$_6$ alkyl (e.g., methyl), halogen (e.g., F or Cl), —CN, and —OR$^3$, wherein the alkyl is optionally substituted with one or more halogen (e.g., methyl); and
R$^3$ is H or C$_1$-C$_6$ alkyl (e.g., methyl), wherein the alkyl is optionally substituted with one or more halogen (e.g., CHF$_2$).

In one embodiment, the disclosure provides compounds of formula (Ib):

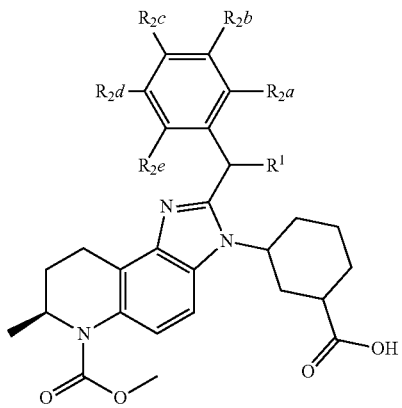

or a pharmaceutically acceptable salt thereof, wherein:
$R^1$ is H;
$R^{2a}$ is selected from H, $C_1$-$C_6$ alkyl (e.g., methyl), halogen (e.g., F or Cl), and —$OR^3$, wherein the alkyl is optionally substituted with one or more halogen (e.g., $CHF_2$);
$R^{2b}$ is selected from H, $C_1$-$C_6$ alkyl (e.g., methyl), halogen (e.g., F or Cl), and —$OR^3$, wherein the alkyl is optionally substituted with one or more halogen (e.g., $CHF_2$);
$R^{2c}$ is selected from H, $C_1$-$C_6$ alkyl (e.g., methyl), halogen (e.g., F or Cl), and —$OR^3$, wherein the alkyl is optionally substituted with one or more halogen;
$R^{2d}$ is selected from H or halogen (e.g., F or Cl);
$R^{2e}$ is selected from H, $C_1$-$C_6$ alkyl (e.g., methyl), halogen (e.g., F or Cl), —CN, and —$OR^3$, wherein the alkyl is optionally substituted with one or more halogen (e.g., methyl); and
$R^3$ is H or $C_1$-$C_6$ alkyl (e.g., methyl), wherein the alkyl is optionally substituted with one or more halogen (e.g., $CHF_2$).

In one embodiment, the disclosure provides compounds of formula (Ib):

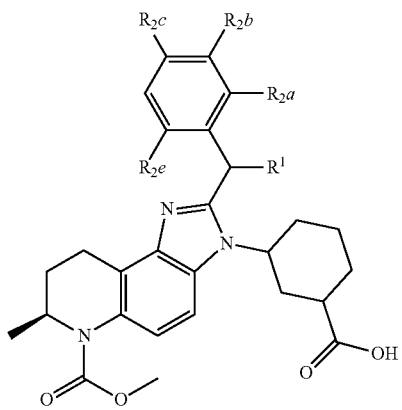

or a pharmaceutically acceptable salt thereof, wherein:
$R^1$ is H or —OH;
$R^{2a}$ is selected from H, $C_1$-$C_6$ alkyl (e.g., methyl), halogen (e.g., F or Cl), and —$OR^3$, wherein the alkyl is optionally substituted with one or more halogen (e.g., $CHF_2$);
$R^{2b}$ is H;
$R^{2c}$ is H;
$R^{2d}$ is independently selected from H or halogen (e.g., F or Cl);
$R^{2e}$ is H; and
$R^3$ is independently H or $C_1$-$C_6$ alkyl (e.g., methyl), wherein the alkyl is optionally substituted with one or more halogen (e.g., $CHF_2$).

In one embodiment, the disclosure provides compounds of formula (Ib):

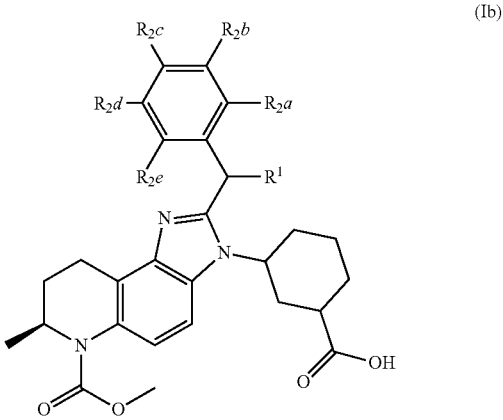

or a pharmaceutically acceptable salt thereof, wherein:
$R^1$ is H or —OH;
$R^{2a}$ is selected from H, and —$OR^3$;
$R^{2b}$ is H;
$R^{2c}$ is H;
$R^{2d}$ is independently selected from H or halogen (e.g., F or Cl);
$R^{2e}$ is H; and
$R^3$ is independently H or $C_1$-$C_6$ alkyl (e.g., methyl), wherein the alkyl is optionally substituted with one or more halogen (e.g., $CHF_2$).

In some embodiments, Selective CBP Inhibitor Compounds of formula (I) are provided. In some embodiments, Selective CBP Inhibitor Compounds of Formula (Ib) are provided. The present disclosure encompasses the recognition that compounds of formula (I) are CBP Inhibitor Compounds, defined herein as compounds having one or more of the following characteristics when tested according to the HTRF biochemical Assay Protocol below in Example 3: (1) a CBP $IC_{50}$ value of less than 1 µM; and (2) a CBP $IC_{50}$ value of between 0.001 and 1 µM.

In some embodiments, the disclosure relates to compounds of formula (I) that are of a formula selected from Group A:

(A1)
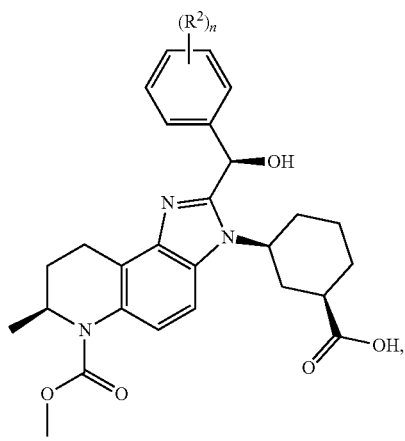
(A2)
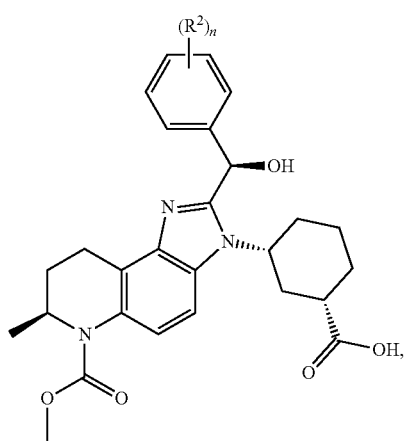
(A3)
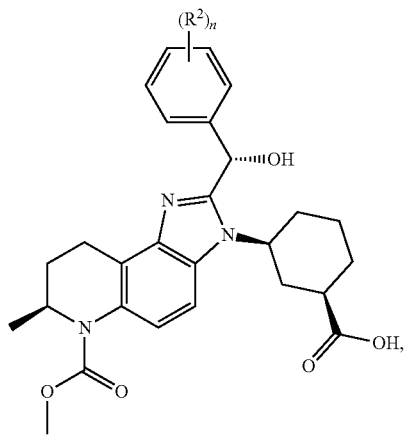
-continued
(A4)
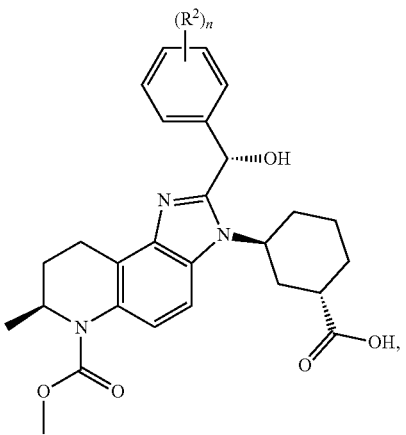
(A5)
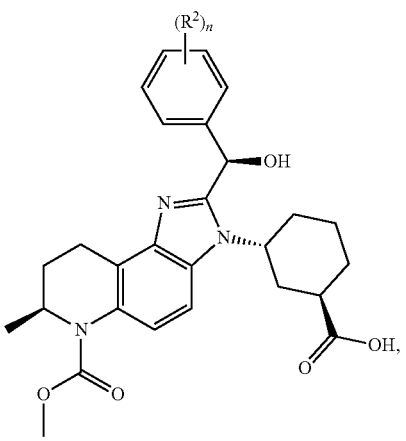
(A6)
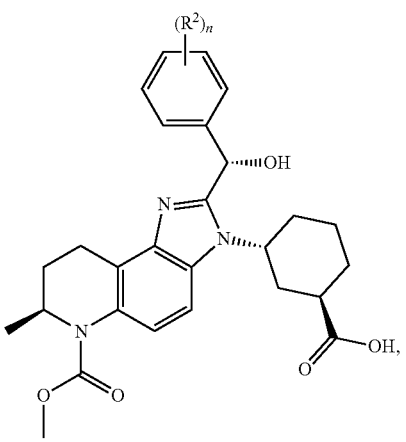

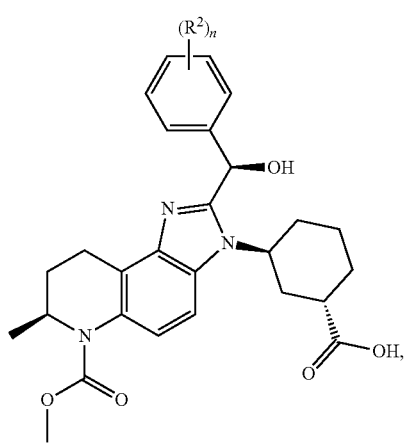
(A7)
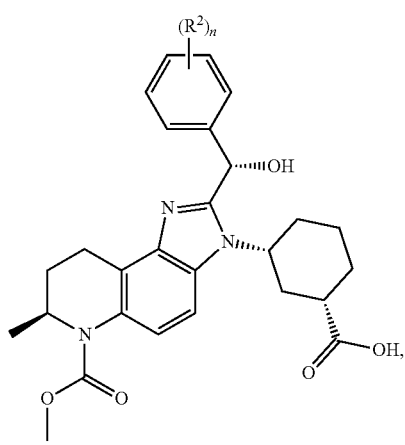
(A8)
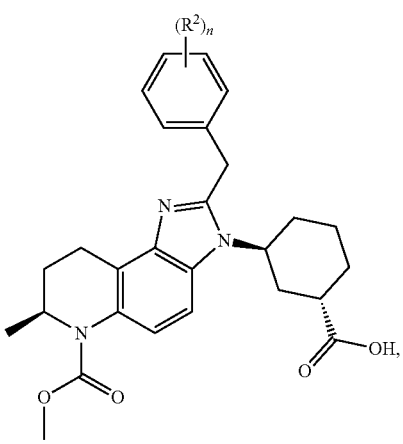
(A9)
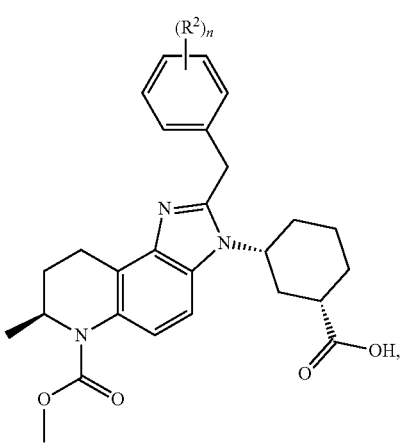
(A10)
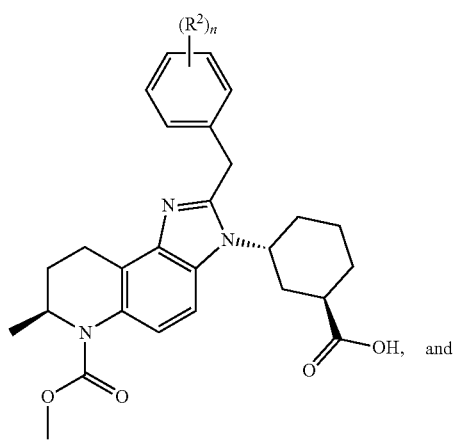
(A11)
and
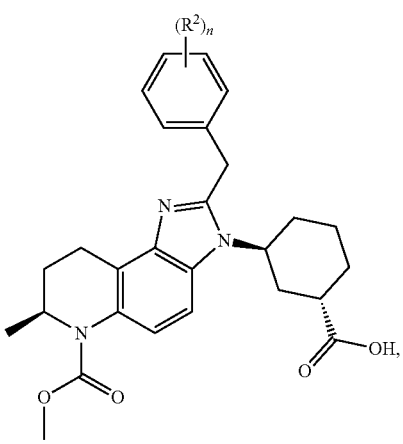
(A12)
and pharmaceutically acceptable salts thereof.

Figure 2:
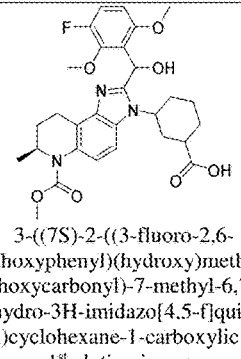
FIG. 2 is a table of compounds in accordance with various embodiments of the disclosure.

In some embodiments, the disclosure relates to a compound of formula (I) selected from FIG. 2. In FIG. 2, "Eluted Isomer" refers to the order in which the compound eluted by preparative HPLC.

In some embodiments, $R^1$ is H or —OH. In some embodiments, $R^1$ is H. In some embodiments, $R^1$ is —OH.

In some embodiments, each $R^2$ is independently selected from $C_1$-$C_6$ alkyl, halogen, —CN, and —$OR^3$, wherein the alkyl is optionally substituted with one or more halogen. In some embodiments, $R^2$ is $C_1$-$C_6$ alkyl, wherein the alkyl is optionally substituted with one or more halogen. In some embodiments, $R^2$ is $C_1$-$C_6$ alkyl, wherein the alkyl is substituted with one halogen. In some embodiments, $R^2$ is $C_1$-$C_6$ alkyl, wherein the alkyl is substituted with two halogens. In some embodiments, $R^2$ is selected from —$CH_3$ and —$CHF_2$. In some embodiments, $R^2$ is —$CH_3$. In some embodiments, $R^2$ is —$CHF_2$. In some embodiments $R^2$ is halogen. In some embodiments, $R^2$ is selected from —F and —Cl. In some embodiments, $R^2$ is —F. In some embodiments, $R^2$ is —Cl. In some embodiments, $R^2$ is —CN. In some embodiments, $R^2$ is —$OR^3$, wherein $R^3$ is as described herein.

In some embodiments, each $R^3$ is independently $C_1$-$C_6$ alkyl, wherein the alkyl is optionally substituted with one or more halogen. In some embodiments, $R^3$ is $C_1$-$C_6$ alkyl, wherein the alkyl is substituted with one halogen. In some embodiments, $R^3$ is $C_1$-$C_6$ alkyl, wherein the alkyl is substituted with two halogens. In some embodiments, $R^3$ is selected from —$CH_3$, —$CHF_2$, and propyl. In some embodiments, $R^3$ is —$CH_3$. In some embodiments, $R^3$ is —$CHF_2$. In some embodiments, $R^3$ is propyl.

In some embodiments, n is selected from 0, 1, 2, and 3. In some embodiments, n is 0. In some embodiments, n is 1. In some embodiments, n is 2. In some embodiments, n is 3.

In some embodiments, n is 2 and $R^2$ is $CH_3$ in one instance and F in the second instance. In some embodiments, n is 2 and $R^2$ is —$OCH_3$ in one instance and Cl in the second instance. In some embodiments, n is 2 and $R^2$ is —$OCH_3$ in one instance and —$OCH_3$ in the second instance. In some embodiments, n is 2 and $R^2$ is —$CH_3$ in one instance and F in the second instance. In some embodiments, n is 2 and $R^2$ is F in one instance and F in the second instance. In some embodiments, n is 2 and $R^2$ is —$CHF_2$ in one instance and F in the second instance. In some embodiments, n is 2 and $R^2$ is —$OCH(CH_3)_2$ in one instance and F in the second instance. In some embodiments, n is 2 and $R^2$ is —$OCHF_2$ in one instance and F in the second instance. In some embodiments, n is 3 and $R^2$ is —$OCH_3$ in one instance, F in the second instance, and F in the third instance. In some embodiments, n is 3 and $R^2$ is —$OCH_3$ in one instance, —$OCH_3$ in the second instance, and F in the third instance.

In some embodiments, $R^1$ is H and n is 0.

In some embodiments, $R^1$ is —OH and n is 0.

In some embodiments, $R^1$ is —OH, n is 2, and $R^2$ is —F in one instance and —$OR^3$ in the second instance, wherein $R^3$ is —$CH_3$.

In some embodiments, $R^1$ is —OH, n is 2, and $R^2$ is —F in one instance and —$OR^3$ in the second instance, wherein $R^3$ is —$CHF_2$.

In some embodiments, the pharmaceutical composition for treating a patient diagnosed with an AR-positive cancer comprises Compound 1:

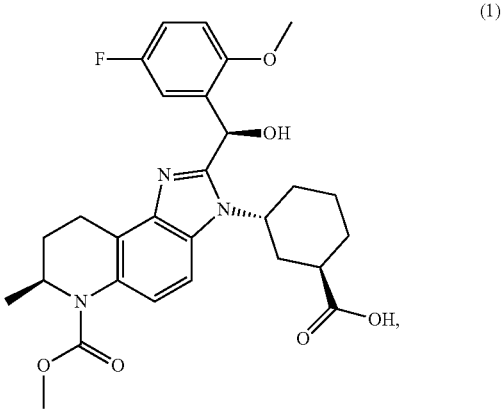 [SMILES: COC(=O)N1c2ccc3c(nc([C@H](O)c4cc(F)ccc4OC)n3[C@@H]3CCC[C@@H](C(=O)O)C3)c2CC[C@@H]1C]

or a pharmaceutically acceptable salt thereof.

In some embodiments, the compound of formula (I) is (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid.

In some embodiments, the compound of formula (I) is (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid.

Compound 1 is a potent and selective oral inhibitor of CBP/p300 BRD interaction with acetylated lysines on histones to disrupt androgen receptor (AR)-related transcriptional programming and induce antiproliferative, and potentially apoptotic effects in AR-dependent tumors. Compound 1 shows a >500-fold selectivity against BRD4 and was inactive when tested against a panel of multiple bromodomains. A reduction in global acetylation of H3K27 (H3K27Ac) was observed with Compound 1, both in vitro and in vivo, in a concentration-dependent manner in models of AR+ prostate cancer, consistent with the notion that inhibition of the bromodomain binding impacts the HAT activity of CBP/p300. These changes were reversible after withdrawal of Compound 1. CBP/p300 are co-activators of the AR and inhibition via Compound 1 resulted in a reduction of AR transcriptional activity, i.e. reduction in gene expression of AR target genes with Compound 1 was observed in a concentration- and time-dependent manner both in vitro and in vivo in models of prostate cancer. Compound 1 also decreased the protein expression of AR and splice variants of AR including AR-v7 in vitro in models of prostate cancer. In AR+ breast cancer, CBP/p300 are co-activators of the estrogen receptor (ER) and inhibition via Compound 1 resulted in a reduction of ER transcriptional activity. In vitro, Compound 1 showed a concentration-dependent anti-proliferative effect in prostate cancer cell lines expressing high levels of AR (or the splice variant AR-v7). Compound 1 also had antitumor activity in a patient-derived xenograft model of prostate cancer.

The potency and selectivity of Compound 1 as a CBP/p300 inhibitor was determined in biochemical time-resolved fluorescence assays using glutathione-S-transferase fusions of the BRDs of CBP, p300 and BRD4 and a tetra-acetylated histone H3 peptide. In these conditions, Compound 1 was determined to be a potent inhibitor of both CBP and p300 with $IC_{50}$ values of less than 2 nM, each. In the BRD4 assay, Compound 1 showed an $IC_{50}$ of about 0.5 μM, providing >500-fold selectivity for CBP relative to BRD4. The selectivity of Compound 1 was also evaluated across a panel of 10 bromodomains; Compound 1 was inactive (>10 µM) in multiple assays in the Examples but active in the CREBBP (CBP) assay (<0.1 µM).

A concentration-dependent reduction of AR target genes after 24 hr exposure to Compound 1 was observed in both androgen-dependent (VCaP) and independent (22Rv1) prostate cancer cell lines, with $IC_{50}$ values less than 0.5 µM in VCaP cells and 22Rv1 cells.

Compound 1 induced a dose dependent reduction of the AR protein level in the androgen-independent and dependent cell lines 22Rv1 and VCaP, respectively, and the AR splice variant AR-v7, was reduced in 22Rv1 cells. In addition, the reduction of full-length AR was observed in both VCaP and 22Rv1 models. The reversibility of the modulation of AR and AR-v7 was also assessed in 22Rv1 over 72 hrs after a 24 hr exposure to Compound 1. Following removal of Compound 1, AR returned to baseline level within 24 hours whereas AR-v7 reduction was maintained for 72 hrs (with 10 µM Compound 1).

The anti-proliferative effects of Compound 1 and enzalutamide were evaluated in a 10-day assay across a panel of prostate cancer cell lines including androgen-dependent (LnCaP and VCaP) and androgen-independent AR-v7+ (22Rv1) cell lines. Enzalutamide was active against androgen-dependent cell lines LnCaP and VCaP ($IC_{50}$ of about 1 and <0.5 µM, respectively) but was inactive in AR negative (PC3 and DU145) and the ARv7 expressing 22Rv1 cell line. Conversely, Compound 1 had a potent and concentration-dependent growth inhibitory effect in all AR+ cell lines (IC50 between about 0.5 and 1.5 µM) including 22Rv1 ($IC_{50}$ between 0.5 and 1 µM).

Figure 10:
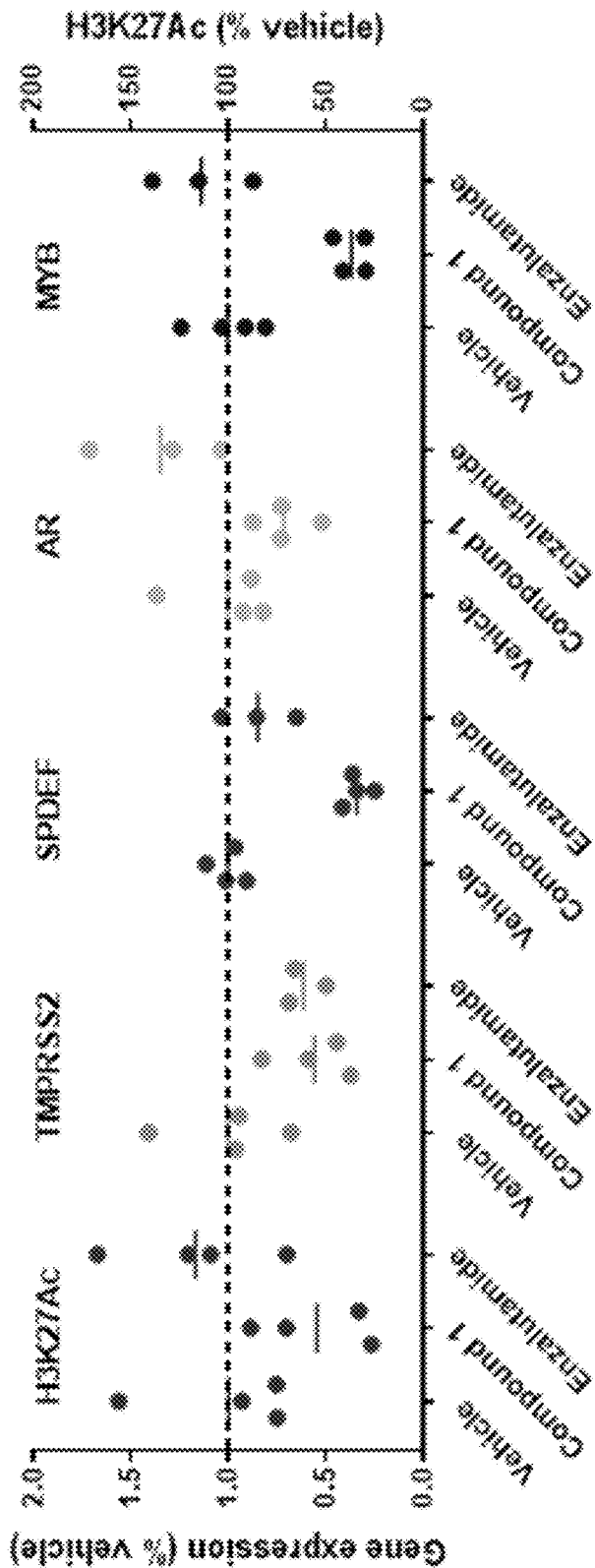
FIG. 10 is a graph showing the reduction of AR target gene expression in tumor tissues of a patient-derived xenograft (PDX) prostate cancer model (4 hours after last administration of Compound 1).
Figure 11:
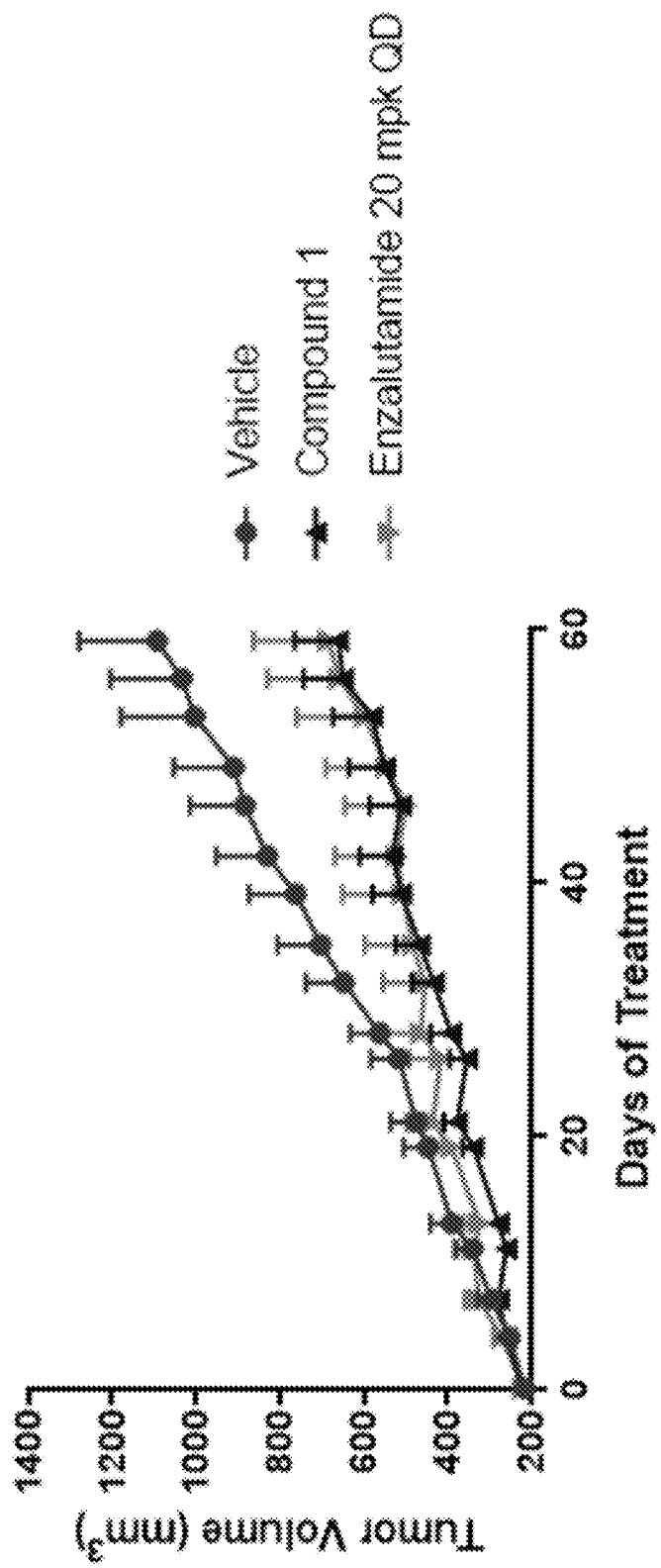
FIG. 11 shows tumor volume over time in the different cohorts of mice bearing xenografts and administered with vehicle, Compound 1, or Enzalutamide.

In a patient-derived xenograft (PDX) mouse model of prostate cancer sensitive to enzalutamide, a reduction of H3K27Ac as well as target gene expression was observed following Compound 1 administration (40 mg/kg/day for four days) (FIG. 10). Consistent with its mechanism of action, enzalutamide (20 mg/kg/day for four days) did not modulate H3K27Ac but did reduce the AR target gene TMPRSS2 to a similar extent as Compound 1. However, Compound 1 reduced the AR target gene SPDEF as well as MYB while enzalutamide did not, consistent with the mechanism of action. In castrated male mice bearing xenografts (enzalutamide-sensitive AR+ prostate cancer), similar tumor growth inhibition was observed following 59 days of Compound 1 (40 mg/kg/day) or enzalutamide (20 mg/kg/day) administration (FIG. 11).

In some embodiments, the present disclosure relates to solid forms of Compound 1, or pharmaceutically acceptable salts or isomers thereof, capable of modulating CBP/p300 family bromodomains, where the solid forms of Compound 1 are useful for the treatment of diseases and disorders associated with modulation of CBP/p300 family bromodomains. In some embodiments, the disclosure further relates to solid forms of compounds, or pharmaceutically acceptable salts or isomers thereof, which are useful for inhibiting CBP/p300 family bromodomains.

In some embodiments, Compound 1 may form acid addition salts, which may be pharmaceutically acceptable salts. For example, acid addition salts of Compound 1 may originate from the addition of hydrochloric acid (HCl) to the compound. In the absence of an acid addition salt, the compounds are referred to as a free base form. The acid addition salts and free base forms may be crystalline. In one aspect, Compound 1 may form a hydrochloric acid addition salt in one or more of three crystalline forms provided herein (hereafter referred to as types A, B, and C hydrochloric acid addition salts), or a free base crystalline form (hereafter referred to as type A free base form) of Compound 1.

Crystalline type A of the hydrochloric acid addition salt is characterized by an X-ray powder diffraction pattern (XRPD) having at least three approximate peak positions (degrees 2θ±0.2) when measured using Cu $K_\alpha$ radiation, selected from the group consisting of: 7.27, 8.98, 10.60, 15.60, and 23.93, when the XRPD is collected from about 3 to about 40 degrees 2θ. FIG. 4 contains a list of peaks from the X-ray powder diffraction pattern of the type A hydrochloric acid addition salt having a relative intensity greater than or equal to 5%. It is also characterized by an endothermic peak having an onset temperature at about 230° C. as measured by differential scanning calorimetry (DSC). The type A hydrochloric acid addition salt is also characterized by a weight loss of approximately 1.1% at temperatures up to 170° C., as measured by thermogravimetric analysis. The type A hydrochloric acid addition salt is also characterized as hygroscopic, evidenced by the water uptake of 6.3% at relative humidity of up to 80%, as measured by dynamic vapor sorption isotherm plots. The type A hydrochloric acid addition salt can be stable for at least two weeks at temperatures up to 40° C. and relative humidity of up to 75%. Crystalline type A of the hydrochloric acid addition salt is an anhydrate (anhydrous).

Crystalline type B of the hydrochloric acid addition salt is characterized by an X-ray powder diffraction pattern (XRPD) having at least three approximate peak positions (degrees 2θ±0.2) when measured using Cu $K_\alpha$ radiation, selected from the group consisting of: 10.23, 18.72, 23.03, 24.77, and 28.03, when the XRPD is collected from about 3 to about 40 degrees 2θ. FIG. 4 contains a list of peaks from the X-ray powder diffraction pattern of the type B hydrochloric acid addition salt having a relative intensity greater than or equal to 5%. It is also characterized by endothermic peaks having onset temperatures at about 139° C. and 232° C. and an exothermic peak at about 104° C. as measured by DSC. The type B hydrochloric acid addition salt is also characterized by a weight loss of approximately 20% at temperatures up to 200° C., as measured by thermogravimetric analysis. In some embodiments, crystalline type B of the hydrochloric acid addition salt is a hydrate or solvate.

Crystalline type C of the hydrochloric acid addition salt is characterized by an X-ray powder diffraction pattern (XRPD) having at least three approximate peak positions (degrees 2θ±0.2) when measured using Cu $K_\alpha$ radiation, selected from the group consisting of: 7.05, 19.84, 21.09, 24.98, and 31.44, when the XRPD is collected from about 3 to about 40 degrees 2θ. FIG. 4 contains a list of peaks from the X-ray powder diffraction pattern of the type C hydrochloric acid addition salt having a relative intensity greater than or equal to 5%. It is also characterized by endothermic peaks having onset temperatures at about 83° C., 143° C., and 179° C. and an exothermic peak at about 230° C. as measured by DSC. The type C hydrochloric acid addition salt is also characterized by a weight loss of approximately 9.4% at temperatures up to 180° C., as measured by thermogravimetric analysis. In some embodiments, crystalline type C of the hydrochloric acid addition salt is a hydrate or solvate.

Crystalline type A free base form is characterized by an X-ray powder diffraction pattern (XRPD) having at least three approximate peak positions (degrees 2θ±0.2) when measured using Cu K$_\alpha$ radiation, selected from the group consisting of: 11.11, 14.11, 18.21, 20.48, and 26.24, when the XRPD is collected from about 3 to about 40 degrees 2θ. FIG. 5 contains a list of peaks from the X-ray powder diffraction pattern of type A free base form having a relative intensity greater than or equal to 5%. It is also characterized by an endothermic peak having an onset temperature at about 209° C. as measured by DSC. The type A free base form is also characterized by negligible weight loss at temperatures up to 210° C., as measured by thermogravimetric analysis.

In some embodiments, the pharmaceutical composition for treating a patient diagnosed with an AR-positive cancer comprises compound 2:

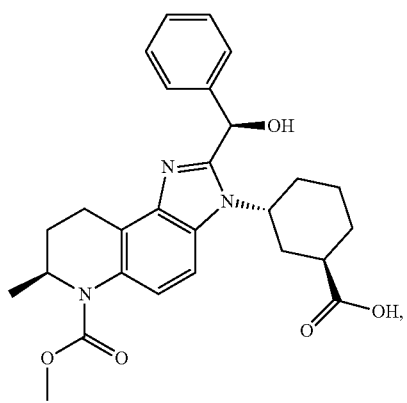

(2)

or a pharmaceutically acceptable salt thereof.

In some embodiments, the compound of formula (I) is 3-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid.

In some embodiments, the compound of formula (I) is the first eluting isomer of 3-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid when eluted from a preparative HPLC using the conditions defined in Example 1-2.

In some embodiments, the compound of formula (I) is (1R,3R)-3-((S)-2-((R)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid.

In some embodiments, the pharmaceutical composition for treating a patient diagnosed with an AR-positive cancer comprises compound 3:

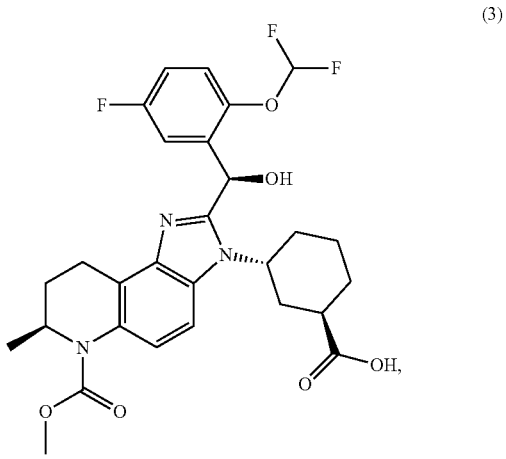 [SMILES: COC(=O)N1c2ccc3c(nc([C@H](O)c4cc(F)ccc4OC(F)F)n3[C@@H]3CCC[C@@H](C(=O)O)C3)c2CC[C@@H]1C]

(3)

or a pharmaceutically acceptable salt thereof.

In some embodiments, the compound of formula (I) is 3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid.

In some embodiments, the compound of formula (I) is the first eluting isomer of 3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl) cyclohexane-1-carboxylic acid when eluted from a preparative HPLC using the conditions defined in Example 1-4.

In some embodiments, the compound of formula (I) is (1R,3R)-3-((S)-2-((R)-(2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid.

In some embodiments, the pharmaceutical composition for treating a patient diagnosed with an AR-positive cancer comprises compound 4:

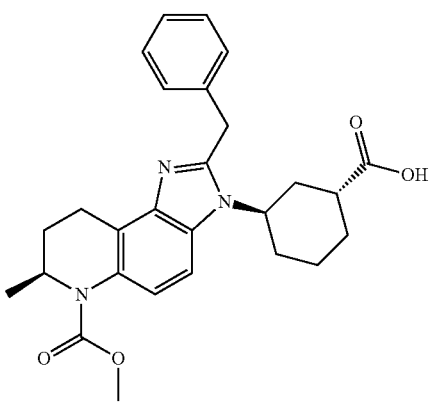

(4)

or a pharmaceutically acceptable salt thereof.

In some embodiments, the compound of formula (I) is 3-((S)-2-benzyl-6-(methoxycarbonyl)-7-methyl-6,7,8,9-tetrahydro-3H-imidazo[4,5-f]quinolin-3-yl)cyclohexane-1-carboxylic acid.

In some embodiments, the compound of formula (I) is (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid.

Compound 4 has a single-digit nanomolar potency against CBP and p300, and is highly selective over BRD4 and other bromodomain proteins representative of the branches of the bromodomain tree, as shown in the examples disclosed herein. Compound 4 induces the rapid reduction of H3K27 acetylation in an AR-positive triple negative breast cancer model. High-content analysis reveals that this reduction of H3K27 acetylation occurs throughout the entire population of cells. Additionally, the reduction of H3K27 acetylation is reversible, returning to baseline within 24 to 48 hours after removal of the compound.

Gene set enrichment analysis of RNAseq data revealed enrichment of ER- and AR-target genes in MDA-MB-453 cells treated with compound 4. SPDEF and XBP1, representative of AR- and ER-target genes, respectively, were validated by qPCR after cells were exposed to the AR agonist R1881 with and without simultaneous exposure to compound 4 (FIG. 12(B)). ChIP-seq analysis revealed reduced CBP and p300 binding upstream of the ER-regulated gene, AQP3. This is concurrent with reduction in H3K27 acetylation at this location. These changes were also associated with the reduction of AQP3 mRNA levels.

Compound 4 is a potent inhibitor of the proliferation of an AR-positive triple negative breast cancer cell model, including MDA-MB-453. This AR-modulator also potently inhibits the proliferation of AR-positive prostate cancer models, including an AR-v7 expressing cell model, 22Rv1. Compound 4 induces time-dependent inhibition of proliferation, with maximum inhibition observed after ten days of continuous exposure. Five days of exposure defines the minimal period to achieve sustained growth inhibition. Compound 4 is forty-times as potent as the AR-antagonist enzalutamide in this model, and is preferentially active against cells expressing high levels of AR.

A dose- and time-dependent pharmacokinetic (PK) and pharmacodynamic (PD) relationship was observed from an oral administration of compound 4 to mice harboring a MDA-MB-453 xenograft. The level of unbound compound 4 in plasma correlated with modulation of H3K27 acetylation and ER- and AR-target genes. This was associated with a reduced proliferative index, as measured by Ki-67 immunohistochemical staining. Additionally, compound 4 induced tumor stasis in the MDA-MB-453 xenografts.

The disclosure is also based in part on the recognition that compounds of formula (I) are Selective CBP Inhibitor Compounds, defined herein as CBP Inhibitors having a BRD4 $IC_{50}$ value greater than that of their CBP $IC_{50}$ value, preferably wherein its BRD4 $IC_{50}$ value is greater than 1 μM (e.g., 1 micromolar to 10 micromolar, or greater), wherein the $IC_{50}$ values are determined as in the procedures set forth in the assay described in Example 3. In some embodiments, compounds of formula (I) can be Selective CBP Inhibitor Compounds, wherein the BRD4 $IC_{50}$ value is greater than 500 nM (e.g., 500 nanomolar to 10 micromolar, or greater), wherein the $IC_{50}$ values are determined as in the procedures set forth in the assay described in Example 3. The disclosure is also based in part on the recognition that Compound 1 is a Selective CBP Inhibitor Compound, defined herein as a CBP Inhibitor having a BRD4 $IC_{50}$ value greater than that of its CBP $IC_{50}$ value, wherein the $IC_{50}$ values are determined as in the procedures set forth in the assay described in Example 3. In some embodiments, compounds of formula (I) can be Selective CBP Inhibitor Compounds, wherein the BRD4 $IC_{50}$ value is greater than 500 nM (e.g., 500 nanomolar to 10 micromolar, or greater), wherein the $IC_{50}$ values are determined as in the procedures set forth in the assay described in Example 3.

The discovery includes the use of one or more compounds of formula (I), and pharmaceutically acceptable salts thereof, in pharmaceutical preparations for the treatment of patients diagnosed with a disease or disorder associated with the inhibition of CBP (e.g., certain forms of cancer). The compositions comprising one or more compounds of formula (I), and pharmaceutically acceptable salts thereof, can be obtained by certain processes also provided herein. In some embodiments, a Selective CBP Inhibitor Compound of formula (I) is used to treat breast cancer (e.g., TNBC, PR+, ER+ and/or Her2+) or prostate cancer. In some embodiments, a Selective CBP Inhibitor Compound of Formula (Ib) is used to treat an AR+ form of cancer, including AR+ breast cancer or prostate cancer. The use of a Selective CBP Inhibitor Compound of formula (I) is provided for treatment of a patient diagnosed with a AR+ form of cancer, such as AR+ breast cancer (e.g., AR+ TNBC) or AR+ prostate cancer (e.g., an AR-v7+ form of prostate cancer).

In some embodiments, the discovery includes the use of (1R,3R)-3-[(7S)-2-[(R)-(5-fluoro-2-methoxyphenyl)(hydroxy)methyl]-6-(methoxycarbonyl)7-methyl-3H,6H,7H,8H,9H-imidazo[4,5-f]quinolin-3-yl]cyclohexane-1-carboxylic acid (Compound 1), and pharmaceutically acceptable salts thereof, in pharmaceutical preparations for the treatment of patients diagnosed with a disease or disorder associated with the inhibition of CBP (e.g., certain forms of cancer). The compositions comprising Compound 1 and pharmaceutically acceptable salts thereof can be obtained by certain processes also provided herein.

In some embodiments, the discovery includes the use of (1R,3R)-3-((S)-2-((R)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid (Compound 2), and pharmaceutically acceptable salts thereof, in pharmaceutical preparations for the treatment of patients diagnosed with a disease or disorder associated with the inhibition of CBP (e.g., certain forms of cancer). The compositions comprising Compound 2 and pharmaceutically acceptable salts thereof can be obtained by certain processes also provided herein.

In some embodiments, the discovery includes the use of (1R,3R)-3-((S)-2-((R)-(2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid (Compound 3), and pharmaceutically acceptable salts thereof, in pharmaceutical preparations for the treatment of patients diagnosed with a disease or disorder associated with the inhibition of CBP (e.g., certain forms of cancer). The compositions comprising Compound 3 and pharmaceutically acceptable salts thereof can be obtained by certain processes also provided herein.

In some embodiments, the discovery includes the use of (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid (Compound 4), and pharmaceutically acceptable salts thereof, in pharmaceutical preparations for the treatment of patients diagnosed with a disease or disorder associated with the inhibition of CBP (e.g., certain forms of cancer). The compositions comprising Compound 4 and pharmaceutically acceptable salts thereof can be obtained by certain processes also provided herein.

Methods of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), or a pharmaceutically acceptable salt thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize stereocenters exist in the compounds of Formula (I). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I), or Group A, may be atropisomers (e.g., substituted biaryls) and are considered as part of this disclosure. Enantiomers can also be separated by use of a chiral HPLC column.

In some embodiments, the free base form of Compound 1 is not amorphous. The amorphous, free base form can be accessed through a synthesis provided in Example 1. This chemical synthesis can produce Compound 1. In one aspect, only trace amounts of the stereoisomeric contaminants of Compound 1 may be present in the end synthetic product, other than as specified herein. The amorphous, free base form can be produced with purities in excess of 99%, as determined by HPLC analysis, as outlined in the examples below. In some embodiments, the salt and crystalline forms used in the preparation of the pharmaceutical compositions are at least 95% pure, as assessed by HPLC analysis, as outlined in the examples below.

The crystalline type A free base form can be prepared by dissolving the free base form in an organic solvent at reflux and subsequently cooling the resulting solution, as provided in Example 2.a. In one aspect, the free base form of Compound 1 is crystalline, partially crystalline, or amorphous in some embodiments.

The crystalline type A of the hydrochloric acid addition salt can be prepared by dissolving the free base form in an organic solvent, adding hydrochloric acid, and heating the resulting solution followed by cooling, as provided in Example 2.b.

The crystalline type B of the hydrochloric acid addition salt can be prepared by dissolving the type A hydrochloric acid addition salt in a mixture of organic solvents, and then heating the resulting solution, followed by cooling and slow evaporation at room temperature as provided in Example 2.c.

The crystalline type C of the hydrochloric acid addition salt can be prepared by dissolving the type A hydrochloric acid addition salt in a mixture of organic solvents, and then heating the resulting solution, followed by cooling and slow evaporation at room temperature as provided in Example 2.d.

Pharmaceutical Compositions Including the Compounds of the Disclosure

In one aspect, the disclosure relates to pharmaceutical compositions comprising a compound of formula (I) in one or more solid forms, which can be a pharmaceutically acceptable salt, hydrate, solvate, and/or tautomer thereof, including acid-addition salts of the foregoing.

For example, in some embodiments, the disclosure relates to pharmaceutical compositions comprising Compound (1) in one or more solid forms and/or pharmaceutically acceptable salts:

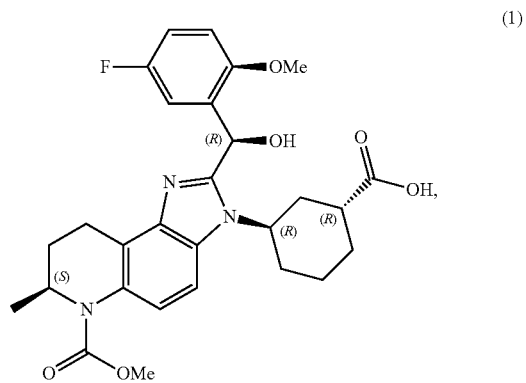

(1)

and hydrates, solvates, and tautomers thereof, and acid addition salts of the foregoing.

Compound 1 may form acid addition salts, which may be pharmaceutically acceptable salts. The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of Compound 1 can be a capsule. In some embodiments, an oral dosage form of a compound of Compound 1 is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

In one aspect, a pharmaceutical composition comprises Compound 1 in one or more solid forms selected from the group consisting of type A hydrochloric acid addition salt, type B hydrochloric acid addition salt, type C hydrochloric acid addition salt, and type A free base form. In one aspect, a pharmaceutical composition comprises Compound 1 in one or more crystalline forms selected from the group consisting of type A hydrochloric acid addition salt, type B hydrochloric acid addition salt, type C hydrochloric acid addition salt, and type A free base form.

In some embodiments, a pharmaceutical composition comprises Compound 1 in a free base form. The free base form may be crystalline. In some embodiments, a pharmaceutical composition comprises Compound 1 in the crystalline type A free base form.

In some embodiments, a pharmaceutical composition comprises an acid addition salt of Compound 1. For example, the acid addition salts of the foregoing may originate from the addition of hydrochloric acid (HCl). The acid addition salts may be crystalline. In one aspect, a pharmaceutical composition can comprise a solid form of a hydrochloric acid addition salt of Compound 1. In one aspect, a pharmaceutical composition comprises Compound 1 hydrochloric acid addition salt in one or more of three crystalline forms provided herein (hereafter referred to as types A, B, and C). In some embodiments, a pharmaceutical composition comprises crystalline type A hydrochloric acid addition salt of Compound 1. In some embodiments, a pharmaceutical composition comprises type B hydrochloric acid addition salt of Compound 1. In some embodiments, a pharmaceutical composition comprises type C hydrochloric acid addition salt of Compound 1.

Methods of Using the Compounds and Pharmaceutical Compositions of the Disclosure In some embodiments, compounds of formula (I) are tool compounds useful for studying the effects of CBP/p300 inhibition in vitro or in an in vivo model. In vitro, the tool compounds of formula (I) may be useful for studying the effects of CBP/p300 inhibition on purified proteins, cellular extracts, in intact cells and cell line models, and the like. In vivo, the tool compounds of formula (I) may be useful for studying the effects of CBP/p300 inhibition in cell line derived xenografts, in patient derived xenografts, in knock-in mouse model, in knock-out mouse models, and the like.

This disclosure is based in part on the discovery that CBP inhibitor compounds can preferentially inhibit proliferation of AR-overexpressing models of breast and prostate cancers. For example, in vivo experiments demonstrate that Compound 1 elicits dose-dependent anti-tumor activity in AR-positive triple negative breast cancer (TNBC), hormone receptor positive breast cancer, and prostate cancer models, as demonstrated in the Examples below. The inhibition of the CBP/p300 bromodomain can antagonize androgen receptor signaling and demonstrate clinical benefit in AR+ breast cancer and castration-resistant prostate cancer (CRPC).

Various methods for measuring and defining AR positivity can be employed to select patients to receive a pharmaceutical composition comprising a CBP inhibitor compound. In the case of prostate cancer, AR expression is largely maintained in the target population of relapse patients. Furthermore, AR and AR-v7 splice form protein or mRNA can be detected in circulating tumor cells (CTC) while AR mutations and AR amplification can be detected from circulating tumor DNA (ctDNA). Current immunohistochemical (IHC) methods for measuring AR vary based on multiple factors including the antibody used, the IHC methodology, and the cut-off criterion for positivity. Overall, the frequency of AR positivity in triple negative breast cancer has been reported to be 20% to 30%.

Methods of treatment (e.g., by inhibiting CBP) can comprise administering to a subject in need thereof a therapeutically effective amount of (1) a compound of formula (I) or a pharmaceutically acceptable salt thereof; or (2) a pharmaceutical composition comprising one or more compounds of formula (I) or a pharmaceutically acceptable salt thereof and a pharmaceutically acceptable carrier.

Methods of treatment (e.g., by inhibiting CBP) can comprise administering to a subject in need thereof a therapeutically effective amount of (1) Compound 1 or a pharmaceutically acceptable salt thereof; or (2) a pharmaceutical composition comprising Compound 1 or a pharmaceutically acceptable salt thereof and a pharmaceutically acceptable carrier.

Methods of treatment (e.g., by inhibiting CBP) can comprise administering to a subject in need thereof a therapeutically effective amount of (1) Compound 2 or a pharmaceutically acceptable salt thereof; or (2) a pharmaceutical composition comprising Compound 2 or a pharmaceutically acceptable salt thereof and a pharmaceutically acceptable carrier.

Methods of treatment (e.g., by inhibiting CBP) can comprise administering to a subject in need thereof a therapeutically effective amount of (1) Compound 3 or a pharmaceutically acceptable salt thereof; or (2) a pharmaceutical composition comprising Compound 3 or a pharmaceutically acceptable salt thereof and a pharmaceutically acceptable carrier.

Methods of treatment (e.g., by inhibiting CBP) can comprise administering to a subject in need thereof a therapeutically effective amount of (1) Compound 4 or a pharmaceutically acceptable salt thereof; or (2) a pharmaceutical composition comprising Compound 4 or a pharmaceutically acceptable salt thereof and a pharmaceutically acceptable carrier.

The pharmaceutical compositions may be orally administered in any orally acceptable dosage form. Accordingly, a patient and/or subject can be selected for treatment using a compound described herein by first evaluating the patient and/or subject to determine whether the subject is in need of inhibition of CBP, and if the subject is determined to be in need of inhibition of CBP, then administering to the subject a composition described herein.

Pharmaceutical compositions comprising CBP inhibitor compounds are useful for the treatment of certain forms of AR-positive breast cancer. For example, the suppression of androgen receptor and/or estrogen receptor transcriptional activity with Compound 1, Compound 2, Compound 3, or Compound 4 (or a pharmaceutical composition comprising Compound 1, Compound 2, Compound 3, or Compound 4) can be useful in promoting antitumor effects in AR-positive breast cancers, via the inhibition of the CBP/P300 bromodomains.

In some embodiments, the AR-positive cancer with which the patient in need of treatment has been diagnosed is a form of an AR-positive breast cancer.

The CBP/p300 inhibitor compounds provided herein are useful for use in methods of treating various subtypes of breast cancer distinguished based on a number of factors including the histopathological type of tumor, the grade of the tumor, the stage of the tumor, and the expression of genes which are characteristic of particular subtypes of breast cancer. Determination of the particular subtype of cancer in a patient is often of critical importance in determining the most appropriate course of treatment for the patient. ER negative (ER−) breast cancer and ER positive (ER+) breast cancer are two recognized subtypes of breast cancer, defined by the presence or absence of expression of the estrogen receptor gene. Triple-negative breast cancer (TNBC) is another recognized subtype of breast cancer. The TNBC subtype is clinically defined by the absence of ER and progesterone receptor (PR) expression, and neither overexpression nor amplification of human epidermal growth factor receptor 2 (HER2).

In some embodiments, this invention relates to the treatment of androgen receptor-positive breast cancer in a subject, for example a female subject. Accordingly, this invention provides methods of: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of estrogen receptor (ER), progesterone receptor (PR), and/or human epidermal growth factor receptor 2 (HER2); i) treating a subject suffering from triple negative breast cancer (TNBC); j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP) bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2− positive breast cancer; r) treating a subject suffering from ER mutant expressing breast cancer, and/or s) treating a subject suffering from Y537 S ER mutant expressing breast cancer, comprising administering to the subject a therapeutically effective amount of a CBP/p300 inhibitor compound of Formula (I).

In some embodiments, the AR-positive breast cancer is an AR-positive triple-negative breast cancer (TNBC). A triple-negative breast cancer is characterized as being negative for the estrogen receptor, progesterone receptor, and HER-2, per College of American Pathologists (CAP) guidelines. In one embodiment, the method of treatment may include administering a therapeutically effective amount of a pharmaceutical composition comprising a CBP inhibitor compound to patients diagnosed with an invasive breast carcinoma with triple-negative status and detectable AR expression in >1% of tumor cells (per CAP guidelines), wherein the breast carcinoma is characterized as a progressive disease and the patient has failed at least two prior systemic therapies with evaluable disease.

In some embodiments, the AR-positive breast cancer may be a hormone receptor positive breast cancer. A hormone receptor positive breast cancer is characterized as being positive for the estrogen receptor and/or the progesterone receptor, per CAP guidelines. In some embodiments, the AR-positive breast cancer may be a HER-2 positive breast cancer. In some embodiments, the AR-positive breast cancer may be both hormone receptor positive and HER-2 positive. In some embodiments, the method of treatment may include administering a therapeutically effective amount of a pharmaceutical composition comprising a CBP inhibitor compound to patients diagnosed with an invasive breast carcinoma with detectable AR expression in >1% of tumor cells and which is ER, PR, or HER2 positive (per CAP guidelines), wherein the breast carcinoma is characterized as a progressive disease and the patient has failed at least three prior systemic therapies.

Pharmaceutical compositions comprising one or more compounds of formula (I) are useful for the treatment of certain forms of AR+ breast cancer. For example, the suppression of AR and/or ER transcriptional activity with a compound of formula (I) (or a pharmaceutical composition comprising one or more compounds of formula (I)) can be useful in treating antitumor effects in AR+ breast cancers, including TNBC and ER+ tumors, via its inhibition of CBP/P300 BRD. In some embodiments, the suppression of AR and/or ER transcriptional activity with a compound of formula (I) (or a pharmaceutical composition comprising one or more compounds of formula (I)) can be useful in treating antitumor effects in AR+ breast cancers, including TNBC and ER+ tumors, via its inhibition of CBP/P300 BRD. In some embodiments, the suppression of AR and/or ER transcriptional activity with Compound 1 (or a pharmaceutical composition comprising Compound 1) can be useful in treating antitumor effects in AR+ breast cancers, including TNBC and ER+ tumors, via its inhibition of CBP/P300 BRD. In some embodiments, the suppression of AR and/or ER transcriptional activity with Compound 1 (or a pharmaceutical composition comprising Compound 1) can be useful in treating antitumor effects in AR+ breast cancers, including TNBC and ER+ tumors, via its inhibition of CBP/P300 BRD. In some embodiments, the suppression of AR and/or ER transcriptional activity with Compound 2 (or a pharmaceutical composition comprising Compound 2) can be useful in treating antitumor effects in AR+ breast cancers, including TNBC and ER+ tumors, via its inhibition of CBP/P300 BRD. In some embodiments, the suppression of AR and/or ER transcriptional activity with Compound 3 (or a pharmaceutical composition comprising Compound 3) can be useful in treating antitumor effects in AR+ breast cancers, including TNBC and ER+ tumors, via its inhibition of CBP/P300 BRD. In some embodiments, the suppression of AR and/or ER transcriptional activity with Compound 4 (or a pharmaceutical composition comprising Compound 4) can be useful in treating antitumor effects in AR+ breast cancers, including TNBC and ER+ tumors, via its inhibition of CBP/P300 BRD. In some embodiments, the breast cancer is characterized as being metastatic breast cancer.

Some methods include administering a therapeutically effective amount of a pharmaceutical composition comprising one or more compounds of formula (I) to patients diagnosed with invasive breast carcinoma with triple negative status (per College of American Pathologists[CAP] guidelines) and detectable AR expression in >1% of tumor cells, with progressive disease; invasive breast carcinoma with triple negative status (per College of American Pathologists [CAP] guidelines) and detectable AR expression in >1% of tumor cells, with progressive disease who has failed at least one prior systemic therapy with evaluable disease; invasive breast carcinoma with triple negative status (per College of American Pathologists [CAP] guidelines) and detectable AR expression in >1% of tumor cells, with progressive disease who has failed at least two prior systemic therapies with evaluable disease; invasive breast carcinoma AR positive >1% and ER, PR, and/or HER2 positive (per CAP guidelines) with progressive disease; invasive breast carcinoma AR positive >1% and ER, PR, and/or HER2 positive (per CAP guidelines) with progressive disease who has failed at least one prior systemic therapy; invasive breast carcinoma AR positive >1% and ER, PR, and/or HER2 positive (per CAP guidelines) with progressive disease who has failed at least two prior systemic therapies; or invasive breast carcinoma AR positive >1% and ER, PR, and/or HER2 positive (per CAP guidelines) with progressive disease who has failed at least three prior systemic therapies. Some methods include administering a therapeutically effective amount of a pharmaceutical composition comprising one or more compounds of formula (I) to patients diagnosed with Her2− breast cancer. Some methods include administering a therapeutically effective amount of a pharmaceutical composition comprising one or more compounds of formula (I) to patients diagnosed with ER−, PR−, or ER−/PR− breast cancer.

Some methods include administering a therapeutically effective amount of a pharmaceutical composition comprising Compound 1 to patients diagnosed with invasive breast carcinoma with triple negative status (per College of American Pathologists [CAP] guidelines) and detectable AR expression in >1% of tumor cells, with progressive disease; invasive breast carcinoma with triple negative status (per College of American Pathologists [CAP] guidelines) and detectable AR expression in >1% of tumor cells, with progressive disease who has failed at least one prior systemic therapy with evaluable disease; invasive breast carcinoma with triple negative status (per College of American Pathologists [CAP] guidelines) and detectable AR expression in >1% of tumor cells, with progressive disease who has failed at least two prior systemic therapies with evaluable disease; invasive breast carcinoma AR positive >1% and ER, PR, and/or HER2 positive (per CAP guidelines) with progressive disease; invasive breast carcinoma AR positive >1% and ER, PR, and/or HER2 positive (per CAP guidelines) with progressive disease who has failed at least one prior systemic therapy; invasive breast carcinoma AR positive >1% and ER, PR, and/or HER2 positive (per CAP guidelines) with progressive disease who has failed at least two prior systemic therapies; or invasive breast carcinoma AR positive >1% and ER, PR, or HER2 positive (per CAP guidelines) with progressive disease who has failed at least three prior systemic therapies. Some methods include administering a therapeutically effective amount of a pharmaceutical composition comprising Compound 1 to patients diagnosed with Her2− breast cancer. Some methods include administering a therapeutically effective amount of a pharmaceutical composition comprising Compound 1 to patients diagnosed with ER−, PR−, or ER−/PR− breast cancer.

Some methods include administering a therapeutically effective amount of a pharmaceutical composition comprising Compound 2 to patients diagnosed with invasive breast carcinoma with triple negative status (per College of American Pathologists [CAP] guidelines) and detectable AR expression in >1% of tumor cells, with progressive disease; invasive breast carcinoma with triple negative status (per College of American Pathologists [CAP] guidelines) and detectable AR expression in >1% of tumor cells, with progressive disease who has failed at least one prior systemic therapy with evaluable disease; invasive breast carcinoma with triple negative status (per College of American Pathologists [CAP] guidelines) and detectable AR expression in >1% of tumor cells, with progressive disease who has failed at least two prior systemic therapies with evaluable disease; invasive breast carcinoma AR positive >1% and ER, PR, and/or HER2 positive (per CAP guidelines) with progressive disease; invasive breast carcinoma AR positive >1% and ER, PR, and/or HER2 positive (per CAP guidelines) with progressive disease who has failed at least one prior systemic therapy; invasive breast carcinoma AR positive >1% and ER, PR, and/or HER2 positive (per CAP guidelines) with progressive disease who has failed at least two prior systemic therapies; or invasive breast carcinoma AR positive >1% and ER, PR, or HER2 positive (per CAP guidelines) with progressive disease who has failed at least three prior systemic therapies. Some methods include administering a therapeutically effective amount of a pharmaceutical composition comprising Compound 2 to patients diagnosed with Her2− breast cancer. Some methods include administering a therapeutically effective amount of a pharmaceutical composition comprising Compound 2 to patients diagnosed with ER−, PR−, or ER−/PR− breast cancer.

Some methods include administering a therapeutically effective amount of a pharmaceutical composition comprising Compound 3 to patients diagnosed with invasive breast carcinoma with triple negative status (per College of American Pathologists [CAP] guidelines) and detectable AR expression in >1% of tumor cells, with progressive disease; invasive breast carcinoma with triple negative status (per College of American Pathologists [CAP] guidelines) and detectable AR expression in >1% of tumor cells, with progressive disease who has failed at least one prior systemic therapy with evaluable disease; invasive breast carcinoma with triple negative status (per College of American Pathologists [CAP] guidelines) and detectable AR expression in >1% of tumor cells, with progressive disease who has failed at least two prior systemic therapies with evaluable disease; invasive breast carcinoma AR positive >1% and ER, PR, and/or HER2 positive (per CAP guidelines) with progressive disease; invasive breast carcinoma AR positive >1% and ER, PR, and/or HER2 positive (per CAP guidelines) with progressive disease who has failed at least one prior systemic therapy; invasive breast carcinoma AR positive >1% and ER, PR, and/or HER2 positive (per CAP guidelines) with progressive disease who has failed at least two prior systemic therapies; or invasive breast carcinoma AR positive >1% and ER, PR, or HER2 positive (per CAP guidelines) with progressive disease who has failed at least three prior systemic therapies. Some methods include administering a therapeutically effective amount of a pharmaceutical composition comprising Compound 3 to patients diagnosed with Her2− breast cancer. Some methods include administering a therapeutically effective amount of a pharmaceutical composition comprising Compound 3 to patients diagnosed with ER−, PR−, or ER−/PR− breast cancer.

Some methods include administering a therapeutically effective amount of a pharmaceutical composition comprising Compound 4 to patients diagnosed with invasive breast carcinoma with triple negative status (per College of American Pathologists [CAP] guidelines) and detectable AR expression in >1% of tumor cells, with progressive disease;

invasive breast carcinoma with triple negative status (per College of American Pathologists [CAP] guidelines) and detectable AR expression in >1% of tumor cells, with progressive disease who has failed at least one prior systemic therapy with evaluable disease; invasive breast carcinoma with triple negative status (per College of American Pathologists [CAP] guidelines) and detectable AR expression in >1% of tumor cells, with progressive disease who has failed at least two prior systemic therapies with evaluable disease; invasive breast carcinoma AR positive >1% and ER, PR, and/or HER2 positive (per CAP guidelines) with progressive disease; invasive breast carcinoma AR positive >1% and ER, PR, and/or HER2 positive (per CAP guidelines) with progressive disease who has failed at least one prior systemic therapy; invasive breast carcinoma AR positive >1% and ER, PR, and/or HER2 positive (per CAP guidelines) with progressive disease who has failed at least two prior systemic therapies; or invasive breast carcinoma AR positive >1% and ER, PR, or HER2 positive (per CAP guidelines) with progressive disease who has failed at least three prior systemic therapies. Some methods include administering a therapeutically effective amount of a pharmaceutical composition comprising Compound 4 to patients diagnosed with Her2– breast cancer. Some methods include administering a therapeutically effective amount of a pharmaceutical composition comprising Compound 4 to patients diagnosed with ER–, PR–, or ER–/PR– breast cancer.

The present invention also relates to the treatment of prostate cancer, including castration-resistant prostate cancer (CRPC) (e.g., metastatic CRPC (mCRPC) or locally confined, inoperable CRPC) by administering to a patient in need thereof a therapeutically effective amount of a CBP/p300 compound of Formula (I). The AR-v7 variant is present in both benign and malignant prostate tissues but is generally enriched in metastatic forms of the disease.

Prostate cancers are frequently dependent upon gene expression programs driven by the AR. Consequently, direct and indirect antagonists of steroid hormone biosynthesis and androgen receptor interaction are central to the treatment of these diseases. The dependence of prostate cancer on AR signaling is well-established and is the basis for the development of androgen deprivation therapy (ADT), including agents luteinizing hormone releasing hormone (LH-RH) receptor agonists and antagonists and cytochrome P450 (CYP) 17 inhibitors antagonizing androgen biosynthesis. These therapies are the mainstay of prostate cancer treatment.

Prostate cancer can become castration-resistant. AR antagonists such as enzalutamide, apalutamide or darolutamide are effective therapies in CRPC. However, the 5-year survival rate for subjects with metastatic castration-resistant prostate cancer (mCRPC) progressing on or after first line chemotherapy is estimated at less than 2% due to resistance to anti-androgen therapies arising from autocrine ligand production, intra-tumoral androgen biosynthesis, AR aberrations including AR gene amplification, somatic mutation in the ligand binding domain (LBD) of AR and altered splicing of AR messenger ribonucleic acid (mRNA) resulting in loss of the LBD, the so-called AR variant 7 (AR-v7) form. Tumors at this stage can remain dependent upon AR-mediated transcriptional programs. This persistent dependence on AR function within these resistant populations recommends novel therapeutic approaches targeting AR functions distinct from ligand binding.

CBP/p300 are critical and essential co-activators of AR, modifying the chromatin environment surrounding the nuclear receptor to increase its transcriptional activity and recruit additional co-factors. Inhibition of CBP/p300 therefore provides a novel approach to target AR in prostate cancer. Compound 1 is a potent and selective inhibitor of CBP/p300 BRD interaction with acetylated lysines on histones. Compound 2 is a potent and selective inhibitor of CBP/p300 BRD interaction with acetylated lysines on histones. Compound 3 is a potent and selective inhibitor of CBP/p300 BRD interaction with acetylated lysines on histones. Compound 4 is a potent and selective inhibitor of CBP/p300 BRD interaction with acetylated lysines on histones. Compounds of Formula (I) can antagonize AR-driven transcriptional activity in preclinical models of mCRPC in vitro and in vivo and demonstrates preclinical antitumor activity.

Treatments for prostate cancers resistant to androgen deprivation therapy or androgen antagonists remain an unmet need. In some examples, the inhibition of the CBP/P300 bromodomain, with its differentiated mechanism of antagonizing the AR-driven transcriptional program, is used as a treatment for these patients, with potential utility as an earlier line of therapy. Pharmaceutical compositions comprising CBP inhibitor compounds can be used to treat certain forms of prostate cancer. Compositions comprising a CBP inhibitor compound are useful for the inhibition of the CBP/P300 bromodomain, which provides a differentiated mechanism of antagonizing the AR-driven transcriptional program, and can be administered as an earlier line of therapy.

Other or additional treatments at the time of the prostate cancer diagnosis, based upon the burden of disease, Gleason score, and age of the patient, range from active surveillance, prostatectomy, or radiation therapy for low risk disease, to aggressive surgical interventions and/or androgen deprivation therapy (ADT). ADT can be administered for those patients with regional or advanced disease or at time of recurrence. ADT is known to provide a decline of prostate-specific antigen (PSA) in most patients. After a mean time of 2 to 3 years, however, the disease progresses despite continuous hormonal manipulation, thus resulting in CRPC. Following advancement to CRPC, subsequent treatment can comprise ADT in combination with androgen synthesis inhibitors (e.g, abiraterone acetate), or anti-androgens (e.g, enzalutamide or apalutamide). The dependence of prostate cancer on AR function is a basis for the development of ADT, including agents antagonizing androgen biosynthesis such as the LHRH receptor agonists and CYP17 inhibitors, as well as the nonsteroidal antiandrogens such as flutamide, bicalutamide, nilutamide, enzalutamide, and apalutamide.

Enzalutamide is an androgen receptor inhibitor indicated for the treatment of patients with castration resistant prostate cancer or metastatic castration-sensitive prostate cancer. Patients receiving enzalutamide can also receive a gonadotropin-releasing hormone (GnRH) analog concurrently or can have had bilateral orchiectomy. Enzalutamide is an androgen receptor inhibitor that acts on different steps in the androgen receptor signaling pathway. Enzalutamide has been shown to competitively inhibit androgen binding to androgen receptors; and consequently, inhibits nuclear translocation of androgen receptors and their interaction with DNA. A major metabolite, N-desmethyl enzalutamide, exhibited similar in vitro activity to enzalutamide. Enzalutamide decreased proliferation and induced cell death of prostate cancer cells in vitro, and decreased tumor volume in a mouse prostate cancer xenograft model.

Enzalutamide is an androgen receptor antagonist indicated for the treatment of patients with castration resistant prostate cancer as well as castration-sensitive prostate cancer. Patients receiving enzalutamide can also receive a luteinizing-releasing hormone (LH-RH) analog concurrently or can have had bilateral orchiectomy. Enzalutamide is an androgen receptor antagonist that acts on different steps in the androgen receptor signaling pathway. Enzalutamide has been shown to competitively inhibit androgen binding to androgen receptors; and consequently, inhibits nuclear translocation of androgen receptors and their interaction with DNA. A major metabolite, N-desmethyl enzalutamide, exhibited similar in vitro activity to enzalutamide. Enzalutamide decreased proliferation and induced cell death of prostate cancer cells in vitro, and decreased tumor volume in a prostate cancer xenograft model in mice.

In some embodiments, the AR-positive cancer with which the patient in need of treatment has been diagnosed may be a form of an AR-positive prostate cancer.

In some embodiments, the AR-positive prostate cancer may be a metastatic castration resistant prostate cancer (mCRPC). A castration resistant prostate cancer is a form of prostate cancer that survives the effects of androgen deprivation therapy. In some embodiments, the method of treatment may include administering a therapeutically effective amount of a pharmaceutical composition comprising a CBP inhibitor compound to patients diagnosed with mCRPC with progressive castration-resistant disease who have failed or been intolerant to at least two prior systemic therapies, including at least one androgen antagonist-based therapy (anti-androgen+luteinizing hormone-releasing hormone (LH-RH) analog, enzalutamide, or abiraterone) and with evaluable disease and a rising PSA per standard definitions. In some embodiments, the mCRPC is further characterized as being refractory or resistant following the administration and completion of a course of anti-androgens.

Structural variations in the ligand binding domain of AR can render the receptor ligand-independent and insensitive to AR antagonists. Approximately twenty AR mRNA splice variants have been identified, with a subset that are constitutively active. Notably, all biologically active forms of AR retain the N-terminal transactivation domain (NTD); drugs that target the NTD have the potential to impact all AR forms, including those that may drive resistance to AR-LBD-targeting therapies. Of the AR variants, only AR-v7 and ARv567es have been detected at the protein level and AR-v7 has been the most studied. Notably, in cases of mCRPC where men were initially treated with an AR antagonist, those with AR-v7-positive circulating tumor cells (CTC) showed poorer PSA response, and shorter PFS and OS, compared to those negative for AR-v7 CTCs. Furthermore, in blood samples from mCRPC patients, the frequency of AR-v7 protein detection in CTC nuclei increased from 3% of samples from patients following first line of therapy to 31% of samples for the third or more lines of therapy. Findings such as these point to the potential for using AR-v7 as a patient selection biomarker, and its likely utility for determining which men with mCRPC may benefit from AR antagonist treatment versus chemotherapy. In addition, other structural variations such as mutations of AR in the LBD have been associated with resistance to anti-androgens. These mutations are detectable in circulating tumor DNA (ctDNA) from patients with prostate cancer. These mutations and a broader set of genetic aberrations associated with resistance to anti-androgens can also be detected from tumor biopsies in patients with prostate cancer.

Without being bound to theory, it is believed that CBP/P300 can interact with AR directly via the NRID domain of CBP/P300. However, contrary to other nuclear receptors, this interaction is not believed to be dependent on ligand binding. Also, CBP/P300 can interact with both the LBD of AR and its N-terminal domain. Both these factors are of relevance in castrate resistant prostate cancer and it is expected that CBP/P300 interacts with AR-v7 very similarly as with AR. CBP/P300 also interact with AR indirectly via the co-factor TIP60/SRC-1 which itself interacts with AR. This approach can differ from direct receptor antagonists and can have the advantage of being unaffected by structural variations in the AR ligand binding domain (LBD). Such CBP/P300 bromodomain inhibitors can have activity in a number of cancers dependent upon nuclear hormone-receptor transcriptional programs, such as metastatic CRPC and locally advanced or metastatic AR-positive breast cancers.

In some embodiments, the patient diagnosed with mCRPC may have the AR-v7 splice variant of the androgen receptor.

In some embodiments, the CBP inhibitor composition may be administered to patients diagnosed with mCRPC in combination with an anti-androgen. In some embodiments, the CBP inhibitor composition may be administered to patients diagnosed with mCRPC following the completion of an administration of an anti-androgen.

Some methods include administering a therapeutically effective amount of a pharmaceutical composition comprising one or more compounds of formula (I) to patients diagnosed with mCRPC with progressive castration-resistant disease. Some methods include administering a therapeutically effective amount of a pharmaceutical composition comprising one or more compounds of formula (I) to patients diagnosed with mCRPC with progressive castration-resistant disease who have failed or been intolerant to at least one prior systemic therapy. Some methods include administering a therapeutically effective amount of a pharmaceutical composition comprising one or more compounds of formula (I) to patients diagnosed with mCRPC with progressive castration-resistant disease who have failed or been intolerant to at least two prior systemic therapies. Some methods include administering a therapeutically effective amount of a pharmaceutical composition comprising one or more compounds of formula (I) to patients diagnosed with mCRPC with progressive castration-resistant disease who have failed or been intolerant to at least two prior systemic therapies, including at least one prior line of treatment for metastatic disease and with evaluable disease and a rising PSA per standard definitions. Compounds of formula (I) are useful for treatment of patients diagnosed with an AR-v7 variant form of AR. In some methods, patients diagnosed with mCRPC with AR-v7 positive circulating tumor cells (CTC) can be treated with the pharmaceutical composition comprising one or more compounds of formula (I). In some methods, patients diagnosed with disease progression after treatment with enzalutamide can be treated with the pharmaceutical composition comprising one or more compounds of formula (I).

Some methods include administering a therapeutically effective amount of a pharmaceutical composition comprising Compound 1 to patients diagnosed with mCRPC with progressive castration-resistant disease. Some methods include administering a therapeutically effective amount of a pharmaceutical composition comprising Compound 1 to patients diagnosed with mCRPC with progressive castration-resistant disease who have failed or been intolerant to at least one prior systemic therapy. Some methods include administering a therapeutically effective amount of a pharmaceutical composition comprising Compound 1 to patients diagnosed with mCRPC with progressive castration-resistant disease who have failed or been intolerant to at least two prior systemic therapies. Some methods include administering a therapeutically effective amount of a pharmaceutical composition comprising Compound 1 to patients diagnosed with mCRPC with progressive castration-resistant disease who have failed or been intolerant to at least two prior systemic therapies, including at least one prior line of treatment for metastatic disease and with evaluable disease and a rising PSA per standard definitions. Compound 1 is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising Compound 1. In some methods, patients diagnosed with disease progression after treatment with enzalutamide can be treated with the pharmaceutical composition comprising Compound 1.

Some methods include administering a therapeutically effective amount of a pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease. Some methods include administering a therapeutically effective amount of a pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least one prior systemic therapy. Some methods include administering a therapeutically effective amount of a pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least two prior systemic therapies. Some methods include administering a therapeutically effective amount of a pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least two prior systemic therapies, including at least one prior line of treatment for metastatic disease and with evaluable disease and a rising PSA per standard definitions. (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid. In some methods, patients diagnosed with disease progression after treatment with enzalutamide can be treated with the pharmaceutical composition comprising (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid.

In some embodiments, Compound 1 is a CBP/p300 inhibitor compound useful for treating patients diagnosed with AR+ prostate cancer. The dependence of prostate cancer on AR signaling is well-established and is the basis for the development of ADT, including luteinizing hormone releasing hormone (LHRH) receptor agonists or antagonists, second generation anti-androgens (e.g., enzalutamide), and cytochrome P450 (CYP) 17 inhibitors capable of antagonizing androgen biosynthesis. These therapies are the mainstay of prostate cancer treatment. Prostate cancer resistance to anti-androgen therapies can arise from autocrine ligand production, intra-tumoral androgen biosynthesis, and AR aberrations such as AR gene amplification, somatic mutation in the ligand binding domain (LBD) of AR, and altered splicing of AR messenger ribonucleic acid (mRNA) resulting in loss of the LBD, as in the so-called AR variant 7 (AR-v7) form. The persistent dependence on AR function within these resistant populations recommends novel therapeutic approaches targeting AR functions distinct from ligand binding. Cyclic adenosine monophosphate (cAMP)-response element binding protein (CREB) binding protein (CBP) and ElA binding protein p300 (p300) are essential co-activators of AR-mediated transcription. The catalytic core of these proteins contains a bromodomain (BRD) and a histone acetyltransferase (HAT) domain. The BRD of CBP/p300 binds acetylated lysines on histones, positioning CBP/p300 on the chromatin so the HAT can acetylate proximal substrates, including histone H3 at lysine 27 (H3K27Ac). This results in a more accessible, transcriptionally permissive chromatin environment. CBP/p300 also binds AR at both the N-terminus and the ligand-binding domain of the receptor, including truncated forms of AR like the AR-v7 form. CBP/p300 also acetylates and stabilizes AR.

Various AR aberrations are known in the art, and have been found in established cell lines or from tumor biopsies. The aberrations may include amino acid substitutions, insertions or deletions. Exemplary mutational AR aberrations include, but are not limited to: E43G, L54 S, Q58L, L57Q, Q64R, AQ86, Q112H, G142V, E166 S, K180R, L192F, Q198G, E211E, D221H, N222D, T227C, M266T, P269 S, A251V, E253K, S296R, P334F, P340L, A356V, P390L, G414 S, W433L, T438P, T438I, L444 S, G449D, G451D, G456 S, G457D, R484C, T497I, A498T, P499P, V508L, G524 S, G524D, D528G, AL547, DR554, T573A, L574P, K580R, A586V, A587 S, L594M, K609E, R629Q, K630T, S646D, S647N, E665D, Q670R, I672T, G683A, V716M, V715M, L701H, L720E, A721T, V730M, R726L, L744V, A748V, M749I, G750 S, F754L, T755A, V757A, S759P, Y763C, W741C, F747L, N756A, V757I, R760K, W741X, AG743, W751X, S782N, R786X, W7960, L797P, Q798E, S791P, I799P, L830P, R846G, Q867X, H874Y, T877A, T877 S, V866M, L880Q, L872P, D879G, M886I, A896T, Q902R, F891L, G909Q, Q919R, D890N, M895V, and K910R.

These point mutations may be categorized into the three main regions of the steroid receptor protein 1) LBD mutants (T877A, D879G, W741C. W741L, M749L, H874Y, F876L) and mutations in the LBD may have altered ligand binding due to receptor protein conformation changes or alterations in amino acid R groups in the ligand binding pocket or conformation resulting in loss of ligand binding, loss of ligand recognition, switching of antagonist to agonist, and/or ligand promiscuity; 2) NTD or hinge region mutants (R629Q, G142V, P533 S) that may affect the ability of receptor transactivation, interaction with the transcription machinery or cofactors/regulators and result in alterations of receptor functions such as DNA binding, regulating gene expression, or nuclear translocation; or 3) DBD mutants (T575A) that may affect the receptor's ability to regulate of gene expression. Examples include: H874Y mutation in the androgen receptor has been shown to allow estradiol, progesterone, hydrocortisone, flutamide, and bicalutamide binding in 22Rv1 and CWR22RV1 cells; D878G has been shown to confer loss of DHT and testosterone binding and activity; W741C mutations confers bicalutamide and flutamide as agonists; F876L changes ARN-509 and enzalutamide from antagonists to agonists; M749L confers a hypersensitivity to estradiol; T575A leads to preferential binding to AR-nonspecific motifs, i.e. GRE; R629Q leads to gain of function with DHT.

In addition, AR aberrations may include splice variants resulting from exon skipping, cryptic splicing donor/acceptor usage, and cryptic exon inclusion. Exemplary splice variant AR aberrations include, but are not limited to, AR-v1, AR-v2, AR-v3, AR-v4, AR-v5, AR-v6, AR-v7, AR-v567es, AR-v9, AR-v12, AR-v13, and AR-v14. In particular, AR-v3 and AR-v4 may demonstrate constitutive transcriptional activity, similar to the AR-v7 splice variant.

In some embodiments, a method of treating AR+ prostate cancer in a patient includes administering to the patient in need thereof a therapeutically effective amount of Compound 1, or a pharmaceutically acceptable salt thereof (e.g. type A, B, or C hydrochloric acid addition salt). In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt). In some embodiments, the pharmaceutical composition includes Compound 1, or the pharmaceutically acceptable salt thereof, in a crystalline form (e.g. crystalline type A free base form, or type A, B, or C hydrochloric acid addition salt).

In some embodiments, a method of treating AR+ prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen deprivation treatment. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis.

In some embodiments, a method of treating AR+ prostate cancer in a patient includes administering to the patient in need thereof a therapeutically effective amount of Compound 1, or a pharmaceutically acceptable salt thereof (e.g. type A, B, or C hydrochloric acid addition salt), in combination with one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the one or more anti-androgens are selected from the group consisting of enzalutamide, abiraterone, darolutamide, and apalutamide.

In some embodiments, a method of treating AR+ prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen deprivation treatment and one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic hormone-sensitive prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment and one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis. In some embodiments, the one or more anti-androgens are selected from the group consisting of enzalutamide, abiraterone, darolutamide, and apalutamide.

In some embodiments, a method of treating AR+ castration-resistant prostate cancer in a patient includes administering to the patient in need thereof a therapeutically effective amount of Compound 1, or a pharmaceutically acceptable salt thereof (e.g. type A, B, or C hydrochloric acid addition salt). In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt). In some embodiments, the pharmaceutical composition includes Compound 1, or the pharmaceutically acceptable salt thereof, in a crystalline form (e.g. crystalline type A free base form, or type A, B, or C hydrochloric acid addition salt).

In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt). In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt). In some embodiments, the pharmaceutical composition includes Compound 1, or the pharmaceutically acceptable salt thereof, in a crystalline form (e.g. crystalline type A free base form, or type A, B, or C hydrochloric acid addition salt).

In some embodiments, Compound 1 is a CBP/p300 inhibitor compound useful for treating patients diagnosed with AR+ prostate cancer in the metastatic setting who are castration-resistant and are progressive after at least one line of treatment and had previously been treated with at least one potent anti-androgen drug (e.g. enzalutamide, darolutamide, apalutamide or abiraterone). In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient is progressive after at least one line of treatment and had previously been treated with at least one potent anti-androgen drug (e.g. enzalutamide, darolutamide, apalutamide, or abiraterone). In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient is progressive after at least one line of treatment and had previously been treated with at least one potent anti-androgen drug (e.g. enzalutamide, darolutamide, apalutamide, or abiraterone). In some embodiments, the pharmaceutical composition includes Compound 1, or the pharmaceutically acceptable salt thereof, in a crystalline form (e.g. crystalline type A free base form, or type A, B, or C hydrochloric acid addition salt).

Compound 1 can inhibit proliferation of androgen-independent cell lines. In some embodiments, Compound 1 is a CBP/p300 inhibitor compound useful for treating patients diagnosed with AR+ prostate cancer in the metastatic castration-resistant setting who are refractory to or relapsing on treatment with enzalutamide or abiraterone. In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient is refractory or relapsing on treatment with enzalutamide or abiraterone. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient is refractory or relapsing on treatment with enzalutamide or abiraterone. In some embodiments, the pharmaceutical composition includes Compound 1, or the pharmaceutically acceptable salt thereof, in a crystalline form (e.g. crystalline type A free base form, or type A, B, or C hydrochloric acid addition salt).

Compound 1 can downregulate the truncated forms of AR, including the AR-v7 variant, and decrease AR target gene expression in AR-v7-positive cell lines, including 22Rv1. In some embodiments, Compound 1 is a CBP/p300 inhibitor compound useful for treating patients diagnosed with AR+ prostate cancer in the metastatic castration-resistant setting who are harboring AR aberrations (e.g. AR gene amplification, somatic mutation in the ligand binding domain (LBD) of AR, and/or altered splicing of AR messenger ribonucleic acid (mRNA) resulting in loss of the LBD, as in the AR-v7 form). In some embodiments, Compound 1 is a CBP/p300 inhibitor compound useful for treating patients diagnosed with AR+ prostate cancer in the metastatic castration-resistant setting who are harboring an AR aberration, where the AR aberration is the AR-v7 form. In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient harbors one or more AR aberrations. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), where the patient harbors one or more AR aberrations. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the patient harbors one or more AR aberrations, where the one or more AR aberrations include the AR-v7 form.

Compound 1 can downregulate AR and the truncated forms of AR, and can induce tumor growth inhibition in enzalutamide-sensitive xenograft models. In some embodiments, Compound 1 is a CBP/p300 inhibitor compound useful for treating patients diagnosed with AR+ prostate cancer who are castrate-resistant in the metastatic setting (mCRPC) who have not previously been treated in that setting. In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient has not been previously treated for metastatic castration-resistant prostate cancer. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), where the patient has not been previously treated for metastatic castration-resistant prostate cancer. In some embodiments, the pharmaceutical composition includes Compound 1, or the pharmaceutically acceptable salt thereof, in a crystalline form (e.g. crystalline type A free base form, or type A, B, or C hydrochloric acid addition salt).

Compound 1 has a different mechanism of action for targeting AR signaling, compared to other potent anti-androgen drugs (e.g. enzalutamide, abiraterone, darolutamide, and apalutamide). In some embodiments, Compound 1 is a CBP/p300 inhibitor compound useful for treating patients diagnosed with AR+ prostate cancer in the metastatic castration-resistant setting, previously untreated or previously treated with at least one line of treatment, in combination with enzalutamide or abiraterone or darolutamide or apalutamide. In some embodiments, a method of treating AR+ metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient has not been previously treated for metastatic castration-resistant prostate cancer or has received one line of treatment for metastatic castration-resistant prostate cancer, and where Compound 1, or the pharmaceutically acceptable salt thereof, is administered in combination with one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), where the patient has not been previously treated for metastatic castration-resistant prostate cancer or has received one line of treatment for metastatic castration-resistant prostate cancer, and where the pharmaceutical composition including Compound 1, or the pharmaceutically acceptable salt thereof, is administered in combination with one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the one or more anti-androgens are selected from the group consisting of enzalutamide, abiraterone, darolutamide, and apalutamide.

Compound can reduce AR target gene expression. In some embodiments, treatment with Compound 1 can delay or slow down progression to the metastatic state in AR+ prostate cancer patients who are castrate-resistant (i.e. non-metastatic castration-resistant prostate cancer (nmCRPC)). In some embodiments, a method of treating AR+ non-metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the administration of Compound 1, or the pharmaceutically acceptable salt thereof, delays or slows the progression of the AR+ non-metastatic castration-resistant prostate cancer to a metastatic state. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ non-metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), where the administration of Compound 1, or the pharmaceutically acceptable salt thereof, delays or slows the progression of the AR+ non-metastatic castration-resistant prostate cancer to a metastatic state. In some embodiments, the pharmaceutical composition includes Compound 1, or the pharmaceutically acceptable salt thereof, in a crystalline form (e.g. crystalline type A free base form, or type A, B, or C hydrochloric acid addition salt).

In some embodiments, Compound 1 is useful for treating patients diagnosed with AR+ prostate cancer who are castrate-resistant but with no metastases (nmCRPC) in combination with androgen-deprivation treatment. In some embodiments, a method of treating AR+ non-metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen-deprivation treatment. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ non-metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis.

In some embodiments, Compound 1 is useful for treating patients diagnosed with AR+ prostate cancer who are castrate-resistant but with no metastases (nmCRPC) in combination with a potent anti-androgen (e.g. enzalutamide, abiraterone, darolutamide, and apalutamide). In some embodiments, a method of treating AR+ non-metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), in combination with one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ non-metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the one or more anti-androgens are selected from the group consisting of enzalutamide, abiraterone, darolutamide, and apalutamide.

In some embodiments, Compound 1 is useful for treating patients diagnosed with AR+ prostate cancer who are castrate-resistant but with no metastases (nmCRPC) in combination with androgen-deprivation treatment and another potent anti-androgen drug such as darolutamide or apalutamide or enzalutamide or abiraterone. In some embodiments, a method of treating AR+ non-metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen-deprivation treatment and one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ non-metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment and one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis. In some embodiments, the one or more anti-androgens are selected from the group consisting of darolutamide, apalutamide, enzalutamide, and abiraterone.

In some embodiments, Compound 1 is a CBP/p300 inhibitor compound useful for treating patients diagnosed with AR+ prostate cancer in the non-metastatic castration-resistant setting who are harboring AR aberrations (e.g. AR gene amplification, somatic mutation in the ligand binding domain (LBD) of AR, and/or altered splicing of AR messenger ribonucleic acid (mRNA) resulting in loss of the LBD, as in the AR-v7 form). In some embodiments, Compound 1 is a CBP/p300 inhibitor compound useful for treating patients diagnosed with AR+ prostate cancer in the non-metastatic castration-resistant setting who are harboring an AR aberration, where the AR aberration is the AR-v7 form. In some embodiments, a method of treating AR+ non-metastatic castration-resistant prostate cancer in a patient includes administering to the patient in need thereof a therapeutically effective amount of Compound 1, or a pharmaceutically acceptable salt thereof (e.g. type A, B, or C hydrochloric acid addition salt), where the patient harbors one or more AR aberrations. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic castration-resistant prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), where the patient harbors one or more AR aberrations. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the patient harbors one or more AR aberrations, where the one or more AR aberrations include the AR-v7 form.

In some embodiments, Compound 1 is also useful for treating patients diagnosed with metastatic hormone-sensitive prostate cancer (mHSPC). In some embodiments, a method of treating AR+ metastatic hormone-sensitive prostate cancer in a patient includes administering to the patient in need thereof a therapeutically effective amount of Compound 1, or a pharmaceutically acceptable salt thereof (e.g. type A, B, or C hydrochloric acid addition salt). In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic hormone-sensitive prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt). In some embodiments, the pharmaceutical composition includes Compound 1, or the pharmaceutically acceptable salt thereof, in a crystalline form (e.g. crystalline type A free base form, or type A, B, or C hydrochloric acid addition salt).

Compound 1 can inhibit proliferation of androgen-dependent prostate cancer cell lines. In some embodiments, Compound 1 is useful for treating patients diagnosed with AR+ prostate cancer who are metastatic hormone-sensitive (mHSPC) in combination with androgen-deprivation treatment. In some embodiments, a method of treating AR+ metastatic hormone-sensitive prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen deprivation treatment. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic hormone-sensitive prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis.

In some embodiments, Compound 1 is useful for treating patients diagnosed with AR+ prostate cancer who are metastatic hormone-sensitive (mHSPC) in combination with an anti-androgen. In some embodiments, a method of treating AR+ metastatic hormone-sensitive prostate cancer in a patient includes administering to the patient in need thereof a therapeutically effective amount of Compound 1, or a pharmaceutically acceptable salt thereof (e.g. type A, B, or C hydrochloric acid addition salt), in combination with one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic hormone-sensitive prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the one or more anti-androgens are selected from the group consisting of enzalutamide, abiraterone, darolutamide, and apalutamide.

In some embodiments, Compound 1 is useful for treating patients diagnosed with AR+ prostate cancer who are metastatic hormone-sensitive (mHSPC) in combination with androgen-deprivation treatment and another potent anti-androgen drug such as darolutamide or apalutamide or enzalutamide or abiraterone. In some embodiments, a method of treating AR+ metastatic hormone-sensitive prostate cancer in a patient includes administering to the patient in need thereof a therapeutically effective amount of Compound 1, or a pharmaceutically acceptable salt thereof (e.g. type A, B, or C hydrochloric acid addition salt), in combination with an androgen deprivation treatment and one or more anti-androgens. In some embodiments, Compound 1, or the pharmaceutically acceptable salt thereof, is administered as a crystalline form (e.g. crystalline type A free base form, or type A, B, or C hydrochloric acid addition salt). In some embodiments, a method of treating AR+ metastatic hormone-sensitive prostate cancer in a patient includes administering to the patient in need thereof a therapeutically effective amount of a pharmaceutical composition including Compound 1, or a pharmaceutically acceptable salt thereof (e.g. type A, B, or C hydrochloric acid addition salt), in combination with an androgen-deprivation treatment and one or more anti-androgens. In some embodiments, the pharmaceutical composition includes Compound 1, or the pharmaceutically acceptable salt thereof, in a crystalline form (e.g. crystalline type A free base form, or type A, B, or C hydrochloric acid addition salt). In some embodiments, the androgen deprivation treatment includes the administration of agents such as luteinizing hormone releasing hormone (LHRH) receptor agonists and antagonists, and/or cytochrome P450 (CYP) 17 inhibitors capable of antagonizing androgen biosynthesis. In some embodiments, the one or more anti-androgens are selected from the group consisting of darolutamide, apalutamide, enzalutamide, and abiraterone.

Overall, CBP/p300 promotes AR transcriptional activity and increases AR target gene expression driving proliferation in AR-driven tumors. Accordingly, methods of treating certain mCRPC can include the administration of a therapeutically effective amount of Compound 1 or a pharmaceutically acceptable salt thereof.

In some embodiments, a method of treatment comprises administering to a patient in need thereof a therapeutically effective amount of Compound 1 or a pharmaceutically acceptable salt thereof. In one aspect, a daily dose of Compound 1 is administered to a human adult patient diagnosed with an androgen receptor positive (AR+) form of cancer, in an amount effective to produce a desired therapeutic biomarker response and/or tumor growth inhibition in the patient. For example, in one embodiment, a total daily dose of 10 mg-300 mg of Compound 1 (based on the weight of the free base) can be administered to a patient, including a total daily dose of 10, 25, 50, 100, 150, 200, 250, or 300 mg of Compound 1 free base in a pharmaceutically acceptable addition salt (e.g., a hydrochloride salt of Compound 1). In one embodiment, a total daily dose of 25 mg-500 mg of Compound 1 (based on the weight of the free base) can be administered to a patient, including a total daily dose of 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg of Compound 1 free base, where Compound 1 is optionally administered as a pharmaceutically acceptable addition salt (e.g. a hydrochloride salt of Compound 1). In one embodiment, Compound 1 is administered to a patient as the type A hydrochloric acid addition salt. In another embodiment, Compound 1 is administered to a patient as the type B hydrochloric acid addition salt. In yet another embodiment, Compound 1 is administered to a patient as the type C hydrochloric acid addition salt.

In one embodiment, a total daily dose of 10 mg of Compound 1 free base in a pharmaceutically acceptable addition salt (e.g., a hydrochloride salt of Compound 1) in an oral unit dosage form to the patient once per day during a dosing period. In one embodiment, a total daily dose of 25 mg of Compound 1 free base in a pharmaceutically acceptable addition salt (e.g., a hydrochloride salt of Compound 1) in an oral unit dosage form to the patient once per day during a dosing period. In one embodiment, a total daily dose of 50 mg of Compound 1 free base in a pharmaceutically acceptable addition salt (e.g., a hydrochloride salt of Compound 1) in an oral unit dosage form to the patient once per day during a dosing period. In one embodiment, a total daily dose of 100 mg of Compound 1 free base in a pharmaceutically acceptable addition salt (e.g., a hydrochloride salt of Compound 1) in an oral unit dosage form to the patient once per day during a dosing period. In one embodiment, a total daily dose of 150 mg of Compound 1 free base in a pharmaceutically acceptable addition salt (e.g., a hydrochloride salt of Compound 1) in an oral unit dosage form to the patient once per day during a dosing period. In one embodiment, a total daily dose of 200 mg of Compound 1 free base in a pharmaceutically acceptable addition salt (e.g., a hydrochloride salt of Compound 1) in an oral unit dosage form to the patient once per day during a dosing period. In one embodiment, a total daily dose of 250 mg of Compound 1 free base in a pharmaceutically acceptable addition salt (e.g., a hydrochloride salt of Compound 1) in an oral unit dosage form to the patient once per day during a dosing period. In one embodiment, a total daily dose of 300 mg of Compound 1 free base in a pharmaceutically acceptable addition salt (e.g., a hydrochloride salt of Compound 1) in an oral unit dosage form to the patient once per day during a dosing period. In one embodiment, a total daily dose of 10-300 mg of Compound 1 free base in a pharmaceutically acceptable addition salt (e.g., a hydrochloride salt of Compound 1) in an oral unit dosage form to the patient once per day during a dosing period.

The pharmaceutical composition can be administered to the patient in need thereof on a planned clinical dosing schedule. The dosing schedule can be an intermittent dosing regimen comprising one or more treatment cycles. Each treatment cycle can comprise: (a) a dosing period during which a therapeutically effective amount of said pharmaceutical composition comprising Compound 1 or a pharmaceutically acceptable salt thereof is administered to a patient in need thereof and, thereafter, (b) a resting period during which the pharmaceutical composition comprising Compound 1 or the pharmaceutically acceptable salt thereof is not administered to the patient. In some embodiments, a method of treatment comprises administering Compound 1 or the pharmaceutically acceptable salt thereof to a patient in need thereof for multiple (e.g., two or more) treatment cycles. In some embodiments, each treatment cycle is a 28-day cycle comprising 21 consecutive treatment days followed by 7 consecutive days without administering Compound 1 or the pharmaceutically acceptable salt thereof to the patient. In some embodiments, Compound 1 is administered once per day (QD) to the patient during a dosing period.

The method of treatment can comprise administering Compound 1 or the pharmaceutically acceptable salt thereof to the patient throughout a duration of treatment of one or more consecutive treatment cycles. In some embodiments, the method of treatment can comprise multiple consecutive treatment cycles for a duration of treatment of at least 2, 3, 4, 5, or 6 consecutive 28-day treatment cycles. In one aspect, the method of treatment comprises administering the therapeutically effective amount of Compound 1 or the pharmaceutically acceptable salt thereof for at least 24 consecutive weeks (e.g., 6 or more consecutive treatment cycles), 25 consecutive weeks, or at least 26 consecutive weeks. In some embodiments, the duration of treatment can be until patient disease progression.

In one embodiment, a method of treating patients diagnosed with metastatic castration-resistant prostate cancer (mCRPC) who have progressed despite treatment with at least one potent anti-androgen therapy. The method of treatment can comprise the oral administration of Compound 1 or a pharmaceutically acceptable salt thereof (e.g., (1R,3R)-3-[(7S)-2-[(R)-(5-fluoro-2-methoxyphenyl)(hydroxy)methyl]-6-(methoxycarbonyl)-7-methyl-3H,6H,7H, 8H,9H-imidazo[4,5-f]quinolin-3-yl]cyclohexane-1-carboxylic acid hydrochloride) for a treatment cycle comprising a twenty-one (21) consecutive day dosing period of administering Compound 1 or the pharmaceutically acceptable salt thereof daily to the patient, followed by a seven (7)-day resting period during which Compound 1 (or the pharmaceutically acceptable salt thereof) is not administered to the patient. In some embodiments, the total daily dose of Compound 1 can be 100 mg or 200 mg of the free base, in a pharmaceutically acceptable salt of Compound 1, such as the Type A HCl addition salt of Compound 1.

In some embodiments, Compound 1, or the pharmaceutically acceptable salt thereof, and pharmaceutically acceptable compositions comprising the same, are useful for treating AR+ breast cancers, including locally advanced or metastatic AR+ breast cancer. For example, the inhibition of CBP/P300 can target AR transcriptional activity through H3K27Ac, reduction of AR target gene expression, or reduction of AR expression with, ultimately, a reduction in proliferation. In addition, CBP/P300 BRD inhibitors present the possibility of suppressing ER-driven signaling in hormone-receptor positive breast cancers.

Compound 1 induced a concentration-dependent reduction of H3K27Ac, a mark specific to CBP/P300, in an AR positive breast cancer cell line. Compound 1 reduced the mRNA expression of TMPRSS2 and XBP1 in an AR positive breast cancer cell line. Compound 1 inhibit proliferation of breast cancer cell lines after 10 days continuous exposure to the drug, and the cell lines with high expression of AR mRNA are more sensitive than those with low expression. Compound 1 treatment produced a tumor growth inhibition in an AR positive breast cancer cell line derived xenograft model. In some embodiments, an AR positive breast cancer cell line can be MDA-MB-453.

Pharmaceutical compositions comprising Compound 1, or a pharmaceutically acceptable salt thereof, are useful for the treatment of certain forms of AR+ breast cancer. For example, the suppression of AR and/or ER transcriptional activity with Compound 1 (or a pharmaceutical composition comprising Compound 1) can be useful in treating antitumor effects in AR+ breast cancers, including TNBC and metastatic ER+ tumors, via its inhibition of CBP/P300 BRD.

Some methods include administering a therapeutically effective amount of a pharmaceutical composition comprising Compound 1 to patients diagnosed with invasive breast carcinoma with triple negative status (per College of American Pathologists [CAP] guidelines) and detectable AR expression in >1% of tumor cells, with progressive disease who have failed at least two prior systemic therapies with evaluable disease or invasive breast carcinoma AR positive >1% and ER, PR, or HER positive (per CAP guidelines) with progressive disease who have failed at least three prior systemic therapies. Some methods include administering a therapeutically effective amount of a pharmaceutical composition comprising Compound 1 to patients diagnosed with Her2-breast cancer. Some methods include administering a therapeutically effective amount of a pharmaceutical composition comprising Compound 1 to patients diagnosed with ER−, PR−, or ER−/PR− breast cancer.

Some methods include administering a therapeutically effective amount of a pharmaceutical composition comprising Compound 2 to patients diagnosed with mCRPC with progressive castration-resistant disease. Some methods include administering a therapeutically effective amount of a pharmaceutical composition comprising Compound 2 to patients diagnosed with mCRPC with progressive castration-resistant disease who have failed or been intolerant to at least one prior systemic therapy. Some methods include administering a therapeutically effective amount of a pharmaceutical composition comprising Compound 2 to patients diagnosed with mCRPC with progressive castration-resistant disease who have failed or been intolerant to at least two prior systemic therapies. Some methods include administering a therapeutically effective amount of a pharmaceutical composition comprising Compound 2 to patients diagnosed with mCRPC with progressive castration-resistant disease who have failed or been intolerant to at least two prior systemic therapies, including at least one prior line of treatment for metastatic disease and with evaluable disease and a rising PSA per standard definitions. Compound 2 is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising Compound 2. In some methods, patients diagnosed with disease progression after treatment with enzalutamide can be treated with the pharmaceutical composition comprising Compound 2.

Some methods include administering a therapeutically effective amount of a pharmaceutical composition comprising Compound 3 to patients diagnosed with mCRPC with progressive castration-resistant disease. Some methods include administering a therapeutically effective amount of a pharmaceutical composition comprising Compound 3 to patients diagnosed with mCRPC with progressive castration-resistant disease who have failed or been intolerant to at least one prior systemic therapy. Some methods include administering a therapeutically effective amount of a pharmaceutical composition comprising Compound 3 to patients diagnosed with mCRPC with progressive castration-resistant disease who have failed or been intolerant to at least two prior systemic therapies. Some methods include administering a therapeutically effective amount of a pharmaceutical composition comprising Compound 3 to patients diagnosed with mCRPC with progressive castration-resistant disease who have failed or been intolerant to at least two prior systemic therapies, including at least one prior line of treatment for metastatic disease and with evaluable disease and a rising PSA per standard definitions. Compound 3 is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising Compound 3. In some methods, patients diagnosed with disease progression after treatment with enzalutamide can be treated with the pharmaceutical composition comprising Compound 3.

Some methods include administering a therapeutically effective amount of a pharmaceutical composition comprising Compound 4 to patients diagnosed with mCRPC with progressive castration-resistant disease. Some methods include administering a therapeutically effective amount of a pharmaceutical composition comprising Compound 4 to patients diagnosed with mCRPC with progressive castration-resistant disease who have failed or been intolerant to at least one prior systemic therapy. Some methods include administering a therapeutically effective amount of a pharmaceutical composition comprising Compound 4 to patients diagnosed with mCRPC with progressive castration-resistant disease who have failed or been intolerant to at least two prior systemic therapies. Some methods include administering a therapeutically effective amount of a pharmaceutical composition comprising Compound 4 to patients diagnosed with mCRPC with progressive castration-resistant disease who have failed or been intolerant to at least two prior systemic therapies, including at least one prior line of treatment for metastatic disease and with evaluable disease and a rising PSA per standard definitions. Compound 4 is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising Compound 4. In some methods, patients diagnosed with disease progression after treatment with enzalutamide can be treated with the pharmaceutical composition comprising Compound 4.

Some methods include administering a therapeutically effective amount of a pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease. Some methods include administering a therapeutically effective amount of a pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least one prior systemic therapy. Some methods include administering a therapeutically effective amount of a pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least two prior systemic therapies. Some methods include administering a therapeutically effective amount of a pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid to patients diagnosed with mCRPC with progressive castration-resistant disease who have failed or been intolerant to at least two prior systemic therapies, including at least one prior line of treatment for metastatic disease and with evaluable disease and a rising PSA per standard definitions. (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid is also useful for treatment of patients diagnosed with an AR-v-7 variant form of AR. In some methods, patients diagnosed with mCRPC with AR-v7 positive circulating tumor cells (CTC) can be treated with the pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid. In some methods, patients diagnosed with disease progression after treatment with enzalutamide can be treated with the pharmaceutical composition comprising (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid.

The therapeutic benefits of AR inhibition have been demonstrated clinically in these cancers, but with limitations that highlight the need for alternative approaches with long term benefit and mechanisms of resistance that are non-overlapping with anti-androgen therapies. For example, the inhibition of the CBP/P300 bromodomain can target AR transcriptional activity through the reduction of H3K27 histone acetylation, inhibiting the expression of AR-dependent genes, inducing the degradation of AR and the AR-v7 splice form, and/or reduction of AR expression, ultimately leading to a reduction in proliferation. CBP/p300 inhibitor-mediated inhibition of AR activities is expected to be insensitive to AR LBD structural variations, and thus insensitive to LBD-related mechanisms of resistance to anti-androgens. Finally, CBP/p300 BRD inhibitors can be useful for suppressing ER-driven signaling in hormone-receptor positive breast cancers.

In some embodiments, the CBP inhibitor pharmaceutical composition is administered to patients with AR-positive cancers at doses sufficient to reduce the expression of androgen receptor-dependent genes within the patients. In some embodiments, the AR-dependent genes inhibited by the CBP inhibitor pharmaceutical composition include Myc, TMPRSS2, KLK3, and SPDEF.

In some embodiments, the CBP inhibitor pharmaceutical composition is administered to patients with AR-positive cancers at doses sufficient to reduce the expression of estrogen receptor-dependent genes within the patients. In some embodiments, the ER-dependent genes inhibited by the CBP inhibitor pharmaceutical composition may include AQP3 and XBP1.

In some embodiments, the CBP inhibitor pharmaceutical composition is administered to patients with AR-positive cancers at doses sufficient to reduce the amount of H3K27 acetylated histone proteins within the patients.

In some embodiments, the CBP inhibitor pharmaceutical composition is administered to patients with AR-positive cancers at doses sufficient to reduce the amount of AR or AR-v7 splice variant proteins present within the patients. In some embodiments, the CBP inhibitor pharmaceutical composition is administered to patients with AR-positive cancers at doses sufficient to reduce the intracellular protein levels of AR or AR-v7 splice variant proteins within the patient. In some embodiments, the CBP inhibitor pharmaceutical composition is administered to patients with AR-positive cancers at doses sufficient to reduce the expression levels of AR and/or AR-v7 splice variant.

Pharmaceutical compositions comprising CBP inhibitor compounds can be prepared using the methods as described in Example 1 below. Preferably, the pharmaceutical composition includes an active pharmaceutical ingredient (API) comprising a CBP inhibitor compound that is at least 95% pure by HPLC (Example 22). In some examples, the API can further include one or more stereoisomers of the CBP inhibitor compound, in any suitable amounts that permit the API to have a desired therapeutically effective potency and purity for an intended medical use. Preferably, the API comprises a CBP inhibitor compound with 95%, 96%, 97%, 98% or 99% (or greater) purity determined by HPLC using the method of Example 22.

In addition to the API, the pharmaceutical composition can further contain pharmaceutically acceptable excipients. Preferably, the pharmaceutical composition is formulated for oral administration to a human or veterinary subject in need thereof. In some embodiments, the pharmaceutical composition is formulated for administration in a capsule form. In some embodiments, the pharmaceutical composition is formulated to contain a dose of 10 mg, 25 mg, or 100 mg of the CBP inhibitor compound. In some embodiments, the pharmaceutical composition is administered to the patient once daily. In some embodiments, the pharmaceutical composition is administered to the patient twice daily. In some embodiments, the pharmaceutical composition is administered to the patient for a period of 14 to 28 days per 28-day cycle. The strength and dosage, as well as administration frequency, of the pharmaceutical composition can be selected depending on the diagnosis and other medically relevant characteristics of the patient.

EXAMPLES

Example 1: Synthesis of CBP Inhibitor Compounds

The following abbreviations are used in the following examples and elsewhere herein:

Abbreviations

ACN acetonitrile
$Ac_2O$ acetic anhydride
($\pm$)BINAP ($\pm$)-2,2'-Bis(diphenylphosphino)-1,1'-binaphthalen
Boc tert-butoxycarbonyl
n-BuOH butanol
cm centimeter
DCE 1,2-dichloroethane
DCM dichloromethane or methylene chloride
DEA diethylamine
DMC 2-Chloro-4,5-dihydro-1,3-dimethyl-1H-imidazolium chloride
DMP Dess-Martin periodinane
DMTMM 4-(4,6-Dimethoxy-1,3,5-triazin-2-yl)-4-methylmorpholinium chloride
DIEA N,N-diisopropylethylamine
DMAP 4-(dimethylamino)pyridine
DMF N,N-dimethylformamide
DMSO dimethylsulfoxide
DPPA diphenylphosphoryl azide
dppf bis(diphenylphosphino)ferrocene
ES electrospray ionization
$Et_3N$ triethylamine
EtOAc ethyl acetate
EtOH ethanol
FA formic acid
FCC flash column chromatography
h hours
HATU 2-(3H-[1,2,3]triazolo[4,5-b]pyridin-3-yl)-1,1,3,3-tetramethylisouronium hexafluorophosphate
HCl hydrogen chloride
HOAc acetic acid
HPLC high performance liquid chromatography
(i-Pr)$_2$NEt N,N-diisopropylethylamine
L liter
LC/MS liquid chromatography/mass spectrometry
LDA lithium diisopropylamine
$K_2CO_3$ potassium carbonate
MeOH methanol
mL milliliter
mmol millimole
mg milligram
MHz megahertz
MS mass spectrometry
m/z mass/charge ratio
NBS N-bromosuccinimide
nm nanometer
NMM 4-methylmorpholine
NMR nuclear magnetic resonance
$Pd_2(dba)_3$ tris(dibenzylideneacetone)dipalladium
$Ph_3P$ triphenylphosphine
PhCHO benzaldehyde
PhMe toluene
ppm parts per million
rt room temperature
RT retention time
SFC supercritical fluid chromatography
STAB sodium triacetoxyborohydride
p-TSA para-toluenesulfonic anhydride
p-TsOH para-toluenesulfonic acid
TFA trifluoroacetic acid
TFAA trifluoroacetic anhydride
THF tetrahydrofuran
UV ultraviolet
XPhos 2-dicyclohexylphosphino-2',4',6'-triisopropylbiphenyl The term "organic solvent" will be readily known to those skilled in the art, but may include chemical solvents such as acetone, acetonitrile, benzene, chloroform, 1,4-dioxane, diethyl ether, dichloromethane, dimethylacetamide, N,N-dimethylformamide, dimethyl sulfoxide, ethanol, ethyl acetate, hexanes, isopropanol, methanol, N-methylpyrolidone, pyridine, tetrahydrofuran, toluene, water, in addition to those not explicitly named.

Materials and Methods

Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Instruments

In the examples that follow, X-Ray Powder Diffraction (XRPD) was performed with a Panalytical X'Pert$^3$ Powder XRPD on a Si zero-background holder. The 2θ position was calibrated against a Panalytical Si reference standard disc. The XRPD parameters used are listed in FIG. 3A.

Thermogravimetric Analysis (TGA) data were collected using a TA Q500 and Q550 from TA Instruments. Differential Scanning Calorimetry (DSC) was performed using a TA Q2000 from TA Instruments. DSC was calibrated with indium reference standard, and the TGA was calibrated using nickel reference standard. Detailed parameters used are listed in FIG. 3B.

Dynamic Vapor Sorption (DVS) data were collected with a SMS DVS Intrinsic from Surface Measurement Systems. Parameters for DVS test are listed in FIG. 3C.

HPLC Assessment of Drug Compound Purity: Drug compound samples for analysis were prepared at concentrations of 0.2 mg/mL in a 70:30 mixture of water and acetonitrile. The samples were subsequently analyzed on a Waters Alliance e2695 liquid chromatography instrument equipped with a Waters QDa mass spectrometer and Waters 2998 photodiode array detector. Parameters for the chromatography method are disclosed in FIG. 3D.

General Methods of Compound Preparation

Described herein are methods of synthesizing the compounds of the present disclosure. Compounds of the present disclosure can be synthesized according to the synthetic schemes provided below. Preparation of the starting material for Schemes 1 and 2 ("Intermediate 1") is described below. Preparation of the starting material for Schemes 3 and 4 can be found in Example 1, Part A of U.S. Pat. No. 4,404,207.

Unless otherwise specified, the substituents $R^4$ and $R^5$ in the following reaction schemes are defined as follows:

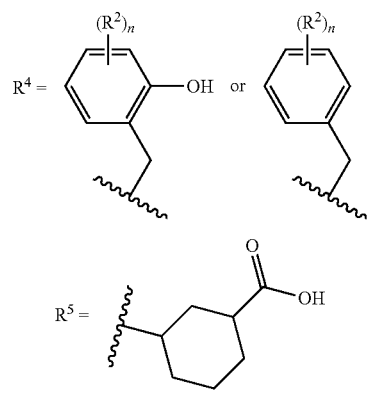

Scheme 1 provides methods useful for synthesizing compounds of Formula I.

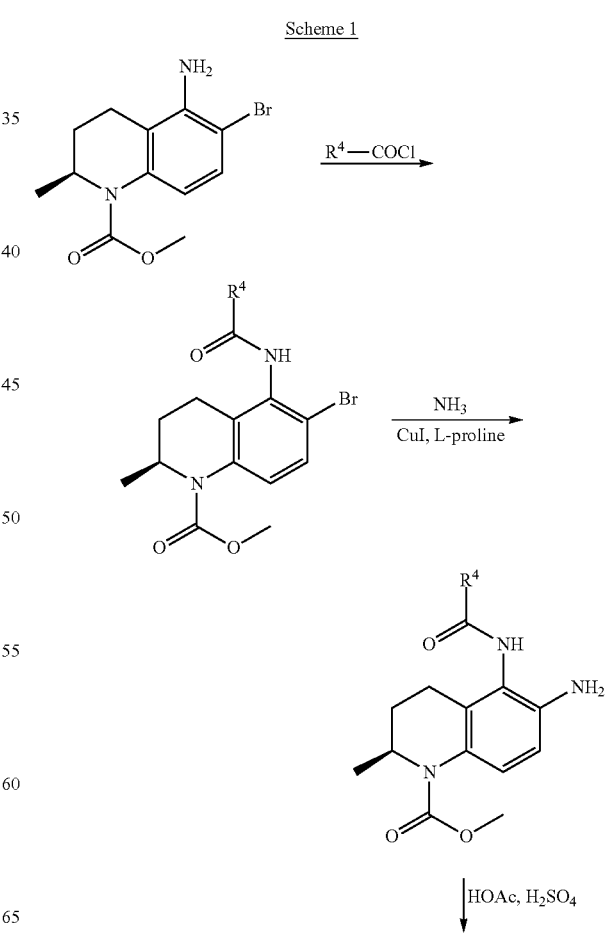

61
-continued
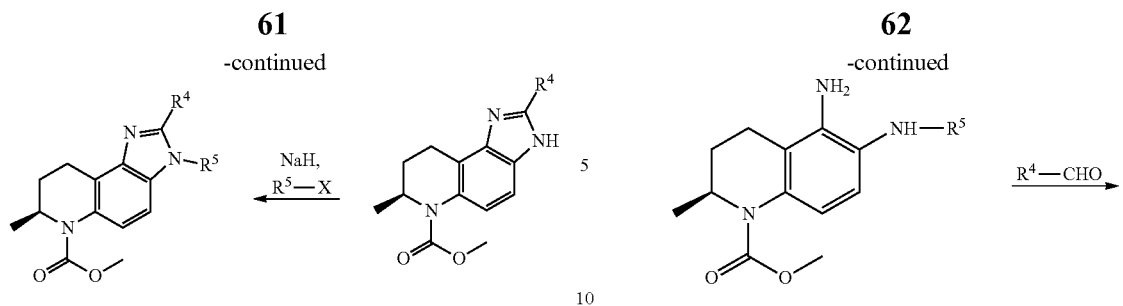
Scheme 2 provides methods useful for synthesizing compounds of Formula I.
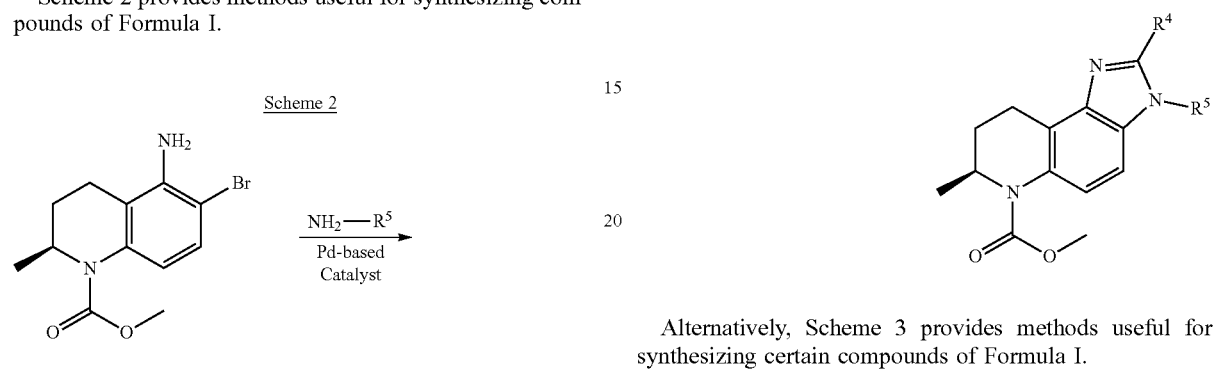
62
-continued
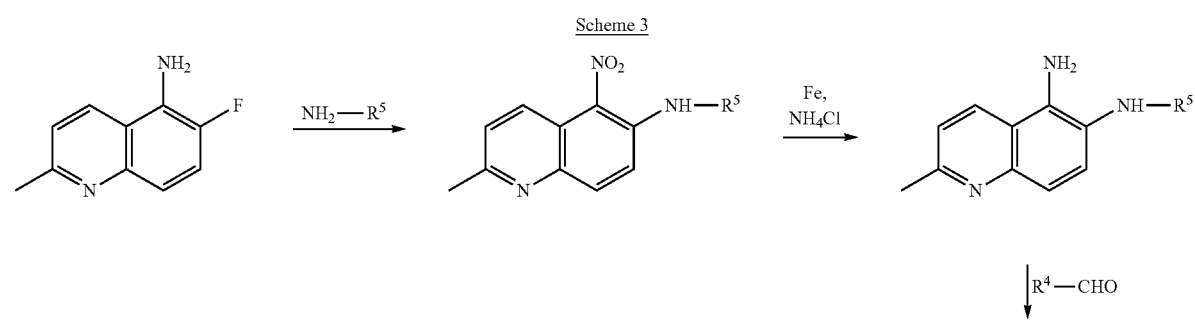
Alternatively, Scheme 3 provides methods useful for synthesizing certain compounds of Formula I.
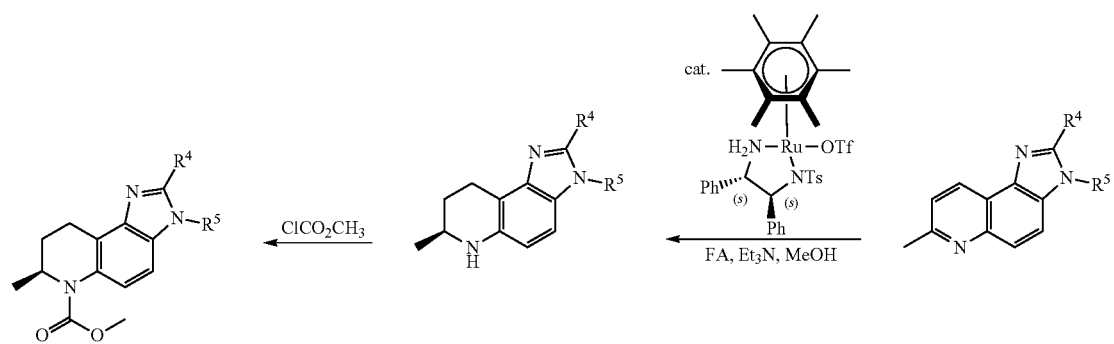

Alternatively, Scheme 4 provides methods useful for synthesizing certain compounds of Formula I.
Scheme 4
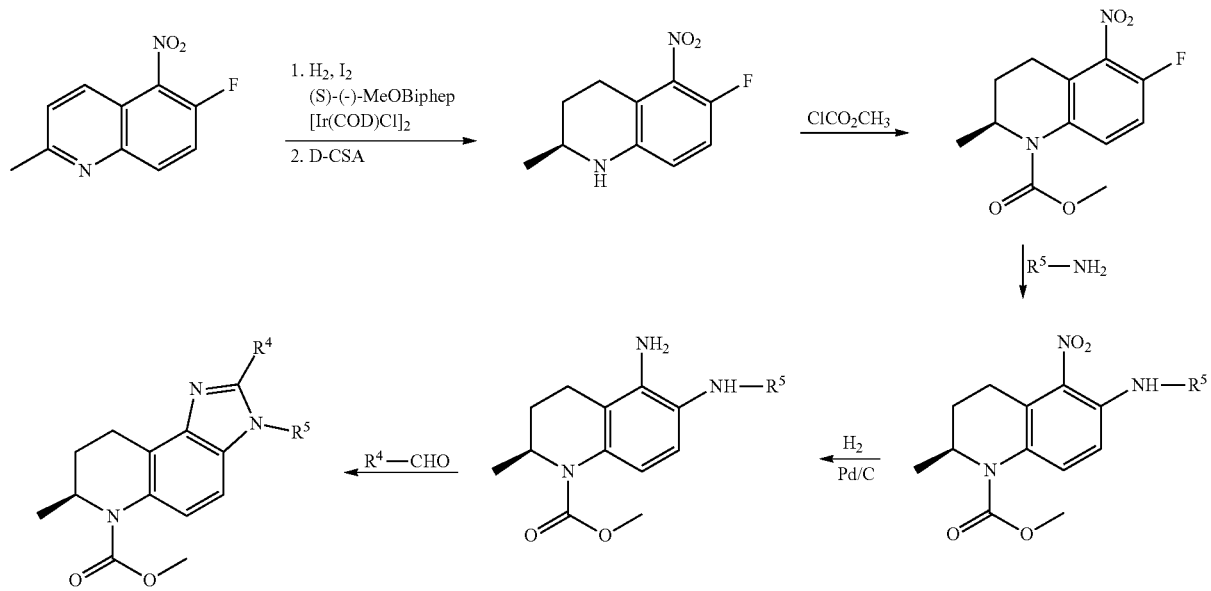
Example 1-1
Preparation of Intermediate 1: methyl (S)-5-amino-6-bromo-2-methyl-3,4-dihydroquinoline-1(2H)-carboxylate
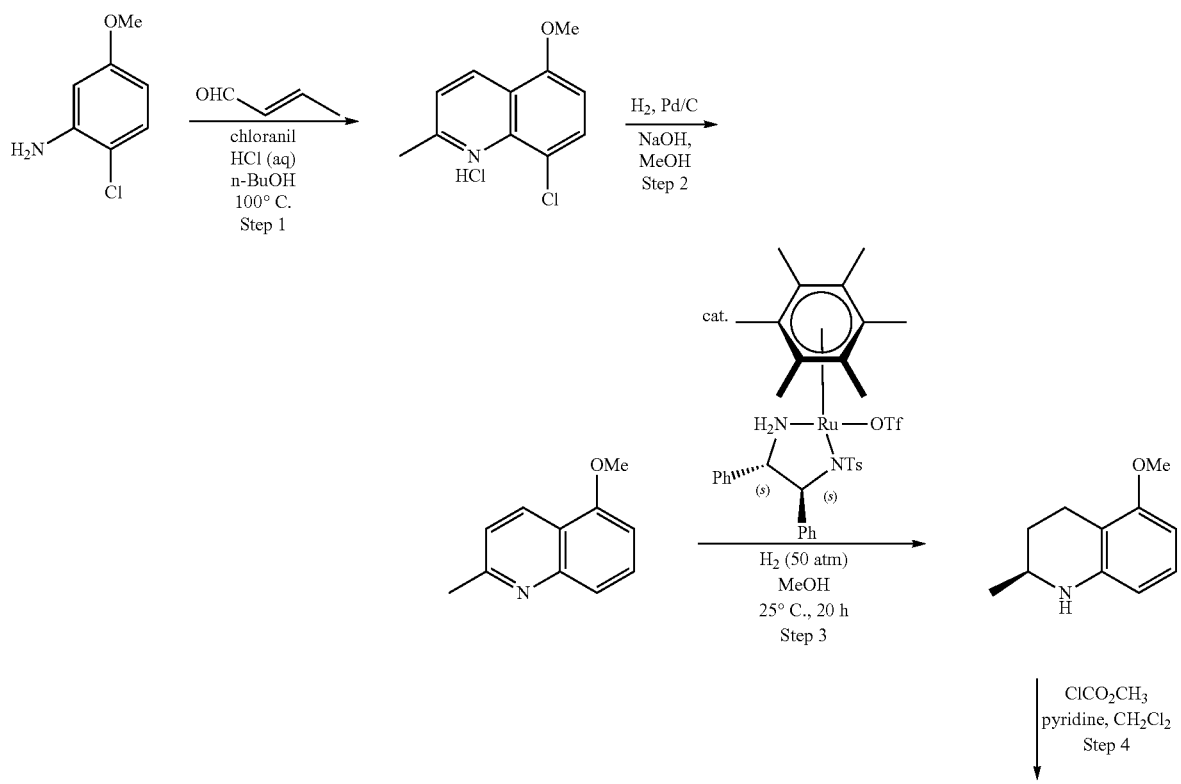

-continued

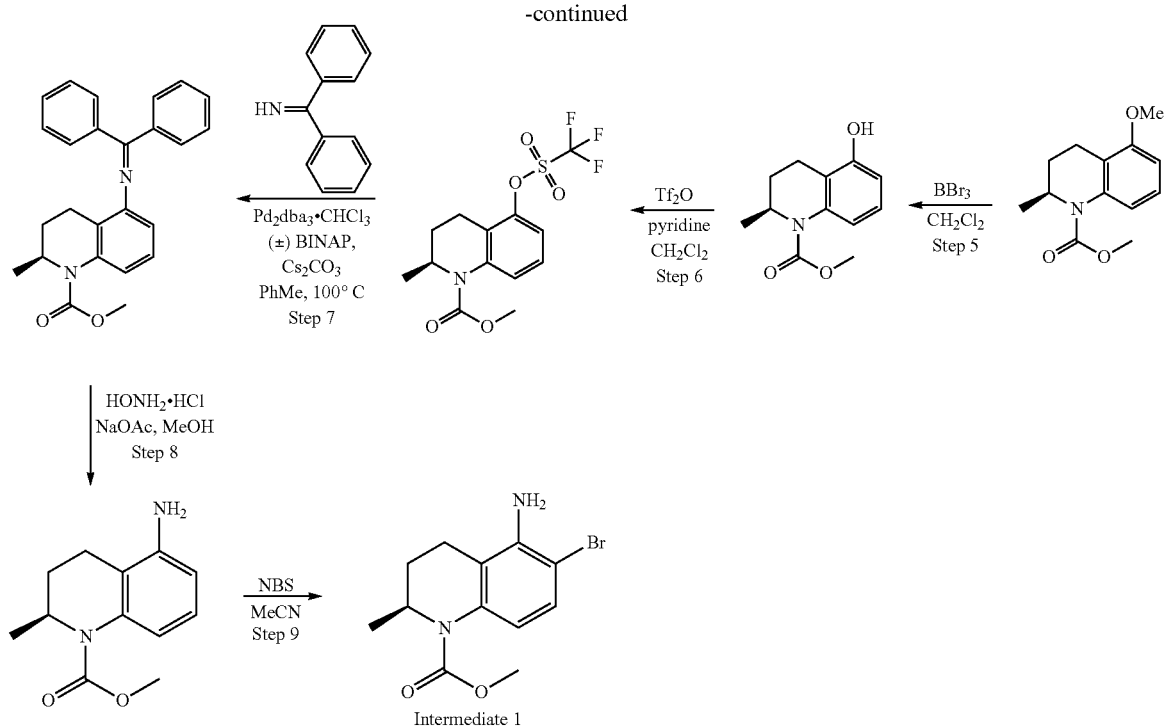

Step 1. 8-chloro-5-methoxy-2-methylquinoline hydrochloride

Into a 5 L 4-necked round-bottom flask purged and maintained with an inert atmosphere of nitrogen, 2-chloro-5-methoxyaniline (250 g, 1.59 mol) was dissolved in 1-butanol (1200 mL). Then hydrochloric acid (aq, 36.5%, 526.5 mL) and chloranil (456.5 g, 1.86 mol) were added. The resulting mixture was stirred for 1 h at 100° C. under nitrogen atmosphere. Then a solution of (E)-but-2-enal (169 mL, 2.06 mol) in 1-butanol (300 mL) was added dropwise. The resulting solution was stirred for 1 h at 100° C. under nitrogen atmosphere. The oil bath was cooled to 70° C. and tetrahydrofuran (1500 mL) was added. Then the resulting mixture was stirred for 1 h at 70° C. The reaction mixture was cooled to 0° C. and the solids were filtered. The solids were washed with tetrahydrofuran (3 L) at 0° C. then dried in an oven to afford 8-chloro-5-methoxy-2-methylquinoline hydrochloride (83.0 g, 74%) as a yellow solid. MS (ES, m/z): 208 [M+H]+.

Step 2. 5-methoxy-2-methylquinoline

Into a 1000-mL 3-necked round-bottom flask, 8-chloro-5-methoxy-2-methylquinoline hydrochloride (50 g, 204.82 mmol) was dissolved in methanol (300 mL). Then sodium hydroxide (3M, 205 mL) and 10% palladium on carbon (25 g) were added. Hydrogen (g) was charged into the reaction mixture. The reaction mixture was stirred under a hydrogen atmosphere for 3 h at room temperature. The reaction was vented to nitrogen and the solids were filtered out over celite. The filtered solution was concentrated under vacuum. The residue was subjected to purification by FCC eluting with ethyl acetate/petroleum ether (1:5). This afforded the title compound (28.5 g, 80%) as a yellow oil. MS (ES, m/z): 174 [M+H]+.

Step 3. (2S)-5-methoxy-2-methyl-1,2,3,4-tetrahydroquinoline

Into a 30-mL pressure tank reactor (50 atm), 5-methoxy-2-methylquinoline (4.0 g, 23.09 mmol) was dissolved in methanol (10 mL). Then Ru(OTf)(η6-hexamethylbenzene) ((S,S)-TsDPEN) ([N-[(1S,2S)-2-(amino-κN)-1,2-diphenylethyl]-4-methylbenzenesulfonamidato-κN][(1,2,3,4,5,6-η)-1,2,3,4,5,6-hexamethylbenzene](1,1,1-trifluoromethanesulfonato-κO)-ruthenium, prepared according to the procedure in J. Am. Chem. Soc. 2011, 133, 9878-9891) (150 mg, 0.23 mmol) was added. To the above hydrogen was introduced in. The resulting solution was stirred for 6 h at room temperature. The resulting mixture was concentrated under vacuum. The residue was subjected to purification by FCC eluting with ethyl acetate/petroleum ether (1:4). This afforded the title compound (3.0 g, 73%) as a yellow oil. MS: (ES, m/z): 178 [M+H]+.

Step 4. methyl (S)-5-methoxy-2-methyl-3,4-dihydroquinoline-1(2H)-carboxylate

Into a 250-mL round-bottom flask, (2S)-5-methoxy-2-methyl-1,2,3,4-tetrahydroquinoline (18 g, 99.52 mmol) was dissolved in dichloromethane (100 mL). Then pyridine (23.6 g, 298.36 mmol) was added, followed by methyl carbonochloridate (9.4 g, 99.47 mmol). The resulting solution was stirred for 1 h at room temperature. The resulting solution was diluted with 100 mL of dichloromethane and washed with 3×200 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (21 g, 89%) as a yellow oil. MS: (ES, m/z): 236 [M+H]+.

Step 5. methyl (S)-5-hydroxy-2-methyl-3,4-dihydroquinoline-1(2H)-carboxylate Into a 500-mL 3-necked round-bottom flask, methyl (2S)-5-methoxy-2-methyl-1,2,3,4-tetrahydroquinoline-1-carboxylate (21 g, 89.36 mmol) was dissolved in dichloromethane (150 mL). Then boron tribromide (150 mL, 0.15 mol, 1 M in CH$_2$Cl$_2$) was added. The resulting solution was stirred for 1 h at room temperature. The reaction was then quenched by the addition of 300 mL of water. The resulting mixture was extracted with 3×300 mL of dichloromethane. The organic layers were combined, dried over anhydrous sodium sulfate, filtered and concentrated under vacuum. The residue was subjected to purification by FCC eluting with ethyl acetate/petroleum ether (1:2). This afforded the title compound (13.5 g, 68%) as a yellow solid. MS: (ES, m/z): 222 [M+H]$^+$.

Step 6. methyl (S)-2-methyl-5-(((trifluoromethyl)sulfonyl)oxy)-3,4-dihydroquinoline-1(2H)-carboxylate Into a 250-mL round-bottom flask, methyl (2S)-5-hydroxy-2-methyl-1,2,3,4-tetrahydroquinoline-1-carboxylate (5 g, 18.08 mmol) was dissolved in dichloromethane (50 mL). Then pyridine (14.3 g, 180.78 mmol) and trifluoromethanesulfonic anhydride (10.2 g, 36.15 mmol) were added. The resulting solution was stirred for 1 h at room temperature. The resulting mixture was washed with 3×100 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (5.5 g, 86%) as a yellow oil. MS: (ES, m/z): 354 [M+H]$^+$.

Step 7. methyl (S)-5-((diphenylmethylene)amino)-2-methyl-3,4-dihydroquinoline-1(2H)-carboxylate Into a 500-mL round-bottom flask purged and maintained with an inert atmosphere of nitrogen, methyl (2S)-2-methyl-5-[(trifluoromethane)sulfonyloxy]-1,2,3,4-tetrahydroquinoline-1-carboxylate (23.5 g, 65.18 mmol) was dissolved in toluene (100 mL). Then diphenylmethanimine (17.9 g, 97.78 mmol), tris(dibenzylideneacetone)dipalladium-chloroform adduct (1.19 μg, 1.30 mmol), (+/−)-2,2'-Bis(diphenylphosphino)-1,1'-binaphthyl (2.43 g, 3.90 mmol) and cesium carbonate (42.4 g, 130.13 mmol) were added. The resulting solution was stirred overnight at 100° C. under nitrogen atmosphere. The reaction mixture was cooled and the solids were filtered out. The residue was subjected to purification by FCC eluting with ethyl acetate/petroleum ether (1:3). This afforded the title compound (33 g, 80%) as a yellow oil. MS: (ES, m/z): 385 [M+H]$^+$.

Step 8. methyl (S)-5-amino-2-methyl-3,4-dihydroquinoline-1(2H)-carboxylate

Into a 500-mL round-bottom flask, methyl (2S)-5-[(diphenylmethylidene)amino]-2-methyl-1,2,3,4-tetrahydroquinoline-1-carboxylate (33 g, 85.93 mmol) was dissolved in methanol (200 mL). Then sodium acetate (17 g, 207.23 mmol) and hydroxylamine hydrochloride (12.3 g, 177.00 mmol) were added. The resulting solution was stirred for 2 h at room temperature. The solids were filtered out. The resulting mixture was concentrated under vacuum. The residue was subjected to purification by FCC eluting with ethyl acetate/petroleum ether (1:2). This afforded the title compound (12.5 g, 66%) as a yellow solid. MS: (ES, m/z): 221 [M+H]$^+$.

Step 9. methyl (S)-5-amino-6-bromo-2-methyl-3,4-dihydroquinoline-1(2H)-carboxylate (Intermediate 1)

Into a 100-mL 3-necked round-bottom flask, methyl (2S)-5-amino-2-methyl-1,2,3,4-tetrahydroquinoline-1-carboxylate (1 g, 4.09 mmol) was dissolved in acetonitrile (20 mL). Then N-bromosuccinimide (730 mg, 4.10 mmol) was added. The resulting solution was stirred for 30 min at room temperature. The resulting mixture was concentrated under vacuum. The residue was subjected to purification by FCC eluting with ethyl acetate/petroleum ether (1:1). This afforded the title compound (1.1 g, 90%) as a yellow solid. MS: (ES, m/z): 299, 301 [M+H]$^+$.
$^1$H-NMR: (400 MHz, CD$_3$OD, ppm): 7.19 (d, J=8.8 Hz, 1H), 6.84 (d, J=8.8 Hz, 1H), 4.73-4.69 (m, 1H), 3.74 (s, 3H), 2.64-2.57 (m, 1H), 2.55-2.44 (m, 1H), 2.12-2.05 (m, 1H), 1.82-1.79 (m, 1H), 1.17 (d, J=6.9 Hz, 3H).

Example 1-2

Synthesis of (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid (2)

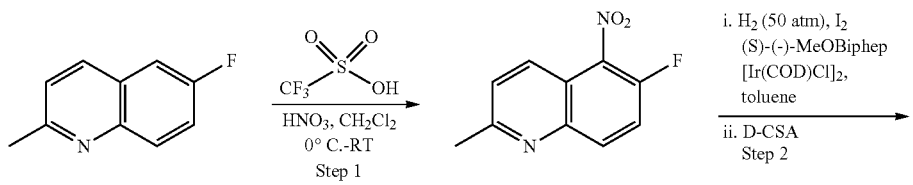

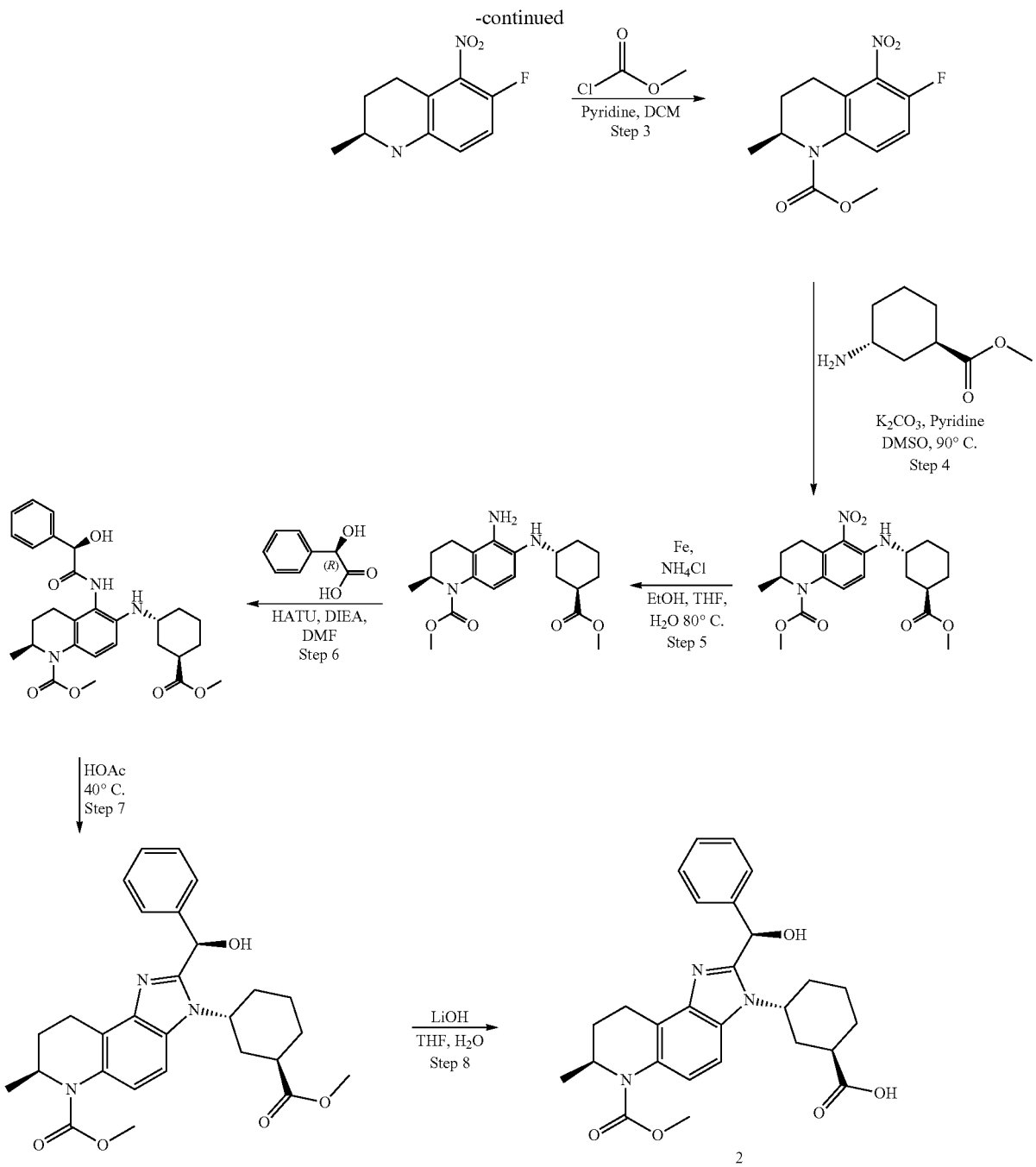

Step 1. 6-fluoro-2-methyl-5-nitroquinoline

A solution of trifluoromethanesulfonic acid (82.0 mL, 0.923 mol) in HNO$_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]$^+$.

Step 2. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of 12 (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]$^+$.

Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrogen chloride (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]$^+$.

Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2 S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 [M+H]$^+$.

Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2 S)-5-amino-6-[1[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 6. methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate A solution of (R)-2-hydroxy-2-phenylacetic acid (972 mg, 6.39 mmol), HATU (1.20 g, 3.16 mmol), methyl (2S)-5-amino-6-[[(1R,3R)-3-(methoxycarbonyl)cyclohexyl]amino]-2-methyl-1,2,3,4-tetrahydroquinoline-1-carboxylate (800 mg, 2.13 mmol), DIEA (1.08 mL, 6.20 mmol) in N,N-dimethylformamide (10 mL) was stirred for 5 h at room temperature (25° C.). The resulting solution was diluted with water (30 mL), and extracted with ethyl acetate (3×50 mL). The organic layers were combined and washed with brine (2×25 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate as a colorless oil (600 mg, 55%). LCMS (ES, m/z): 510 [M+H]$^+$ Step 7. methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate (600 mg, 1.18 mmol) in glacial acetic acid (5 mL, 98%) was stirred for overnight at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 69%) as a colorless oil. LCMS (ES, m/z): 492 [M+H]$^+$.

Step 8. (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid (2)

A solution of methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 0.81 mmol), LiOH (100 mg, 4.17 mmol) in tetrahydrofuran (5 mL) and water (2 mL) was stirred for overnight at room temperature (25° C.). The resulting mixture was concentrated under vacuum. The crude product was purified by Prep-HPLC (Column: XBridge Shield RP18 OBD Column, 5 m, 19×150 mm; Mobile Phase, A: water (containing 10 mmol/L NH$_4$HCO$_3$) and B: ACN (3% to 30% over 21 min); Detector: UV 254 nm). The product fractions were lyophilized to afford (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid (2) as a white solid (83.7 mg, 22%). Enantiomeric excess was determined via HPLC: Column: CHIRALPAK IE-3, Column size: 0.46×5 cm; 3 μm; Mobile phase: Hex (0.1% FA): EtOH=85:15, Flow: 1.0 ml/min.

$^1$H-NMR (CD$_3$OD, 400 MHz) δ (ppm): 7.47-7.28 (m, 7H), 6.12 (s, 1H), 4.84-4.74 (m, 2H), 3.79 (s, 3H), 3.33-3.25 (m, 1H), 3.03-2.96 (m, 1H), 2.86-2.82 (m, 1H), 2.38-2.25 (m, 2H), 2.25-2.07 (m, 3H), 1.79-1.72 (m, 1H), 1.64-1.57 (m, 2H), 1.40-1.29 (m, 2H), 1.16 (d, J=6.8 Hz, 3H). LCMS (ES, m/z): 478 [M+H]$^+$; 99.13% ee.

A composition of Formula (I) can comprise a compound of one or more of Formula (III-a), (III-b), (III-c), (III-d), (III-e), (III-f), (III-g), (III-h), (III-i), (III-j), (III-k), (III-l), (III-m), (III-n), and/or (III-o). For example, in some embodiments the disclosure provides a composition comprising compound 2 of the foregoing structure or a pharmaceutically acceptable salt thereof at a purity of at least 90% wherein the composition comprises less than 10%, e.g. less than 9%, less than 8%, less than 7%, less than 6%, less than 5%, less than 4%, less than 3%, less than 2% or less than 1%, collectively of one or more of the following stereoisomers of compound 2, represented as Formulae (III-a)-(III-o) below:

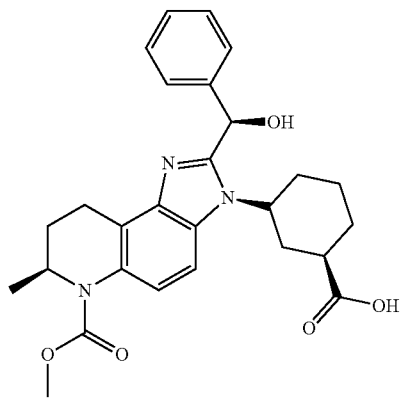

(III-a)

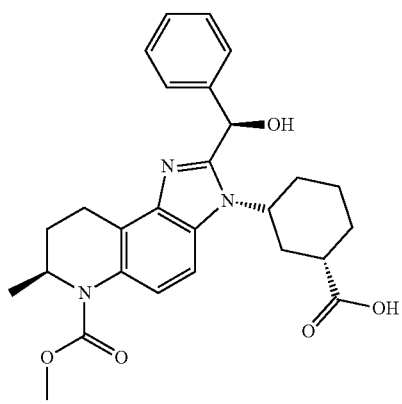

(III-b)

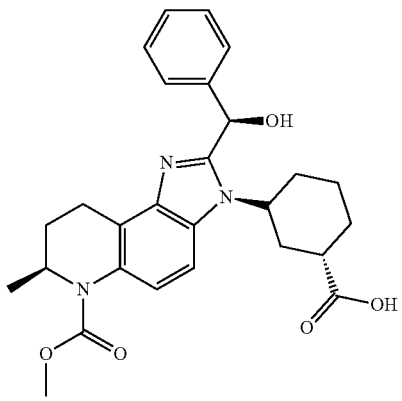

(III-c)

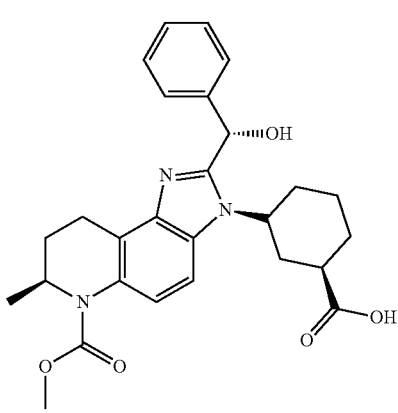

(III-d)

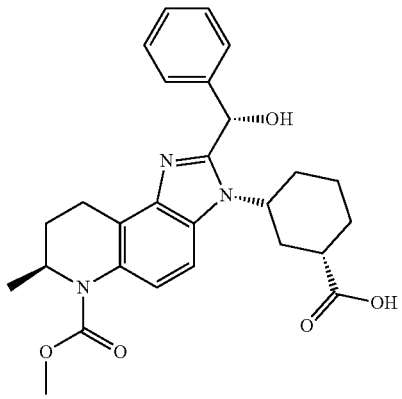

(III-e)

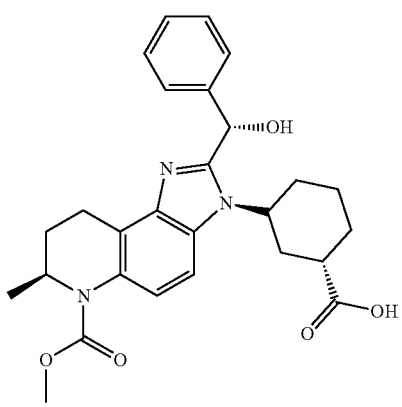

(III-f)

-continued
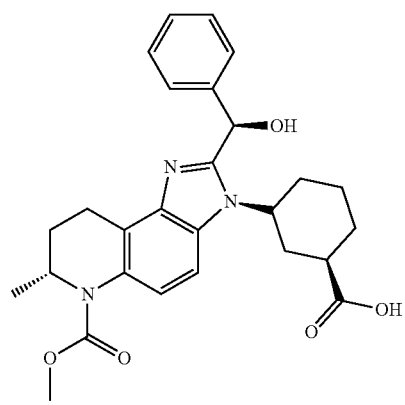
(III-g)
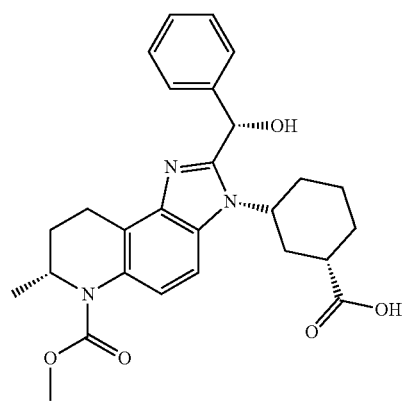
(III-k)
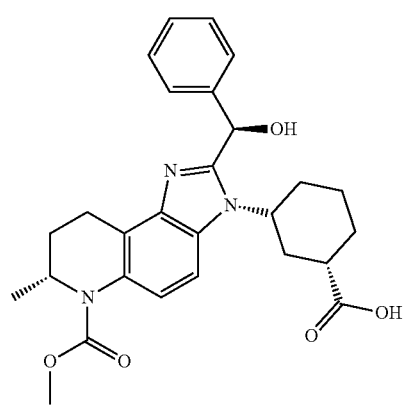
(III-h)
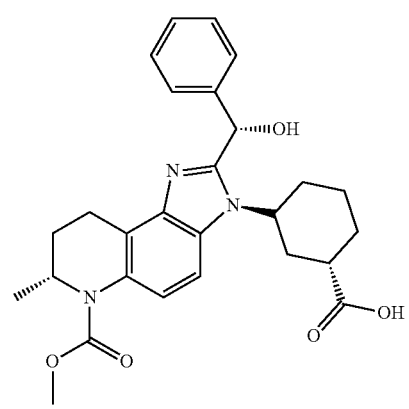
(III-l)
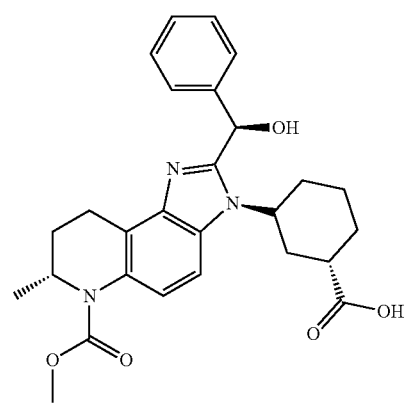
(III-i)
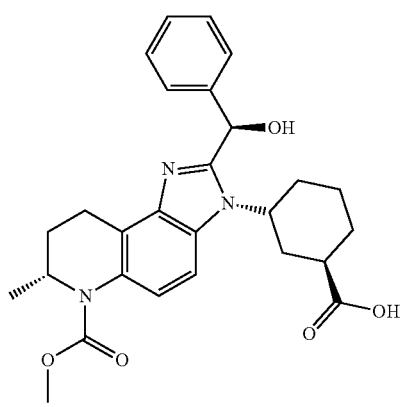
(III-m)
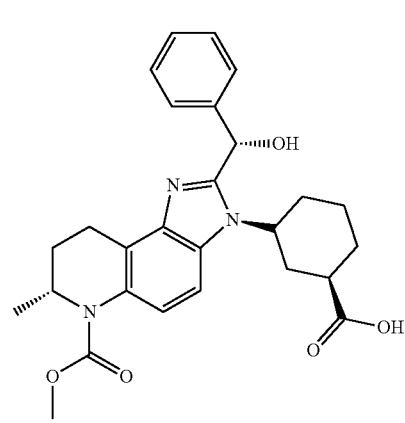
(III-j)
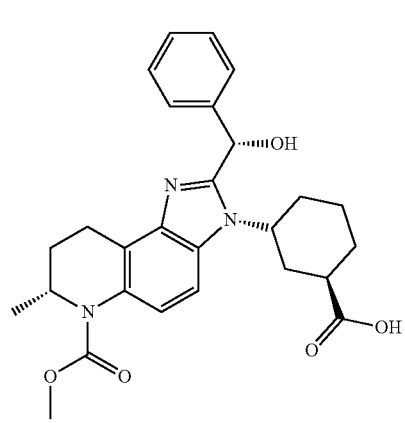
(III-n)

-continued (III-o)

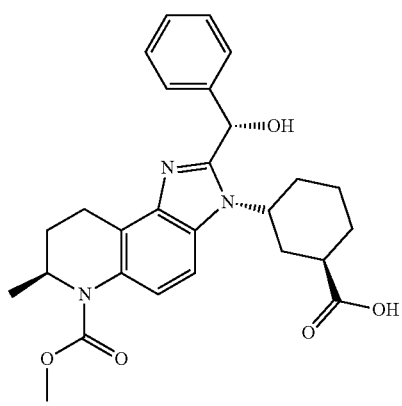

For instance, the disclosure provides a pharmaceutical composition comprising compound 2 or a pharmaceutically acceptable salt thereof at a purity of at least 95% as determined by the above HPLC method of Example 22. The disclosure also provides a pharmaceutical composition comprising compound 2 at a purity of at least 95% as determined by the above HPLC method.

Example 1-3

Synthesis of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1) and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1')

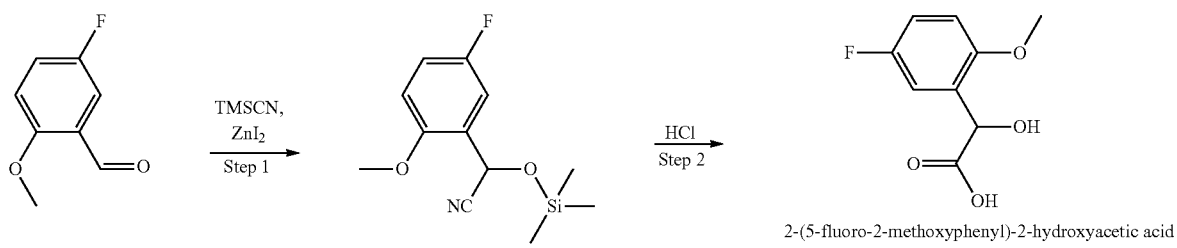

2-(5-fluoro-2-methoxyphenyl)-2-hydroxyacetic acid

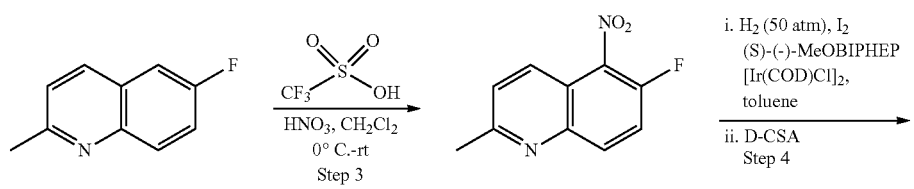

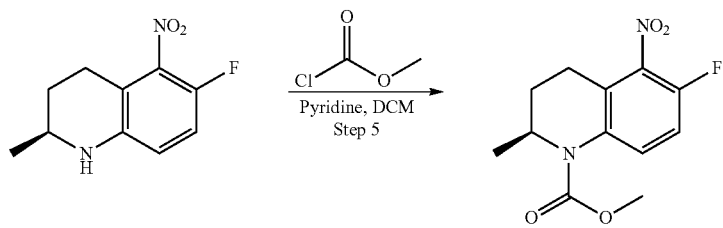

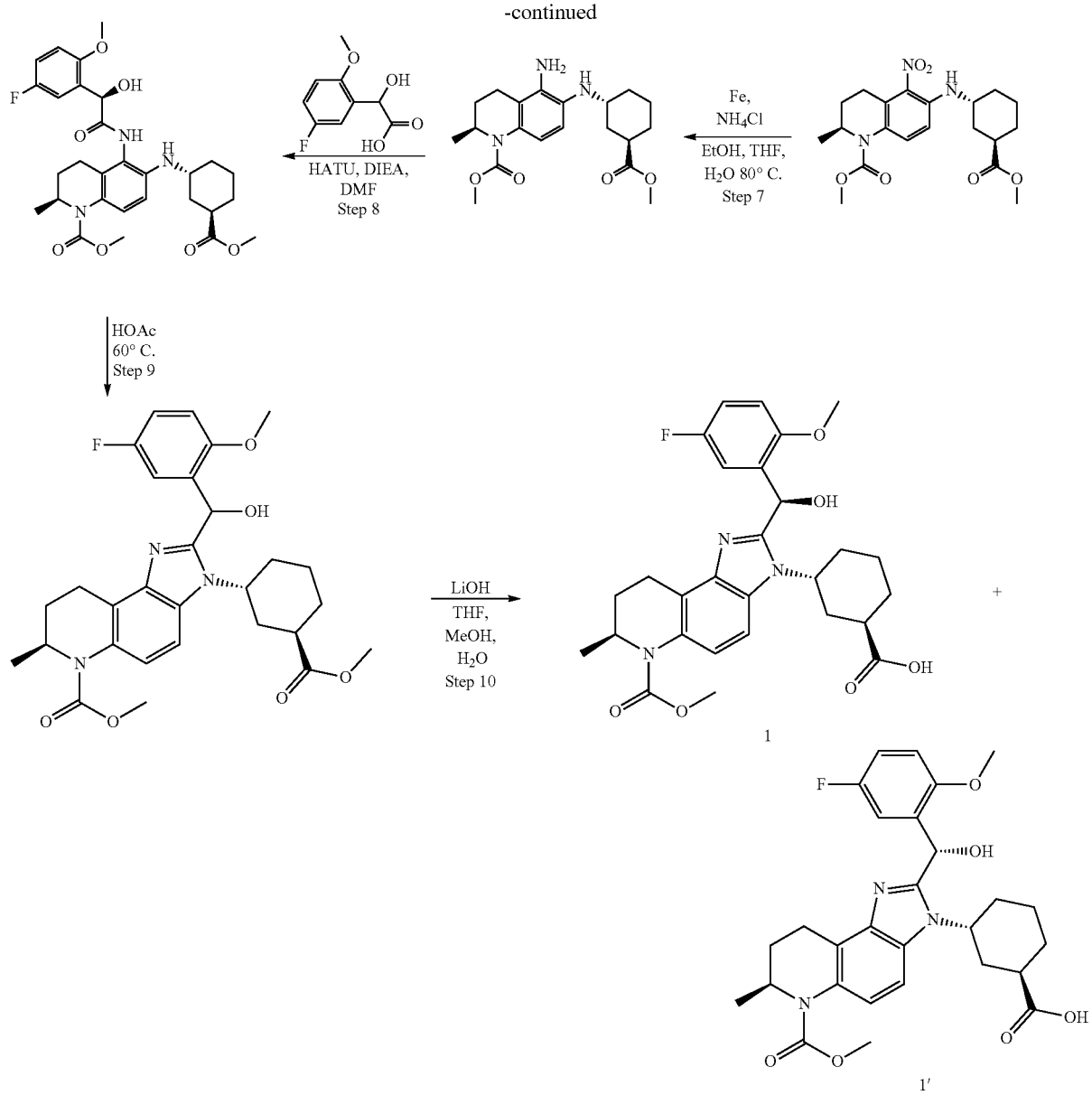

Step 1. 2-(5-fluoro-2-methoxyphenyl)-2-[(trimethylsilyl)oxy]acetonitrile

A solution of $ZnI_2$ (1.6 mg, 0.01 mmol), 5-fluoro-2-methoxybenzaldehyde (1.54 g, 9.99 mmol) in trimethylsilanecarbonitrile (1.5 mL, 11.25 mmol) was stirred for 1 h at room temperature. The resulting mixture was concentrated under vacuum. The resulting crude product was purified by silica gel chromatography (eluting with 1:1 ethyl acetate/petroleum ether) to afford 2-(5-fluoro-2-methoxyphenyl)-2-[(trimethylsilyl)oxy]acetonitrile as a white solid (2.0 g, 79%).

Step 2. 2-(5-fluoro-2-methoxyphenyl)-2-hydroxyacetic acid

A solution of 2-(5-fluoro-2-methoxyphenyl)-2-[(trimethylsilyl)oxy]acetonitrile (1.50 g, 5.92 mmol) in hydrochloric acid (10 mL, 12 M) was stirred for 1 h at 25° C., and then stirred for 2 h at 70° C. The reaction mixture was cooled and concentrated under vacuum. The crude product was purified by reverse phase chromatography (Column: C18; Mobile phase, A: water (containing 0.05% TFA) and B: ACN (5% to 20% over 30 min); Detector, UV 254 nm) to afford 2-(5-fluoro-2-methoxyphenyl)-2-hydroxyacetic acid as a white solid (1.10 g, 93%).

Step 3. 6-fluoro-2-methyl-5-nitroquinoline

A solution of trifluoromethanesulfonic acid (82.0 mL, 0.923 mol) in $HNO_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]$^+$.

Step 4. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of 12 (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]$^+$.

Step 5. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrochloric acid (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]$^+$.

Step 6. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2 S)-6-[[(1R,3R)-3-(methoxycarbonyl) cyclohexyl] amino]-2-methyl-5-nitro-1,2,3,4-tetrahydroquinoline-1-carboxylate as a red oil (32 g, 72%). LCMS (ES, m/z): 406 [M+H]$^+$.

Step 7. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), and water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 8. methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate A solution of 2-(5-fluoro-2-methoxyphenyl)-2-hydroxyacetic acid (240 mg, 1.20 mmol), HATU (228 mg, 0.60 mmol), methyl (2S)-5-amino-6-[[(1R,3R)-3-(methoxycarbonyl) cyclohexyl]amino]-2-methyl-1,2,3,4-tetrahydroquinoline-1-carboxylate (150 mg, 0.40 mmol), DIEA (0.19 mL, 1.20 mmol) in N,N-dimethylformamide (10 mL) was stirred for 1 h at 25° C. The resulting solution was diluted with H$_2$O (10 mL). The resulting solution was extracted with ethyl acetate (3×15 mL) and the organic layers combined. The resulting mixture was washed with brine (2×20 mL). The mixture was dried over anhydrous sodium sulfate and concentrated under vacuum. The resulting crude product was purified by silica gel chromatography (eluting with 3:2 ethyl acetate/petroleum ether) to afford methyl (2S)-5-[2-(5-fluoro-2-methoxyphenyl)-2-hydroxyacetamido]-6-[[(1R, 3R)-3-(methoxycarbonyl)cyclohexyl]amino]-2-methyl-1,2, 3,4-tetra-hydroquinoline-1-carboxylate as a yellow solid (180 mg, 81%). LCMS (ES, m/z): 558 [M+H]$^+$.

Step 9. methyl (7S)-2-[(5-fluoro-2-methoxyphenyl) (hydroxy)methyl]-3-[(1R,3R)-3-(methoxycarbonyl) cyclohexyl]-7-methyl-3H,6H,7H,8H,9H-imidazo[4, 5-f]quinoline-6-carboxylate A solution of methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate (180 mg, 0.32 mmol) in AcOH (8 mL) was stirred for overnight at 60° C. The reaction mixture was cooled and concentrated under vacuum. The resulting crude product was purified by silica gel chromatography (eluting with 1:1 ethyl acetate/petroleum ether) to afford methyl (7S)-2-[(5-fluoro-2-methoxyphenyl)(hydroxy)methyl]-3-[(1R,3R)-3-(methoxycarbonyl)cyclohexyl]-7-methyl-3H, 6H,7H,8H,9H-imidazo[4,5-f]quinoline-6-carboxylate as a yellow solid (120 mg, 69%). LCMS (ES, m/z): 540 [M+H]+.

Step 10. (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1) and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1')

A solution of methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate (120 mg, 0.22 mmol), and LiOH (16 mg, 0.67 mmol) in tetrahydrofuran (2.0 mL), methanol (2.0 mL) and water (2.0 mL) was stirred overnight at 25° C. The resulting mixture was concentrated under vacuum. The crude product was purified by Prep-HPLC (Column, XBridge Prep C18 OBD Column, 19×150 mm, 5 m; Mobile phase, A: water (containing 10 mmol/L NH4HCO3) and B: ACN (15.0% to 29.0% over 14 min); Detector, UV 220/254 nm). The product was separated by Chiral-Prep-HPLC (Column, CHIRALPAK IE, 2×25 cm, 5 μm; Mobile phase, A: Hex (containing 0.1% FA) and B: ethanol (hold 50.0% ethanol over 12 min); Detector, UV 220/254 nm). The product fractions were concentrated to afford (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1) as a white solid (23.6 mg, 20%); and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1') as a white solid (23.8 mg, 20%). Stereoisomeric purity was determined via HPLC: Column: CHIRALPAK IE-3, Column size: 0.46×5 cm; 3 μm; Mobile phase: Hex (0.1% FA): EtOH=50:50, Flow: 1.0 ml/min.

First eluting isomer (1): 1H-NMR (CD3OD, 400 MHz) δ (ppm): 7.56-7.47 (m, 1H), 7.47-7.31 (m, 1H), 7.21-7.09 (m, 1H), 7.09-6.89 (m, 2H), 6.53 (s, 1H), 4.81-4.61 (m, 2H), 3.85 (s, 3H), 3.78 (s, 3H), 3.31-3.18 (m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.16 (d, J=6.8 Hz, 3H). LCMS (ES, m/z): 526 [M+H]+.

Second eluting isomer (1'): 1H-NMR (CD3OD, 400 MHz) δ (ppm): 7.69-7.44 (m, 2H), 7.44-7.29 (m, 1H), 7.12-6.99 (m, 1H), 6.98-6.82 (m, 1H), 6.37 (s, 1H), 5.03-4.91 (m, 1H), 4.81-4.69 (m, 1H), 3.78 (s, 3H), 3.61 (s, 3H), 3.22-3.04 (m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J=6.4 Hz, 3H). LCMS (ES, m/z): 526 [M+H]+.

A composition of Formula (I) can comprise a compound of one or more of Formula (II-a), (II-b), (II-c), (II-d), (II-e), (II-f), (II-g), (II-h), (II-i), (II-j), (II-k), (II-l), (II-m), (II-n), and/or (II-o). For example, in some embodiments the disclosure provides a composition comprising compound 1 of the foregoing structure or a pharmaceutically acceptable salt thereof at a purity of at least 90% wherein the composition comprises less than 10%, e.g. less than 9%, less than 8%, less than 7%, less than 6%, less than 5%, less than 4%, less than 3%, less than 2% or less than 1%, collectively of one or more of the following stereoisomers of compound 1, represented as Formulae (II-a)-(II-o) below:

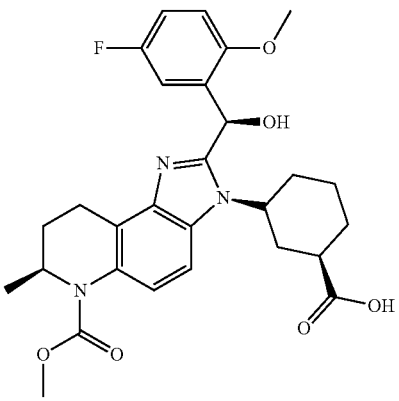
(II-a)

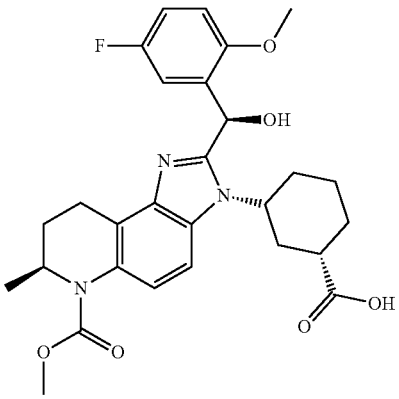
(II-b)

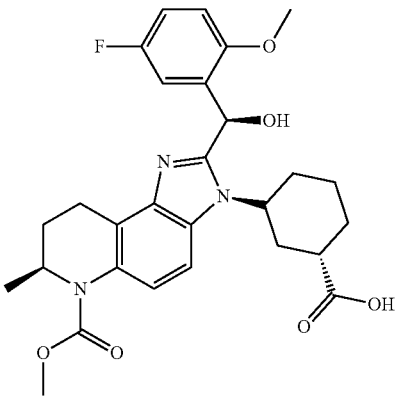
(II-c)

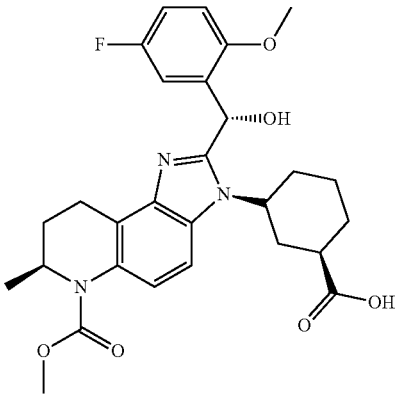
(II-d)

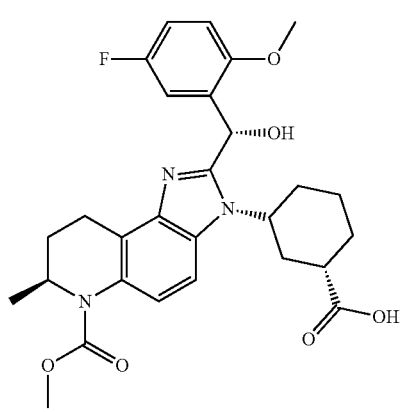
(II-e)
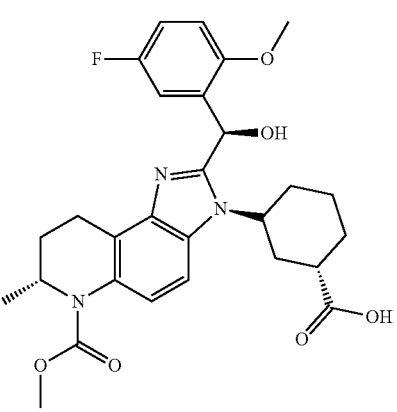
(II-i)
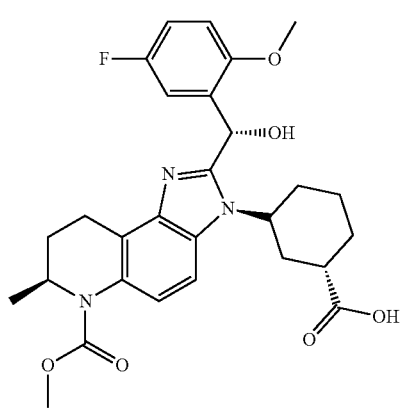
(II-f)
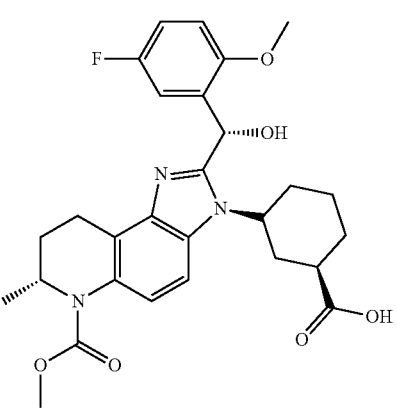
(II-j)
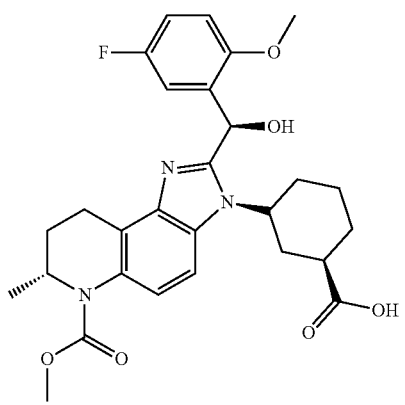
(II-g)
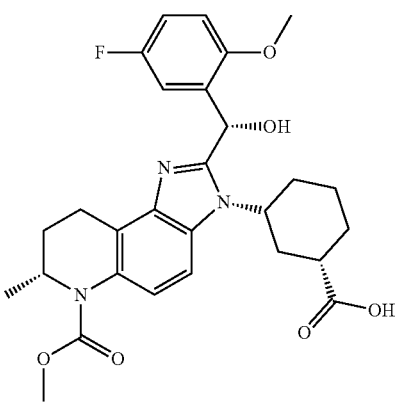
(II-k)
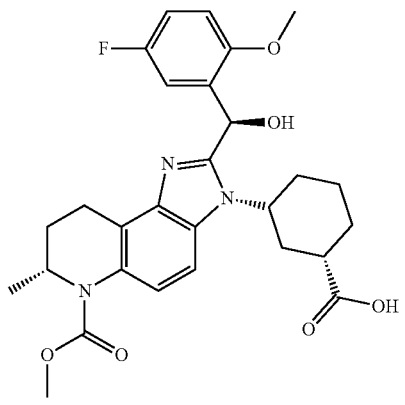
(II-h)
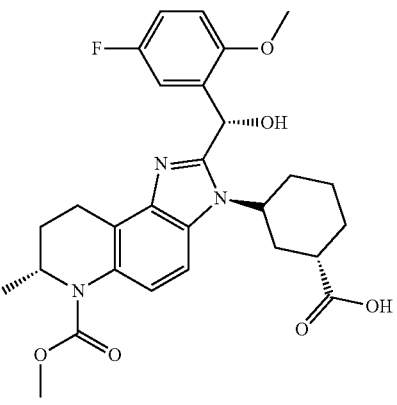
(II-l)

87

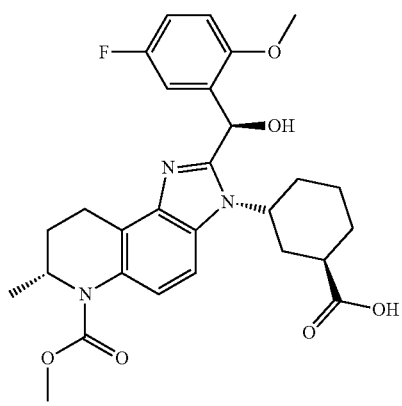

(II-m)

(II-n)

(II-o)/compound 1'

For instance, the disclosure provides a pharmaceutical composition comprising compound 1 or a pharmaceutically acceptable salt thereof at a purity of at least 95% as determined by the above HPLC method of Example 22. The disclosure also provides a pharmaceutical composition comprising compound 1 at a purity of at least 95% as determined by the above HPLC method.

The disclosure provides a compound of Formula II obtained by the foregoing method exemplified in Example 1-3:

88

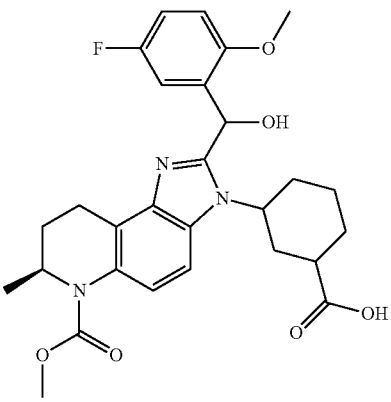

(II)

or a pharmaceutically acceptable salt, enantiomer, hydrate, solvate, isomer or tautomer thereof.

It will be apparent to the skilled reader that each of the stereoisomers of the compound of Formula (II) can be obtained by varying the stereochemistry of the appropriate reagents utilized in the method of Example 1-3 above. For instance, by adjusting the reagent used in Step 4 of Example 1-3, compounds such as those of Formulae (II-m) and (II-n) can be synthesized. Similarly, in Step 6 of Example 1-3, the reagent methyl (1S,3R)-3-aminocyclohexane-1-carboxylate can be used in place of methyl (1R,3R)-3-aminocyclohexane-1-carboxylate to obtain compounds of Formulae (II-b) and (II-e). It will be apparent to the skilled reader that by making a combination of these types of modifications to the process set out in Example 1-3, each of compounds (II-a) to (II-o) depicted above can be synthesized.

Example 1-4

Synthesis of (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid and (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (3)

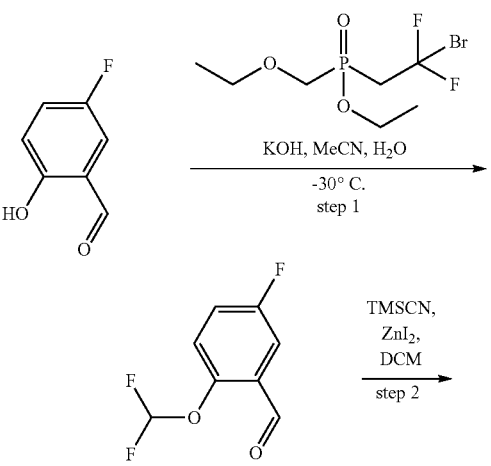

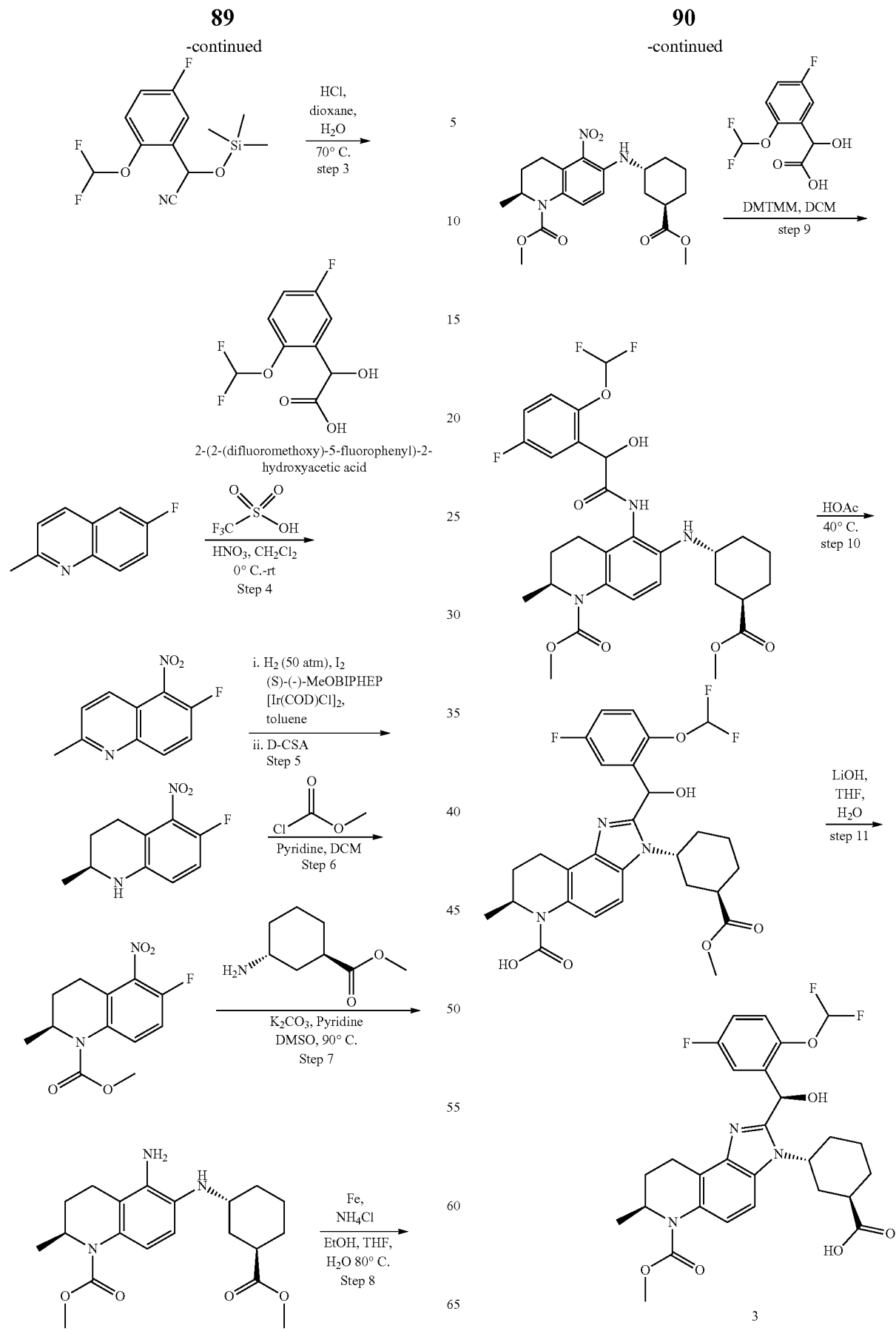

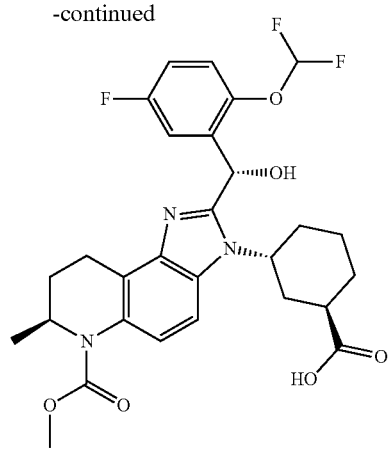

452

Step 1. 2-(difluoromethoxy)-5-fluorobenzaldehyde

A solution of 5-fluoro-2-hydroxybenzaldehyde (2.0 μg, 14.3 mmol), diethyl (bromodifluoromethyl)phosphonate (5.69 g, 21.3 mmol), potassium hydroxide (16.0 g, 285 mmol) in MeCN (100 mL) and water (50 mL) was stirred for 1 h at −30° C. The reaction mixture was diluted with water (20 mL). The resulting solution was extracted with ethyl acetate (3×100 mL) and the organic layers combined and dried over anhydrous sodium sulfate. The solids were filtered out. The resulting mixture was concentrated under vacuum. The resulting crude product was purified by silica gel chromatography (eluting with 1:1 ethyl acetate/petroleum ether) to afford 2-(difluoromethoxy)-5-fluorobenzaldehyde as a yellow solid (1.46 g, 54%). LCMS (ES, m/z): 191 [M+H]⁺.

Step 2. 2-[2-(difluoromethoxy)-5-fluorophenyl]-2-[(trimethylsilyl)oxy]acetonitrile A solution of 2-(difluoromethoxy)-5-fluorobenzaldehyde (1.46 g, 7.68 mmol), TMSCN (760 mg, 7.66 mmol), ZnI₂ (50 mg, 0.16 mmol) in dichloromethane (3 mL) was stirred for 2 h at room temperature (25° C.). The resulting mixture was concentrated under vacuum. The resulting crude product was purified by silica gel chromatography (eluting with 1:1 ethyl acetate/petroleum ether) to afford 2-[2-(difluoromethoxy)-5-fluorophenyl]-2-[(trimethylsilyl) oxy]acetonitrile as a yellow solid (800 mg, 36%). LCMS (ES, m/z):290 [M+H]⁺-Step 3. 2-[2-(difluoromethoxy)-5-fluorophenyl]-2-hydroxyacetic acid A solution of 2-[2-(difluoromethoxy)-5-fluorophenyl]-2-[(trimethylsilyl)oxy] acetonitrile (800 mg, 2.77 mmol), 1,4-dioxane (2.0 mL), hydrogen chloride (1.0 mL, 12M) in water (2 mL) was stirred for 12 h at 70° C. and then cooled to room temperature. The resulting solution was concentrated under vacuum. The crude product was purified by reverse phase column chromatography (water (containing 0.05% TFA)/MeCN) to afford 2-[2-(difluoromethoxy)-5-fluorophenyl]-2-hydroxyacetic acid (400 mg, 61%). LCMS (ES, m/z): 237 [M+H]⁺.

Step 4. 6-fluoro-2-methyl-5-nitroquinoline

A solution of trifluoromethanesulfonic acid (82.0 mL, 0.923 mol) in HNO₃ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]⁺.

Step 5. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of 12 (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]⁺.

Step 6. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrogen chloride (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]⁺.

Step 7. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2 S)-6-[[(1R,3R)-3-(methoxycarbonyl)cyclohexyl] amino]-2-methyl-5-nitro-1,2,3,4-tetrahydroquinoline-1-carboxylate as a red oil (32 g, 72%). LCMS (ES, m/z): 406 [M+H]$^+$.

Step 8. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 9. methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate A solution of methyl (2S)-5-amino-6-[[(1R,3R)-3-(methoxycarbonyl)cyclohexyl] amino]-2-methyl-1,2,3,4-tetrahydroquinoline-1-carboxylate (200 mg, 0.53 mmol), 2-[2-(difluoromethoxy)-5-fluorophenyl]-2-hydroxyacetic acid (220 mg, 0.93 mmol), DMTMM (350 mg, 1.26 mmol) in dichloromethane (5 mL) was stirred for 1 h room temperature (25° C.). The resulting solution was concentrated under vacuum. The resulting crude product was purified by silica gel chromatography (eluting with 1:1 ethyl acetate/ petroleum ether) to afford methyl (2S)-5-[2-[2-(difluoromethoxy)-5-fluorophenyl]-2-hydroxyacetamido]-6-[[(1R, 3R)-3-(methoxycarbonyl)cyclohexyl]amino]-2-methyl-1,2, 3,4-tetrahydroquinoline-1-carboxylate as a yellow solid (70.0 mg, 22%). LCMS (ES, m/z): 594 [M+H]$^+$.

Step 10. methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate (70.0 mg, 0.12 mmol) in glacial acetic acid (2.0 mL) was stirred for overnight at 40° C. and then cooled to room temperature. The resulting solution was concentrated under vacuum. The resulting crude product was purified by silica gel chromatography (eluting with 1:2 ethyl acetate/petroleum ether) to afford methyl (7 S)-2-[[2-(difluoromethoxy)-5-fluorophenyl](hydroxy)methyl]-3-[(1R,3R)-3-(methoxycarbonyl) cyclohexyl]-7-methyl-3H,6H,7H,8H,9H-imidazo[4,5-f]quinoline-6-carboxylate as a yellow solid (50.0 mg, 74%). LCMS (ES, m/z): 576 [M+H]$^+$.

Step 11. (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (452); (1R,3R)-3-[(7S)-2-[(R)-[2-(difluoromethoxy)-5-fluorophenyl](hydroxy) methyl]-6-(methoxycarbonyl)-7-methyl-3H,6H,7H, 8H,9H-imidazo[4,5-f]quinolin-3-yl]cyclohexane-1-carboxylic acid (3)

A solution of methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4, 5-f] quinoline-6-carboxylate (50.0 mg, 0.09 mmol), LiOH (10.0 mg, 0.42 mmol) in tetrahydrofuran (2.0 mL) and water (2.0 mL) was stirred for overnight at room temperature (25° C.). The resulting mixture was concentrated under vacuum. The crude product was purified by Prep-HPLC (Column, XBridge Shield RP18 OBD Column, 30×150 mm, 5 m; Mobile phase, A: water (containing 10 mmol/L NH$_4$HCO$_3$) and B: ACN (25.0% to 35.0% over 8 min); Detector, UV 254/220 nm). The product fractions were concentrated to afford (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (452) as a white solid (4.50 mg, 9%), and (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (3) as a white solid (4.30 mg, 9%). Enantiomeric excess was determined via HPLC: Column: CHIRALPAK IE-3, Column size: 0.46×5 cm; 3 μm; Co-Solvent: IPA (20 mM NH$_3$) Gradient (B %): 10% to 50% in 4.0 min, hold 2.0 min at 50%.

First eluting isomer: $^1$H-NMR (CD$_3$OD, 400 MHz) δ (ppm): 7.63-7.61 (m, 1H), 7.53 (d, J=8.8 Hz, 1H), 7.41 (d, J=9.2 Hz, 1H) 7.20-7.13 (m, 2H), 6.67-6.30 (m, 2H), 4.98-4.95 (m, 1H), 4.76-4.71 (m, 1H), 3.78 (s, 3H), 3.15-2.86 (m, 3H), 2.46-2.20 (m, 5H), 1.81-1.53 (m, 5H), 1.13 (d, J=6.8 Hz, 3H). LCMS (ES, m/z): 562 [M+H]$^+$.

Second eluting isomer: $^1$H-NMR (CD$_3$OD, 400 MHz) δ (ppm): 7.55-7.53 (m, 1H), 7.47-7.42 (m, 2H), 7.40-7.12 (m, 2H), 6.85-6.44 (m, 2H), 4.94-4.91 (m, 1H), 4.76-4.71 (m, 1H), 3.78 (s, 3H), 3.22-2.84 (m, 3H), 2.46-2.23 (m, 5H), 1.84-1.61 (m, 5H), 1.14 (d, J=6.4 Hz, 3H). LCMS (ES, m/z): 562 [M+H]$^+$; >99.99% ee.

In some embodiments, the disclosure provides the first eluting isomer obtained from Step 11 of the process described in Example 1-4. In some embodiments, the disclosure provides the second eluting isomer obtained from Step 11 of the process described in Example 1-4.

A composition of Formula (I) can comprise a compound of one or more of Formula (IV-a), (IV-b), (IV-c), (IV-d), (IV-e), (IV-f), (IV-g), (IV-h), (IV-i), (IV-j), (IV-k), (IV-l), (IV-m), (IV-n), and/or (IV-o). For example, in some embodiments the disclosure provides a composition comprising compound 3 of the foregoing structure or a pharmaceutically acceptable salt thereof at a purity of at least 90% wherein the composition comprises less than 10%, e.g. less than 9%, less than 8%, less than 7%, less than 6%, less than 5%, less than 4%, less than 3%, less than 2% or less than 1%, collectively of one or more of the following stereoisomers of compound 3, represented as Formulae (IV-a)-(IV-o) below:

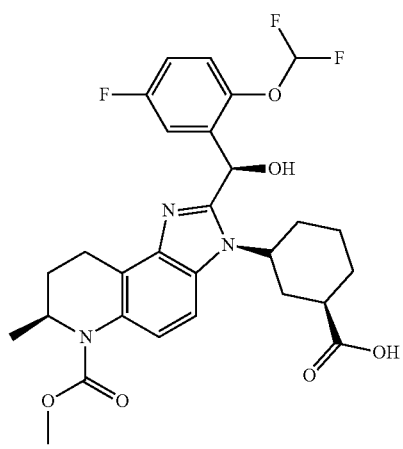
(IV-a)
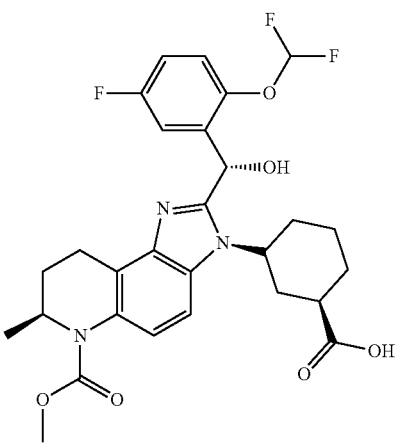
(IV-d)
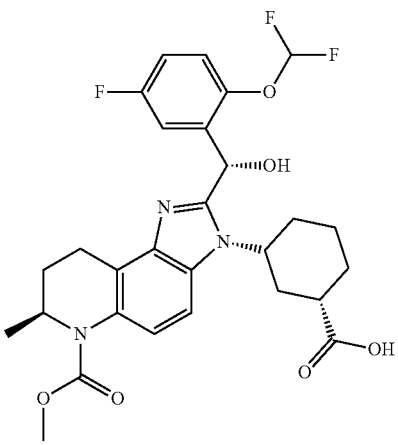
(IV-e)
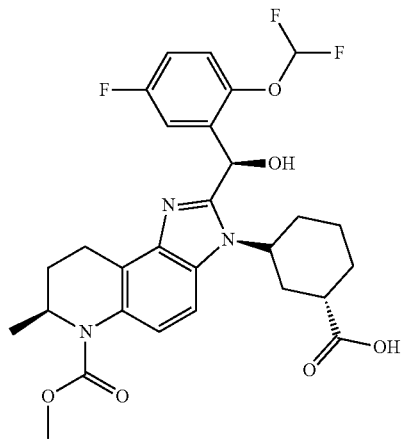
(IV-b)
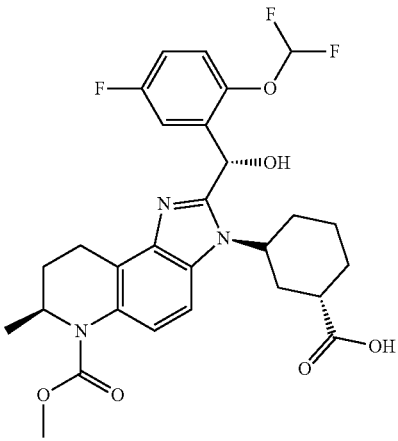
(IV-f)
(IV-c)

-continued
(IV-g)
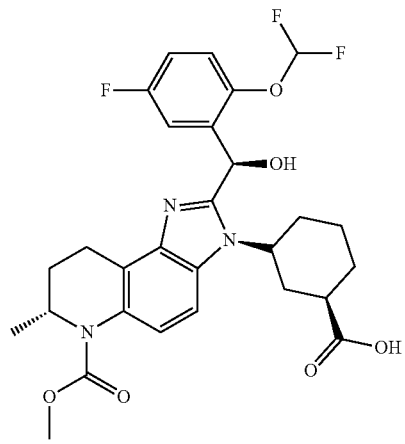
(IV-h)
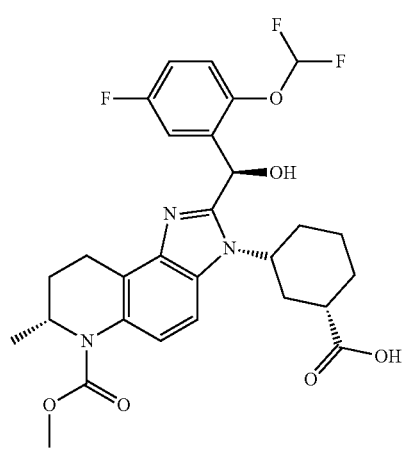
(IV-i)
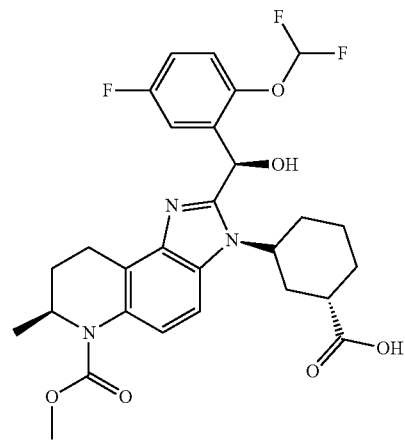
-continued
(IV-j)
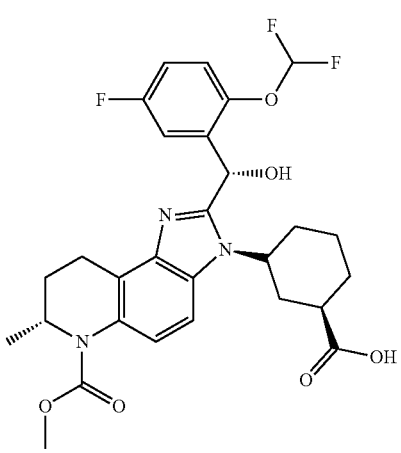
(IV-k)
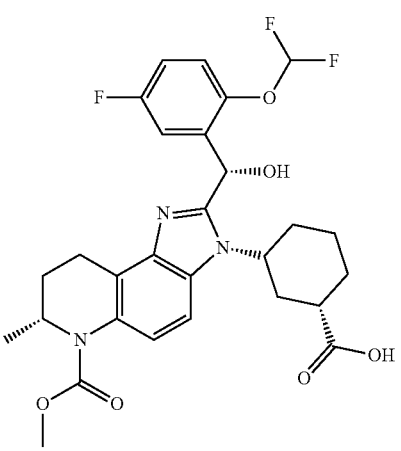
(IV-l)
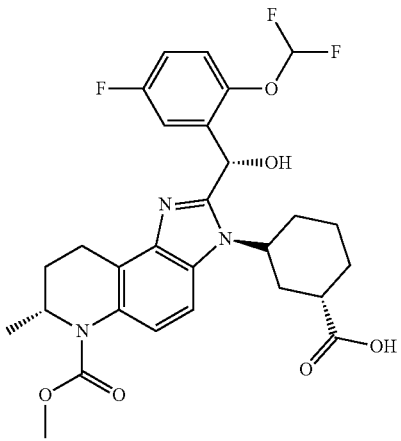

-continued (IV-m)

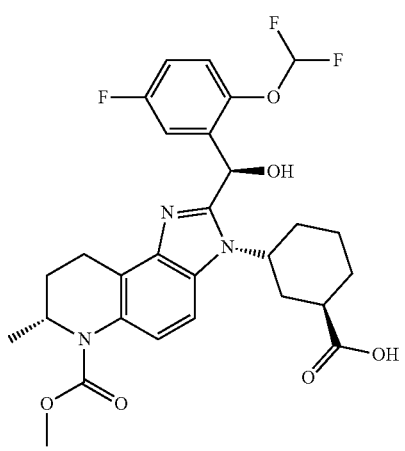

(IV-n)

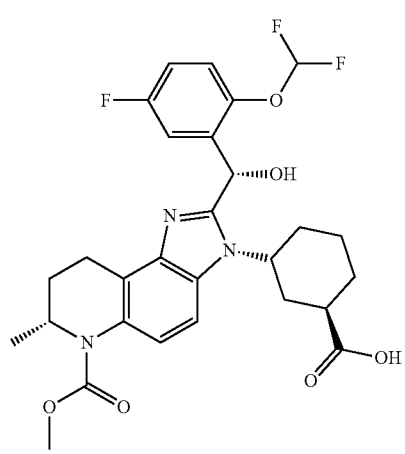

(IV-o)

For instance, the disclosure provides a pharmaceutical composition comprising compound 3 or a pharmaceutically acceptable salt thereof at a purity of at least 95% as determined by the above HPLC method of Example 22. The disclosure also provides a pharmaceutical composition comprising compound 3 at a purity of at least 95% as determined by the above HPLC method.

Example 1-5

(1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid (4)

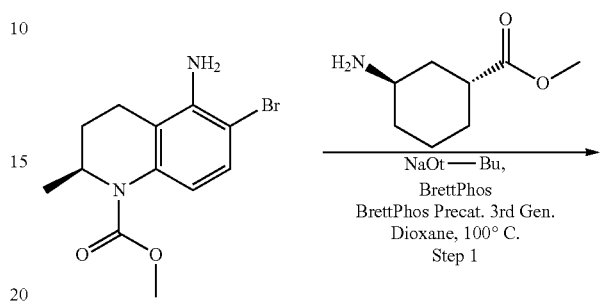

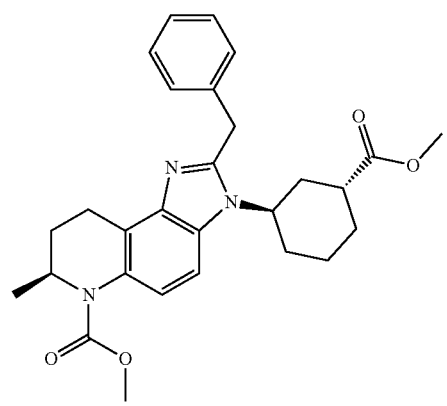

4

Step 1. methyl (S)-5-amino-6-(((1R,3R)-3-(methoxycarbonyl)cyclohexyl)amino)-2-methyl-3,4-dihydroquinoline-1-(2H)-carboxylate Into a 10-mL round-bottom flask purged and maintained with an inert atmosphere of nitrogen, methyl (1R,3R)-3-aminocyclohexane-1-carboxylate hydrochloride (130 mg, 0.67 mmol) was dissolved in dioxane (4 mL). Then methyl (2S)-5-amino-6-bromo-2-methyl-1,2,3,4-tetrahydroquinoline-1-carboxylate (100 mg, 0.33 mmol, Intermediate 1), Brettphos (72 mg, 0.13 mmol), 3$^{rd}$ Generation Brettphos pre-catalyst (61 mg, 0.07 mmol) and sodium tert-butoxide (97 mg, 1.01 mmol) were added. The resulting solution was stirred for 1 h at 100° C. under nitrogen atmosphere. The reaction mixture was cooled and the solids were filtered out. The resulting mixture was concentrated under vacuum. The residue was subjected to purification by FCC eluting with ethyl acetate/petroleum ether (2:1). This afforded the title compound (41.3 mg, 33%) as a dark green solid. MS: (ES, m/z): 376 [M+H]$^+$.

Step 2. methyl (S)-2-benzyl-3-((1R,3R)-3-(methoxycarbonyl)cyclohexyl)-7-methyl-3,7,8,9-tetrahydro-6H-imidazo[4,5-f]quinoline-6-carboxylate Into a 25-mL round-bottom flask, methyl (S)-5-amino-6-(((1R,3R)-3-(methoxycarbonyl)cyclohexyl)amino)-2-methyl-3,4-dihydroquinoline-1(2H)-carboxylate (165.4 mg, 0.44 mmol) was dissolved in dichloromethane (5 mL). Then 2-phenylacetaldehyde (158.8 mg, 1.32 mmol) was added. The resulting solution was stirred for 2 h at room temperature. The resulting mixture was concentrated under vacuum. The residue was subjected to purification by FCC eluting with ethyl acetate/petroleum ether (2:1). This afforded the title compound (122.9 mg, 59%) as a yellow solid. MS: (ES, m/z): 476 [M+H]$^+$.

Step 3. (1R,3R)-3-[(7S)-2-benzyl-6-(methoxycarbonyl)-7-methyl-3H,6H,7H,8H,9H-imidazo[4,5-f]quinolin-3-yl]cyclohexane-1-carboxylic acid (4)

Into a 25-mL round-bottom flask, methyl (S)-2-benzyl-3-((1R,3R)-3-(methoxycarbonyl)cyclohexyl)-7-methyl-3,7,8,9-tetrahydro-6H-imidazo[4,5-f]quinoline-6-carboxylate (30 mg, 0.06 mmol) was dissolved in tetrahydrofuran (0.5 mL). Then water (0.5 mL) was added, followed by lithium hydroxide (7.0 mg, 0.29 mmol). The resulting solution was stirred for 3 h at 85° C. The pH value of the solution was adjusted to 5-6 with hydrochloric acid (1 mol/L). The resulting solution was extracted with ethyl acetate (3×20 mL). The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase, A: Water (containing 10 mmol/L NH$_4$HCO$_3$) and B: ACN (10.0% to 30.0% ACN over 10 min); UV Detector: 254 nm. This afforded the title compound (15.2 mg, 52%) as a white solid.

$^1$H NMR (CD$_3$OD, 400 MHz) δ (ppm): 7.47 (d, J=9.0 Hz, 1H), 7.39 (d, J=8.9 Hz, 1H), 7.35-7.19 (m, 5H), 4.84-4.68 (m, 2H), 4.45-4.25 (m, 2H), 3.79 (s, 3H), 3.22-3.14 (m, 1H), 2.98-2.85 (m, 2H), 2.40-2.02 (m, 5H), 1.83-1.70 (m, 1H), 1.64-1.54 (m, 2H), 1.33-1.13 (m, 5H). MS: (ES, m/z): 462 [M+H]$^+$.

Compound 17, Compound 18, and Compound 19 were prepared using standard chemical manipulations and procedures similar to those used for the preparation of Example 1-5.

Example 1-6

3-((7S)-2-((4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid (413); and (1R,3R)-3-((S)-2-((S)-(4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid (501)

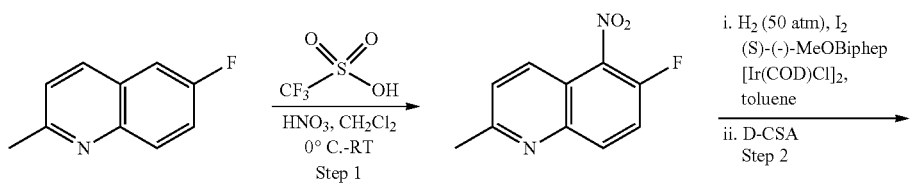

103 104
-continued
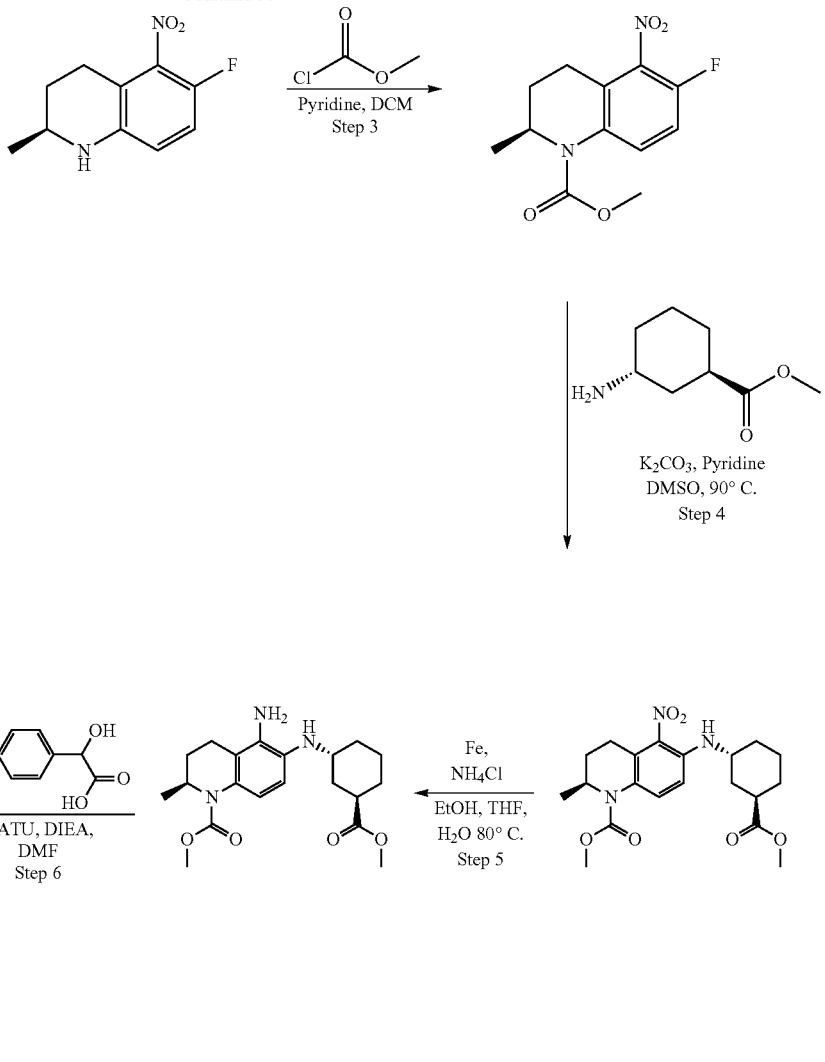
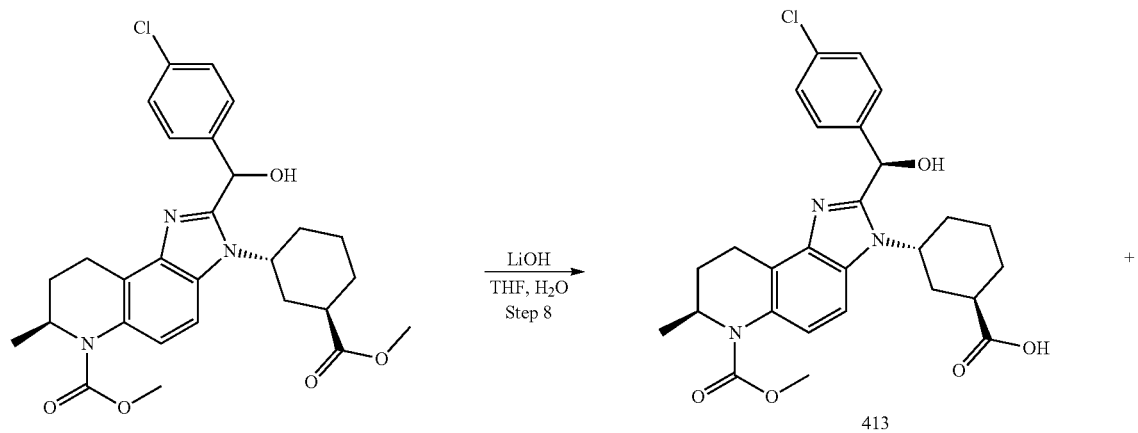

-continued

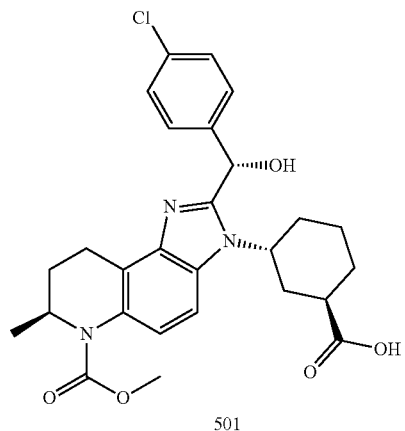

501

Step 1. 6-fluoro-2-methyl-5-nitroquinoline

A solution of trifluoromethanesulfonic acid (82.0 mL, 0.923 mol) in HNO$_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 hours at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]$^+$.

Step 2. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of 12 (410 mg, 1.62 mmol), and 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]$^+$.

Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), and methyl carbonochloridate (18.7 mL, 0.242 mol) in dichloromethane (150 mL) was stirred for 3 h at room temperature (25° C.). The reaction was washed with iN hydrogen chloride (aq., 2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]$^+$.

Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), and methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2 S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 [M+H]$^+$.

Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-2-methyl-5-nitro-6-[[(1R,3R)-4-(methoxycarbonyl)cyclohexyl]amino]-1,2,3,4-tetrahydroquinoline-1-carboxylate (31.0 g, 76.46 mmol), NH$_4$Cl (24.3 g, 454.28 mmol), and Fe (powder, 64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-((R)-2-hydroxy-2-phenylacetamido)-6-[[(1R,3R)-3-(methoxycarbonyl)cyclohexyl] amino]-2-methyl-1,2,3,4-tetrahydroquinoline-1-carboxylate as a dark green solid (27.5 g, 92%). LCMS (ES, m/z): 376 [M+H]$^+$.

Step 6. methyl (2S)-5-[2-(4-chlorophenyl)-2-hydroxyacetamido]-6-[[(1R,3R)-3-(methoxycarbonyl) cyclohexyl]amino]-2-methyl-1,2,3,4-tetrahydroquinoline-1-carboxylate A solution of 2-(4-chlorophenyl)-2-hydroxyacetic acid (112 mg, 0.60 mmol), HATU (304 mg, 0.80 mmol), methyl (2S)-5-amino-6-[[(1R,3R)-3-(methoxycarbonyl)cyclohexyl]amino]-2-methyl-1,2,3,4-tetrahydroquinoline-1-carboxylate (150 mg, 0.40 mmol), and DIEA (155 mg, 1.20 mmol) in N,N-dimethylformamide (2 mL) was stirred for 15 h at room temperature (25° C.). The resulting solution was diluted with water (30 mL), and extracted with ethyl acetate (3×50 mL). The organic layers were combined and washed with brine (2×25 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate as yellow oil (70.0 mg, 32%). LCMS (ES, m/z): 544 [M+H]$^+$.

Step 7. methyl (7S)-2-[(4-chlorophenyl)(hydroxy) methyl]-3-[(1R,3R)-3-(methoxycarbonyl)cyclohexyl]-7-methyl-3H,6H,7H,8H,9H-imidazo[4,5-f] quinoline-6-carboxylate A solution of methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate (60.0 mg, 0.11 mmol) in AcOH (2 mL) was stirred for 15 h at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(4-chlorophenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate as yellow oil (46.0 mg, 79%). LCMS (ES, m/z): 526 [M+H]$^+$.

Step 8. (1R,3R)-3-[(7S)-2-[(R)-(4-chlorophenyl) (hydroxy)methyl]-6-(methoxycarbonyl)-7-methyl-3H,6H,7H,8H,9H-imidazo[4,5-f]quinolin-3-yl]cyclohexane-1-carboxylic acid (413); (1R,3R)-3-[(7S)-2-[(S)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid (501)

A solution of methyl (7S)-2-[(4-chlorophenyl)(hydroxy) methyl]-3-[(1R,3R)-3-(methoxycarbonyl)cyclohexyl]-7-methyl-3H,6H,7H,8H,9H-imidazo[4,5-f]quinoline-6-carboxylate (50.0 mg, 0.10 mmol), and LiOH (11.4 mg, 0.48 mmol) in tetrahydrofuran (1 mL) and water (1 mL) was stirred for 15 h at 25° C. The resulting mixture was concentrated under vacuum. The crude product was purified by Prep-HPLC (Column: XBridge Shield RP18 OBD Column, 5 um, 19×150 mm; Mobile Phase, A: water (containing 10 mmol/L NH$_4$HCO$_3$) and B: ACN (10% to 37% over 12 min); Detector: UV 254 nm). The product fractions were lyophilized to afford (1R,3R)-3-[(7S)-2-[(R)-(4-chlorophenyl)(hydroxy)methyl]-6-(methoxycarbonyl)-7-methyl-3H, 6H,7H,8H,9H-imidazo[4,5-f]quinolin-3-yl]cyclohexane-1-carboxylic acid (413) as a white solid (10.5 mg, 43%); and (1R,3R)-3-[(7S)-2-[(S)-(4-chlorophenyl)(hydroxy)methyl]-6-(methoxycarbonyl)-7-methyl-3H,6H,7H,8H,9H-imidazo [4,5-f]quinolin-3-yl]cyclohexane-1-carboxylic acid (501) as a white solid (7.0 mg, 29%).

First eluting isomer (413): $^1$H-NMR (CD$_3$OD, 400 MHz) δ (ppm): 7.49 (d, J=9.0 Hz, 1H), 7.42-7.33 (m, 5H), 6.19 (s, 1H), 4.92-4.90 (m, 1H), 4.82-4.72 (m, 1H), 3.79 (s, 3H), 3.34-3.20 (m, 1H), 3.02-2.94 (m, 1H), 2.90-2.87 (m, 1H), 2.36-2.09 (m, 4H), 1.99-1.96 (m, 1H), 1.80-1.42 (m, 5H), 1.16 (d, J=6.6 Hz, 3H). LCMS (ES, m/z): 512 [M+H]$^+$.

Second eluting isomer (501): $^1$H-NMR (CD$_3$OD, 400 MHz) δ (ppm): 7.52-7.33 (m, 6H), 6.22 (s, 1H), 4.84-4.73 (m, 2H), 3.78 (s, 3H), 3.27-3.16 (m, 1H), 3.04-2.92 (m, 1H), 2.90-2.88 (m, 1H), 2.46-2.35 (m, 2H), 2.30-2.22 (m, 1H), 2.15-2.02 (m, 2H), 1.82-1.71 (m, 1H), 1.63-1.55 (m, 2H), 1.40-1.28 (m, 1H), 1.15 (d, J=6.6 Hz, 4H). LCMS (ES, m/z): 512 [M+H]$^+$.

Example 2: Preparation of Crystalline Solid Forms of Compound 1

Example 2.a—Preparation of Crystalline Type A Free Base Form

The (1R,3R)-3-((S)-2-((R)-(5-fluoro-2-methoxyphenyl) (hydroxy)methyl)-6-(methoxy carbonyl)-7-methyl-6,7,8,9-tetrahydro-3H-imidazo[4,5-f]quinolin-3-yl)cyclohexane-1-carboxylic acid (5.00 g, 9.51 mmol) was completely dissolved in hot ethyl acetate (67 mL) at reflux. Cloudiness occurs after briefly cooling over several minutes. The hot slurry was cooled slowly to ambient temperature and was then stirred for 1 h. The slurry was then cooled to 0° C. and stirred for 2 h in ice bath before filtering and washing solids with cold ethyl acetate. Isolation gave 3.70 g (74% recovery), white powder of increased purity after drying. LCMS (ES, m/z): 526 [M+H]$^+$. The samples were further characterized by XRPD, DSC, and TGA. These results indicated that the sample is crystalline by XRPD and conformed to Freeform Type A.

Example 2.b—Preparation of Hydrochloric Acid Addition Salt: Type A 900 mg of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 16.5 mL of ethyl acetate and 37% hydrochloric acid was added in 3 aliquots (57 μL each) with vigorous stirring. Solids precipitate and re-dissolve after the first two aliquots but the third addition has solids persist. The slurry is stirred in 50° C. oil bath for two hours and is then slowly cooled to ambient temperature overnight. The white slurry was cooled in ice bath for 90 minutes and filtered/washed with cold ethyl acetate. The white solids were air dried to 908 mg (94% yield). LCMS (ES, m/z): 526 [M+H]⁺ The samples were further characterized by XRPD, DSC and TGA. The results indicated that the sample is crystalline by XRPD and conformed to HCl Salt Type A.

Example 2.c—Preparation of Hydrochloric Acid Addition Salt: Type B 20 mg of the type A hydrochloric acid addition salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL of a 1:1 mixture of dichloromethane and isopropanol. The solution was heated to 50° C., subsequently cooled to 5° C. at a rate of 0.1° C. per minute, and then stirred at 5° C. overnight. The solution was then warmed to room temperature and a precipitate was observed following the slow, unassisted evaporation of a portion of the solvent. The precipitate was collected via centrifugation, dried at 40° C. under vacuum, and subsequently characterized by XRPD, DSC, and TGA. The results indicated that the sample is crystalline via XRPD and conformed to the type B hydrochloric acid addition salt.

Example 2.d—Preparation of Hydrochloric Acid Addition Salt: Type C 20 mg of the type A hydrochloric acid addition salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL of a 9:1 mixture of 1,4-dioxane and water. The solution was heated to 50° C., subsequently cooled to 5° C. at a rate of 0.1° C. per minute, and then stirred at 5° C. overnight. The solution was then warmed to room temperature and a precipitate was observed following the slow, unassisted evaporation of a portion of the solvent. The precipitate was collected via centrifugation, dried at 40° C. under vacuum, and subsequently characterized by XRPD, DSC, and TGA. The results indicated that the sample is crystalline via XRPD and conformed to the type C hydrochloric acid addition salt.

Example 3: HTRF Biochemical Assay for CBP and BRD4 Activity

The potency and selectivity of the CBP/p300 inhibitors were determined in biochemical time-resolved fluorescence assays using glutathione-S-transferase fusions of the BRDs of CBP, p300 and BRD4 and a tetra-acetylated histone H3 peptide.

The ability of compounds of Formula (I) to selectively inhibit CBP was determined using the following HTRF biochemical assay for CBP and BRD4 activity. The assay was performed in a final volume of 6 μL in assay buffer containing 50 mM Hepes pH 7.5, 0.5 mM GSH, 0.01% BGG, 0.005% BSA and 0.01% Triton X-100. Nanoliter quantities of 10-point, 3-fold serial dilution in DMSO were pre-dispensed into 1536 assay plates with a top concentration of 33 μM and half log dilutions. 3 μL of 2× Protein and 3 μL of 2× Peptide Ligand were added to assay plates (pre-stamped with compound). Plates were incubated for varying times up to 4 hours at room temperature prior to measuring the TR-FRET signal. IC50 values are shown in FIG. 2. As set forth in FIG. 2, an IC50 value of greater than or equal to 0.001 μM and less than or equal to 0.01 μM is marked "++++"; a value greater than 0.01 μM and less than or equal to 0.1 μM is marked "+++"; a value greater than 0.1 μM and less than or equal to 1 μM is marked "++"; and a value greater than 1 μM and less than 1000 μM is marked "+".

In some embodiments, the disclosure relates to Compound 1 having an $IC_{50}$ of less than or equal to 0.01 μM for the inhibition of CBP, and an $IC_{50}$ value of greater than 1 μM for the inhibition of BRD4 as determined by the HTRF biochemical assay for CBP and BRD4 activity described herein in Example 3.

The ability of amorphous Compound 1 to selectively inhibit CBP was determined using the following HTRF biochemical assay for CBP and BRD4 activity. The assay was performed in a final volume of 6 μL in assay buffer containing 50 mM Hepes (pH 7.5, (0.5M Hepes, pH 7.5 solution; Teknova H1575)), 0.5 mM GSH, 0.01% BGG (0.22 μM filtered, Sigma, G7516-25G), 0.005% BSA (0.22 μM filtered, EMD Millipore Corporation, 126575) and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 33 μM to 1.7 nM, top to lowest dose, respectively. 3 μL of 2× Protein and 3 μL of 2× Peptide Ligand were added to assay plates (pre-stamped with compound). Plates were incubated for varying times at room temperature prior to measuring the signal. TR-FRET (Time-Resolved Fluorescence Resonance Energy Transfer) was measured on a PHERAstar plate reader (BMG, equipped with HTRF optic module [337/520/490]) or on an Envision plate reader (PerkinElmer, equipped with the TRF Laser unit, TRF dual mirror D400/D505 and emission filters M520 and M495). Data were reported as percent inhibition compared with control wells based on the following equation: % inh=1−((TR-FRET ratio−AveLow)/(AveHigh−AveLow)) where TR-FRET ratio=(Fluorescence at 520 nm/Fluorescence at 490 nm)*10000), AveLow=average TR-FRET ratio of no enzyme control (n=32), and AveHigh=average TR-FRET ratio of DMSO control (n=32). $IC_{50}$ values were determined by curve fitting of the standard 4 parameter logistic fitting algorithm included in the Activity Base software package: IDBS XE Designer Model205. Data is fitted using the Levenburg Marquardt algorithm. For all assay formats data were reported as percent inhibition compared with control wells based on the following equation: % inh=100*((FLU−AveLow)/(AveHigh−AveLow)) where FLU=measured Fluorescence, AveLow=average Fluorescence of no enzyme control (n=32), and AveHigh=average Fluorescence of DMSO control (n=32). $IC_{50}$ values were determined by curve fitting of the standard 4 parameter logistic fitting algorithm included in the Activity Base software package: IDBS XE Designer Model205. Data is fitted using the Levenburg Marquardt algorithm.

In these conditions, Compound 1 was determined to be a potent inhibitor of CBP and p300 with IC50 values of about 1 and 1 nM, respectively. In the BRD4 assay, Compound 1 showed an IC50 of >0.5 μM, while providing >500-fold selectivity for CBP relative to BRD4.

In some embodiments, the disclosure relates to compound 2 having an $IC_{50}$ of less than or equal to 0.01 μM for the inhibition of CBP, and an $IC_{50}$ value of greater than 1 μM for the inhibition of BRD4 as determined by the HTRF biochemical assay for CBP and BRD4 activity described herein in Example 3.

In some embodiments, the disclosure relates to compound 3 having an $IC_{50}$ of less than or equal to 0.01 μM for the inhibition of CBP, and an $IC_{50}$ value of greater than 1 μM for the inhibition of BRD4 as determined by the HTRF biochemical assay for CBP and BRD4 activity described herein in Example 3.

In some embodiments, the disclosure relates to compound 4 having an $IC_{50}$ of less than or equal to 0.01 μM for the inhibition of CBP, and an $IC_{50}$ value of greater than 1 μM for the inhibition of BRD4 as determined by the HTRF biochemical assay for CBP and BRD4 activity described herein in Example 3.

Example 4: Compounds 1, 1', 2, and 4 Demonstrated In Vitro Activity Against CBP

The potency and selectivity of CBP/P300 inhibitor compounds including Compound 1 were determined in biochemical time resolved fluorescence assays using GST fusions of the bromodomains of CBP and BRD4. Briefly, CBP inhibitors were pre-dispensed into 1536 assay plates for a final test concentration of 33 μM to 1.7 nM. Plates and incubated for 4 h. Data were reported as percent inhibition compared with control wells. $IC_{50}$ values were determined by curve fitting of the standard 4 parameter logistic fitting algorithm. In these conditions, Compound 1 was determined to be a potent inhibitor of CBP with an $IC_{50}$<2 nM (N=16). In a similar assay, BRD4 potency was determined and Compound 1 showed an $IC_{50}$ of <500 nM (N=15), indicating >200-fold selectivity.

Selectivity of Compound 1 was evaluated in screening assays for kinase inhibition and BRD binding. Compound 1 showed no to low binding affinity for the human kinases and disease-relevant mutant variants evaluated in a KINOMEscan™ screen. A panel of 10 BRD representing the various branches of the bromodomain tree were tested using an AlphaScreen. Of the 10 bromodomains surveyed, Compound 1 was inactive against 8. Compound 1 $IC_{50}$ values for bromodomains of CREBBP and BRD4 (tandem BD1/BD2) were 0.1 and >10 μM, respectively, confirming the high selectivity of Compound 1 for CBP.

Selectivity of Compound 4 was evaluated in screening assays against a panel of 13 BRD representing the various branches of the bromodomain tree using an AlphaScreen method commonly known to those of ordinary skill in the art (denoted by *) and a TRF assay analogous to the one disclosed in Example 3 (denoted by **). Results are shown in the table below:

| Bromodomain | Compound 4 $IC_{50}$ (μM) |
| --- | --- |
| CBP* | <0.10 |
| BRD4* | >5 |
| TAF1-2* | >5 |
| ATAD2* | >10 |
| BPTF* | >10 |
| BRPF3* | >10 |
| BRWD1* | >10 |
| CECR2* | >10 |
| SMARCA4* | >10 |
| SP140* | >10 |
| BRD9** | >25 |
| ASH1L** | >30 |
| BRWD3** | >30 |

The ability of Compound 1 and Compound 1', as well as Compound 2 and Compound 4, to selectively inhibit CBP was determined using the biochemical assay of Example 3 for CBP and BRD4 activity. Results are shown in the table below:

| Compound | CBP ($IC_{50}$) | P300 ($IC_{50}$) | Selectivity Ratio of BRD4 ($IC_{50}$)/CBP ($IC_{50}$) |
| --- | --- | --- | --- |
| 1 | <10 nM | | >240 |
| 1' | <20 nM | | >76 |
| 2 | <10 nM | | 530 |
| 4 | <10 nM | <10 nM | 742 |

Both Compound 1 and Compound 1' potently inhibited (e.g., $IC_{50}$<100 nM) CBP in the HTRF biochemical assay of Example 3, while Compound 1 was about 3.5-times more selective for CBP inhibition compared to BRD4 using this assay.

Example 5: Determination of the Antiproliferative Effects of Compound 1, Compound 2, and Compound 4 in Breast Cancer Cell Lines The antiproliferative effects of Compound 1, Compound 2, and Compound 4 were determined across a panel of breast cancer cell lines with a range of AR mRNA expression levels using a CellTiter-Glo assay (Promega) following a 10-day independent exposure to each of Compounds 1, 2, 3 and 4.

Breast cell lines were cultured according to the distributor's recommendations. The following day, cells were exposed to compounds up to 10 days. Cell viability was assessed using a CellTiter-Glo® assay (Promega) at the end of the incubation period. The growth inhibitory effect was assessed by the concentration inhibiting growth by 50% using a nonlinear regression equation and a variable slope (Graphpad Prism). The mRNA expression levels for the androgen receptor (HUGO: AR) was determined from the DepMap Portal database (release 19Q2).

A time-dependent antiproliferative activity was assessed with compound 4 and showed that a minimum of 5 days drug exposure was necessary to induce a significant antiproliferative effect. However, washing out the drug after that did not compromise the antiproliferative activity. Maximum sensitivity was observed after 10 days continuous exposure to Compound 4 (FIG. 6A). The antiproliferative activity of Compound 4 was also compared to the AR antagonist enzalutamide in MDA-MB-453 cells using a CTG assay. Compound 4 decreased cell viability with an IC50 of less than 300 nM (less than 0.3 μM) after 10 days exposure to the compound. Enzalutamide tested in the same conditions reduced proliferation with an IC50 of >11 μM (FIG. 6B). Compound 4 was also preferentially active against breast cancer cell lines expressing high levels of AR (FIG. 6C). Compounds 1, 2, and 4 all show antiproliferative activity against a panel of breast cancer cell lines (Table 1).

As set forth in Table 1, below, an IC50 value of less than 0.2 μM is marked "++++"; a value greater than 0.2 μM and less than 0.5 μM is marked "+++"; a value greater than 0.5 μM and less than 1 μM is marked "++"; and a value greater than 1 μM is marked "+".

CBP/p300 inhibitor compounds of Formula (I) inhibit proliferation in estrogen receptor (ER) positive models of breast cancer as shown in Table 1, confirming that CBP/p300 inhibition has potential utility in ER+ breast cancer.

TABLE 1

| Cell Line Name | AR Status | ER Status | Her2 Status | Compound 1 IC$_{50}$ (µM) | Compound 2 IC$_{50}$ (µM) | Compound 4 IC$_{50}$ (µM) |
|---|---|---|---|---|---|---|
| MDA-MB-453 | High | − | +/− | ++++ | +++ | ++++ |
| CAMA1 | High | + | − | ++++ | ++++ | ++++ |
| HCC1500 | High | + | − | ++ | ++ | + |
| HCC1187 | High | − | − | +++ | +++ | +++ |
| BT549 | Low | − | − | + | + | + |
| CAL148 | Low | − | − | + | + | + |
| MFM223 | Low | − | − | + | + | + |
| MDA-MB-231 | Low | − | − | + | + | + |

Example 6: Antiproliferative Activity of Compound 1, Compound 2, and Compound 4 in Prostate Cancer Cell Lines The anti-proliferative effects of Compound 1, 2 and 4 and enzalutamide were evaluated in a 10-day assay across a panel of prostate cancer cell lines including androgen-dependent (LnCaP and VCaP) and androgen-independent AR-v7+(22Rv1) cell lines. Two AR-negative prostate cancer cell lines DU145 and PC-3 were also evaluated.

As shown in Table 2 Enzalutamide was active against the androgen-dependent cell lines LnCaP and VCaP, but was inactive in the AR-negative PC-3 and DU145 cell lines. Enzalutamide was additionally inactive against the AR-v7 expressing 22Rv1 cell line. Compounds 1, 2 and 4 show an antiproliferative effect in androgen-dependent cell lines as well as the AR-v7-expressing cell line 22Rv1. However, Compounds 1, 2 and 4 were inactive against AR-negative cell lines. As shown in Table 2, CBP/p300 inhibitor compounds of Formula (I) inhibit proliferation in prostate cancer cell lines with AR amplification or AR-v7 expression, which are both clinically-relevant mechanisms of enzalutamide resistance to a similar degree than in models of non-amplified intact AR (LNCaP for example).

As set forth in Table 2, below, an IC50 value of less than 0.5 µM is marked "+++"; a value greater than 0.5 µM and less than 1 µM is marked "++"; and a value greater than 1 µM is marked "+".

TABLE 2

| Cell Line | AR aberrations | Androgen dependence | Compound 4 | Compound 1 | Compound 2 | Enzalutamide |
|---|---|---|---|---|---|---|
| LNCaP | T878A/WT | Androgen-dependent | +++ | + |  | + |
| VCAP | WT, AR amplification | Androgen-dependent | +++ | ++ | + | +++ |
| 22Rv1 | H857Y/H857Y, AR v7+ | Androgen-independent | ++ | ++ | ++ | + |
| PC-3 | AR negative | Androgen-independent | + | + |  | + |
| DU 145 | AR negative | Androgen-independent | + | + |  | + |
| BPH1 | AR negative | Androgen-independent | + |  |  |  |

Prostate cell lines were obtained from ATCC or DSMZ and cultured according to the distributor's recommendations. Prostate cancer cells were plated and incubated overnight. The following day, cells were exposed to Compounds 1, 2, 4, or Enzalutamide (final top concentration 10 µM, half-log dilutions) continuously. Cell viability was assessed using a CellTiter-Glo® assay (Promega) after 10 days drug exposure. The growth inhibitory effect was assessed by the concentration inhibiting growth by 50% using a nonlinear regression equation and a variable slope (Graphpad Prism).

Bromodomain inhibitors of CBP/p300 of Formula (I) can be used to treat enzalutamide resistant prostate cancer carrying mutations of the ligand binding domain (LBD) of the androgen receptor. In some cases, these mutations, F876L, T877A and W741L, can render the AR resistant to enzalutamide and other AR antagonists, and in some cases convert these antagonists into agonists. The CBP/p300 bromodomain inhibitors that are active against splice variants which lack the LBD (i.e. AR-v7) are selected to treat AR LBD mutants because these compounds interact with AR and inhibit AR signaling regardless of the presence of the LBD. CBP/p300 inhibitor compounds of Formula (I) inhibit AR signaling in AR-v7+ prostate models, which is consistent with the lack of requirement of the LBD function for CBP/p300 inhibitors to inhibit AR signaling. CBP/p300 inhibitor compounds of Formula (I) are evaluated in transient transfection assays in which cDNAs encoding the wild type AR and the 3 point mutants can be individually co-transfected into cells with an AR driven luciferase reporter construct. The ability of these mutants to activate transcription through the androgen response element (ARE) can be assessed following activation with the AR agonist, dihydroxytestosterone or testosterone, in hormone depleted media. The transfected cells expressing the wild-type AR and the AR F876L, T877A and W741L mutants can be treated with CBP/300 inhibitors and the impact on ARE driven transcription are measured using the Dual-Glo® luciferase assay system. This allows assessment of the impact of CBP/p300 bromodomain inhibitors on AR driven signaling by enzalutamide resistant mutants of the AR.

Example 7: Compound 1 Demonstrates In Vivo Efficacy in AR-Positive, Human-Derived Triple Negative Breast Cancer Xenografts The antitumor activity of Compound 1 was tested in an AR-positive cell line derived xenograft model of AR+ triple negative breast cancer (Robinson et al., "Androgen receptor driven transcription in molecular apocrine breast cancer is mediated by FoxA1," The EMBO Journal (2011) 30, 3019-3027 (2011), incorporated herein by reference in its entirety). Briefly, AR-positive breast cancer tumor cells ($1\times10^7$) were implanted subcutaneously in the flank of 6-8-week-old NOD SCID mice. Mice were randomized, and treatment started when mean tumor size reached 160 mm$^3$ (8 mice per cohort). 50 mg/kg Compound 1 was administered orally daily for the duration of the experiment. Tumor volume (TV) was measured twice weekly by caliper and the tumor volume (mm$^3$) calculated as follows: TV=a×b×b/2, where "a" and "b" are long and short diameters of a tumor, respectively.

Figure 7:
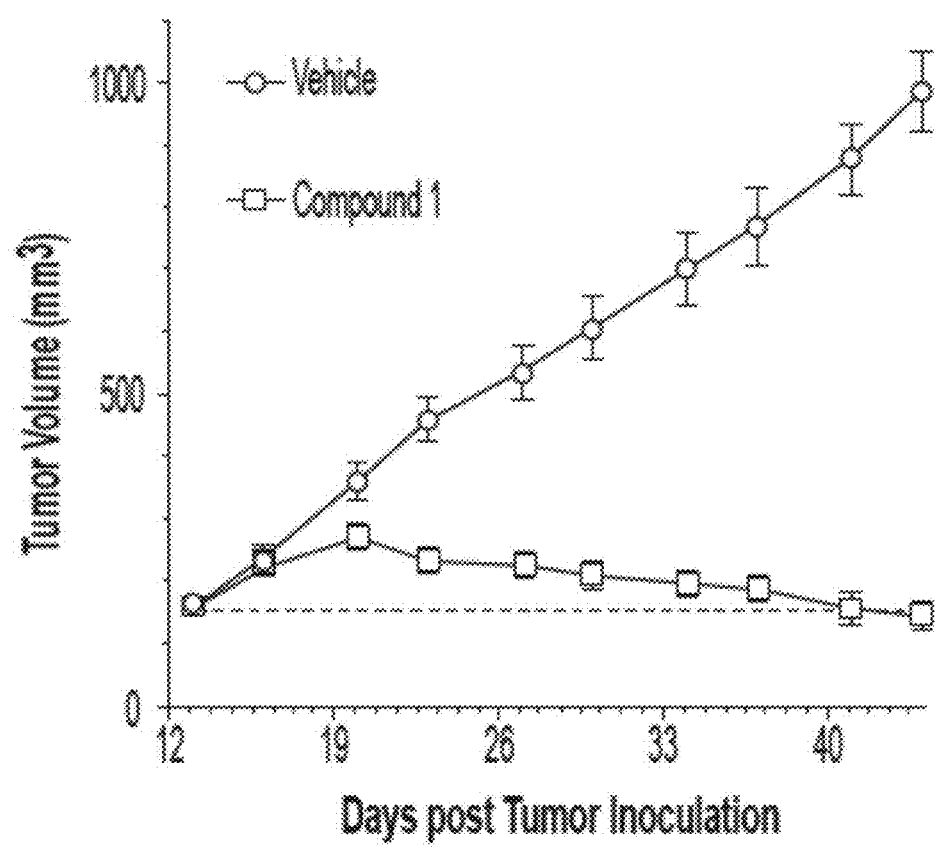
FIG. 7 is a graph showing the in vivo activity of Compound 1 in a cell-line-derived xenograft model of AR+ triple negative breast cancer.

Results are shown in FIG. 7. At the end of the treatment period, Compound 1 treatment produced a tumor growth inhibition (TGI) of 104% (p<0.001) compared with vehicle control (TGI=[1-(TreatedTVfinal-TreatedTVinitial)/(VehicleTVfinal-VehicleTVinitial)]$^+$100 where "TVfinal" and "TVinitial" are the mean tumor volumes on the final day and initial day of dosing). The average body weight loss was 3.7%.

Example 8: Antitumor Activity of Compound 2 Following Repeated Administration in AR-Positive Triple Negative Breast Cancer Xenografts The antitumor activity of Compound 2 was evaluated over time in the human breast cancer xenograft model of AR+ triple negative breast cancer.

The study was completed using methods analogous to those described in Example 7, above. Mice harboring AR-positive breast cancer xenograft tumors were dosed with vehicle, 20 mg/kg Compound 2, 30 mg/kg Compound 2, 40 mg/kg Compound 2, or 60 mg/kg Compound 2.

Mice in the 20 mg/kg, 40 mg/kg, and 60 mg/kg cohorts were dosed on a cycle in which they received the indicated dose of Compound 2 for 4 days, followed by a 3-day dosing holiday. Three dosing cycles were completed for mice within these cohorts.

Mice in the 30 mg/kg cohort were dosed daily for three weeks.

Figure 8:
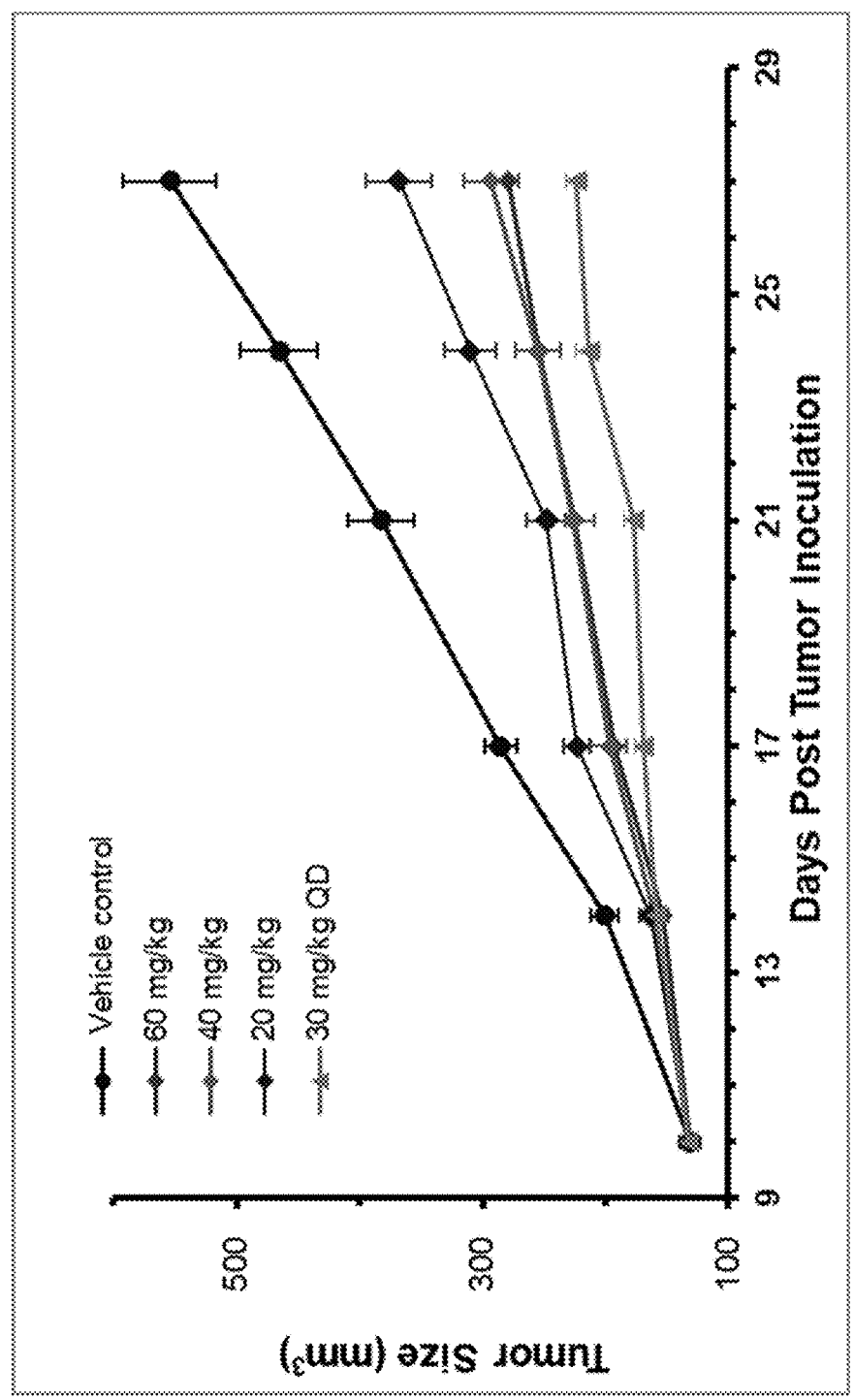
FIG. 8 shows tumor volumes over time in mice bearing AR+ triple-negative breast cancer xenografts administered Compound 2 at 20 mg/kg, 30 mg/kg, 40 mg/kg, or 60 mg/kg.

Tumor volume was assessed at Day 14, Day 17, Day 21, Day 24, and Day 27 of the study. Repeated dosing of Compound 2 resulted in a concentration and dosing frequency dependent reduction in tumor volume, relative to the vehicle control, as shown in FIG. 8.

Example 9: Compound 4 Induces Pharmacodynamic and Anti-Tumor Effects in AR-Positive Triple-Negative Breast Cancer Xenografts The temporal and dose-dependent effects of proximal (H3K27Ac), as well as downstream (ER/AR target genes), biomarkers of CBP/p300 modulation following administration of Compound 4 to mice bearing MDA-MB-453 xenografts were evaluated.

Figure 9A:
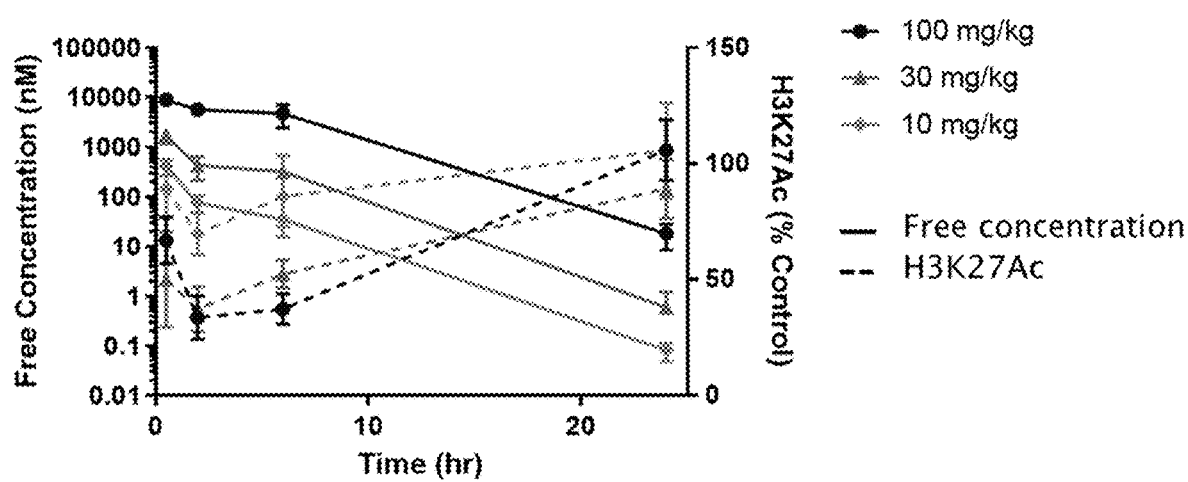
FIG. 9(A) shows the level of unbound Compound 4 in plasma correlated with the modulation of H3K27Ac in AR-positive breast cancer xenografts.
Figure 9B:
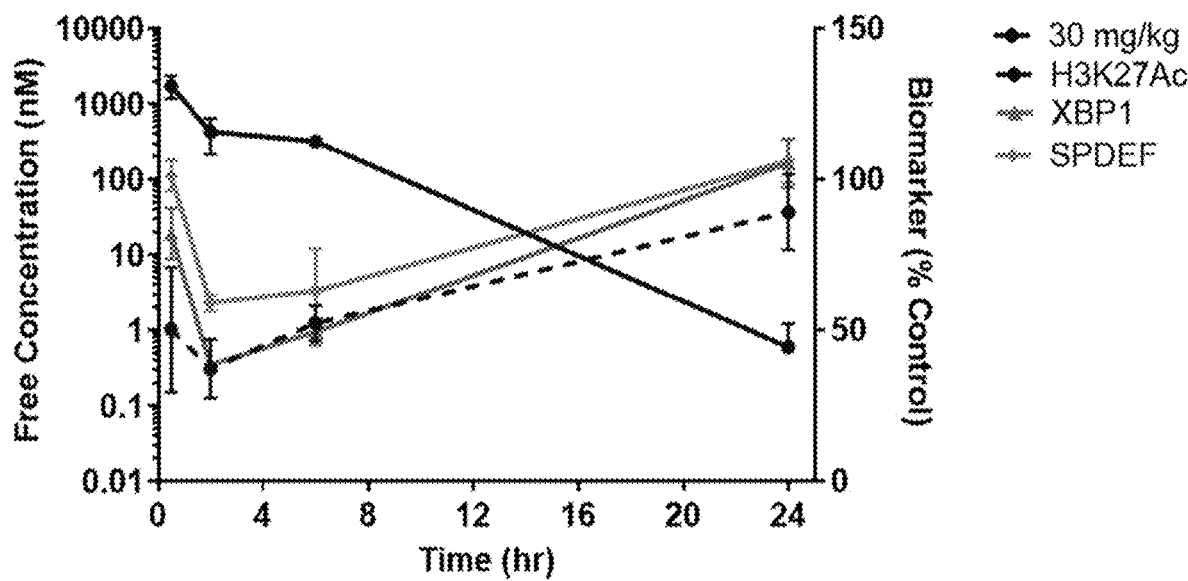
FIG. 9(B) shows the level of unbound Compound 4 in plasma correlated with the modulation of ER- and AR-target genes in AR-positive breast cancer xenografts.
Figure 9C:
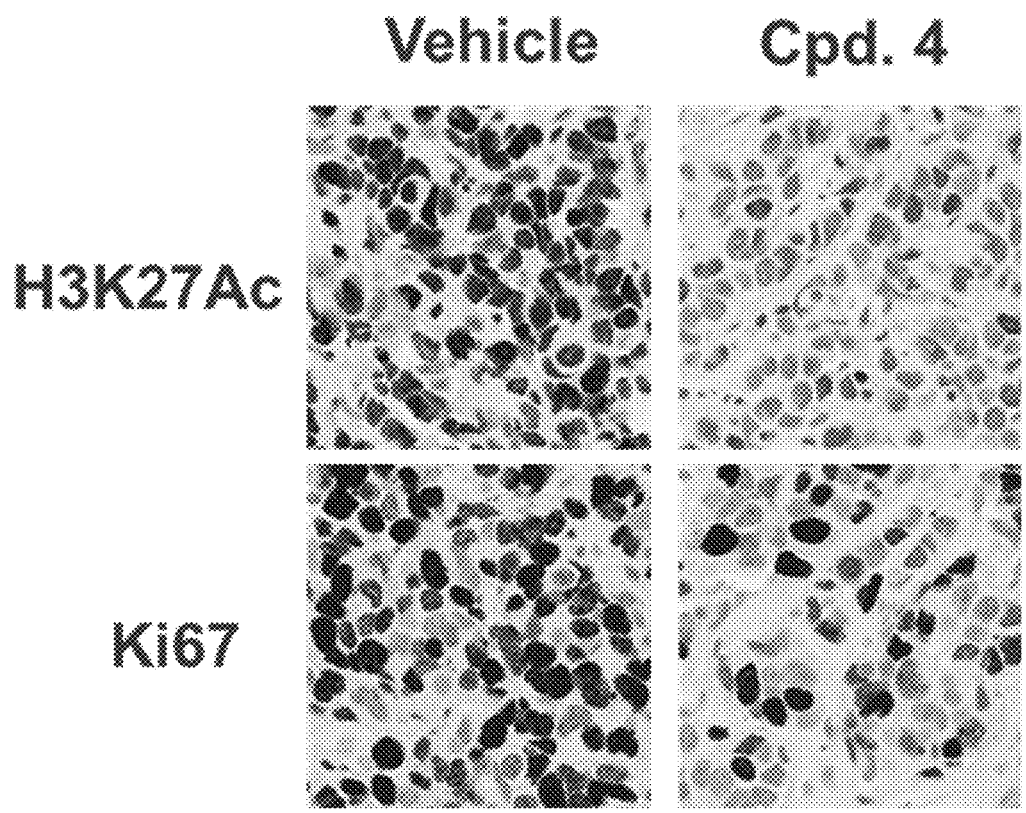
FIG. 9(C) shows Ki67 immunohistochemical staining of samples collected from mice with an AR-positive breast cancer xenograft treated with vehicle or compound 4.
Figure 9D:
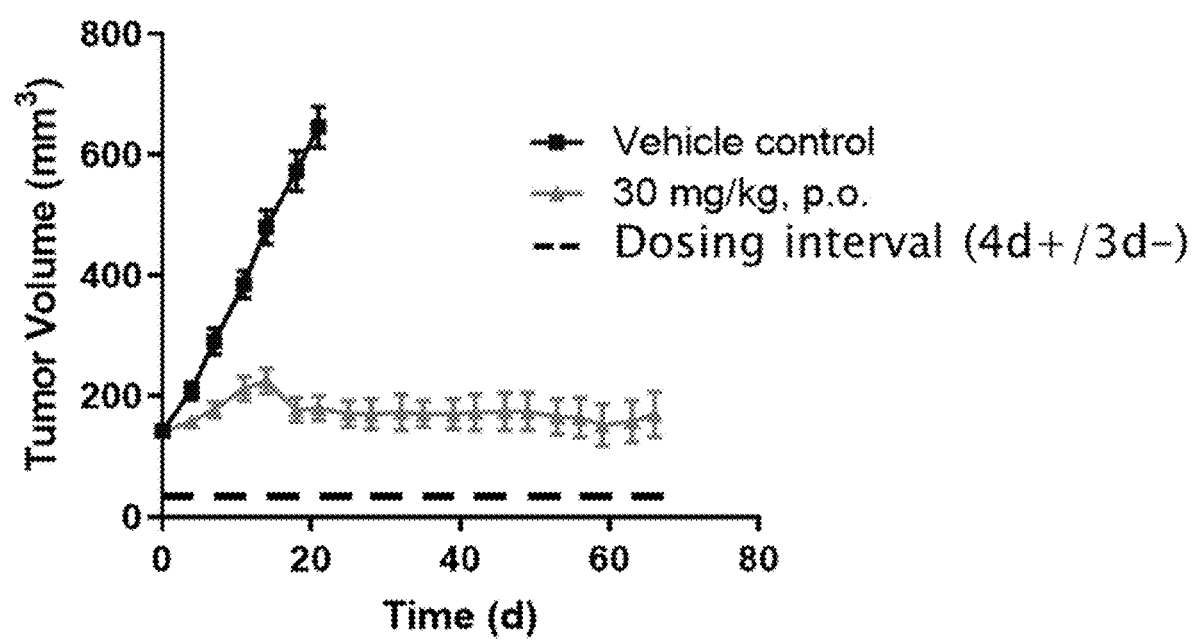
FIG. 9(D) shows the reduction of tumor volume over time in mice with an AR-positive breast cancer xenograft treated with compound 4, compared to a vehicle control.

A dose- and time-dependent pharmacokinetic (PK) and pharmacodynamic (PD) relationship was observed after oral dosing of compound 4 to mice harboring a MDA-MB-453 AR+ triple-negative breast cancer cell xenograft. The level of unbound compound 4 in plasma correlated with modulation of H3K27 acetylation and ER- and AR-target genes (FIGS. 9(A) and (B)). This was associated with a reduced proliferative index, as measured by Ki-67 staining with immunohistochemistry using methods commonly known to those of ordinary skill in the art (FIG. 9(C)). Additionally, compound 4 induced tumor stasis in the MDA-MB-453 xenografts (FIG. 9(D)).

Female SCID mice (6-8 weeks of age) were implanted with MDA-MB-453 cells. When tumors reached an average tumor volume of ~300 mm$^3$, animals were randomized into different cohort groups and dosing initiated. For the PK/PD, Compound 4 was administered by oral gavage at doses of 10, 30 and 100 mg/Kg daily Mon-Thu repeated weekly. At specific time-points, tumors and plasma were harvested. Drug concentrations were determined in plasma. Tumors were pulverized and histone extracted using a histone extraction kit. RNA was also extracted from tumors and analyzed by qPCR using Taqman® primer-probes for XBP1 and SPDEF. GAPDH was used as a housekeeping gene. For the efficacy study, Compound 4 was administered by oral gavage at a dose 30 mg/Kg daily Mon-Thu repeated weekly. Animals were weighed twice weekly. Tumors were measured twice weekly. The maximum tumor volume of control animals was 1500 mm$^3$.

Example 10: Antitumor Activity of Compound 1 in a Patient-Derived Xenograft Model of Prostate Cancer Sensitive to Enzalutamide The temporal and dose-dependent modulation of proximal (H3K27Ac) as well as downstream AR target genes TMPRSS2 and SPDEF were evaluated after administration of Compound 1 in a patient-derived xenograft (PDX) models of AR+ prostate cancer known to be sensitive to the standard of care, enzalutamide. The antitumor activity of Compound 1 was also assessed in this model alongside enzalutamide. The antitumor activity was determined based by tumor volume during the course of the study.

Male NOG mice (6-8 weeks of age) were implanted with tumor fragments. When tumors reached an average tumor volume of 150-200 mm$^3$ animals were randomized into different cohort groups and dosing initiated on the same day (Day 0). Animals were weighed twice weekly.

In the patient-derived xenograft (PDX) mouse model of prostate cancer sensitive to enzalutamide, a reduction of H3K27Ac as well as target gene expression was observed following Compound 1 administration (40 mg/kg/day for four days) (FIG. 10). Consistent with its mechanism of action, enzalutamide (20 mg/kg/day for four days) did reduce the AR target gene TMPRSS2 to a similar extent as Compound 1. However, Compound 1 reduced the AR target gene SPDEF while enzalutamide did not. A similar tumor growth inhibition was observed following 59 days of Compound 1 (40 mg/kg/day) or enzalutamide (20 mg/kg/day) administration (FIG. 11).

The antitumor activity of Compound 1 and enzalutamide was determined by measurements of tumor volume during the study. Tumor growth inhibition (TGI), calculated as $100*(1-\Delta T/\Delta C)$, was evaluated from the start of dosing to day 59, as shown in FIG. 11. TGI at the end of study was comparable for both Compound 1 and enzalutamide.

Example 11: Compound 1, 2 and 4 Reduce AR Target Gene TMPRSS2 and ER Target Gene XBP1 in AR-Positive Breast Cancer Cells AR-positive breast cancer cells were exposed to increasing concentrations of compounds for 24 hours. RNA was extracted and gene expression measured using Taqman® assays for TMPRSS2 and XBP1.

All compounds reduced the mRNA expression of TMPRSS2 and XBP1 in an AR-positive breast cancer cell line.

As set forth in Table 3, below, an IC50 value less than 100 nM is marked "+++"; a value greater than 100 nM and less than 500 nM is marked "++"; and a value greater than 500 nM is marked "+".

TABLE 3

|  | Compound 4 | Compound 1 | Compound 2 |
|---|---|---|---|
| TMPRSS2 | ++ | +++ | + |
| XBP1 | ++ | +++ | +++ |

Example 12: Compound 4 Modulates ER and AR Pathways in AR-Positive Triple-Negative Breast Cancer Cells The transcriptional profile of compound 4 was evaluated using RNA sequencing and gene set enrichment analysis in MDA-MB-453 triple-negative breast cancer cells. In addition, the impact of compound 4 on activated AR target genes was determined in MDA-MB-453 cells exposed to the AR agonist R1881 by qPCR.

Figure 12C:
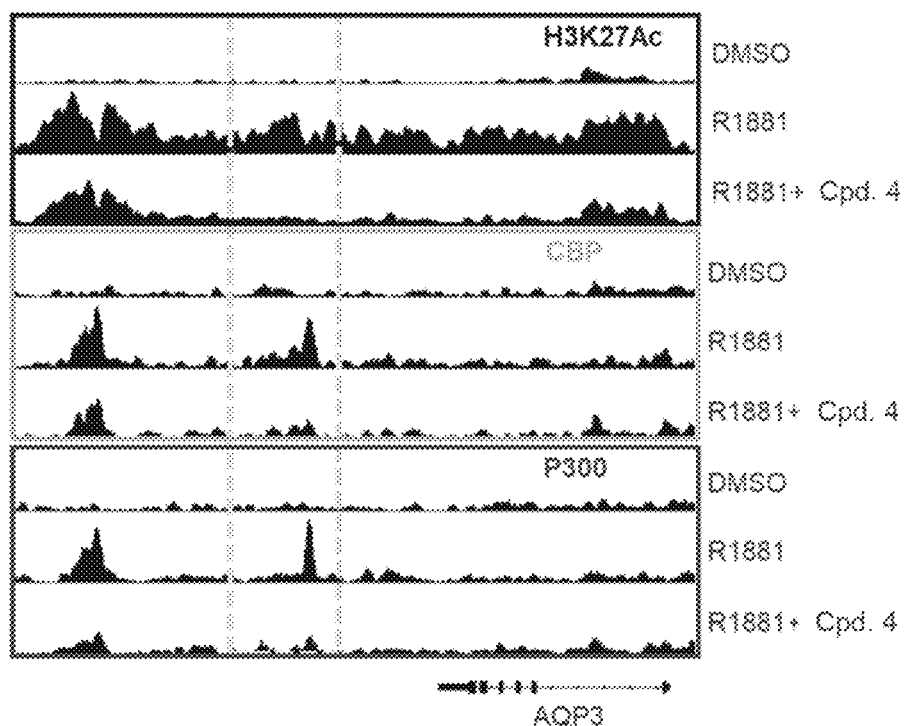
FIG. 12(C) shows ChIP-seq analysis of CBP and p300 binding to the AQP3 gene in cells exposed to R1881 in the presence and absence of compound 4.
Figure 12D:
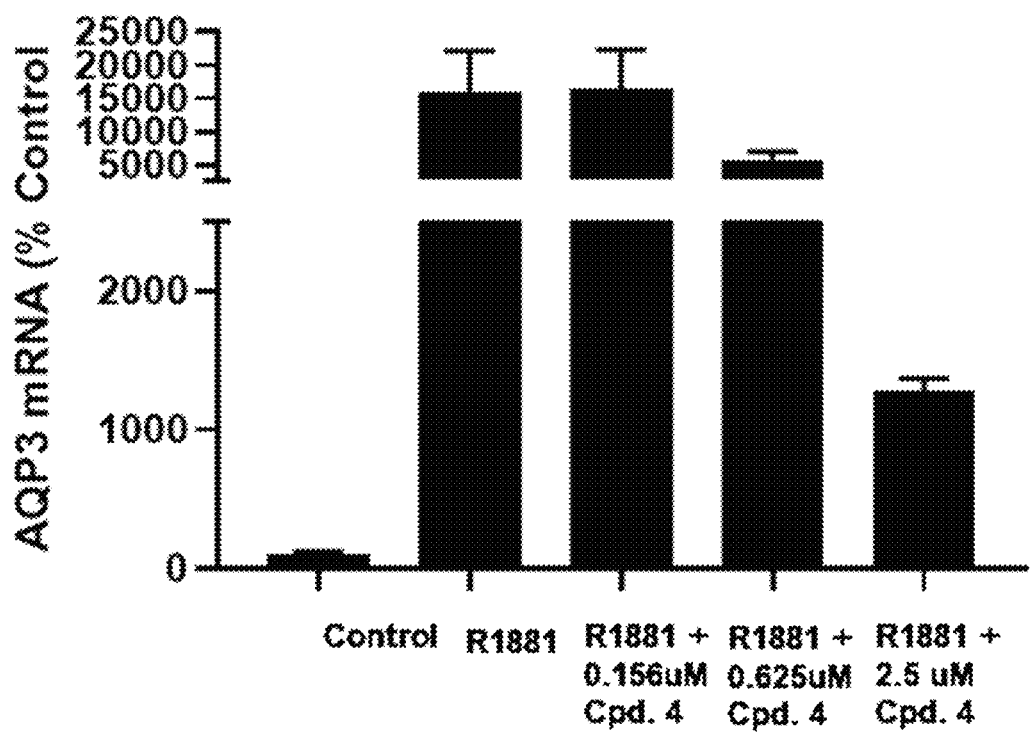
FIG. 12(D) shows the qPCR analysis of AQP3 mRNA levels in cells exposed to R1881 in the presence and absence of compound 4.

Gene set enrichment analysis using methods and techniques commonly known to those of ordinary skill in the art of RNAseq data revealed enrichment of ER- and AR-pathway genes in MDA-MB-453 cells treated compound 4 for 24 hours (FIG. 12(A); "NES" is "normalized enrichment scores" and "FDR" is "false discovery rate"). SPDEF and XBP1, representative of AR- and ER-target genes, respectively, were validated by qPCR after cells were exposed to the AR agonist R1881 with and without simultaneous exposure to compound 4 (FIG. 12(B)). ChIP-seq analysis using methods and techniques commonly known to those of ordinary skill in the art revealed reduced CBP and p300 binding upstream of the ER-regulated gene, AQP3 upon exposure of MDA-MB-453 with compound 4 (FIG. 12(C)). This is concurrent with reduction in H3K27 acetylation at this location. These changes were also associated with the reduction of AQP3 mRNA levels (FIG. 12(D)), again validated by qPCR.

Example 13: Determination of the Modulation of AR Target Genes with Compound 1, Compound 2, Compound 3, and Compound 4 in AR-v7+ Prostate Cancer Cells AR-v7+ prostate cancer cells were exposed to compounds 1, 2, 3, or 4 for 24 h. RNA was extracted and gene expression was measured by qPCR using Taqman® primer-probes. GAPDH was used as a housekeeping gene.

In the conditions tested, all 4 compounds reduced AR target genes TMPRSS2 and KLK3, as well as MYC in a concentration-dependent manner in the AR-v7+ prostate cancer cells.

As set forth in Table 4, below, an IC50 value of less than 10 nM is marked "++++"; a value greater than 10 nM and less than 50 nM is marked "+++"; a value greater than 50 nM and less than 100 nM is marked "++"; and a value greater than 100 nM is marked "+".

TABLE 4

| Target gene | Compound 4 | Compound 1 | Compound 2 | Compound 3 |
|---|---|---|---|---|
| KLK3 | +++ | +++ | ++ | +++ |
| TMPRSS2 | +++ | ++++ | ++ | +++ |
| MYC | N/A | + | + | ++ |

Example 14: Compound 1 Modulates AR Target Genes in Androgen-Dependent VCaP and AR-v7+22Rv1 Prostate Cancer Cells Prostate cancer cells, androgen-dependent (VCaP) and AR-v7+(22Rv1), were exposed to Compound 1 for 24 h. RNA was extracted using Qiacube RNAeasy Mini (Qiagen). For all genes tested, the qPCR reactions were carried out in triplicate with 250 ng RNA per reaction and Taqman® primer-probes. GAPDH was used as a housekeeping gene.

In the conditions tested, Compound 1 reduced AR target genes TMPRSS2, SPDEF and KLK3, as well as MYC in a concentration-dependent manner in both prostate cancer cell lines.

As set forth in Table A, below, an IC50 value of less than 10 nM is marked "++++"; a value greater than 10 nM and less than 50 nM is marked "+++"; a value greater than 50 nM and less than 100 nM is marked "++"; and a value greater than 100 nM is marked "+".

TABLE A

| Gene | VCaP $IC_{50}$ (µM) | 22Rv1 $IC_{50}$ (µM) |
|---|---|---|
| KLK3 (PSA) | +++ | +++ |
| TMPRSS2 | +++ | ++++ |
| SPDEF | + | + |
| MYC | ++ | + |
| FKBP5 | + | + |
| SORD | + | + |

Example 15: Modulation of Histone H3K27 Acetylation by Compound 1 and Compound 4 in AR-Positive Breast Cancer Cells The effects of Compound 1 and 4 on the acetylation of histone H3 at lysine 27 (H3K27Ac), a mark specific to CBP/p300, in AR-positive MDA-MB-453 breast cancer cells were evaluated via western blot of lysates prepared from cells exposed to a range of Compound 1 concentrations.

H3K27Ac is a specific mark of CBP/p300 activity and thus offers a means to directly assess the impact of CBP/p300 inhibition in cells. MDA-MB-453 (AR-positive breast cancer) cells were exposed to increasing concentrations of Compound 1 and Compound 4 for 24 hrs and H3K27Ac levels were assessed by western blot.

MDA-MB-453 cells were plated overnight and exposed to the compounds for 24 hours. Lysates were prepared from the cells in E-PAGE loading buffer (Invitrogen) and analyzed by western blot with antibodies diluted 1:1000 for anti-H3K27Ac, 1:2000 for anti-total H3 and 1:10,000 for anti-β actin. The blots were scanned and analyzed on a LI-COR Odyssey image analyzer. H3K27Ac levels were normalized to β-Actin.

Figure 13A:
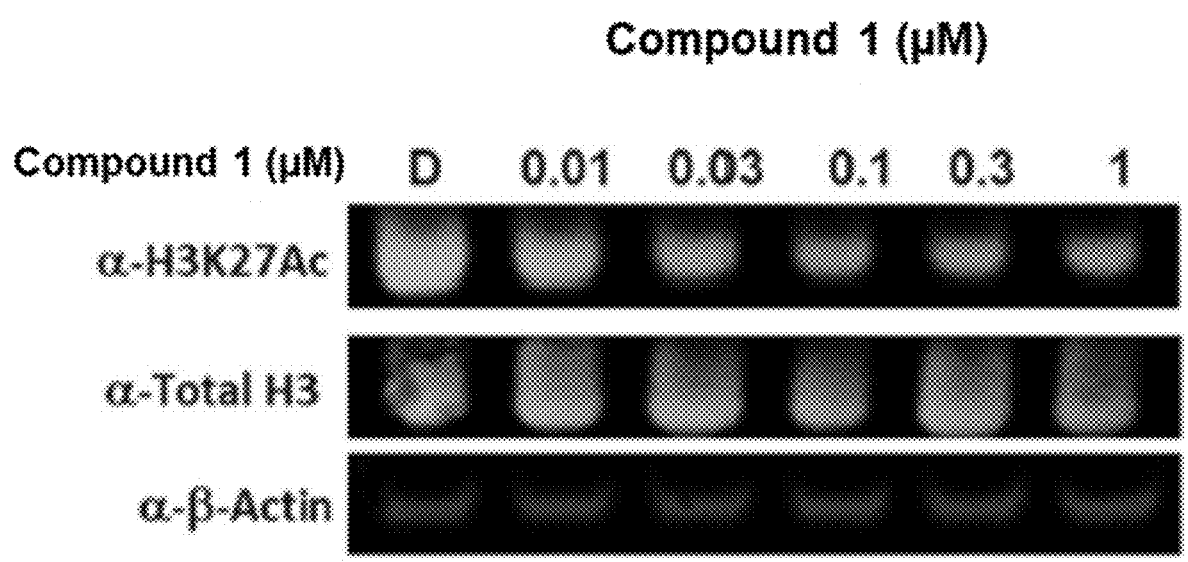
FIG. 13(A) shows a representative western blot of the concentration dependent reduction of H3K27Ac in AR+ triple-negative breast cancer cells. Cells were exposed to DMSO (D) or Compound 1 at the indicated concentrations for 24 hours.
Figure 13B:
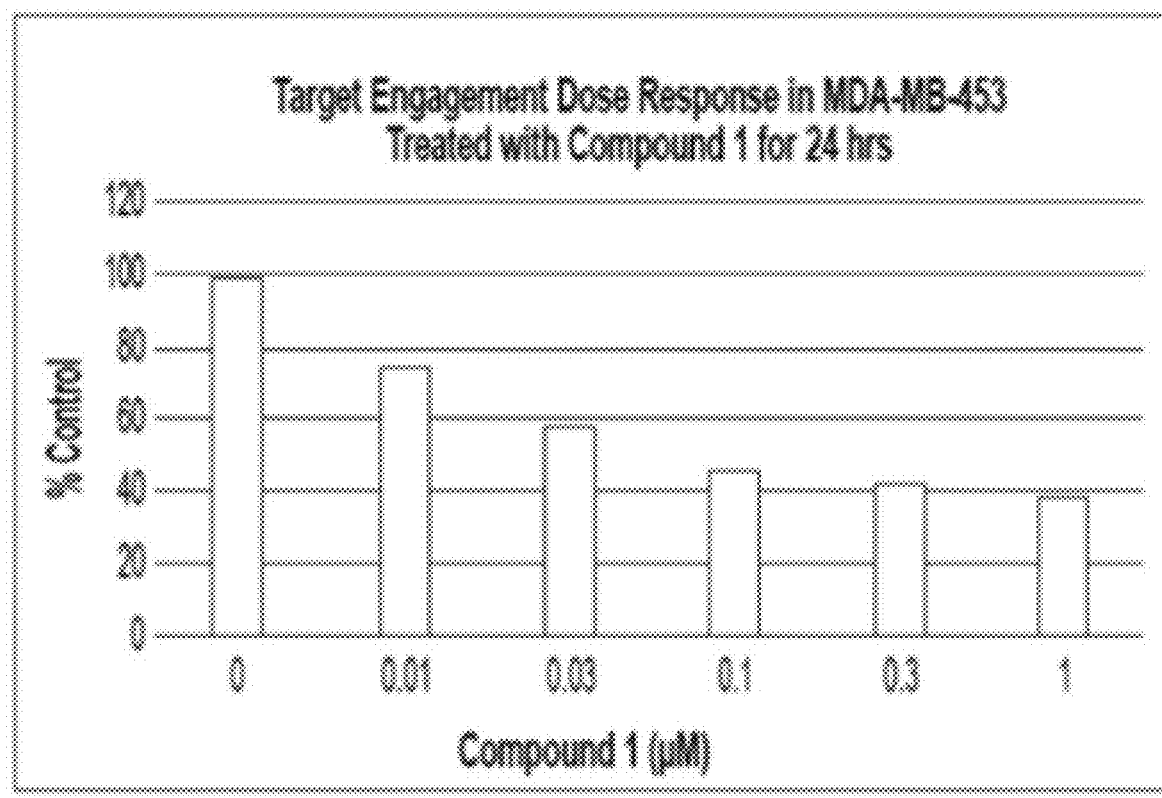
FIG. 13(B) shows quantification of the western blot of FIG. 10(A) expressed as % H3K27Ac/Total H3 (each normalized to (3-actin).
Figure 14A:
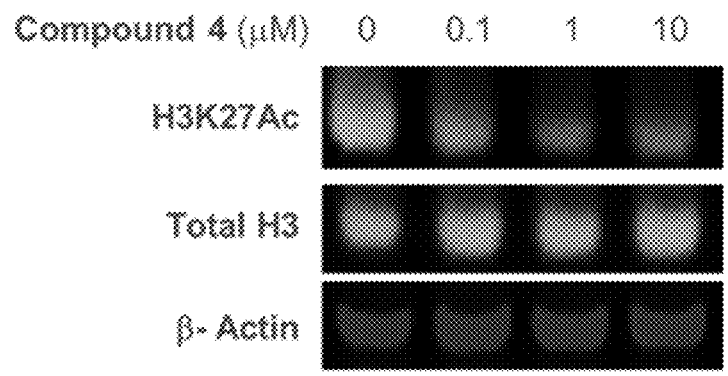
FIG. 14(A) shows a western blot demonstrating the reduction of H3K27Ac in cells treated with compound 4.
Figure 14B:
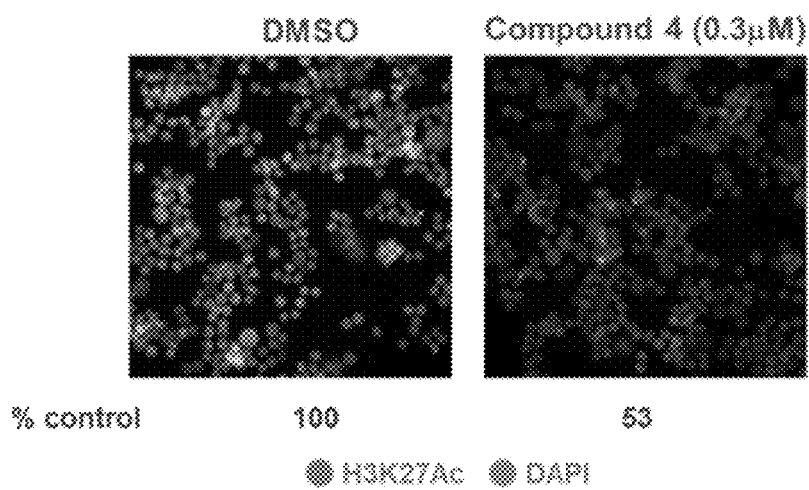
FIG. 14(B) shows high-content analysis of the reduction in H3K27Ac in cells treated with compound 4.

Compound 1 (FIG. 13) and Compound 4 (FIG. 14(A)) induced a concentration dependent reduction of H3K27Ac. In addition, when H3K27Ac was measured by high content imaging using methods and techniques commonly known to those of ordinary skill in the art, the reduction in H3K27Ac with compound 4 affected the majority of the cells (FIG. 14(B)).

Figure 14C:
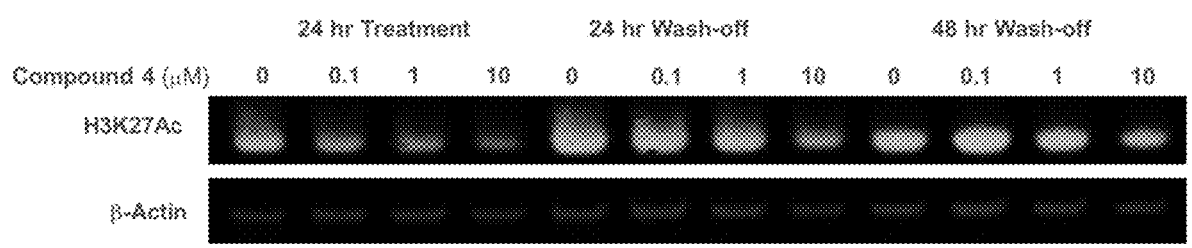
FIG. 14(C) shows a western blot demonstrating that the reduction of H3K27 following treatment with compound 4 is reversible.

Finally, a washout experiments was carried out with compound 4 to assess the recovery of the biomarker after removal of the compound. For the washout arm of the study, cells were treated with Compound 4 (0.1, 1 and 10 μM) for 24 hours and then incubated in the absence of compound for an additional 24 or 48 hours. Lysates were prepared and analyzed by western blot, as described above. Compound 4 shows that the reduction in H3K27Ac was reversible within 24 hrs of compound removal (FIG. 14(C)).

Example 16: Concentration Dependent Reduction of H3K27Ac in a Prostate Cancer Cell Line The effect of Compound 1 on the acetylation of histone H3 at lysine 27 (H3K27Ac), a mark specific to CBP/p300, in a prostate cancer cell line was evaluated via western blot of lysates prepared from cells exposed to a range of Compound 1 concentrations using a process analogous to Example 15.

Figure 15:
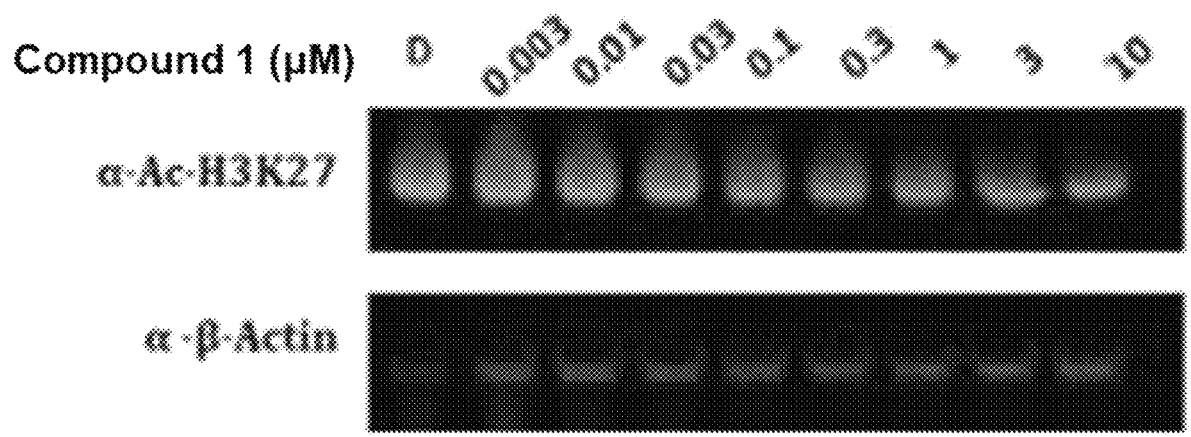
FIG. 15 shows a representative western blot of the concentration dependent reduction of H3K27Ac in a prostate cancer cell line. Cells were exposed to DMSO (D) or Compound 1 at the indicated concentrations.

As illustrated in FIG. 15, Compound 1 reduces H3K27Ac in a concentration-dependent manner in a prostate cancer cell line. DMSO is the vehicle used to deliver the drug and is thus a negative control. Actin is used as to demonstrate consistent loading across the samples.

Example 17: Modulation of AR and AR-v7 Splice Variant Protein Expression by Compound 2 in Androgen-Independent and Androgen-Dependent Prostate Cancer Cells AR-v7+ Prostate cancer cells were exposed to Compound 2 for 24 hours at which time lysates were prepared and the impact of the compound on the protein level of AR was assessed by western blot. The results are shown in FIG. 16. Treatment of prostate cancer cells with Compound 2 led to the reduction of both full length and variant forms of the AR including AR-v7.

Example 18: Impact of CBP/p300 Inhibition on AR and AR-v7 Levels in Androgen-Independent and Androgen-Dependent Prostate Cancer Cells The effect of Compound 1 on the modulation and recovery of AR and AR-v7 splice variant protein expression was evaluated via western blot of lysates prepared from androgen-dependent and androgen-independent prostate cancer cells incubated with Compound 1 using a process analogous to Example 17.

Figure 17:
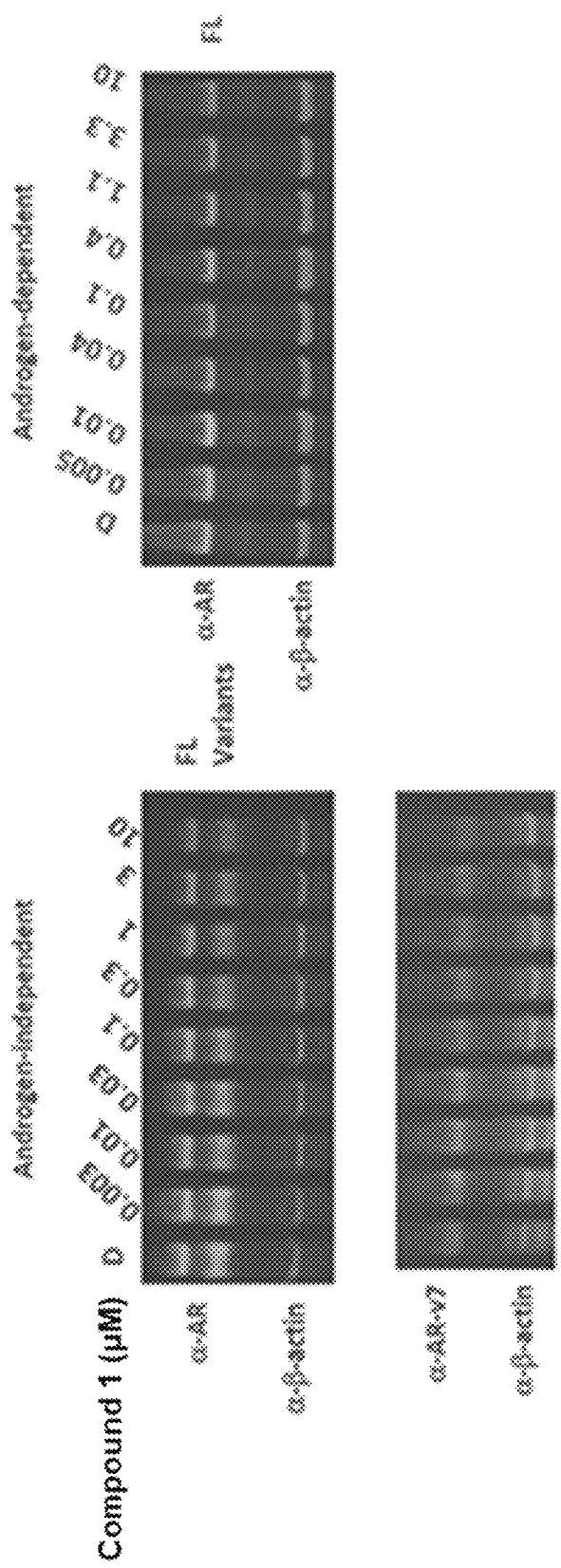
FIG. 17 shows a series of immunoblots of AR, AR-v7, and β-actin protein demonstrating the reduction of AR and AR-v7 protein levels in androgen-dependent and androgen-independent cells following treatment with compound 1.
Figure 18:
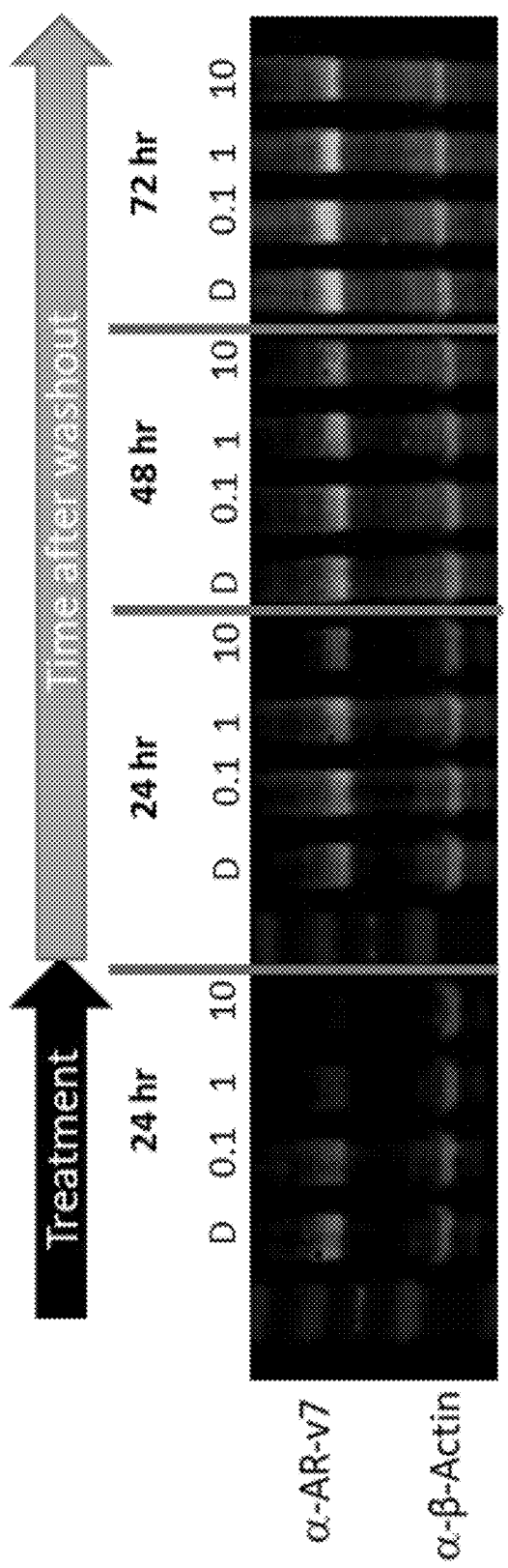
FIG. 18 shows a series of western blots demonstrating the reduction and recovery of AR-v7 after exposure of androgen-independent prostate cancer cells to Compound 1.
Figure 19:
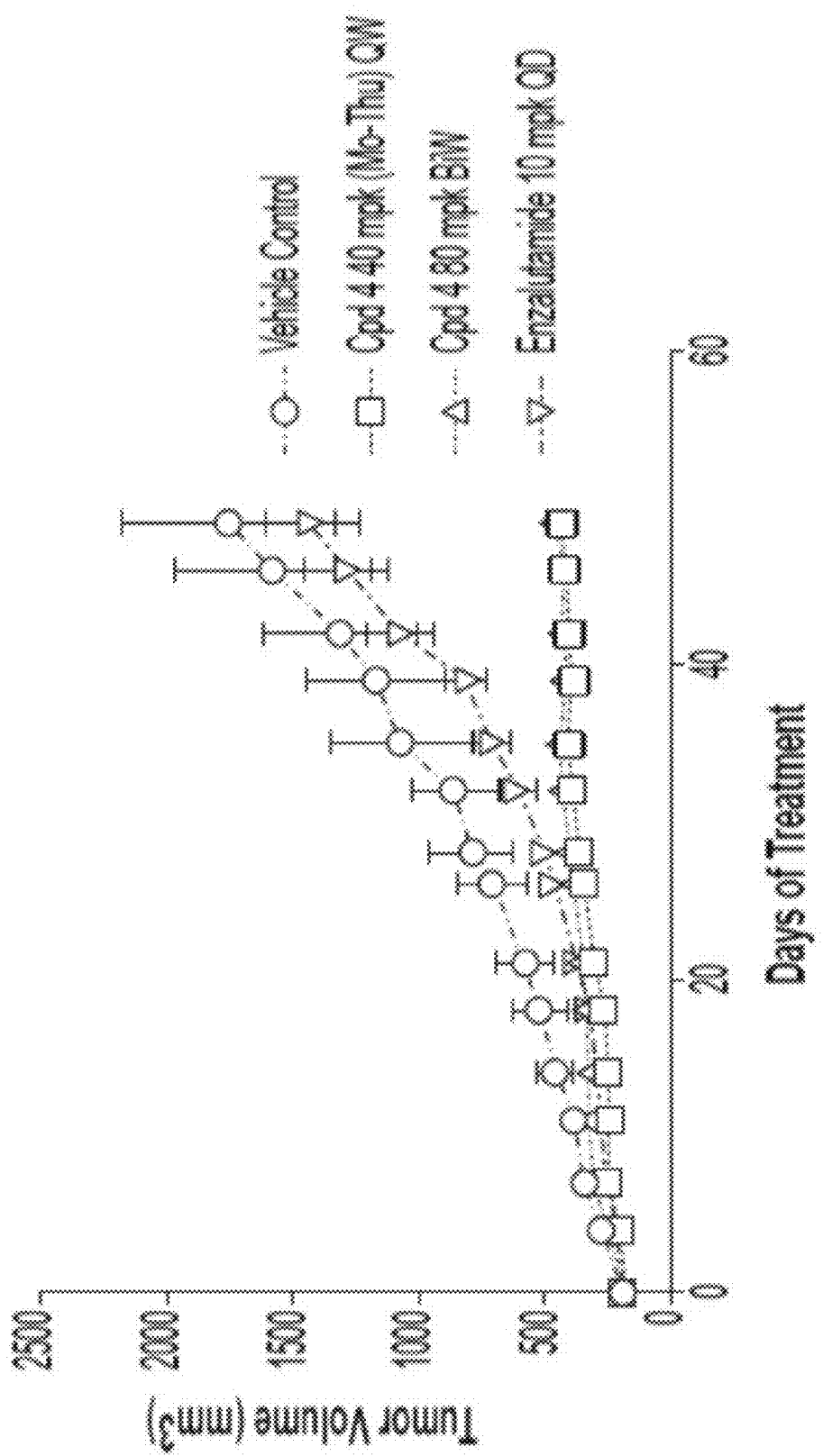
FIG. 19 is a graph showing the in vivo activity of Compound 4 in a patient-derived xenograft model of prostate cancer resistant to enzalutamide.

As illustrated in FIG. 17, the inhibition of CBP/p300 activity by Compound 1 induced a dose dependent reduction of AR protein levels in the androgen independent and androgen-dependent prostate cancer cell lines. AR-v7 was reduced in the androgen-independent prostate cancer cell line. DMSO is the vehicle used to deliver the drug and is thus a negative control. Actin is used as to demonstrate consistent loading across the samples.

The reversibility of the modulation of AR and AR-v7 was also assessed in 22Rv1 over 72 hrs after a 24 hr exposure to Compound 1 (FIG. 6). Following removal of Compound 1, AR returned to baseline level within 24 hours whereas AR-v7 reduction was maintained for 72 hrs.

Example 19: Compound 4 Demonstrates Antitumor Activity in a Patient-Derived Xenograft Model of Prostate Cancer Resistant to Enzalutamide Male NOG mice (6-8 weeks of age) were implanted with prostate PDX tumor fragments. When tumors reached an average tumor volume of 100-300 mm$^3$ animals were randomized into different cohort groups and dosing initiated on the same day (Day 0). Compound 4 was formulated in (0.5 CMC/0.5% Tween 80) pH 8 and administered as a solution. Animals were weighed twice weekly. Tumors were measured twice weekly. The maximum tumor volume of control animals was 1500 mm$^3$.

Compound 4 was administered by oral gavage at a dose and schedule of 40 mg/kg/dose daily Mon-Thu repeated weekly or 80 mg/kg/dose Mo and Thu (twice weekly) repeated weekly.

Treatment with Compound 4 at 40 mg/kg/dose daily Mon-Thu repeated weekly or 80 mg/kg/dose Mo and Thu (twice weekly) repeated weekly resulted in a strong antitumor response (FIG. 15) with tumor growth inhibition values of 84% and 82%, respectively. Enzalutamide had modest activity (TGI=21%).

Example 20: Pharmaceutical Composition Comprising a CBP Inhibitor Compound

A pharmaceutical composition can comprise one or more CBP inhibitor compounds, as provided herein, including Compound 1, Compound 2, or Compound 3 and may also contain stereoisomers, pharmaceutically acceptable salts, or tautomers thereof.

In one example, an active pharmaceutical ingredient (API) can comprise about 90% or more of Compound 1. In one example, an active pharmaceutical ingredient (API) can comprise about 90% or more of Compound 2. In one example, an active pharmaceutical ingredient (API) can comprise about 90% or more of Compound 3. In one example, an active pharmaceutical ingredient (API) can comprise about 90% or more of Compound 4.

Example 21: Pharmaceutical Composition Including Compound 1

A pharmaceutical composition can comprise Compound 1 or a pharmaceutically acceptable salt provided herein.

In one example, an active pharmaceutical ingredient (API) can comprise about 90% or more of Compound 1 or a pharmaceutically acceptable salt thereof.

Oral dosage forms comprising Compound 1 can be prepared as a drug-in-capsule (DIC), encapsulated simple dry-blend granulation, and lipid-based solution in hard shell capsule. The capsules can contain pharmaceutically acceptable excipients, and encapsulated capsules can be packaged in high-density polyethylene induction sealed bottles.

The oral unit dosage form can be capsules incorporating one or more solid forms of Compound 1 (e.g., crystalline type A free base form, crystalline type A hydrochloric acid addition salt, crystalline type B hydrochloric acid addition salt, and/or crystalline type C hydrochloric acid addition salt, or partially crystalline solid forms thereof) as the API powder blended with compendial grade excipients to impart suitable flow and dissolution properties. The formulated blend is subsequently filled into opaque hydroxypropyl methylcellulose (HPMC) V Caps® Plus® capsules. Compound 1 Capsules can be provided on one or more different dose strengths for oral administration. In some embodiments, the Compound 1 Capsules contain 10, 25, or 100 mg Compound 1 (equivalent to free base) by weight per capsule, as the pharmaceutically acceptable solid form. To differentiate the dose strengths, the various dose strengths can be presented as capsules with distinct capsule sizes and/or appearances.

Example 22: Analysis of Compound 1 Purity by HPLC

As disclosed herein, the purity of Compound 1 determined by HPLC (% purity HPLC) refers to a determination of the % purity under the following HPLC conditions: Drug compound samples for analysis were prepared at concentrations of 0.2 mg/mL in a 70:30 mixture of water and acetonitrile. The samples were subsequently analyzed on a Waters Alliance e2695 liquid chromatography instrument equipped with a Waters QDa mass spectrometer and Waters 2998 photodiode array detector. Additional parameters for the chromatography method are disclosed in Table 5 below.

TABLE 5

| Parameters | Values | |
| --- | --- | --- |
| Mobile Phase A | 10 mM Ammonium Acetate | |
| Mobile Phase B | Acetonitrile | |
| Column | Waters XSelect Phenyl-Hexyl, 3.5 µm, 4.6 × 150 mm | |
| Column Temperature | 35° C. | |
| LC Gradient | 0 min | 10% B |
| | 5 min | 30% B |
| | 15 min | 45% B |
| | 21 min | 80% B |
| | 22 min | 80% B |
| | 22.1 min | 10% B |
| Runtime | 25 min | |
| LC Flow Rate | 1 mL/min | |
| UV Wavelength | 238 nm | |
| Ionization Mode | Electrospray Ionization-Positive Mode | |
| Injection Volume | 8 µL | |

Example 23: Pharmaceutical Composition Comprising a CBP Inhibitor Compound for Treatment of mCRPC In one embodiment, a pharmaceutical composition comprising Compound 1, or pharmaceutically acceptable salt form thereof, can be indicated for the treatment of metastatic castrate-resistant prostate cancer (mCRPC). The pharmaceutical composition can be useful for treating patients diagnosed with mCRPC having failed 2 or more prior lines of therapy (including at least one androgen antagonist) and/or in patients having rising PSA or neuroendocrine disease. The pharmaceutical composition can be useful for treating patients diagnosed with mCRPC having failed 2 or more prior lines of therapy (including at least one androgen antagonist) and having rising PSA or neuroendocrine disease. Patients diagnosed with mCRPC can be treated for a course of treatment of 12 weeks or 24 weeks (e.g., in a clinical trial having a PFS primary endpoint, with radiographic progression).

In another embodiment, a pharmaceutical composition comprising Compound 2, or pharmaceutically acceptable salt form thereof, can be indicated for the treatment of metastatic castrate-resistant prostate cancer (mCRPC). The pharmaceutical composition can be useful for treating patients diagnosed with mCRPC having failed 2 or more prior lines of therapy (including at least one androgen antagonist) and/or in patients having rising PSA or neuroendocrine disease. The pharmaceutical composition can be useful for treating patients diagnosed with mCRPC having failed 2 or more prior lines of therapy (including at least one androgen antagonist) and having rising PSA or neuroendocrine disease. Patients diagnosed with mCRPC can be treated for a course of treatment of 12 weeks or 24 weeks (e.g., in a clinical trial having a PFS primary endpoint, with radiographic progression).

In another embodiment, a pharmaceutical composition comprising Compound 3, or pharmaceutically acceptable salt form thereof, can be indicated for the treatment of metastatic castrate-resistant prostate cancer (mCRPC). The pharmaceutical composition can be useful for treating patients diagnosed with mCRPC having failed 2 or more prior lines of therapy (including at least one androgen antagonist) and/or in patients having rising PSA or neuroendocrine disease. The pharmaceutical composition can be useful for treating patients diagnosed with mCRPC having failed 2 or more prior lines of therapy (including at least one androgen antagonist) and having rising PSA or neuroendocrine disease. Patients diagnosed with mCRPC can be treated for a course of treatment of 12 weeks or 24 weeks (e.g., in a clinical trial having a PFS primary endpoint, with radiographic progression).

In another embodiment, a pharmaceutical composition comprising Compound 4, or pharmaceutically acceptable salt form thereof, can be indicated for the treatment of metastatic castrate-resistant prostate cancer (mCRPC). The pharmaceutical composition can be useful for treating patients diagnosed with mCRPC having failed 2 or more prior lines of therapy (including at least one androgen antagonist) and/or in patients having rising PSA or neuroendocrine disease. The pharmaceutical composition can be useful for treating patients diagnosed with mCRPC having failed 2 or more prior lines of therapy (including at least one androgen antagonist) and having rising PSA or neuroendocrine disease. Patients diagnosed with mCRPC can be treated for a course of treatment of 12 weeks or 24 weeks (e.g., in a clinical trial having a PFS primary endpoint, with radiographic progression).

Example 24: Pharmaceutical Composition Comprising a CBP Inhibitor Compound for Treatment of AR-Positive Breast Cancer In one embodiment, a pharmaceutical composition comprising Compound 1, or pharmaceutically acceptable salt form thereof, can be indicated for the treatment of androgen receptor positive (AR+) breast cancer. The pharmaceutical composition can be useful for treating patients diagnosed with AR+ triple negative breast cancer (AR+TNBC) who have failed two or more prior systemic therapies and have AR+ disease that is ER+, PR+ or HER2+ and/or have failed 3 or more prior systemic therapies. The pharmaceutical composition can be useful for treating patients diagnosed with AR+ triple negative breast cancer (AR+TNBC) who have failed two or more prior systemic therapies and have AR+ disease that is ER+, PR+ or HER2+. The pharmaceutical composition can be useful for treating patients diagnosed with AR+ triple negative breast cancer (AR+TNBC) who have failed two or more prior systemic therapies and have failed 3 or more prior systemic therapies. The pharmaceutical composition can be used in a clinical trial with ORR primary endpoint.

In one embodiment, a pharmaceutical composition comprising Compound 2, or pharmaceutically acceptable salt form thereof, can be indicated for the treatment of androgen receptor positive (AR+) breast cancer. The pharmaceutical composition can be useful for treating patients diagnosed with AR+ triple negative breast cancer (AR+TNBC) who have failed two or more prior systemic therapies and have AR+ disease that is ER+, PR+ or HER2+ and/or have failed 3 or more prior systemic therapies. The pharmaceutical composition can be useful for treating patients diagnosed with AR+ triple negative breast cancer (AR+TNBC) who have failed two or more prior systemic therapies and have AR+ disease that is ER+, PR+ or HER2+. The pharmaceutical composition can be useful for treating patients diagnosed with AR+ triple negative breast cancer (AR+TNBC) who have failed two or more prior systemic therapies and have failed 3 or more prior systemic therapies. The pharmaceutical composition can be used in a clinical trial with ORR primary endpoint.

In one embodiment, a pharmaceutical composition comprising Compound 3, or pharmaceutically acceptable salt form thereof, can be indicated for the treatment of androgen receptor positive (AR+) breast cancer. The pharmaceutical composition can be useful for treating patients diagnosed with AR+ triple negative breast cancer (AR+TNBC) who have failed two or more prior systemic therapies and have AR+ disease that is ER+, PR+ or HER2+ and/or have failed 3 or more prior systemic therapies. The pharmaceutical composition can be useful for treating patients diagnosed with AR+ triple negative breast cancer (AR+TNBC) who have failed two or more prior systemic therapies and have AR+ disease that is ER+, PR+ or HER2+. The pharmaceutical composition can be useful for treating patients diagnosed with AR+ triple negative breast cancer (AR+TNBC) who have failed two or more prior systemic therapies and have failed 3 or more prior systemic therapies. The pharmaceutical composition can be used in a clinical trial with ORR primary endpoint.

In one embodiment, a pharmaceutical composition comprising Compound 4, or pharmaceutically acceptable salt form thereof, can be indicated for the treatment of androgen receptor positive (AR+) breast cancer. The pharmaceutical composition can be useful for treating patients diagnosed with AR+ triple negative breast cancer (AR+TNBC) who have failed two or more prior systemic therapies and have AR+ disease that is ER+, PR+ or HER2+ and/or have failed 3 or more prior systemic therapies. The pharmaceutical composition can be useful for treating patients diagnosed with AR+ triple negative breast cancer (AR+TNBC) who have failed two or more prior systemic therapies and have AR+ disease that is ER+, PR+ or HER2+. The pharmaceutical composition can be useful for treating patients diagnosed with AR+ triple negative breast cancer (AR+TNBC) who have failed two or more prior systemic therapies and have failed 3 or more prior systemic therapies. The pharmaceutical composition can be used in a clinical trial with ORR primary endpoint.

Example 25: Study of Compound 1 in Men with Metastatic Castration-Resistant Prostate Cancer This is a multicenter, Phase 1, open-label, study examining Compound 1 for the treatment of men with mCRPC who have progressed despite prior therapy and had been treated with at least one potent anti-androgen therapy (enzalutamide, apalutamide, abiraterone acetate, or darolutamide).

This study enrolls up to 45 men with metastatic castration-resistant prostate cancer (mCRPC) who have progressed despite treatment with at least one potent anti-androgen therapy. The study can last approximately 24 months. The total duration of study treatment for each patient can be approximately 26 weeks. Patients can remain on study treatment until they are deemed to be no longer clinically benefiting (NLCB) by the treating Investigator or until unacceptable toxicity. Patients may be followed for survival for up to 24 months from last dose of study treatment.

Compound 1 is administered in a pharmaceutically acceptable oral unit dosage form described in Example 21. The starting dose, 25 mg once daily (QD).

Compound 1 is administered as a fixed dose. Patients should make all attempts to take Compound 1 Capsules at the same time on scheduled dose days. Capsules may be taken with 240 mL of water. No food should be consumed for at least 2 hours before and 1 hour after drug intake. Patients should avoid grapefruit juice, Seville oranges, and foods containing those products. If a patient vomits at any time after dosing, the dose of Compound 1 should not be re-administered. The site personnel will train the patients and their caregivers on procedures for drug administration. The pharmacist or study nurse can provide the patients with the correct amount of drug for the subsequent dosing period. Compound 1 capsules shall be stored according to storage conditions provided on the drug product label.

The primary endpoints are dose limiting toxicities (DLTs), serious adverse events (SAEs), and clinically relevant adverse events (AEs) and clinically relevant safety laboratory values.

The secondary endpoints are:
Prostate-specific antigen (PSA) at 12 weeks: (Percent change from baseline to 12 weeks) and PSA maximum decrease from baseline (by confirmed decline of PSA)
PSA TTP: Time to a PSA progression, defined as:
  After decline from baseline: record time from start of therapy to first PSA increase that is ≥25% and ≥2 ng/mL above the nadir, and which is confirmed by a second value 3 weeks later (i.e., a confirmed rising trend)
  No decline from baseline: a ≥25% increase from the baseline value along with an increase in absolute value of ≥2 ng/mL after a minimum of 12 weeks of treatment
rTTP: time to a radiographic progression [soft tissue per RECIST 1.1 and bone lesions per Prostate Cancer Working Group 3 (PCWG3)]
Overall response rate (ORR): Radiographic response rate for soft tissue lesions per RECIST 1.1 and bone lesions per PCWG3

Plasma PK parameters (including but not limited to): maximum observed plasma concentration (Cmax), time to maximum observed plasma concentration (Tmax), area under the plasma concentration-time curve from time zero until the 24-hour time point (AUC0-24), area under the plasma concentration-time curve from time zero until the last quantifiable time point (AUC0-last), area under the plasma concentration-time curve from time zero to infinity (AUC0-inf), terminal elimination half-life (t½), apparent clearance (CL/F), apparent volume of distribution (Vd/F) and terminal disposition rate constant Model-based estimate of ΔQTcF and 90% confidence interval at the estimated $C_{max}$ All patients must meet the following criteria for inclusion:
1. Signed and dated Institutional Review Board (IRB)/Independent Ethics Committee (IEC)-approved informed consent form prior to beginning study and undergoing procedures
2. Diagnosis
   (a) mCRPC with either adenocarcinoma or mixed histology:
      (i) Metastatic prostate cancer with progressive castration resistant disease after at least one prior line of treatment for metastatic disease and with evaluable disease at enrollment
      AND
      (ii) Rising PSA (a rising PSA requires at least 3 measurements obtained at least 1 week apart showing increase from nadir with the last level above 2 ng/mL by local testing)
3. Previously failed at least one potent anti-androgen therapy (e.g, abiraterone, enzalutamide, apalutamide, or darolutamide)
4. ≥18 years of age
5. Life expectancy of ≥3 months
6. Castrate levels of serum testosterone (<0.5 ng/mL=1.73 nmol/L)
7. Recovered to ≤Grade 2 toxicity from prior therapy (per CTCAE Version 5.0)
8. Eastern Cooperative Oncology Group (ECOG) performance status 0-2
9. Adequate bone marrow function
   Absolute neutrophil count (ANC)≥1.2×109/L without any growth factors in prior 7 days
   Hemoglobin ≥9.0 g/dL with no blood transfusion in the prior 14 days
   Platelet count ≥75×109/L with no platelet transfusion in the prior 7 days
10. Adequate hepatic function
    Total bilirubin ≤1.5×ULN (≤3×ULN for Gilbert's syndrome)
    AST (serum glutamic oxaloacetic transaminase [SGOT])/ALT (serum glutamic pyruvate transaminase [SGPT])≤3× institutional ULN
11. Adequate renal function
    Creatinine clearance per Cockcroft-Gault equation (or institutional equivalent) of >50 m/min
12. Adequate cardiac function
    Left ventricular ejection fraction (LVEF)>40% by echocardiogram (ECHO) or multi-gated acquisition (MUGA) scan
13. Willingness of patients who are not surgically sterile or with partners who are not postmenopausal to use medically acceptable methods of birth control for the duration of the study treatment, including 90 days after the last dose of study drug
14. Ability to adhere to the study visit schedule and all protocol requirements Patients are to be excluded from the study if they meet any of the following criteria:
1. Previous solid organ transplant
2. Prior anticancer treatment
   Prior treatment with small molecules including chemotherapy, antibody, or other experimental anticancer therapeutic within 4 weeks of first dose of study treatment
   Prior radiation therapy within 4 weeks prior to initiation of study treatment (including radiofrequency ablation)
   Prior androgen antagonist therapy (enzalutamide, apalutamide, abiraterone acetate, or darolutamide) within 2 weeks
   Prior radium-223 therapy within 6 weeks
3. Congestive heart failure (New York Heart Association Class III or IV) or unstable angina pectoris; previous history of myocardial infarction within one year prior to study entry, uncontrolled hypertension, or uncontrolled arrhythmias.
4. Baseline QT interval corrected with Fridericia's method (QTcF)>480 ms (average of triplicate readings)
   NOTE: criterion does not apply to patients with a right or left bundle branch block (BBB). For patients with BBB or conditions interfering with QT assessment, cardiology consult recommended to ensure QTcF within eligible limit.
5. Concomitant medication(s) known to cause Torsades de Pointes (TdP) initiated less than the duration required to reach steady-state plasma concentration (approximately five half-lives) before first dose of study drug (medications used as needed [PRN] (e.g., Zofran) are exempt)
6. Concomitant medication(s) known to be a strong inhibitor or inducer of CYP3A4 or an inhibitor of P-gp
7. Other malignancy within the last 3 years except adequately treated non-melanoma skin cancer or in-situ carcinoma.
8. Major surgery requiring general anesthesia within 3 weeks of starting study treatment (limited biopsy or line placement is acceptable)
9. Symptomatic, untreated, or actively progressing central nervous system (CNS) metastasis
10. Patients with gastrointestinal disorders likely to interfere with absorption of the study drug
11. Known history of infection with human immunodeficiency virus (HIV)
12. Active infection with hepatitis B, or hepatitis C virus
13. Unstable or severe uncontrolled medical condition (eg, unstable pulmonary condition including pneumonitis and/or interstitial lung disease, uncontrolled diabetes, active or uncontrolled infection requiring systemic therapy) or any important medical illness or abnormal laboratory finding that would, in the Investigator's judgment, increase the risk to the patient associated with his participation in the study During study treatment and for 3 months following Compound 1, receipt of live vaccines is prohibited (including the yellow fever vaccine). Annual influenza vaccine is permitted.

Concomitant medication(s) known to cause TdP must have reached steady-state plasma concentration (approximately five half-lives) before first dose of study drug. Medications used PRN (eg, Zofran) are permitted. Initiation of this category of medications on study is prohibited through Cycle 2 Day 15 (to allow for evaluation of QT interval via Central ECG), then allowed afterwards.

During the study treatment period, patients are not to receive any additional anticancer therapy or other investigational agents.

Efficacy will be assessed per the PCWG3 recommendation in all participating patients and response will be assessed by the Investigator. Baseline and on treatment evaluations should include physical examinations, symptom assessments, PSA measurement, imaging which includes cross-sectional imaging of the chest, abdomen, and pelvis, as well as bone scintigraphy, regardless of whether the patient has involvement of those sites at baseline. The same local lab should be used for baseline and on treatment measurement of PSA. The same imaging technique used at baseline should be used on treatment. The type of progression at study entry should be reported.

Example 26: A Study of Compound 1 in Men with mCRPC

This is a Phase 1, open-label study that will evaluate the safety and tolerability of Compound 1 and determine the recommended Phase 2 dose (RP2D), as well as pharmacokinetics (PK), preliminary anti-tumor activity, and pharmacodynamics (PD) of Compound 1 in men with metastatic castration resistant prostate cancer who have progressed despite prior therapy and had been treated with at least one potent anti-androgen therapy.

The study enrolls up to 45 men with metastatic castration-resistant prostate cancer who have progressed despite prior therapy and had been treated with at least one potent anti-androgen therapy. The study can last approximately 18 months. The total duration of study treatment for each patient can be approximately 26 weeks.

Compound 1 is administered in a pharmaceutically acceptable oral unit dosage form described in Example 21. The starting dose, 25 mg once daily (QD), of Compound 1 administered discontinuously (21 days on/7 days off) in 28-day cycles.

In one arm, a dose escalation study of Compound 1 can be performed. Compound 1 can be administered in dose levels of 10 mg, 25 mg, 50 mg, 100 mg, 150 mg, 200 mg, 250 mg, and/or 300 mg. Capsules available in strengths of 10 mg, 25 mg, and 100 mg that are orally administered per the protocol frequency and dose level.

The primary outcome measures are:
1. Incidence of dose limiting toxicities (DLTs);
   [Time Frame: Within first 4 weeks of treatment]
2. Serious adverse effects (SAEs) and clinically relevant adverse events (AEs); and
   [Time Frame: The treatment duration, predicted average 26 weeks]
3. Clinically relevant laboratory values.
   [Time Frame: The treatment duration, predicted average 26 weeks]

The secondary outcome measures are:
1. Prostate-specific antigen (PSA): Decrease from Baseline;
   [Time Frame: The treatment duration, predicted average 26 weeks]
2. Prostate-specific antigen (PSA): Time to Progression;
   [Time Frame: The treatment duration, predicted average 26 weeks]
3. Time to radiographic progression (rTTP);
   [Time Frame: The treatment duration, predicted average 26 weeks]
4. Overall response rate: radiographic response rate;
   [Time Frame: The treatment duration, predicted average 26 weeks]
5. Complete response rate;
   [Time Frame: The treatment duration, predicted average 26 weeks]
6. Area under the plasma concentration versus time curve (AUC);
   [Time Frame: Blood samples for PK analysis collected at multiple visits during the first 90 days of treatment]
7. Peak Plasma Concentration (Cmax);
   [Time Frame: Blood samples for PK analysis collected at multiple visits during the first 90 days of treatment]
8. Time of peak plasma concentration (Tmax);
   [Time Frame: Blood samples for PK analysis collected at multiple visits during the first 90 days of treatment]
9. Terminal elimination half-life (T ½);
   [Time Frame: Blood samples for PK analysis collected at multiple visits during the first 90 days of treatment]
10. Apparent plasma clearance (CL/F);
    [Time Frame: Blood samples for PK analysis collected at multiple visits during the first 90 days of treatment]
11. Apparent volume of distribution (Vd/F); and
    [Time Frame: Blood samples for PK analysis collected at multiple visits during the first 90 days of treatment]
12. Effect on QTc interval.
    [Time Frame: Electrocardiogram collected at multiple timepoints during the first 45 days of treatment]

In order to be eligible for participation in the study, participants must be at least 18 years of age and male. There is no maximum age for participants and healthy volunteers are not eligible.

In addition, all patients must meet the following criteria for inclusion:
1. Signed informed consent;
2. Diagnosis of progressive metastatic castration-resistant prostate cancer (mCRPC);
3. Previously failed at least one potent anti-androgen therapy;
4. Castrate levels of serum testosterone;
5. ECOG performance status 0-2;
6. Adequate bone marrow function;
7. Adequate bone marrow function; and
8. Adequate kidney, heart, and liver function.

Patients are to be excluded from the study if they meet any of the following criteria:
1. Prior solid organ transplant;
2. Prior treatment with small molecules including chemotherapy, antibody, or other experimental anticancer therapeutic within 4 weeks of first dose of study treatment;
3. Prior radiation therapy within 4 weeks prior to initiation of study treatment (including radiofrequency ablation);
4. Prior androgen antagonist therapy (enzalutamide, apalutamide, abiraterone acetate, or darolutamide) within 2 weeks;
5. Prior radium-223 therapy within 6 weeks;
6. Symptomatic, untreated, or actively progressing central nervous system (CNS) metastasis;
7. Unstable or severe, uncontrolled medical condition (e.g. unstable cardiac function, unstable pulmonary condition including pneumonitis and/or interstitial lung disease, uncontrolled diabetes, active or uncontrolled infection requiring systemic therapy) or any important medical illness or abnormal laboratory finding that would, in the Investigator's judgement, increase the risk to the patient associated with participation in the study;
8. Concomitant medications that cause Torsades de Pointes that have not reached steady state before the first dose of the study drug;
9. Concomitant medications that are strong inhibitors or inducers of CYP3A4 or an inhibitor of P-gp;
10. History of infection with human immunodeficiency virus (HIV); and
11. Active infection with hepatitis B, or hepatitis C virus.

Example 27: A Study of Compound 1 in Advanced Tumors

This is a Phase 1/2a, open-label study that can assess the safety, tolerability, PK, and biological activity of Compound 1 in patients with metastatic castration-resistant prostate cancer or advanced solid tumors.

The study can enroll up to 120 participants diagnosed with advanced or metastatic tumors to evaluate the safety and efficacy of Compound 1 as a monotherapy, or in combination with other therapeutics. The study can last approximately 30 months. The total duration of study treatment for each patient can be approximately 12 months. Patients can remain on study treatment until they are deemed to no longer be clinically benefiting (NLCB) by the treating Investigator, or until unacceptable toxicity. Patients may be followed for survival for up to 24 months from the last does of study treatment.

In one arm of the study, a dose escalation study of Compound 1 can be performed in patients diagnosed with metastatic castration-resistant prostate cancer, where Compound 1 is administered orally as the pharmaceutical composition of Example 21 described herein. The pharmaceutical composition can be administered in a capsule formulation.

In another arm, a study of Compound 1 as monotherapy for treating metastatic castration-resistant prostate cancer can be performed in patients, where Compound 1 is administered orally as the pharmaceutical composition of Example 21 described herein. The pharmaceutical composition can be administered in a capsule formulation.

In another arm, a study of Compound 1 in combination with abiraterone for treating metastatic castration-resistant prostate cancer can be performed in patients, where Compound 1 is administered orally as the pharmaceutical composition of Example 21 described herein and abiraterone is administered as a 500 mg tablet that also includes prednisone and/or prednisolone. The pharmaceutical composition can be administered in a capsule formulation.

In another arm, a study of Compound 1 in combination with enzalutamide for treating metastatic castration-resistance prostate cancer can be performed in patients, where Compound 1 is administered orally as the pharmaceutical composition of Example 21 described herein. The pharmaceutical composition can be administered in a capsule formulation.

In another arm, a study of Compound 1 as a monotherapy for treating an advanced solid tumor can be performed in patients, where Compound 1 is administered orally as the pharmaceutical composition of Example 21 described herein and the patients have a tumor with a mutation in CBP and/or p300. The pharmaceutical composition can be administered in a capsule formulation.

Compound 1 is administered as a fixed dose. Patients should make all attempts to take Compound 1 Capsules at the same time on scheduled dose days. Capsules may be taken with 240 mL of water. No food should be consumed for at least 2 hours before and 1 hour after drug intake. Patients should avoid grapefruit juice, Seville oranges, and foods containing those products. If a patient vomits at any time after dosing, the dose of Compound 1 should not be re-administered. The site personnel will train the patients and their caregivers on procedures for drug administration. The pharmacist or study nurse can provide the patients with the correct amount of drug for the subsequent dosing period. Compound 1 capsules shall be stored according to storage conditions provided on the drug product label.

The primary outcome measures are incidence of treatment-related adverse events, serious adverse events, and laboratory assessments, including clinical chemistry and hematology assessments. Each of the primary outcome measures are monitored for the duration of treatment, which can have an average of about 12 months.

The secondary outcome measures are:
Prostate Specific Antigen (PSA) response, as defined by Prostate Cancer Clinical Trial Working Group 3 (PCWG-3) guidelines for the duration of treatment, which can be up to 12 months;
CTC response, defined as a change from unfavorable (five or more cells) at baseline to favorable (four or fewer cells) post treatment for the duration of treatment, which can be up to 12 months;
Objective response rate (ORR), as measured for the duration of treatment, which can be up to 12 months, and includes:
  Malignant soft tissue response rate, as defined by Response Evaluation Criteria in Solid Tumors (RECIST) v1.1; and
  Metastatic bone disease status, as defined by PCWG-3 bone scan criteria;
Radiological progression-free survival (rPFS), measured for the duration of treatment, which can be up to 12 months, and is defined as the time from start of treatment until object disease progression as defined by RECIST 1.1 or PCWG-3 or death;
AUC of Compound 1, as measured for up to 16 days following the first dose of Compound 1 and defined as the area under the plasma concentration-time curve (AUC) from time 0 to the time of the last measureable concentration of Compound 1; and
Cmax of Compound 1, as measured for up to 16 days following the first dose of Compound 1 and defined as the maximum observed plasma concentration (Cmax) of Compound 1.

In order to be eligible for the study, patients must be at least 18 years of age. There is no maximum age for participants and healthy volunteers are not eligible.

All patients must meet the following criteria for inclusion:
1. Provision of consent;
2. ECOG performance status 0-1;
3. Assessable disease (by CT, MRI, bone scan or X-ray);
4. Adequate organ function; and
5. Highly effective contraception measures for duration of study.

All patients with mCRPC must also meet the following criteria for inclusion:
1. Previously received abiraterone and/or enzalutamide (or equivalent anti-androgen), and docetaxel (unless ineligible or refused);
2. Progressive disease documented by one or more of the following:
   a. Biochemical progression defined as at least 2 stepwise increases in a series of any 3 PSA values;
   b. Progression as defined by RECIST v1.1 guidelines for assessment of malignant soft tissue disease; and
   c. Progression defined as two or more new metastatic bone lesions confirmed on bone scan from a previous assessment;
3. PSA at screening ≥2 μg/L;
4. Serum testosterone concentration ≤50 ng/dL; and
5. Serum albumin >2.5 g/dL.

Patients for inclusion in the combination study of Compound 1 with abiraterone must also meet the following criteria for inclusion:
1. Patients must have previously progressed on abiraterone treatment; and
2. Patients whose last dose of abiraterone is greater than 6 months prior to start of study treatment will receive a 4-week-run-in treatment with abiraterone to confirm refractoriness to abiraterone treatment.

Patients for inclusion in the combination study of Compound 1 with enzalutamide must also meet the following criteria for inclusion:
1. Patients must have previously progressed on enzalutamide treatment; and
2. Patients whose last dose of enzalutamide is greater than 6 months prior to start of study treatment will receive a 4-week run-in treatment with enzalutamide to confirm refractoriness to enzalutamide treatment.

Patients for inclusion in the monotherapy study for treating advanced solid tumors that harbor a CBP/p300 mutation must also meet the following criteria for inclusion:
1. Advanced solid tumor with a confirmed mutation in p300/CBP.

Patients are to be excluded from the study if they meet any of the following criteria:
1. Intervention with any chemotherapy, investigational agents or other anti-cancer drugs within 14 days or 5 half-lives of the first dose;
2. Radiotherapy with a wide field of radiation or to more than 30% of the bone marrow within 4 weeks of the first dose of study treatment;
3. Major surgical procedure or significant traumatic injury within 4 weeks of the first dose of study treatment;
4. Strong inhibitors of CYP3A4 or CYP3A4 substrates with a narrow therapeutic range taken within 2 weeks of the first dose of study treatment;
5. Strong inducers of CYP3A4 within 4 weeks of the first dose of study treatment;
6. Statins; patients should discontinue statins prior to starting study treatment;
7. Any unresolved reversible toxicities from prior therapy >CTCAE grade 1 at the time of starting study treatment;
8. Any evidence of severe or uncontrolled systemic diseases;
9. Any known uncontrolled inter-current illness;
10. QTcF prolongation (>480 msec); and/or
11. Primary brain tumors or known or suspected brain metastases.

Patients are to be excluded from the combination study of Compound 1 with abiraterone if they meet any of the following criteria:
1. Clinically significant cardiac abnormalities.

Patients are to be excluded from the combination study of Compound 1 with enzalutamide if they meet any of the following criteria:
1. History of seizures or other predisposing factors;
2. Use of substrates with a narrow therapeutic index metabolized by CYP2C9 or CYP2C19 within 2 weeks of the first dose of study treatment; and/or
3. Clinically significant cardiac abnormalities.

Example 28: A Study of Compound 1 in AR-v7-Positive Metastatic Castration-Resistant Prostate Cancer This is a multicenter, randomized Phase II study that will investigate the effects of Compound 1 on AR-v7+ metastatic castration-resistant prostate cancer. All patients will be required to have previously received docetaxel and to have progression of disease as defined by three rising PSA measurements at least two weeks apart, or a PSA rise of >2.0 μg/L, or radiological disease progression.

The study enrolls up to about 45 men with metastatic castration-resistant prostate cancer who has been shown to harbor the AR-v7 form of the androgen receptor. The study can least approximately 24 months. Patients can remain on study treatment until they are deemed to be no longer clinically benefiting (NLCB) by the treating Investigator or until unacceptable toxicity. Patients may be followed for survival for up to 24 months from last dose of study treatment.

Compound 1 can be administered in a pharmaceutically acceptable oral unit dosage form, as described in Example 21.

Compound 1 is administered as a fixed dose. Patients should make all attempts to take Compound 1 Capsules at the same time on scheduled dose days. Capsules may be taken with 240 mL of water. No food should be consumed for at least 2 hours before and 1 hour after drug intake. Patients should avoid grapefruit juice, Seville oranges, and foods containing those products. If a patient vomits at any time after dosing, the dose of Compound 1 should not be re-administered. The site personnel will train the patients and their caregivers on procedures for drug administration. The pharmacist or study nurse can provide the patients with the correct amount of drug for the subsequent dosing period. Compound 1 capsules shall be stored according to storage conditions provided on the drug product label.

The primary outcome measures are CTC response rate to Compound 1, defined as a decrease from >10 CTC to <5 CTC per 7.5 mL of blood after two or more treatment cycles with Compound 1.

The secondary outcome measures are:
PSA response, defined as a 30% or 50% decline in PSA from baseline to 12 weeks or earlier, in the case of treatment discontinuation;
Best PSA response during treatment; and
Overall survival, defined as the interval between registration and death or last date the patient was known to be alive, In order to be eligible for participation in the study, participants must be at least 18 years of age and male. There is no maximum age for participants and healthy volunteers are not eligible.

In addition, all patients must meet the following criteria for inclusion:
Metastatic castration-resistant prostate cancer with documented disease progression, defined as:
Rising PSA levels; at least two consecutive rises over a reference value and at least one week apart, or a PSA rise of ≥2.0 µg/L; or
Appearance of new lesions or documented disease progression on a CT scan or bone scan;
Previous treatment with docetaxel;
WHO performance status ≤1;
Adequate renal function (serum creatinine ≤1.5× upper limit of normal (ULN) and/or MDRD calculated creatinine clearance >50 mL/min) and hepatic function (total bilirubin ≤1.0×ULN, alanine aminotransferase and aspartate aminotransferase <2.5×ULN, or in case of liver metastases <5×ULN, and alkaline phosphatase <5×ULN, or in case of bone metastases <10×ULN), within 21 days before randomization;
Adequate hematological blood counts (absolute neutrophil count >1.5×10⁹/L and platelets >10×10⁹/L) within 21 days before randomization;
Castration, either surgically or by continued LHRH agonist therapy; and
Written informed consent.
Patients are to be excluded from the study if they meet any of the following criteria:
Impossibility or unwillingness to take oral drugs;
Serious illness or medical unstable conditions requiring treatment, symptomatic central nervous system metastases, or history of psychiatric disorder that would hinder the understanding and obtaining of informed consent;
Use of medications or dietary supplements known to induce or inhibit CYP3A;
Use of hormonal agents other than GnRH agonists;
Known hypersensitivity to corticosteroids;
Any active systemic or local bacterial, viral, or fungal infection;
Ulcerative colitis, Crohn's disease, or celiac disease (active or in medical history);
Ostomy;
Planned/active simultaneous yellow fever vaccine; and
Geographical, psychological, or other non-medical conditions interfering with follow up.
Blood can be drawn by venipuncture before the start of the first and subsequent cycles of treatment with Compound 1. Enumeration of CTCs can be carried out by methods commonly known in the art. mRNA can be harvested from collected blood samples and analyzed for the expression levels of wild type AR and the AR-v7 variant using RT-qPCR via methods commonly known in the art.
During study treatment and for 3 months following Compound 1, receipt of live vaccines is prohibited (including the yellow fever vaccine). Annual influenza vaccine is permitted.
Concomitant medication(s) known to cause TdP must have reached steady-state plasma concentration (approximately five half-lives) before first dose of study drug. Medications used PRN (eg, Zofran) are permitted. Initiation of this category of medications on study is prohibited through Cycle 2 Day 15 (to allow for evaluation of QT interval via Central ECG), then allowed afterwards.
During the study treatment period, patients are not to receive any additional anticancer therapy or other investigational agents.

Efficacy will be assessed per the PCWG3 recommendation in all participating patients and response will be assessed by the Investigator. Baseline and on treatment evaluations should include physical examinations, symptom assessments, PSA measurement, imaging which includes cross-sectional imaging of the chest, abdomen, and pelvis, as well as bone scintigraphy, regardless of whether the patient has involvement of those sites at baseline. The same local lab should be used for baseline and on treatment measurement of PSA. The same imaging technique used at baseline should be used on treatment. The type of progression at study entry should be reported.

Further embodiments of the disclosure are set out in the following numbered embodiments:

1. A method of treating an androgen receptor positive cancer, comprising: administering to a patient in need thereof a therapeutically effective amount of a pharmaceutical composition comprising a compound of formula (I):

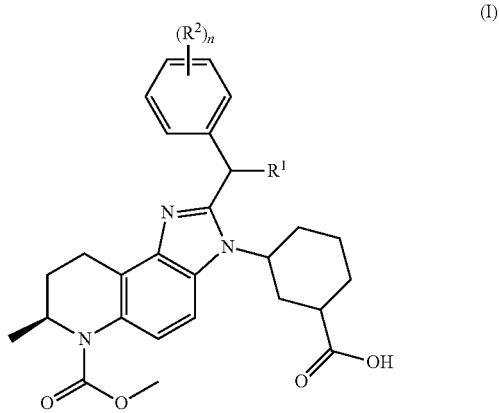

or a pharmaceutically acceptable salt thereof, wherein:
$R^1$ is H or —OH;
each R2 is independently selected from C1-C6 alkyl, halogen, —CN, and —OR3, wherein the alkyl is optionally substituted with one or more halogen;
each R3 is independently C1-C6 alkyl, wherein the alkyl is optionally substituted with one or more halogen; and
n is 0, 1, 2, or 3.

2. The method of embodiment 1, wherein the compound is:

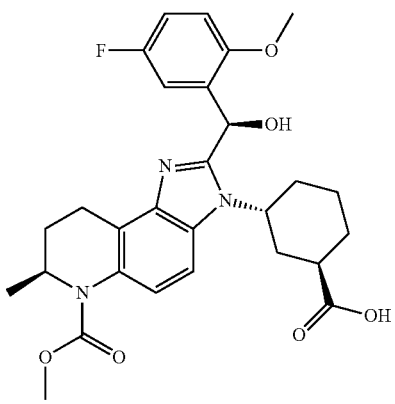 [SMILES: COC(=O)N1c2ccc3c(nc([C@H](O)c4cc(F)ccc4OC)n3[C@@H]3CCC[C@@H](C(=O)O)C3)c2CC[C@@H]1C]

or a pharmaceutically acceptable salt thereof.

3. The method of embodiment 1, wherein the compound is:

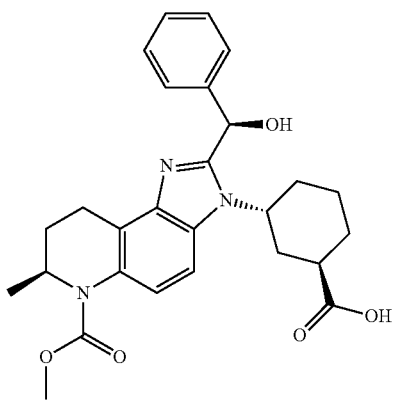 [SMILES: COC(=O)N1c2ccc3c(nc([C@H](O)c4ccccc4)n3[C@@H]3CCC[C@@H](C(=O)O)C3)c2CC[C@@H]1C]

or a pharmaceutically acceptable salt thereof.

4. The method of embodiment 1, wherein the compound is:

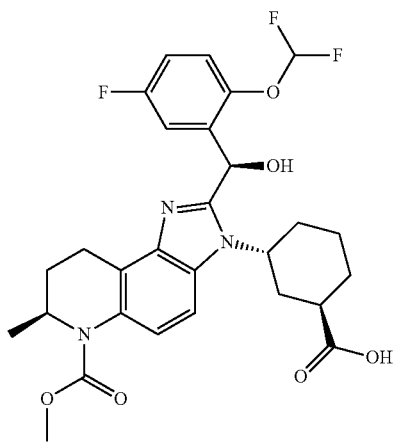 [SMILES: COC(=O)N1c2ccc3c(nc([C@H](O)c4cc(F)ccc4OC(F)F)n3[C@@H]3CCC[C@@H](C(=O)O)C3)c2CC[C@@H]1C]

or a pharmaceutically acceptable salt thereof.

5. The method of embodiment 1, wherein the compound is:

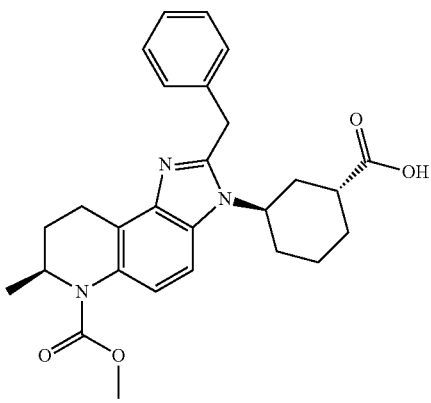 [SMILES: COC(=O)N1c2ccc3c(nc(Cc4ccccc4)n3[C@@H]3CCC[C@@H](C(=O)O)C3)c2CC[C@@H]1C]

or a pharmaceutically acceptable salt thereof.

6. The method of any one of embodiments 1-5, wherein the androgen receptor positive cancer is breast cancer.

7. The method of any one of embodiments 1-6, wherein the androgen receptor positive cancer is triple negative breast cancer.

8. The method of any one of embodiments 1-6 wherein the androgen receptor positive cancer is selected from the group consisting of a HR+/Her2− breast cancer, a HR−/Her2+ breast cancer, and a HR+/Her2+ breast cancer.

9. The method of any one of embodiments 1-5, wherein the androgen receptor positive cancer is prostate cancer.

10. The method of any one of embodiments 1-5, wherein the androgen receptor positive cancer is a metastatic castration-resistant prostate cancer.

11. The method of embodiment 10, wherein the patient in need thereof is further diagnosed as having a metastatic castration resistant prostate cancer that is characterized as being refractory or resistant after an administration of an androgen deprivation therapy.

12. The method of any one of embodiments 9-11, wherein the patient is diagnosed with disease progression following treatment with enzalutamide.

13. The method of any one of embodiments 9-12, wherein the patient in need thereof has an AR-v7 splice form of the androgen receptor.

14. The method of any one of embodiments 9-13, wherein the pharmaceutical composition is administered to the patient in need thereof in combination with an androgen deprivation therapy.

15. The method of any one of embodiments 9-13, wherein the pharmaceutical composition is administered to the patient in need thereof following the completion of an administration of an androgen deprivation therapy.

16. The method of any one of embodiments 1-15, wherein the patient in need thereof is diagnosed as having failed one or more systemic therapies for treating the androgen receptor positive cancer prior to administration of the pharmaceutical composition.

17. The method of any one of embodiments 1-15, wherein the patient in need thereof is diagnosed as having failed two or more systemic therapies for treating the androgen receptor positive cancer prior to administration of the pharmaceutical composition.

18. The method of any one of embodiments 1-15, wherein the patient in need thereof is diagnosed as having failed three or more systemic therapies for treating the androgen receptor positive cancer prior to administration of the pharmaceutical composition.

19. The method of any one of embodiments 1-18, wherein the pharmaceutical composition is administered to the patient in need thereof at a dose sufficient to reduce the expression of an androgen receptor-dependent gene within the patient.

20. The method of any one of embodiments 1-19, wherein the pharmaceutical composition is administered to the patient in need thereof at a dose sufficient to reduce the expression of an estrogen receptor-dependent gene within the patient.

21. The method of any one of embodiments 1-20, wherein the pharmaceutical composition is administered to the patient in need thereof at a dose sufficient to reduce the expression of at least one gene selected from the list consisting of: AQP3, Myc, SPDEF, TMPRSS2, XBP1, and KLK3 within the patient.

22. The method of any one of embodiments 1-21 wherein the pharmaceutical composition is administered at a dose sufficient to reduce an amount of acetylated H3K27 histone proteins within the patient.

23. The method of any one of embodiments 1-22 wherein the pharmaceutical composition is administered at a dose sufficient to reduce an amount of androgen receptor or AR-v7 splice form variant proteins within the patient.

24. The method of any one of embodiments 1-23 wherein the pharmaceutical composition is administered at a dose sufficient to reduce the expression of androgen receptor or AR-v7 splice form variant proteins within the patient.

25. The method of any one of embodiments 1-24, wherein the pharmaceutical composition is formulated for administration as an oral unit dosage form.

26. The method of any one of embodiments 1-25, wherein the pharmaceutical composition is formulated for administration in a capsule form.

27. The method of embodiment 26, wherein the capsule form comprises a pharmaceutical excipient.

28. The method of any one of embodiments 26-27, wherein the capsule form comprises a dose of the compound selected from the group consisting of: 10 mg of the compound, 25 mg of the compound, or 100 mg of the compound.

29. The method of any one of embodiments 26-28, wherein the capsule form is administered to the patient in need thereof once daily.

30. The method of any one of embodiments 26-28, wherein the capsule form is administered to the patient in need thereof twice daily.

31. The method of any one of embodiments 26-30, wherein the capsule form is administered to the patient in need thereof for a period of 14 to 28 days per a 28-day cycle.

32. A method of treating an androgen receptor positive cancer comprising the step of administering to a patient in need thereof a therapeutically effective amount of a pharmaceutical composition comprising a compound, or a pharmaceutically acceptable salt thereof, selected from the group consisting of:

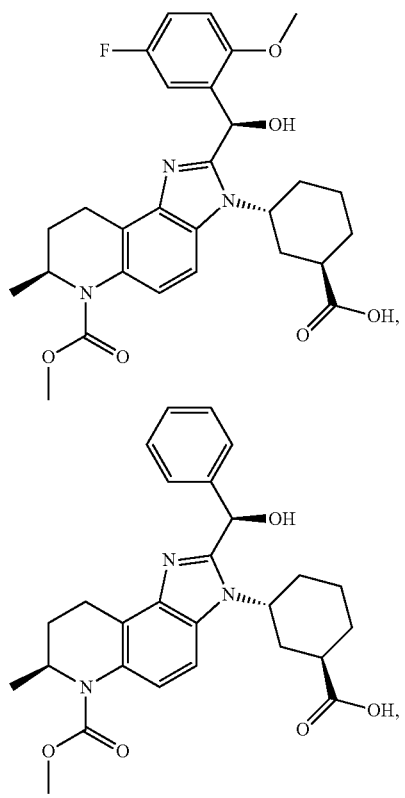

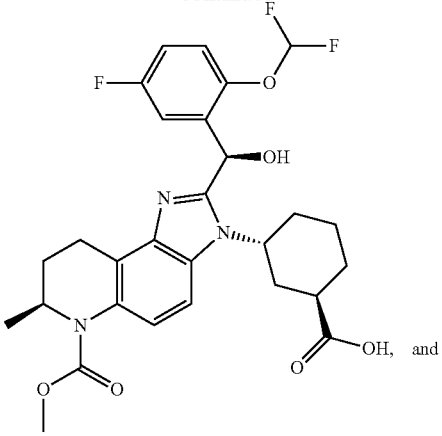

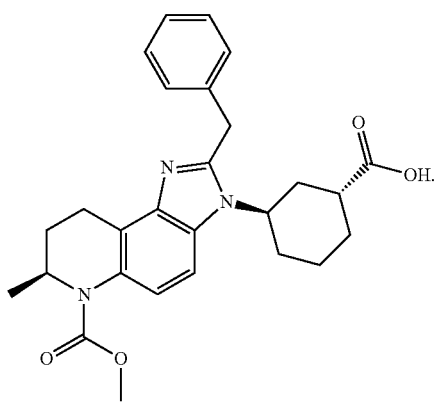

33. The method of embodiment 32, wherein the compound is:

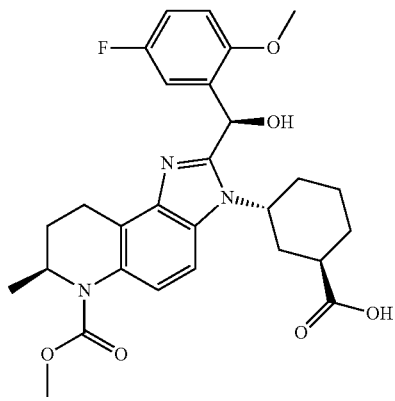 [SMILES: COC(=O)N1c2ccc3c(nc([C@H](O)c4cc(F)ccc4OC)n3[C@@H]3CCC[C@@H](C(=O)O)C3)c2CC[C@@H]1C]

or a pharmaceutically acceptable salt thereof.

34. The method of embodiment 32, wherein the compound is:

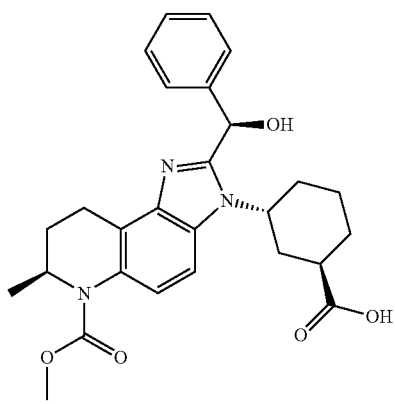 [SMILES: COC(=O)N1c2ccc3c(nc([C@H](O)c4ccccc4)n3[C@@H]3CCC[C@@H](C(=O)O)C3)c2CC[C@@H]1C]

or a pharmaceutically acceptable salt thereof.

35. The method of embodiment 32, wherein the compound is:

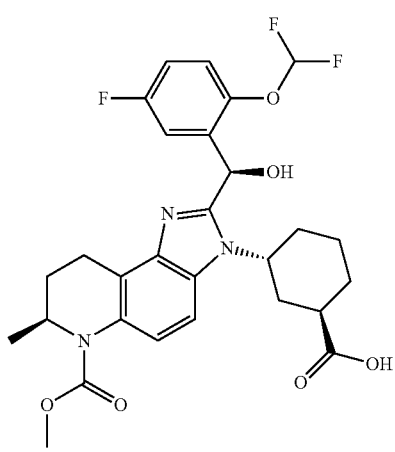 [SMILES: COC(=O)N1c2ccc3c(nc([C@H](O)c4cc(F)ccc4OC(F)F)n3[C@@H]3CCC[C@@H](C(=O)O)C3)c2CC[C@@H]1C]

or a pharmaceutically acceptable salt thereof.

36. The method of embodiment 32, wherein the compound is:

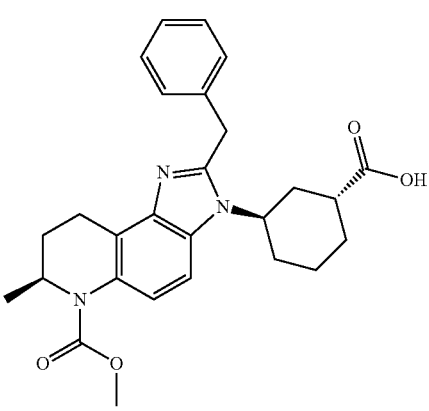 [SMILES: COC(=O)N1c2ccc3c(nc(Cc4ccccc4)n3[C@@H]3CCC[C@@H](C(=O)O)C3)c2CC[C@@H]1C]

or a pharmaceutically acceptable salt thereof.

37. The method of any one of embodiments 32-36, wherein the androgen receptor positive cancer is breast cancer.

38. The method of any one of embodiments 32-37, wherein the androgen receptor positive cancer is a triple negative breast cancer.

39. The method of any one of embodiments 32-37, wherein the androgen receptor positive cancer is selected from the group consisting of a HR+/Her2– breast cancer, a HR–/Her2+ breast cancer, and a HR+/Her2+ breast cancer.

41. The method of any one of embodiments 32-36, wherein the androgen receptor positive cancer is prostate cancer.

42. The method of any one of embodiments 32-36 or embodiment 41, wherein the androgen receptor positive cancer is a metastatic castration-resistant prostate cancer.

43. The method of embodiment 42, wherein the patient in need thereof is further diagnosed as having a metastatic castration resistant prostate cancer that is characterized as being refractory or resistant after an administration of an androgen deprivation therapy.

44. The method of any one of embodiments 41-43, wherein the patient is diagnosed with disease progression following treatment with enzalutamide.

45. The method of any one of embodiments 41-44, wherein the patient in need thereof has an AR-v7 splice form of the androgen receptor.

46. The method of any one of embodiments 41-45, wherein the pharmaceutical composition is administered to the patient in need thereof in combination with an androgen deprivation therapy.

47. The method of any one of embodiments 41-45, wherein the pharmaceutical composition is administered to the patient in need thereof following the completion of an administration of an androgen deprivation therapy.

48. The method of any one of embodiments 32-47, wherein the patient in need thereof is diagnosed as having failed one or more systemic therapies for treating the androgen receptor positive cancer prior to administration of the pharmaceutical composition.

49. The method of any one of embodiments 32-47, wherein the patient in need thereof is diagnosed as having failed two or more systemic therapies for treating the androgen receptor positive cancer prior to administration of the pharmaceutical composition.

50. The method of any one of embodiments 32-47, wherein the patient in need thereof is diagnosed as having failed three or more systemic therapies for treating the androgen receptor positive cancer prior to administration of the pharmaceutical composition.

51. The method of any one of embodiments 32-50, wherein the pharmaceutical composition is administered to the patient in need thereof at a dose sufficient to reduce the expression of an androgen receptor-dependent gene within the patient.

52. The method of any one of embodiments 32-51, wherein the pharmaceutical composition is administered to the patient in need thereof at a dose sufficient to reduce the expression of an estrogen receptor-dependent gene within the patient.

53. The method of any one of embodiments 32-52, wherein the pharmaceutical composition is administered to the patient in need thereof at a dose sufficient to reduce the expression of at least one gene selected from the list consisting of: AQP3, Myc, SPDEF, TMPRSS2, XBP1, and KLK3 within the patient.

54. The method of any one of embodiments 32-53, wherein the pharmaceutical composition is administered at a dose sufficient to reduce an amount of acetylated H3K27 histone proteins within the patient.

55. The method of any one of embodiments 32-54, wherein the pharmaceutical composition is administered at a dose sufficient to reduce an amount of androgen receptor or AR-v7 splice form variant proteins within the patient.

56. The method of any one of embodiments 32-55 wherein the pharmaceutical composition is administered at a dose sufficient to reduce the expression of androgen receptor or AR-v7 splice form variant proteins within the patient.

57. The method of any one of embodiments 32-56, wherein the pharmaceutical composition is formulated for administration as an oral unit dosage form.

58. The method of embodiment 57, wherein the pharmaceutical composition is formulated for administration in a capsule form.

59. The method of embodiment 58, wherein the capsule form further comprises a pharmaceutical excipient.

60. The method of embodiment 58 or 59, wherein the capsule form comprises a dose of the compound selected from the group consisting of: 10 mg of the compound, 25 mg of the compound, or 100 mg of the compound.

61. The method of any one of embodiments 58-60, wherein the capsule form is administered to the patient in need thereof once daily.

62. The method of any one of embodiments 58-60, wherein the capsule form is administered to the patient in need thereof twice daily.

63. The method of any one of embodiments 58-62, wherein the capsule form is administered to the patient in need thereof for a period of 14 to 28 days per a 28-day cycle.

64. A method of treating an androgen receptor positive cancer comprising the step of administering to a patient in need thereof a therapeutically effective amount of a pharmaceutical composition comprising the compound:

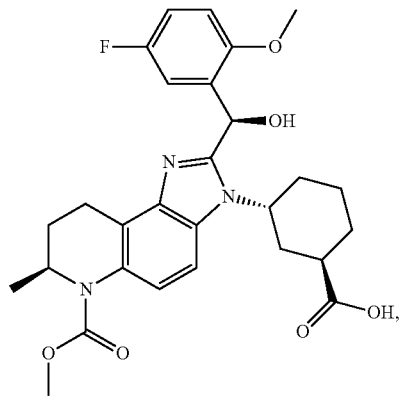 [SMILES: COC(=O)N1c2ccc3c(nc([C@H](O)c4cc(F)ccc4OC)n3[C@@H]3CCC[C@@H](C(=O)O)C3)c2CC[C@@H]1C]

or a pharmaceutically acceptable salt thereof.

65. The method of embodiment 64, wherein the androgen receptor positive cancer is breast cancer.

66. The method of embodiment 64 or 65, wherein the androgen receptor positive cancer is a triple negative breast cancer.

67. The method of embodiment 64 or 65, wherein the androgen receptor positive cancer is selected from the group consisting of a HR+/Her2– breast cancer, a HR–/Her2+ breast cancer, and a HR+/Her2+ breast cancer.

68. The method of embodiment 64, wherein the androgen receptor positive cancer is prostate cancer.

69. The method of embodiment 64 or 68, wherein the androgen receptor positive cancer is a metastatic castration-resistant prostate cancer.

70. The method of embodiment 68 or 69, wherein the patient in need thereof is further diagnosed as having a metastatic castration resistant prostate cancer that is characterized as being refractory or resistant after an administration of an androgen deprivation therapy.

71. The method of any one of embodiments 68-70, wherein the patient is diagnosed with disease progression following treatment with enzalutamide.

72. The method of any one of embodiments 68-71, wherein the patient in need thereof has an AR-v7 splice form of the androgen receptor.

73. The method of any one of embodiments 68-72, wherein the pharmaceutical composition is administered to the patient in need thereof in combination with an androgen deprivation therapy.

74. The method of any one of embodiments 68-72, wherein the pharmaceutical composition is administered to the patient in need thereof following the completion of an administration of an androgen deprivation therapy.

75. The method of any one of embodiments 64-74, wherein the patient in need thereof is diagnosed as having failed one or more systemic therapies for treating the androgen receptor positive cancer prior to administration of the pharmaceutical composition.

76. The method of any one of embodiments 64-74, wherein the patient in need thereof is diagnosed as having failed two or more systemic therapies for treating the androgen receptor positive cancer prior to administration of the pharmaceutical composition.

77. The method of any one of embodiments 64-74, wherein the patient in need thereof is diagnosed as having failed three or more systemic therapies for treating the androgen receptor positive cancer prior to administration of the pharmaceutical composition.

78. The method of any one of embodiments 64-77, wherein the pharmaceutical composition is administered to the patient in need thereof at a dose sufficient to reduce the expression of an androgen receptor-dependent gene within the patient.

79. The method of any one of embodiments 64-78, wherein the pharmaceutical composition is administered to the patient in need thereof at a dose sufficient to reduce the expression of an estrogen receptor-dependent gene within the patient.

80. The method of any one of embodiments 64-79, wherein the pharmaceutical composition is administered to the patient in need thereof at a dose sufficient to reduce the expression of at least one gene selected from the list consisting of: AQP3, Myc, SPDEF, TMPRSS2, XBP1, and KLK3 within the patient.

81. The method of any one of embodiments 64-80 wherein the pharmaceutical composition is administered at a dose sufficient to reduce an amount of acetylated H3K27 histone proteins within the patient.

82. The method of any one of embodiments 64-81 wherein the pharmaceutical composition is administered at a dose sufficient to reduce an amount of androgen receptor or AR-v7 splice form variant proteins within the patient.

83. The method of any one of embodiments 64-82 wherein the pharmaceutical composition is administered at a dose sufficient to reduce the expression of androgen receptor or AR-v7 splice form variant proteins within the patient.

84. The method of any one of embodiments 64-83, wherein the pharmaceutical composition is formulated for administration as an oral unit dosage form.

85. The method of embodiment 84, wherein the pharmaceutical composition is formulated for administration in a capsule form.

86. The method of embodiment 85, wherein the capsule form further comprises a pharmaceutical excipient.

87. The method of embodiment 85 or 86, wherein the capsule form comprises a dose of the compound selected from the group consisting of: 10 mg of the compound, 25 mg of the compound, or 100 mg of the compound.

88. The method of any one of embodiments 85-87, wherein the capsule form is administered to the patient in need thereof once daily.

89. The method of any one of embodiments 85-87, wherein the capsule form is administered to the patient in need thereof twice daily.

90. The method of any one of embodiments 85-89, wherein the capsule form is administered to the patient in need thereof for a period of 14 to 28 days per a 28-day cycle.

91. A method of treating breast cancer in a patient comprising administering to the patient in need thereof a therapeutically effective amount of a pharmaceutical composition comprising a compound of formula (I):

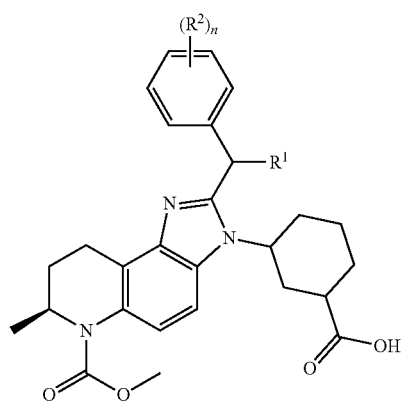

(I)

or a pharmaceutically acceptable salt thereof, wherein:

R$^1$ is H or —OH;

each R$^2$ is independently selected from C$_1$-C$_6$ alkyl, halogen, —CN, and —OR$^3$, wherein the alkyl is optionally substituted with one or more halogen;

each R$^3$ is independently C$_1$-C$_6$ alkyl, wherein the alkyl is optionally substituted with one or more halogen; and n is 0, 1, 2, or 3.

92. The method of embodiment 91, wherein the breast cancer is triple negative breast cancer.

93. The method of embodiment 91, wherein the breast cancer is AR+.

94. The method of embodiment 91, wherein the compound is selected from:

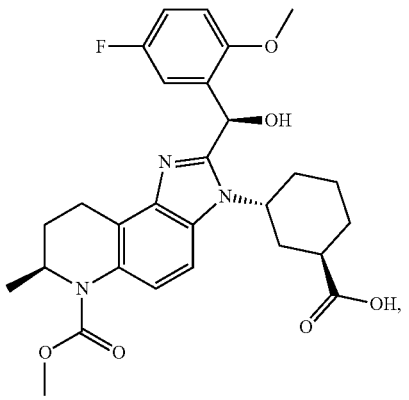

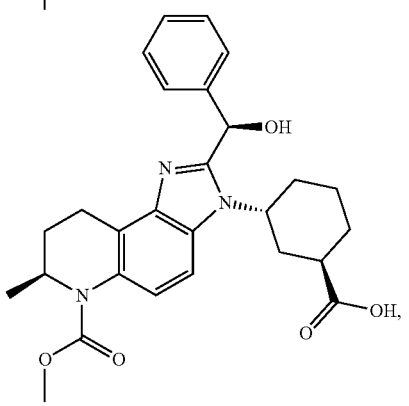

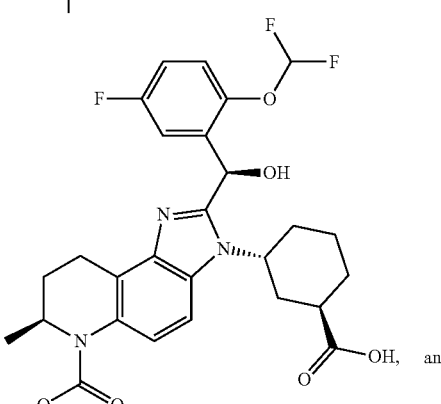

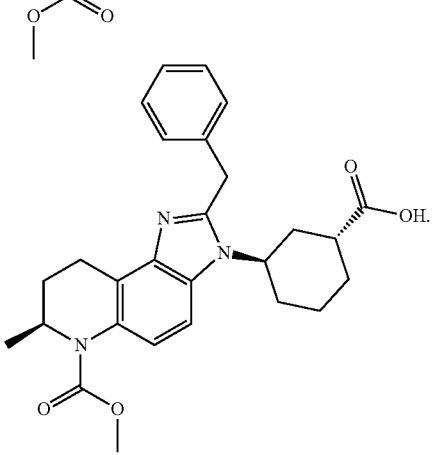

95. The method of embodiment 94, wherein the breast cancer is triple negative breast cancer.

96. The method of embodiment 94, wherein the breast cancer is AR+.
97. The method of embodiment 91, wherein the compound is:
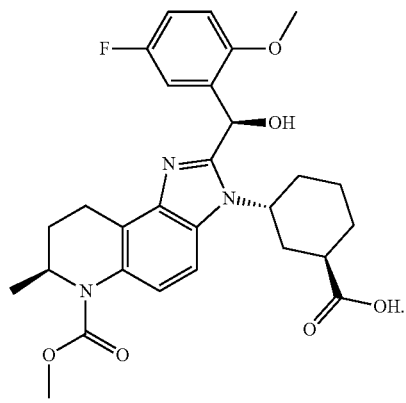 [SMILES: COC(=O)N1c2ccc3c(nc([C@H](O)c4cc(F)ccc4OC)n3[C@@H]3CCC[C@@H](C(=O)O)C3)c2CC[C@@H]1C]
98. The method of embodiment 91, wherein the compound is:
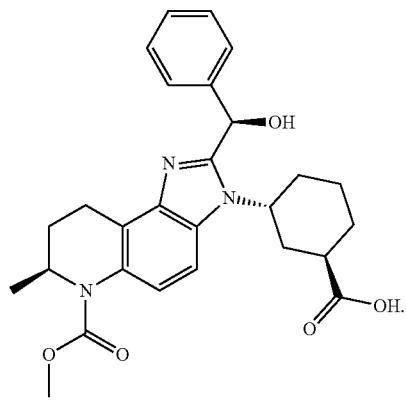 [SMILES: COC(=O)N1c2ccc3c(nc([C@H](O)c4ccccc4)n3[C@@H]3CCC[C@@H](C(=O)O)C3)c2CC[C@@H]1C]
99. The method of embodiment 91, wherein the compound is:
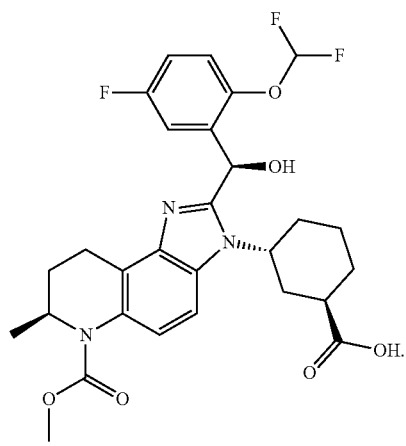 [SMILES: COC(=O)N1c2ccc3c(nc([C@H](O)c4cc(F)ccc4OC(F)F)n3[C@@H]3CCC[C@@H](C(=O)O)C3)c2CC[C@@H]1C]
100. The method of embodiment 91, wherein the compound is:
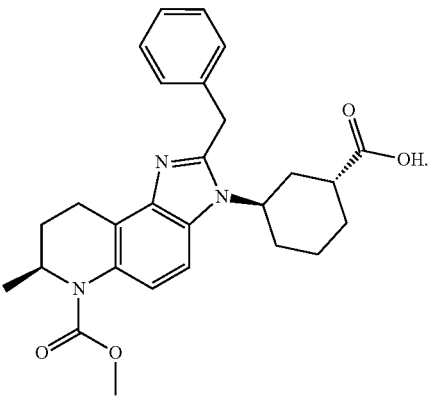 [SMILES: COC(=O)N1c2ccc3c(nc(Cc4ccccc4)n3[C@@H]3CCC[C@@H](C(=O)O)C3)c2CC[C@@H]1C]
101. The method of embodiment 91, wherein the breast cancer is AR+, and wherein the compound is selected from:
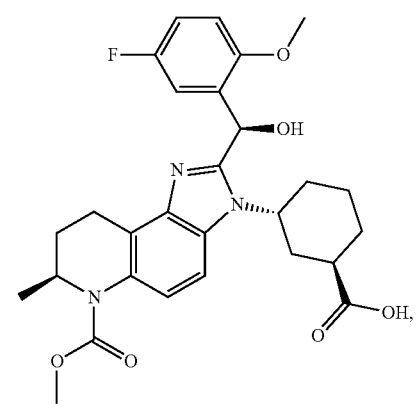

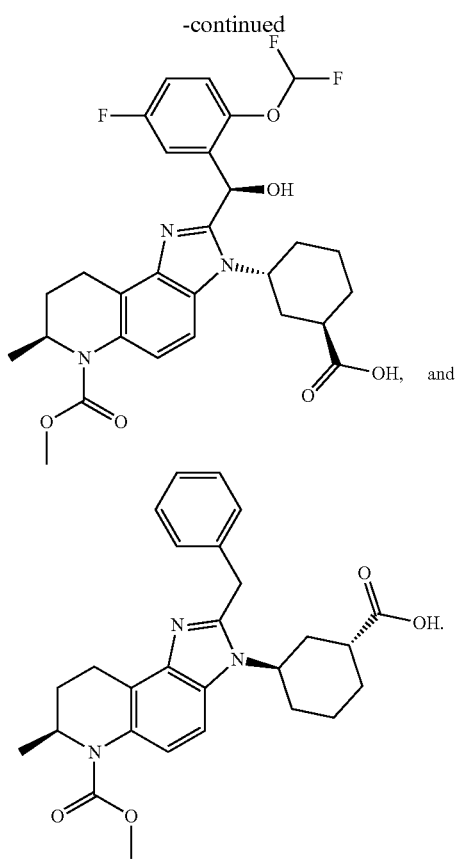

and

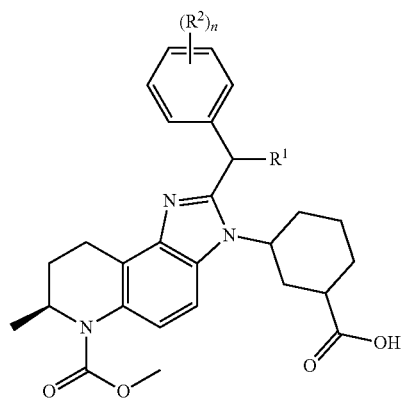

102. The method of embodiment 101, wherein the breast cancer is triple negative breast cancer.

103. A method of treating prostate cancer in a patient comprising administering to the patient in need thereof a therapeutically effective amount of a pharmaceutical composition comprising a compound of formula (I):

(I)

or a pharmaceutically acceptable salt thereof, wherein:
R$^1$ is H or —OH;
each R$^2$ is independently selected from C$_1$-C$_6$ alkyl, halogen, —CN, and —OR$^3$, wherein the alkyl is optionally substituted with one or more halogen;
each R$^3$ is independently C$_1$-C$_6$ alkyl, wherein the alkyl is optionally substituted with one or more halogen; and
n is 0, 1, 2, or 3.

104. The method of embodiment 103, wherein the prostate cancer is AR+.

105. The method of embodiment 103, wherein the prostate cancer is AR-v7+.

106. The method of embodiment 103, wherein the patient is diagnosed with castration-resistant prostate cancer or metastatic castration-sensitive prostate cancer.

107. The method of embodiment 103, wherein the compound is selected from:

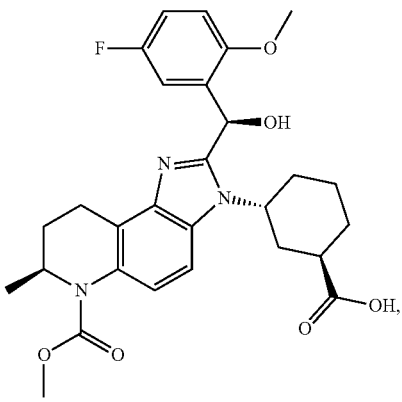

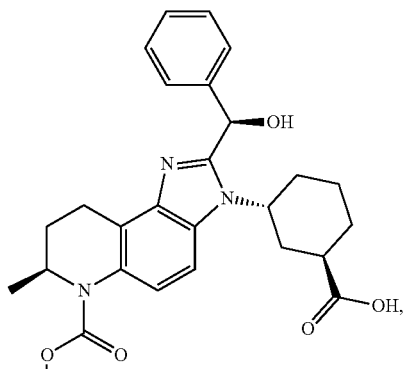

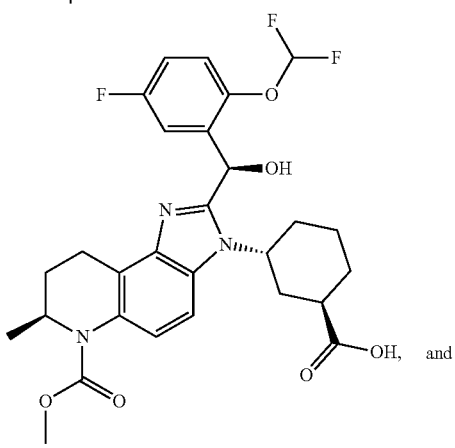

and

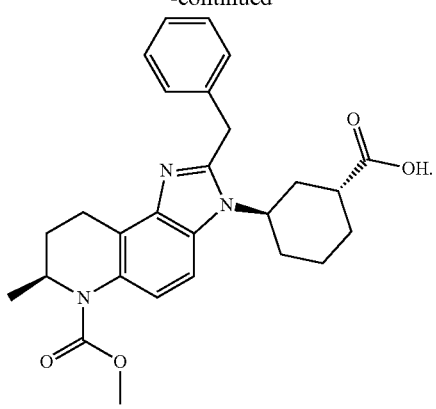

108. The method of embodiment 107, wherein the patient is diagnosed with disease progression following treatment with enzalutamide.

109. The method of embodiment 103, wherein the compound is selected from:

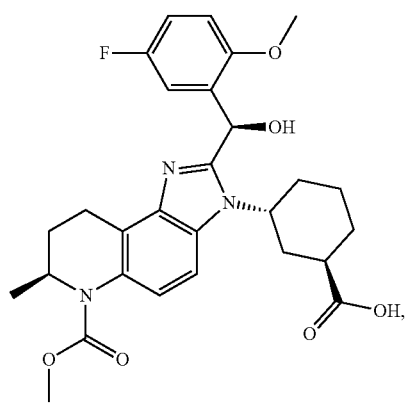

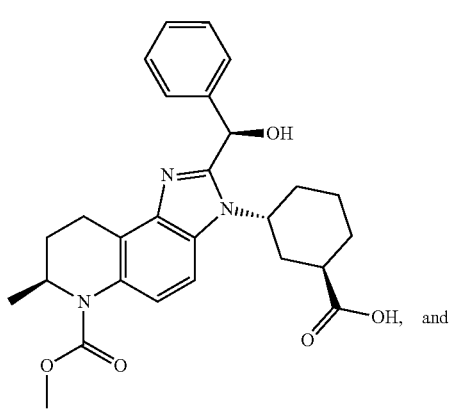

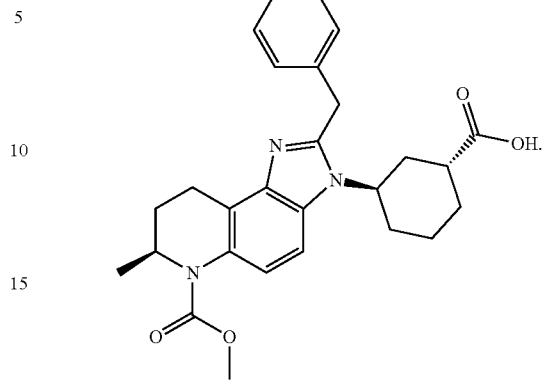

110. The method of embodiment 109, wherein the prostate cancer is AR+.

111. The method of embodiment 110, wherein the prostate cancer is AR-v7+.

112. The method of embodiment 109, wherein the patient is diagnosed with castration-resistant prostate cancer or metastatic castration-sensitive prostate cancer.

113. A method of treating an androgen receptor-expressing cancer in a patient comprising administering to the patient in need thereof a therapeutically effective amount of a pharmaceutical composition comprising (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid, or a pharmaceutically acceptable salt thereof.

114. The method of embodiment 113, wherein the androgen receptor-expressing cancer is AR+ breast cancer.

115. The method of embodiment 114, wherein the AR+ breast cancer is triple negative breast cancer.

116. The method of embodiment 114, wherein the AR+ breast cancer is Her2− breast cancer.

117. The method of embodiment 114, wherein the AR+ breast cancer is selected from ER− breast cancer, PR− breast cancer, and ER−/PR− breast cancer.

118. The method of embodiment 113, wherein the androgen receptor-expressing cancer is AR+ prostate cancer.

119. The method of embodiment 118, wherein the AR+ prostate cancer is AR-v7+. 120. The method of embodiment 113, wherein the androgen receptor-expressing cancer is castration-resistant prostate cancer or metastatic castration-sensitive prostate cancer.

121. The method of embodiment 119, wherein the patient is diagnosed with disease progression following treatment with enzalutamide.

122. A method of treating an androgen receptor-expressing cancer in a patient comprising administering to the patient in need thereof a therapeutically effective amount of a pharmaceutical composition comprising:

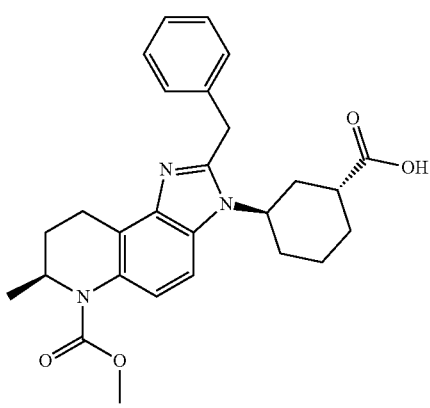 [SMILES: COC(=O)N1c2ccc3c(nc(Cc4ccccc4)n3[C@@H]3CCC[C@@H](C(=O)O)C3)c2CC[C@@H]1C]

or a pharmaceutically acceptable salt thereof.

123. The method of embodiment 122, wherein the androgen receptor-expressing cancer is AR+ breast cancer.

124. The method of embodiment 122, wherein the AR+ breast cancer is triple negative breast cancer.

125. The method of embodiment 122, wherein the androgen receptor-expressing cancer is AR+ prostate cancer.

126. The method of embodiment 125, wherein the AR+ prostate cancer is AR-v7+.

Additional embodiments of the disclosure are set out in the following numbered embodiments:

1. A method of treating AR+ prostate cancer in a patient comprising administering to the patient in need thereof a therapeutically effective amount of Compound 1, or a pharmaceutically acceptable salt thereof, wherein Compound 1 is (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid.

2. The method of embodiment 1, wherein the Compound 1, or a pharmaceutically acceptable salt thereof, is administered to the patient in need thereof in an oral unit dosage form.

3. The method of embodiment 1 or 2, wherein the Compound 1 is administered as a hydrochloric acid addition salt.

4. The method of any one of embodiments 1-3, wherein the Compound 1 is administered as a type A hydrochloric acid addition salt of Compound 1.

5. The method of any one of embodiments 1-3, wherein the Compound 1 is administered as a type B hydrochloric acid addition salt of compound 1.

6. The method of any one of embodiments 1-3, wherein the Compound 1 is administered as a type C hydrochloric acid addition salt of compound 1.

7. The method of embodiment 1 or 2, wherein the Compound 1 is administered as a type A free base form of Compound 1.

8. The method of any one of embodiments 1-4, wherein the Compound 1 is the active pharmaceutical ingredient an anhydrate solid form.

9. The method of any one of embodiments 1-8, wherein the AR+ prostate cancer is AR+ castration-resistant prostate cancer.

10. The method of any one of embodiments 1-9, wherein the AR+ prostate cancer is metastatic castration-resistant prostate cancer.

11. The method of embodiment 10, wherein the patient is progressive after at least one line of treatment and had previously been treated with at least one anti-androgen.

12. The method of embodiment 10 or 11, wherein the patient is refractory or relapsing on treatment with enzalutamide or abiraterone.

13. The method of any one of embodiments 10-12, wherein the patient harbors an AR aberration.

14. The method of any one of embodiments 10-13, wherein the patient harbors the AR-v7 form.

15. The method of embodiment 10, wherein the patient has not previously been treated for metastatic castration-resistant prostate cancer.

16. The method of any one of embodiments 10-15, wherein the Compound 1, or a pharmaceutically acceptable salt thereof, is administered in combination with an anti-androgen.

17. The method of embodiment 16, wherein the anti-androgen is selected from the group consisting of enzalutamide, abiraterone, darolutamide, and apalutamide.

18. The method of any one of embodiments 1-9, wherein the AR+ castration-resistant prostate cancer is non-metastatic castration-resistant prostate cancer.

19. The method of embodiment 18, wherein the administration of the Compound 1, or a pharmaceutically acceptable salt thereof, delays or slows the progression of the non-metastatic castration-resistant prostate cancer to a metastatic state.

20. The method of embodiment 18 or 19, wherein the Compound 1, or a pharmaceutically acceptable salt thereof, is administered in combination with an androgen-deprivation treatment.

21. The method of embodiment 18 or 19, wherein the Compound 1, or a pharmaceutically acceptable salt thereof, is administered in combination with an anti-androgen.

22. The method of any one of embodiments 18-21, wherein the Compound 1, or a pharmaceutically acceptable salt thereof, is administered in combination with an androgen-deprivation therapy and an anti-androgen.

23. The method of embodiment 21 or 22, wherein the anti-androgen is selected from the group consisting of enzalutamide, abiraterone, darolutamide, and apalutamide.

24. The method of any one of embodiments 18-23, wherein the patient harbors an AR aberration.

25. The method of embodiment 24, wherein the AR aberration is the AR-v7 form.

26. The method of any one of embodiments 1-8, wherein the AR+ cancer is AR+ hormone-sensitive prostate cancer.

27. The method of embodiment 26, wherein the Compound 1, or a pharmaceutically acceptable salt thereof, is administered in combination with an androgen-deprivation therapy.

28. The method of embodiment 26, wherein the Compound 1, or a pharmaceutically acceptable salt thereof, is administered in combination with an anti-androgen.

29. The method of any one of embodiments 26-28, wherein the Compound 1, or a pharmaceutically acceptable salt thereof, is administered in combination with an androgen-deprivation therapy and an anti-androgen.

30. The method of embodiment 28 or 29, wherein the anti-androgen is selected from the group consisting of: enzalutamide, abiraterone, darolutamide, and apalutamide.

31. The method of any one of embodiments 1-30, wherein the Compound 1, or pharmaceutically acceptable salt thereof, is administered to the patient on a clinical dosing schedule comprising one or more treatment cycles, wherein each treatment cycle comprises:

(a) a dosing period during which a therapeutically effective amount of said pharmaceutical composition comprising Compound 1 or a pharmaceutically acceptable salt thereof is administered to a patient in need thereof; and, thereafter, (b) a resting period during which the pharmaceutical composition comprising Compound 1 or the pharmaceutically acceptable salt thereof is not administered to the patient.

32. The method of embodiment 31, wherein each treatment cycle is a 28-day cycle.

33. The method of embodiment 31 or 32, wherein the Compound 1 or the pharmaceutically acceptable salt thereof is administered to the patient throughout a duration of treatment of one or more consecutive treatment cycles.

34. The method of any one of embodiments 31-33, comprising multiple consecutive treatment cycles for a total of at least 26 consecutive weeks.

35. The method of any one of embodiments 31-34, wherein Compound 1 is administered to the patient once per day (QD) during the dosing period.

36. The method of any one of embodiments 31-35, wherein the patient does not meet any of the exclusion criteria in Example 21.

37. The method of any one of embodiments 31-36, wherein the pharmaceutical composition is an oral unit dosage form of a pharmaceutical composition disclosed in Example 21.

38. A method of treating a patient diagnosed with metastatic castration-resistant prostate cancer (mCRPC), comprising administering to the patient in need thereof a therapeutically effective amount of (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid ("Compound 1"), or a pharmaceutically acceptable salt thereof.

39. The method of embodiment 38, wherein the Compound 1, or a pharmaceutically acceptable salt thereof is administered to the patient in an oral unit dosage form.

40. The method of embodiment 38 or 39, wherein the Compound 1 is administered as a hydrochloric acid addition salt.

41. The method of any one of embodiments 38-40, wherein the Compound 1 is administered as a Type A hydrochloride salt of Compound 1.

42. The method of any one of embodiments 38-40, wherein the Compound 1 is administered as a Type B hydrochloride salt of Compound 1.

43. The method of any one of embodiments 38-40, wherein the Compound 1 is administered as a Type C hydrochloride salt of Compound 1.

44. The method of embodiment 38 or 39, wherein the Compound 1 is administered as a Type A free base form of Compound 1.

45. The method of any one of embodiments 38-41, wherein the Compound 1 is the active pharmaceutical ingredient in an anhydrate solid form.

46. The method of any one of embodiments 38-45, wherein the Compound 1 or pharmaceutically acceptable salt thereof is administered to the patient on a clinical dosing schedule comprising one or more treatment cycles, wherein each treatment cycle comprises (a) a dosing period during which a therapeutically effective amount of said pharmaceutical composition comprising Compound 1 or a pharmaceutically acceptable salt thereof is administered to a patient in need thereof and, thereafter, (b) a resting period during which the pharmaceutical composition comprising Compound 1 or the pharmaceutically acceptable salt thereof is not administered to the patient.

47. The method of embodiment 46, wherein each treatment cycle is a 28-day cycle comprising 21 consecutive treatment days followed by 7 consecutive days without administering Compound 1 or the pharmaceutically acceptable salt thereof to the patient.

48. The method of embodiment 47, wherein the Compound 1 or the pharmaceutically acceptable salt thereof is administered to the patient throughout a duration of treatment of one or more consecutive treatment cycles.

49. The method of embodiment 47, wherein Compound 1 is administered to the patient once per day (QD) during the dosing period.

50. The method of embodiment 47, wherein the patient is diagnosed with metastatic castration-resistant prostate cancer (mCRPC) and has progressed despite treatment with at least one potent anti-androgen therapy.

51. The method of embodiment 50, comprising multiple consecutive treatment cycles for a total of at least 26 consecutive weeks.

52. The method of embodiment 51, wherein Compound 1 is administered to the patient once per day (QD) during each dosing period.

53. The method of embodiment 52, wherein the patient does not meet any of the exclusion criteria in Example 25. 54. The method of embodiment 52, wherein the patient has previously failed at least one anti-androgen therapy.

55. The method of embodiment 54, wherein the anti-androgen therapy is selected from the group consisting of abiraterone, enzalutamide, apalutamide, and darolutamide.

56. The method of embodiment 52, wherein the patient is diagnosed with AR+ mCRPC characterized by either (a) adenocarcinoma or (b) a mixed histology consisting of (i) metastatic prostate cancer with progressive castration resistant disease after at least one prior line of treatment for metastatic disease and with evaluable disease at enrollment, and (ii) rising PSA (a rising PSA requires at least 3 measurements obtained at least 1 week apart showing increase from nadir with the last level above 2 ng/mL by local testing).

57. The method of embodiment 56, wherein the pharmaceutical composition is an oral unit dosage form of a pharmaceutical composition disclosed in Example 21.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. The present disclosure provides methods for the treatment of certain AR-positive cancers using compounds which are CBP bromodomain inhibitors.

The invention claimed is:

1. A method of treating breast cancer in a patient comprising administering to the patient in need thereof a therapeutically effective amount of a pharmaceutical composition comprising a compound of formula (I):

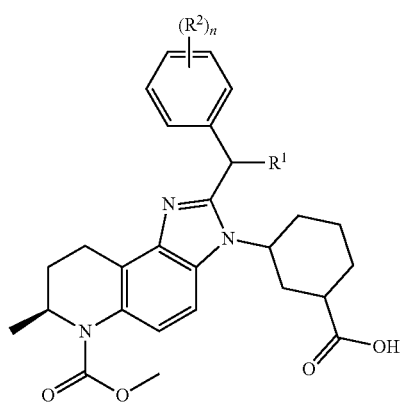

(I)

or a pharmaceutically acceptable salt thereof, wherein:

$R^1$ is H or —OH;

each $R^2$ is independently selected from $C_1$-$C_6$ alkyl, halogen, —CN, and —$OR^3$, wherein the alkyl is optionally substituted with one or more halogen;

each $R^3$ is independently $C_1$-$C_6$ alkyl, wherein the alkyl is optionally substituted with one or more halogen; and n is 0, 1, 2, or 3.

2. The method of claim 1, wherein the breast cancer is triple negative breast cancer.

3. The method of claim 1, wherein the breast cancer is AR+.

4. The method of claim 1, wherein the compound is selected from:

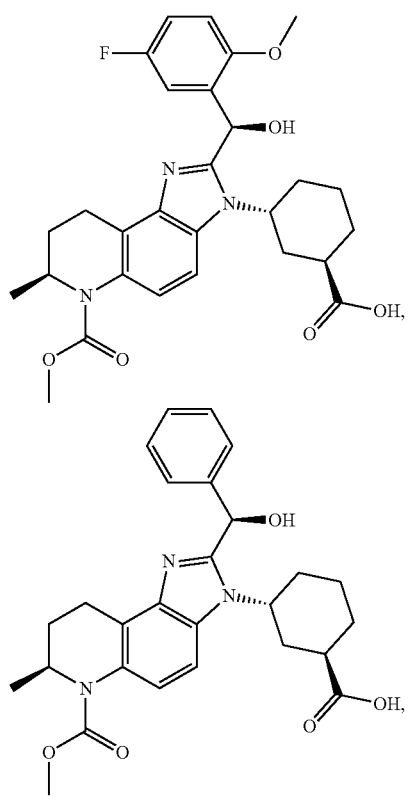

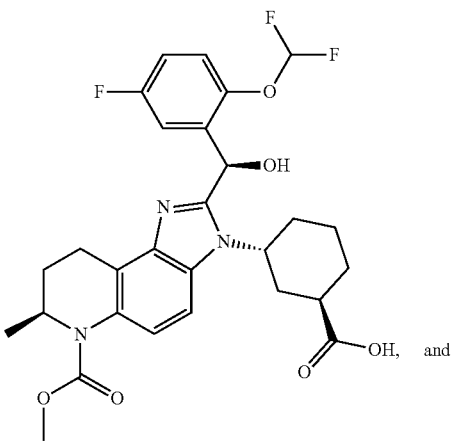

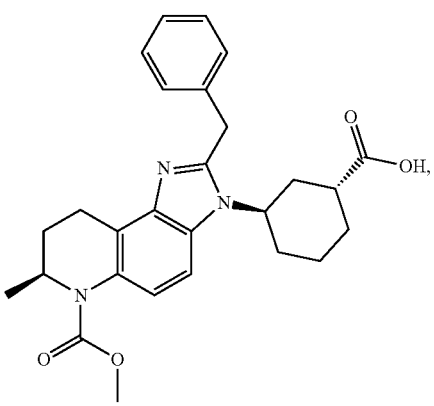

optionally wherein:

the breast cancer is triple negative breast cancer; and/or the breast cancer is AR+.

5. The method of claim 1, wherein the compound is:

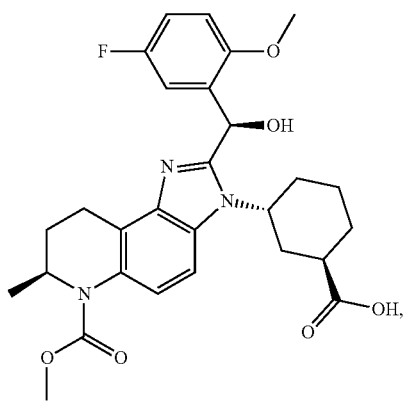 [SMILES: COC(=O)N1c2ccc3c(nc([C@H](O)c4cc(F)ccc4OC)n3[C@@H]3CCC[C@@H](C(=O)O)C3)c2CC[C@@H]1C]

optionally wherein:

the breast cancer is triple negative breast cancer; and/or the breast cancer is AR+.

6. The method of claim 1, wherein the compound is:

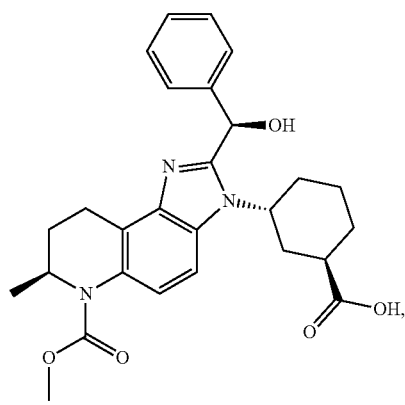 [SMILES: COC(=O)N1c2ccc3c(nc([C@H](O)c4ccccc4)n3[C@@H]3CCC[C@@H](C(=O)O)C3)c2CC[C@@H]1C]

optionally wherein:
the breast cancer is triple negative breast cancer; and/or
the breast cancer is AR+.

7. The method of claim 1, wherein the compound is:

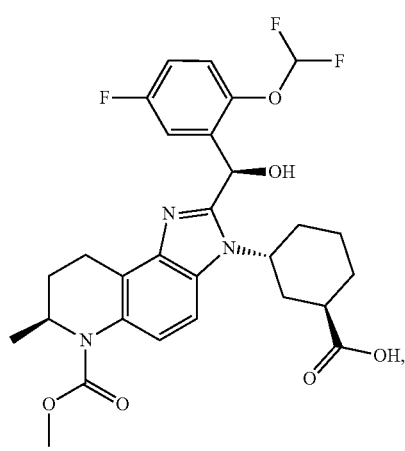 [SMILES: COC(=O)N1c2ccc3c(nc([C@H](O)c4cc(F)ccc4OC(F)F)n3[C@@H]3CCC[C@@H](C(=O)O)C3)c2CC[C@@H]1C]

optionally wherein:
the breast cancer is triple negative breast cancer; and/or
the breast cancer is AR+.

8. The method of claim 1, wherein the compound is:

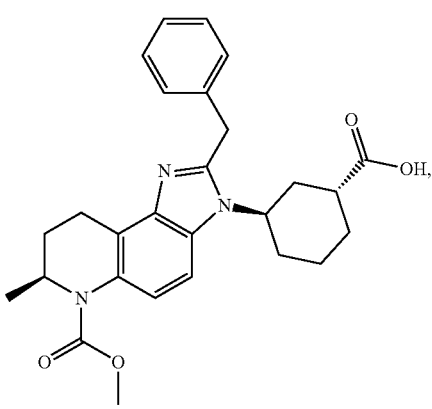 [SMILES: COC(=O)N1c2ccc3c(nc(Cc4ccccc4)n3[C@@H]3CCC[C@@H](C(=O)O)C3)c2CC[C@@H]1C]

optionally wherein:
the breast cancer is triple negative breast cancer; and/or
the breast cancer is AR+.

9. A method of treating prostate cancer in a patient comprising administering to the patient in need thereof a therapeutically effective amount of a pharmaceutical composition comprising a compound of formula (I):

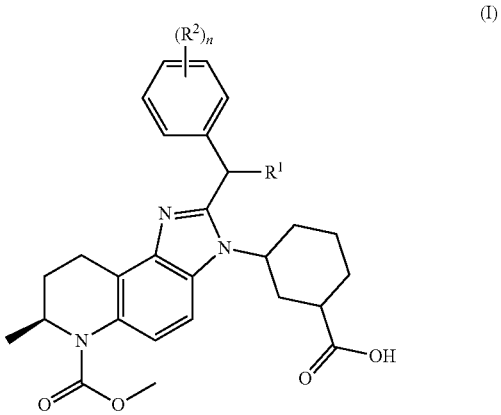

or a pharmaceutically acceptable salt thereof, wherein:
$R^1$ is H or —OH;
each $R^2$ is independently selected from $C_1$-$C_6$ alkyl, halogen, —CN, and —$OR^3$, wherein the alkyl is optionally substituted with one or more halogen;
each $R^3$ is independently $C_1$-$C_6$ alkyl, wherein the alkyl is optionally substituted with one or more halogen; and
n is 0, 1, 2, or 3.

10. The method of claim 9, wherein the prostate cancer is AR+.

11. The method of claim 9, wherein the prostate cancer is AR-v7+.

12. The method of claim 9, wherein the patient is diagnosed with castration-resistant prostate cancer or metastatic castration-sensitive prostate cancer.

13. The method of claim 9, wherein the compound is selected from:

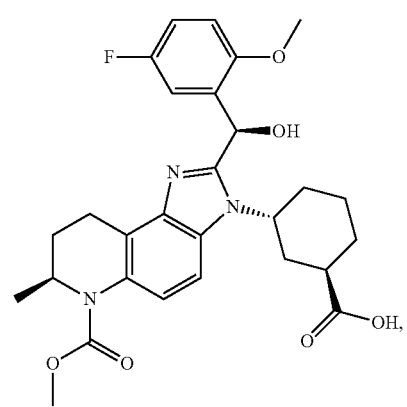

-continued

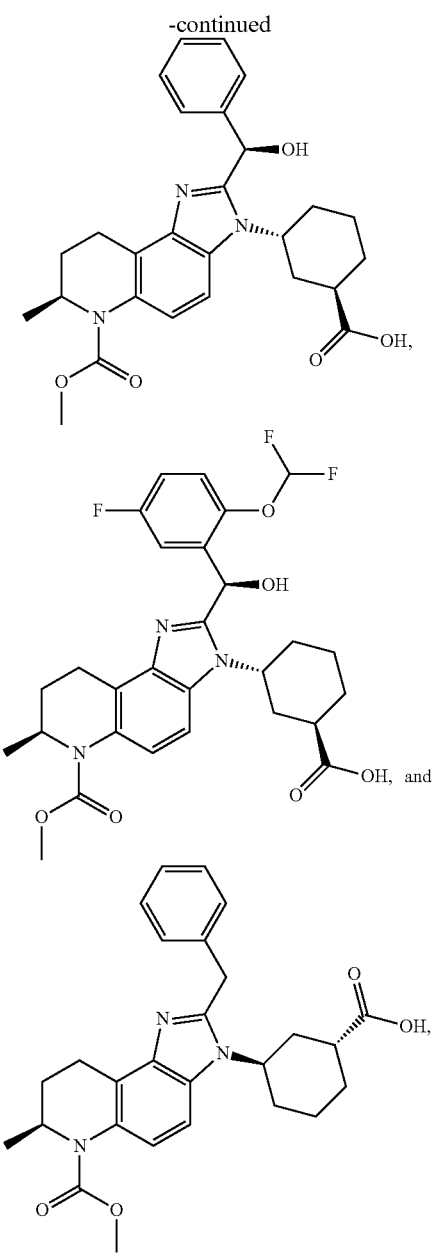

optionally wherein:
the prostate cancer is AR+; and/or
the prostate cancer is AR-v7+.

14. The method of claim 13, wherein the patient is diagnosed with disease progression following treatment with enzalutamide.

15. The method of claim 13, wherein the patient is diagnosed with castration-resistant prostate cancer or metastatic castration-sensitive prostate cancer.

16. A method of treating an Androgen Receptor-expressing cancer in a patient comprising administering to the patient in need thereof a therapeutically effective amount of a pharmaceutical composition comprising (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid, or a pharmaceutically acceptable salt thereof.

17. The method of claim 16, wherein the Androgen Receptor-expressing cancer is AR+breast cancer,
optionally wherein:
the AR+breast cancer is triple negative breast cancer; or
the AR+breast cancer is Her2– breast cancer; or
the AR+breast cancer is selected from ER– breast cancer, PR– breast cancer, and ER–/PR– breast cancer.

18. The method of claim 16, wherein the Androgen Receptor-expressing cancer is AR+prostate cancer, optionally wherein the AR+prostate cancer is AR-v7+.

19. The method of claim 16, wherein the Androgen Receptor-expressing cancer is castration-resistant prostate cancer or metastatic castration-sensitive prostate cancer.

20. The method of claim 19, wherein the patient is diagnosed with disease progression following treatment with enzalutamide.

21. A method of treating an Androgen Receptor-expressing cancer in a patient comprising administering to the patient in need thereof a therapeutically effective amount of a pharmaceutical composition comprising:

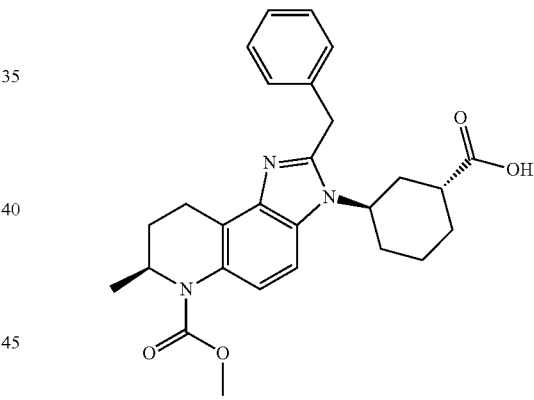

or a pharmaceutically acceptable salt thereof.

22. The method of claim 21, wherein the Androgen Receptor-expressing cancer is AR+breast cancer, optionally wherein the AR+breast cancer is triple negative breast cancer.

23. The method of claim 21, wherein the Androgen Receptor-expressing cancer is AR+prostate cancer, optionally wherein the AR+prostate cancer is AR-v7+.

* * * * *